United States Patent
Zucherman et al.

(10) Patent No.: US 7,621,939 B2
(45) Date of Patent: *Nov. 24, 2009

(54) SUPPLEMENTAL SPINE FIXATION DEVICE AND METHOD

(75) Inventors: James F. Zucherman, San Francisco, CA (US); Ken Y. Hsu, San Francisco, CA (US); Charles J. Winslow, Walnut Creek, CA (US); Henry A. Klyce, Piedmont, CA (US)

(73) Assignee: Kyphon SARL, Neuchatel (CH)

( * ) Notice: Subject to any disclaimer, the term of this patent is extended or adjusted under 35 U.S.C. 154(b) by 605 days.

This patent is subject to a terminal disclaimer.

(21) Appl. No.: 11/092,862

(22) Filed: Mar. 29, 2005

(65) Prior Publication Data

US 2005/0240182 A1    Oct. 27, 2005

Related U.S. Application Data

(60) Division of application No. 09/842,819, filed on Apr. 26, 2001, now Pat. No. 7,201,751, and a continuation-in-part of application No. 09/579,039, filed on May 26, 2000, now Pat. No. 6,451,019, which is a continuation-in-part of application No. 09/473,173, filed on Dec. 28, 1999, now Pat. No. 6,235,030, which is a continuation of application No. 09/179,570, filed on Oct. 27, 1998, now Pat. No. 6,048,342, which is a continuation-in-part of application No. 09/175,645, filed on Oct. 20, 1998, now Pat. No. 6,068,630, which is a continuation-in-part of application No. 08/958,281, filed on Oct. 27, 1997, now Pat. No. 5,860,977, which is a continuation-in-part of application No. 08/778,093, filed on Jan. 2, 1997, now Pat. No. 5,836,948.

(60) Provisional application No. 60/219,985, filed on Jul. 21, 2000.

(51) Int. Cl.
*A61F 2/30* (2006.01)
(52) U.S. Cl. ....................... 606/249; 606/247
(58) Field of Classification Search .................... 606/61, 606/246–279
See application file for complete search history.

(56) References Cited

U.S. PATENT DOCUMENTS 2,456,806 A    12/1948    Wolffe (Continued)

FOREIGN PATENT DOCUMENTS

CA    2015507    1/1991

(Continued)

OTHER PUBLICATIONS

Minns, R.J., et al., *Preliminary Design and Experimental Studies of a Novel Soft Implant for Correcting Sagittal Plane Instability in the Lumbar Spine*, Spine vol. 22, No. 16, pp. 1819-1825, © 1997, Lippincott-Raven Publishers.

(Continued)

*Primary Examiner*—Eduardo C Robert
*Assistant Examiner*—Mary Hoffman
(74) *Attorney, Agent, or Firm*—Coats and Bennett, P.L.L.C.

(57) ABSTRACT

A supplemental spine fixation device and method is used in association with a primary spine fixation device. The supplemental spine fixation device includes a guide and spacer for distracting apart adjacent spinous processes and the device has hook members which hook about the first and second spinous processes. With the spinous processes distracted and the hook members about the spinous processes, the hook members can be rigidly secured to a hub in order to rigidly affix the spinous processes about the spacer. The rigidity between the spinous processes assures that the vertebral bodies will be held rigidly in place in order to promote bone growth and fusion. Further additional freedom of movement between the spacer and hub is accomplished with the spacer being pivotably mounted relative to the hub. The hooks have a tissue distracting lead-in guide for allowing the hooks to be easily urged between spinous processes.

18 Claims, 102 Drawing Sheets

U.S. PATENT DOCUMENTS

| | | | |
|---|---|---|---|
| 2,677,369 A | 5/1954 | Knowles | |
| 3,426,364 A * | 2/1969 | Lumb | 623/17.15 |
| 3,643,658 A | 2/1972 | Steinemenan | |
| 3,648,691 A | 3/1972 | Lumb | |
| 3,867,728 A | 2/1975 | Stubstad | |
| 3,875,595 A | 4/1975 | Froning | |
| 4,003,376 A * | 1/1977 | McKay et al. | 606/61 |
| 4,034,418 A | 7/1977 | Jackson | |
| 4,219,015 A | 8/1980 | Steinemenan | |
| 4,309,777 A | 1/1982 | Patil | |
| 4,349,921 A | 9/1982 | Kuntz | |
| 4,369,769 A | 1/1983 | Edwards | |
| 4,401,112 A | 8/1983 | Rezaian | |
| 4,455,690 A | 6/1984 | Homsy | |
| 4,479,491 A | 10/1984 | Martin | |
| 4,501,269 A | 2/1985 | Bagby | |
| 4,553,273 A | 11/1985 | Wu | |
| 4,554,914 A | 11/1985 | Kapp | |
| 4,599,084 A | 7/1986 | Nashef | |
| 4,599,086 A | 7/1986 | Doty | |
| 4,604,995 A | 8/1986 | Stephens | |
| 4,611,582 A | 9/1986 | Duff | |
| 4,636,217 A | 1/1987 | Ogilvie | |
| 4,643,178 A | 2/1987 | Nastari | |
| 4,657,550 A | 4/1987 | Daher | |
| 4,685,447 A | 8/1987 | Iversen | |
| 4,696,290 A | 9/1987 | Steffee | |
| 4,714,469 A | 12/1987 | Kenna | |
| 4,743,256 A | 5/1988 | Brantigan | |
| 4,772,287 A | 9/1988 | Ray | |
| 4,790,303 A | 12/1988 | Steffee | |
| 4,834,757 A | 5/1989 | Brantigan | |
| 4,502,161 A | 7/1989 | Wall | |
| 4,878,915 A | 11/1989 | Brantigan | |
| 4,904,260 A | 2/1990 | Ray | |
| 4,904,261 A | 2/1990 | Dove | |
| 4,913,134 A | 4/1990 | Luque | |
| 4,923,471 A | 5/1990 | Morgan | |
| 4,932,975 A | 6/1990 | Main | |
| 4,936,848 A | 6/1990 | Bagby | |
| 4,946,378 A | 8/1990 | Hirayama | |
| 4,961,740 A | 10/1990 | Ray | |
| 4,969,888 A | 11/1990 | Scholten | |
| 5,011,484 A | 4/1991 | Breard | |
| 5,015,247 A | 5/1991 | Michelson | |
| 5,015,255 A | 5/1991 | Kuslich | |
| 5,026,373 A | 6/1991 | Ray | |
| 5,035,716 A | 7/1991 | Downey | |
| 5,047,055 A | 9/1991 | Bao | |
| 5,055,104 A | 10/1991 | Ray | |
| 5,059,193 A | 10/1991 | Kuslich | |
| 5,059,194 A | 10/1991 | Michelson | |
| 5,062,845 A | 11/1991 | Kuslich | |
| 5,062,850 A | 11/1991 | MacMillan | |
| 5,074,864 A | 12/1991 | Cozad | |
| 5,084,049 A | 1/1992 | Asher et al. | |
| 5,088,869 A | 2/1992 | Greenslade | |
| 5,092,866 A | 3/1992 | Breard | |
| 5,105,255 A | 4/1992 | Shannon | |
| 5,122,130 A | 6/1992 | Keller | |
| 5,123,926 A | 6/1992 | Pisharodi | |
| 5,127,912 A | 7/1992 | Ray | |
| 5,147,404 A | 9/1992 | Downey | |
| 5,167,662 A | 12/1992 | Hayes | |
| 5,167,665 A | 12/1992 | McKinney | |
| 5,180,381 A | 1/1993 | Aust | |
| 5,192,327 A | 3/1993 | Brantigan | |
| 5,258,031 A | 11/1993 | Salib | |
| 5,263,953 A | 11/1993 | Bagby | |
| 5,275,601 A | 1/1994 | Gogolewski | |
| 5,290,312 A | 3/1994 | Kojimoto | |
| 5,300,073 A | 4/1994 | Ray | |
| 5,304,178 A | 4/1994 | Stahurski | |
| 5,306,275 A | 4/1994 | Bryan | |
| 5,306,309 A | 4/1994 | Wagner | |
| 5,352,225 A | 10/1994 | Yuan | |
| 5,366,455 A | 11/1994 | Dove | |
| 5,387,213 A | 2/1995 | Breard | |
| 5,390,683 A | 2/1995 | Pisharodi | |
| 5,391,168 A | 2/1995 | Sanders | |
| 5,395,372 A | 3/1995 | Holt | |
| 5,403,316 A * | 4/1995 | Ashman | 606/61 |
| 5,415,659 A * | 5/1995 | Lee et al. | 606/61 |
| 5,415,661 A | 5/1995 | Holmes | |
| 5,437,672 A | 8/1995 | Alleyne | |
| 5,443,514 A | 8/1995 | Steffee | |
| 5,454,812 A | 10/1995 | Lin | |
| 5,456,722 A | 10/1995 | McLeod | |
| 5,458,638 A | 10/1995 | Kuslich | |
| 5,458,641 A | 10/1995 | Ramirez Jimenez | |
| 5,458,643 A | 10/1995 | Oka | |
| 5,468,242 A | 11/1995 | Reisberg | |
| 5,470,333 A | 11/1995 | Ray | |
| 5,491,882 A | 2/1996 | Walston | |
| 5,496,318 A | 3/1996 | Howland | |
| 5,505,732 A | 4/1996 | Michelson | |
| 5,507,745 A | 4/1996 | Logroscino | |
| 5,507,823 A | 4/1996 | Walston | |
| 5,514,180 A | 5/1996 | Heggeness | |
| 5,527,312 A | 6/1996 | Ray | |
| 5,531,747 A | 7/1996 | Ray | |
| 5,534,028 A | 7/1996 | Bao | |
| 5,534,029 A | 7/1996 | Shima | |
| 5,540,689 A | 7/1996 | Sanders | |
| 5,549,679 A | 8/1996 | Kuslich | |
| 5,554,191 A | 9/1996 | Lahille | |
| 5,562,736 A | 10/1996 | Ray | |
| 5,571,191 A | 11/1996 | Fitz | |
| 5,577,995 A | 11/1996 | Walker | |
| 5,584,832 A | 12/1996 | Schlapfer | |
| 5,593,409 A | 1/1997 | Michelson | |
| 5,601,553 A | 2/1997 | Trebing | |
| 5,603,713 A | 2/1997 | Aust | |
| 5,609,634 A | 3/1997 | Voydeville | |
| 5,616,142 A | 4/1997 | Yuan | |
| 5,623,984 A | 4/1997 | Nozaki | |
| 5,628,756 A | 5/1997 | Barker, Jr. | |
| 5,645,597 A | 7/1997 | Krapiva | |
| 5,645,599 A | 7/1997 | Samani | |
| 5,653,761 A | 8/1997 | Pisharodi | |
| 5,658,286 A | 8/1997 | Sava | |
| 5,667,506 A * | 9/1997 | Sutterlin | 606/61 |
| 5,672,177 A | 9/1997 | Seldin | |
| 5,674,295 A | 10/1997 | Ray | |
| 5,674,296 A | 10/1997 | Bryan | |
| 5,676,702 A | 10/1997 | Ratron | |
| 5,702,455 A | 12/1997 | Saggar | |
| 5,725,582 A | 3/1998 | Bevan | |
| 5,741,261 A | 4/1998 | Moskovitz | |
| 5,766,251 A | 6/1998 | Koshino | |
| 5,766,252 A | 6/1998 | Henry | |
| 5,800,438 A | 9/1998 | Tuke | |
| 5,824,098 A | 10/1998 | Stein | |
| 5,836,948 A | 11/1998 | Zucherman | |
| 5,860,977 A | 1/1999 | Zucherman | |
| 5,865,846 A | 2/1999 | Bryan | |
| 5,876,402 A | 3/1999 | Errico | |
| 5,876,404 A | 3/1999 | Zucherman | |
| 5,879,396 A | 3/1999 | Walston | |
| 5,885,299 A | 3/1999 | Winslow | |
| 5,888,224 A | 3/1999 | Beckers | |
| 5,888,226 A | 3/1999 | Rogozinski | |
| 5,951,555 A | 9/1999 | Rehak | |
| 5,976,186 A | 11/1999 | Bao | |

| | | | | | | |
|---|---|---|---|---|---|---|
| 6,001,130 | A | 12/1999 | Bryan | 2002/0151895 A1 | 10/2002 | Soboleski |
| 6,022,376 | A | 2/2000 | Assell | 2002/0183756 A1 | 12/2002 | Michelson |
| 6,030,162 | A | 2/2000 | Huebner | 2002/0183757 A1 | 12/2002 | Michelson |
| 6,045,554 | A | 4/2000 | Grooms | 2002/0188296 A1 | 12/2002 | Michelson |
| 6,048,204 | A | 4/2000 | Klardie | 2003/0004572 A1 | 1/2003 | Goble |
| 6,048,342 | A | 4/2000 | Zucherman | 2003/0028250 A1 | 2/2003 | Reiley |
| 6,048,344 | A | 4/2000 | Schenk | 2003/0040746 A1 | 2/2003 | Mitchell |
| 6,068,630 | A | 5/2000 | Zucherman | 2003/0060828 A1 | 3/2003 | Michelson |
| RE36,758 | E | 6/2000 | Fitz | 2003/0078668 A1 | 4/2003 | Michelson |
| 6,099,531 | A | 8/2000 | Bonutti | 2003/0181912 A1 | 9/2003 | Michelson |
| 6,113,639 | A | 9/2000 | Ray | 2003/0191471 A1 | 10/2003 | Michelson |
| 6,129,730 | A | 10/2000 | Bono | 2003/0191472 A1 | 10/2003 | Michelson |
| 6,132,464 | A | 10/2000 | Martin | 2003/0191532 A1 | 10/2003 | Goble |
| 6,139,550 | A | 10/2000 | Michelson | 2003/0204259 A1 | 10/2003 | Goble |
| 6,152,927 | A | 11/2000 | Farris | 2004/0006391 A1 | 1/2004 | Reiley |
| 6,156,067 | A | 12/2000 | Bryan | 2004/0049272 A1 | 3/2004 | Reiley |
| 6,190,414 | B1 | 2/2001 | Young | 2004/0049273 A1 | 3/2004 | Reiley |
| 6,193,721 | B1 | 2/2001 | Michelson | 2004/0049274 A1 | 3/2004 | Reiley |
| 6,200,322 | B1 | 3/2001 | Branch | 2004/0049275 A1 | 3/2004 | Reiley |
| 6,206,922 | B1 | 3/2001 | Zdeblick | 2004/0049276 A1 | 3/2004 | Reiley |
| 6,217,580 | B1 | 4/2001 | Levin | 2004/0049277 A1 | 3/2004 | Reiley |
| 6,224,602 | B1 | 5/2001 | Hayes | 2004/0049278 A1 | 3/2004 | Reiley |
| 6,224,607 | B1 | 5/2001 | Michelson | 2004/0049281 A1 | 3/2004 | Reiley |
| 6,228,900 | B1 | 5/2001 | Shen | 2004/0087948 A1 | 5/2004 | Suddaby |
| 6,234,705 | B1 | 5/2001 | Troxell | 2004/0111154 A1 | 6/2004 | Reiley |
| 6,261,296 | B1 | 7/2001 | Aebi | 2004/0116927 A1 | 6/2004 | Graf |
| 6,293,949 | B1 | 9/2001 | Justis | 2004/0122427 A1 | 6/2004 | Holmes |
| 6,306,136 | B1 | 10/2001 | Baccelli | 2004/0127989 A1 | 7/2004 | Dooris |
| 6,352,537 | B1 | 3/2002 | Strnad | 2004/0143268 A1 | 7/2004 | Falahee |
| 6,368,351 | B1 | 4/2002 | Glenn | 2004/0181226 A1 | 9/2004 | Michelson |
| 6,383,186 | B1 | 5/2002 | Michelson | 2004/0181229 A1 | 9/2004 | Michelson |
| 6,395,030 | B1 | 5/2002 | Songer | 2004/0186475 A1 | 9/2004 | Falahee |
| 6,398,783 | B1 | 6/2002 | Michelson | 2004/0186476 A1 | 9/2004 | Michelson |
| 6,402,756 | B1 | 6/2002 | Ralph | 2004/0210313 A1 | 10/2004 | Michelson |
| 6,419,703 | B1 | 7/2002 | Fallin | 2004/0210314 A1 | 10/2004 | Michelson |
| 6,428,542 | B1 | 8/2002 | Michelson | 2004/0220678 A1 | 11/2004 | Chow |
| 6,436,145 | B1 | 8/2002 | Miller | 2004/0230201 A1 | 11/2004 | Yuan |
| 6,440,169 | B1 | 8/2002 | Elberg et al. | 2004/0230304 A1 | 11/2004 | Yuan |
| 6,454,771 | B1 | 9/2002 | Michelson | 2004/0236334 A1 | 11/2004 | Michelson |
| 6,458,131 | B1 | 10/2002 | Ray | 2004/0236335 A1 | 11/2004 | Michelson |
| 6,527,776 | B1 | 3/2003 | Michelson | 2005/0027297 A1 | 2/2005 | Michelson |
| 6,558,423 | B1 | 5/2003 | Michelson | 2005/0027298 A1 | 2/2005 | Michelson |
| 6,558,686 | B1 | 5/2003 | Darouiche | | | |
| 6,565,570 | B2 | 5/2003 | Sterett | | | |
| 6,565,605 | B2 | 5/2003 | Goble | | | |

FOREIGN PATENT DOCUMENTS

| | | |
|---|---|---|
| DE | 2821678 A1 | 4/1980 |
| DE | 3113142 A1 | 1/1982 |
| DE | 4012622 C1 | 7/1991 |
| DE | 4409833 | 10/1995 |
| DE | 4414781 | 11/1995 |
| DE | 201 12 123 U1 | 9/2001 |
| DE | 101 35 771 A1 | 2/2003 |
| EP | 140790 A2 | 10/1984 |
| EP | 146347 A1 | 12/1984 |
| EP | 322334 A1 | 12/1988 |
| EP | 0307241 B1 | 12/1992 |
| EP | 0677277 A2 | 10/1995 |
| EP | 0767636 B1 | 4/1997 |
| EP | 1138268 A1 | 10/2001 |
| FR | 2623085 | 5/1989 |
| FR | 2681525 A1 | 3/1993 |
| FR | 2705227 | 11/1994 |
| FR | 2707864 A1 | 1/1995 |
| FR | 2717066 | 9/1995 |
| FR | 2717068 | 9/1995 |
| FR | 2717675 | 9/1995 |
| FR | 2722088 | 1/1996 |
| FR | 2722980 A1 | 2/1996 |
| FR | 2724554 | 3/1996 |
| FR | 2780269 A1 | 12/1999 |
| FR | 2782911 A1 | 3/2000 |
| FR | 2806614 A1 | 9/2001 |
| FR | 2806616 A1 | 9/2001 |

| | | | |
|---|---|---|---|
| 6,579,318 | B2 | 6/2003 | Varga |
| 6,579,319 | B2 | 6/2003 | Goble |
| 6,582,437 | B2 | 6/2003 | Dorchak |
| 6,592,586 | B1 | 7/2003 | Michelson |
| 6,610,091 | B1 | 8/2003 | Reiley |
| 6,620,163 | B1 | 9/2003 | Michelson |
| 6,626,944 | B1 | 9/2003 | Taylor |
| 6,669,729 | B2 | 12/2003 | Chin |
| 6,699,246 | B2 | 3/2004 | Zucherman et al. |
| 6,712,852 | B1 | 3/2004 | Chung |
| 6,730,127 | B2 | 5/2004 | Michelson |
| 6,752,831 | B2 | 6/2004 | Sybert |
| 6,755,841 | B2 | 6/2004 | Fraser |
| 6,761,720 | B1 | 7/2004 | Senegas |
| 6,783,527 | B2 | 8/2004 | Drewry |
| 6,800,670 | B2 | 10/2004 | Shen |
| 6,811,567 | B2 | 11/2004 | Reiley |
| 2001/0012938 | A1 | 8/2001 | Zucherman |
| 2001/0018614 | A1 | 8/2001 | Bianchi |
| 2002/0004683 | A1 | 1/2002 | Michelson |
| 2002/0016595 | A1 | 2/2002 | Michelson |
| 2002/0022843 | A1 | 2/2002 | Michelson |
| 2002/0065557 | A1 | 5/2002 | Goble |
| 2002/0072800 | A1 | 6/2002 | Goble |
| 2002/0077700 | A1 | 6/2002 | Varga |
| 2002/0099376 | A1 | 7/2002 | Michelson |
| 2002/0128655 | A1 | 9/2002 | Michelson |
| 2002/0133155 | A1 | 9/2002 | Ferree |

| | | |
|---|---|---|
| GB | 780652 | 8/1957 |
| JP | 10-179622 | 7/1998 |
| SU | 1484348 A1 | 6/1989 |
| WO | WO 90/00037 | 1/1990 |
| WO | WO 91/16018 | 10/1991 |
| WO | WO 94/21185 | 9/1994 |
| WO | WO 94/26192 | 11/1994 |
| WO | WO 94/26193 | 11/1994 |
| WO | WO 95/35067 | 12/1995 |
| WO | WO 96/08206 A1 | 3/1996 |
| WO | WO 96/39975 | 12/1996 |
| WO | WO 98/48717 | 11/1998 |
| WO | WO 98/55038 | 12/1998 |
| WO | WO 99/26562 | 6/1999 |
| WO | WO 99/40866 | 8/1999 |
| WO | WO 99/42051 | 8/1999 |
| WO | WO 99/56653 | 11/1999 |
| WO | WO 99/59669 | 11/1999 |
| WO | WO 00/04851 | 2/2000 |
| WO | WO 00/13619 | 3/2000 |
| WO | WO 00/13620 | 3/2000 |
| WO | WO 00/38582 | 7/2000 |
| WO | WO 00/53126 | 9/2000 |
| WO | WO 01/26566 A1 | 4/2001 |
| WO | WO 01/28442 A1 | 4/2001 |
| WO | WO 02/34120 A2 | 5/2002 |
| WO | WO 02/085226 A1 | 10/2002 |
| WO | WO 03/057055 A1 | 7/2003 |
| WO | WO 03/101350 A1 | 12/2003 |
| WO | WO 2004/071358 A1 | 8/2004 |
| WO | WO 2004/098465 A1 | 11/2004 |

OTHER PUBLICATIONS

Waldemar Link, brochure entitled *Wirbelsäulen-Chirurgie: Instrumentarium Und Implantate Zur Wirbelsäulen-Chirurgie* (Spinal Surgery: Instrumentation and Implants for Spinal Surgery), Waldermar Link, Hamburg, Germany.

Haruo Tsuji, et al., *Ceramic Interspinous Block (CISB) Assisted Anterior Interbody Fusion*, Journal of Spinal Disorders, vol. 3, No. 1, pp. 77-86, © 1990 Raven Press, Ltd., New York.

Richard W. Porter, MD, FRCS, FRCSE, *Spinal Stenosis and Neurogenic Claudication*, Spine vol. 21, No. 17, pp. 2046-2052, © 1996, Lippincott-Raven Publishers.

International Search Report for PCT/US06/10521 (mailed Nov. 22, 2006).

* cited by examiner

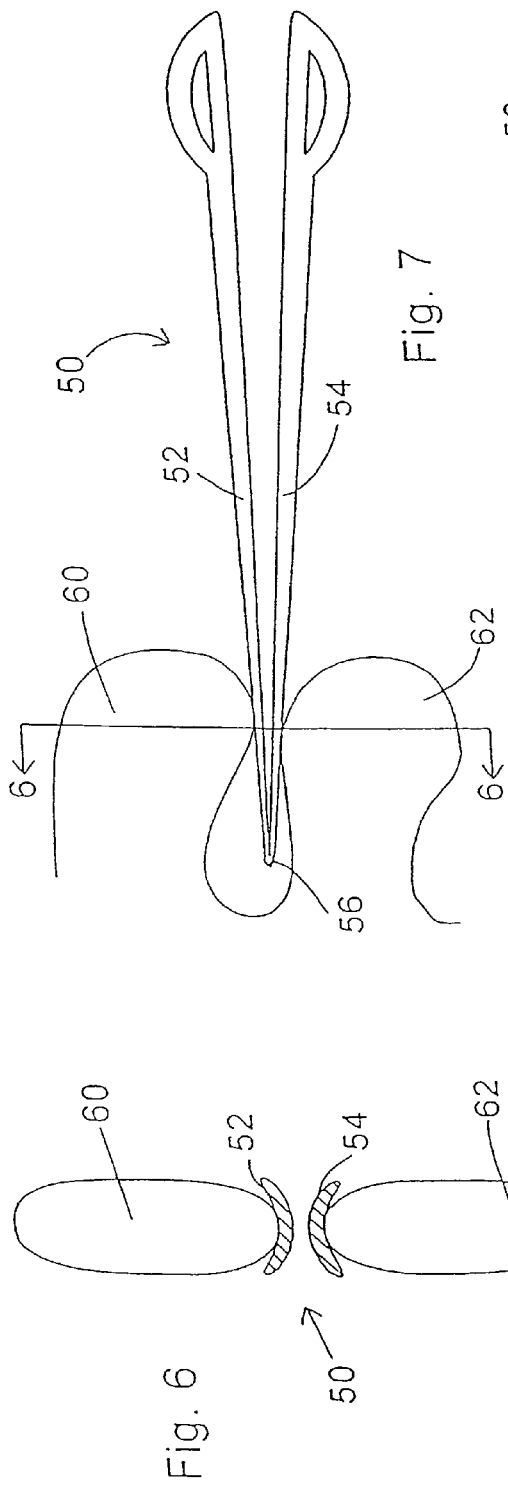
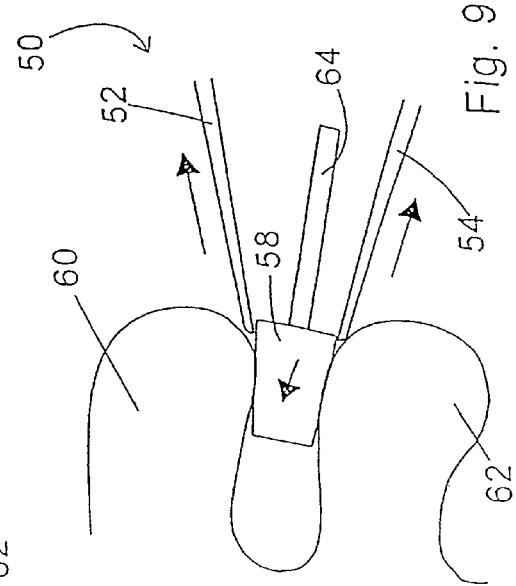
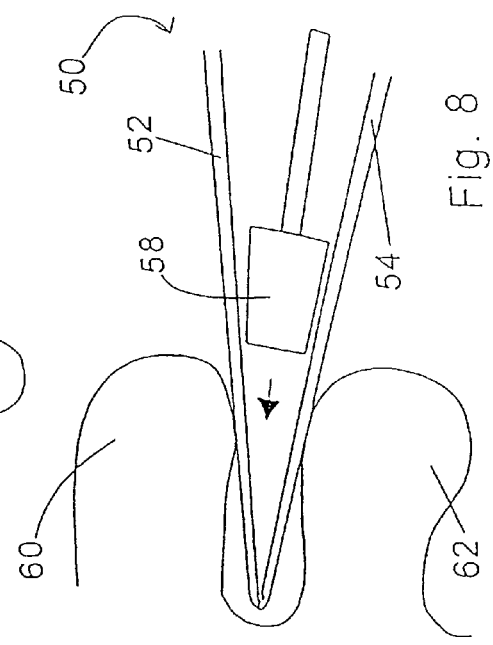

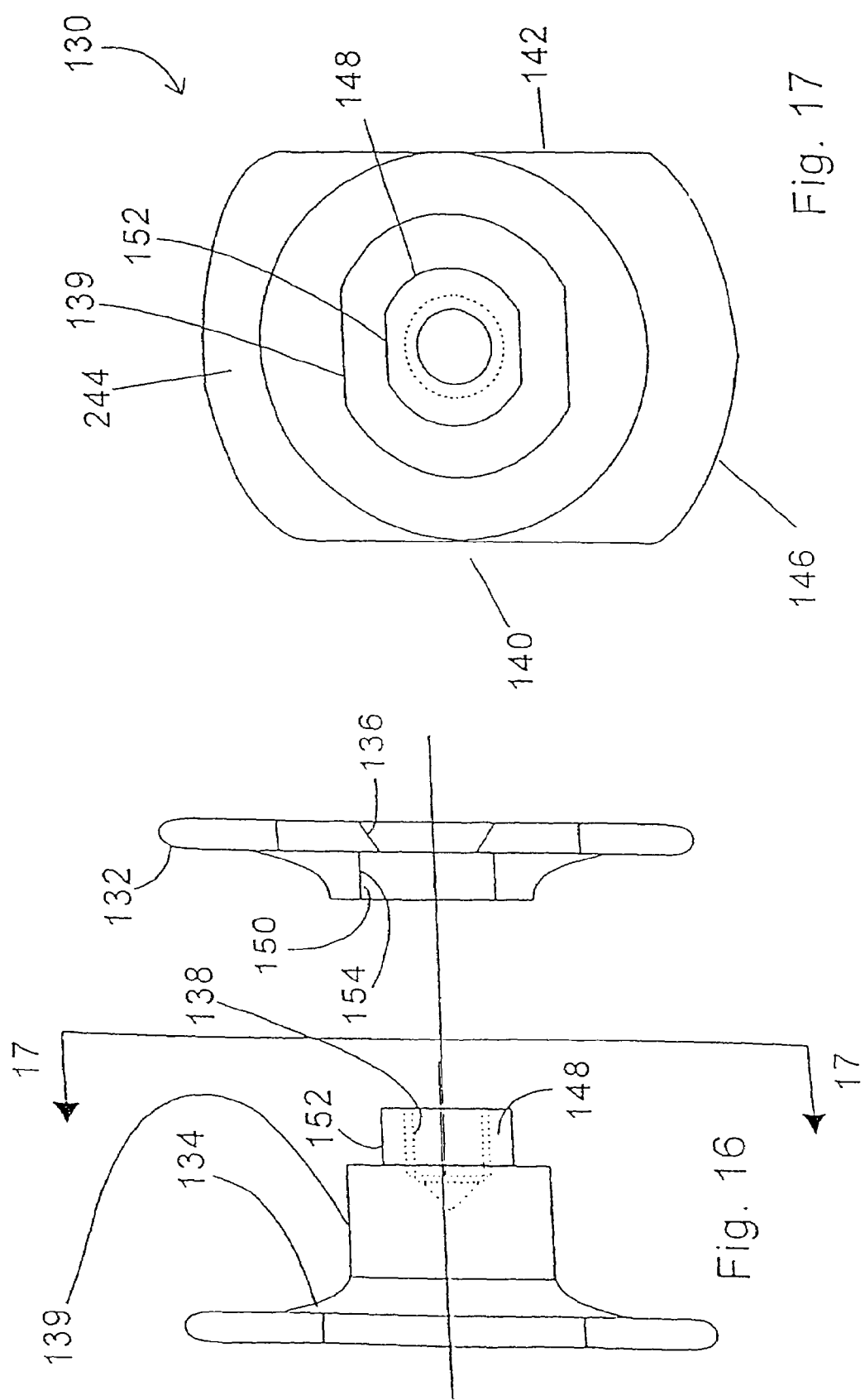

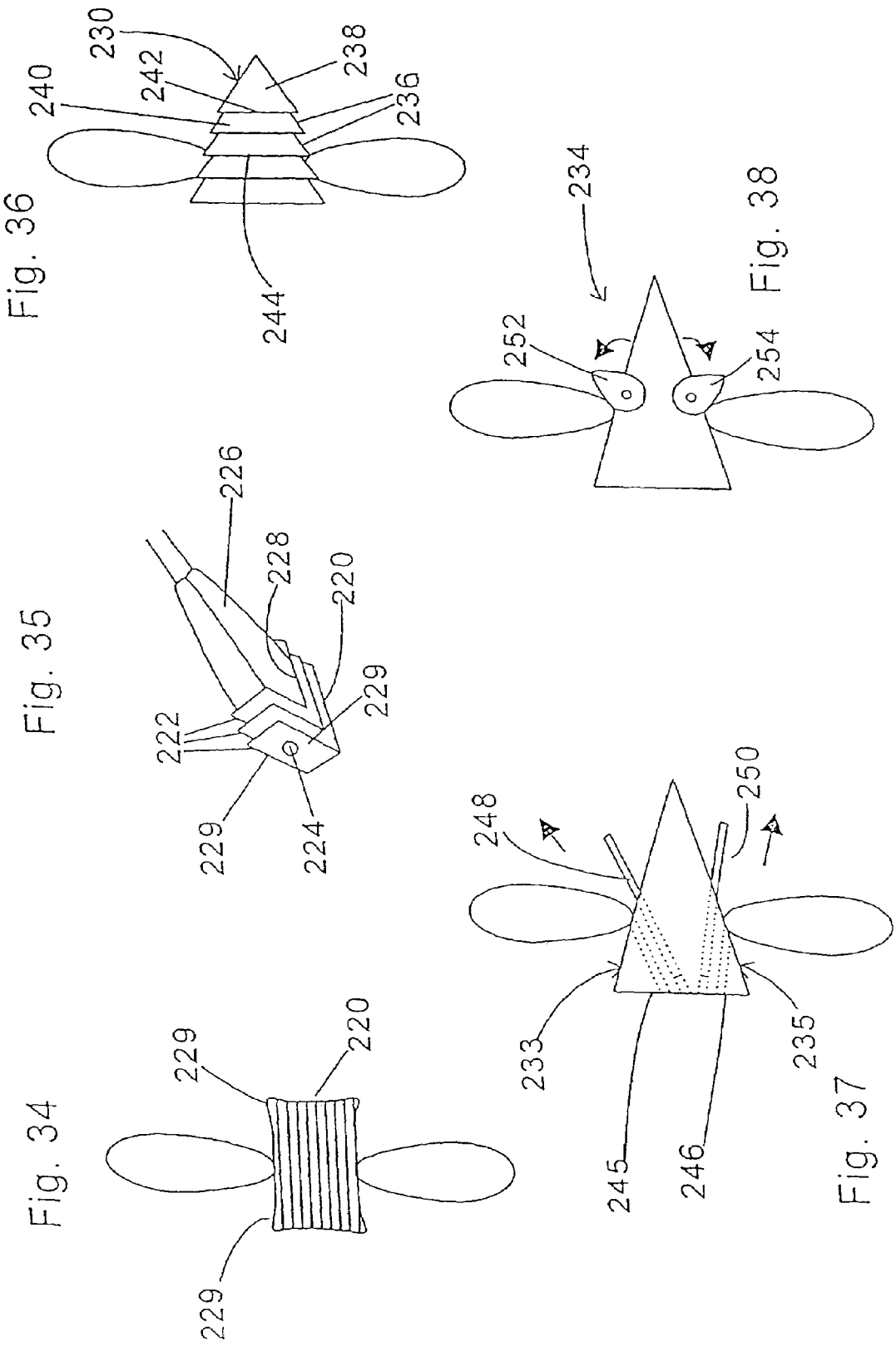

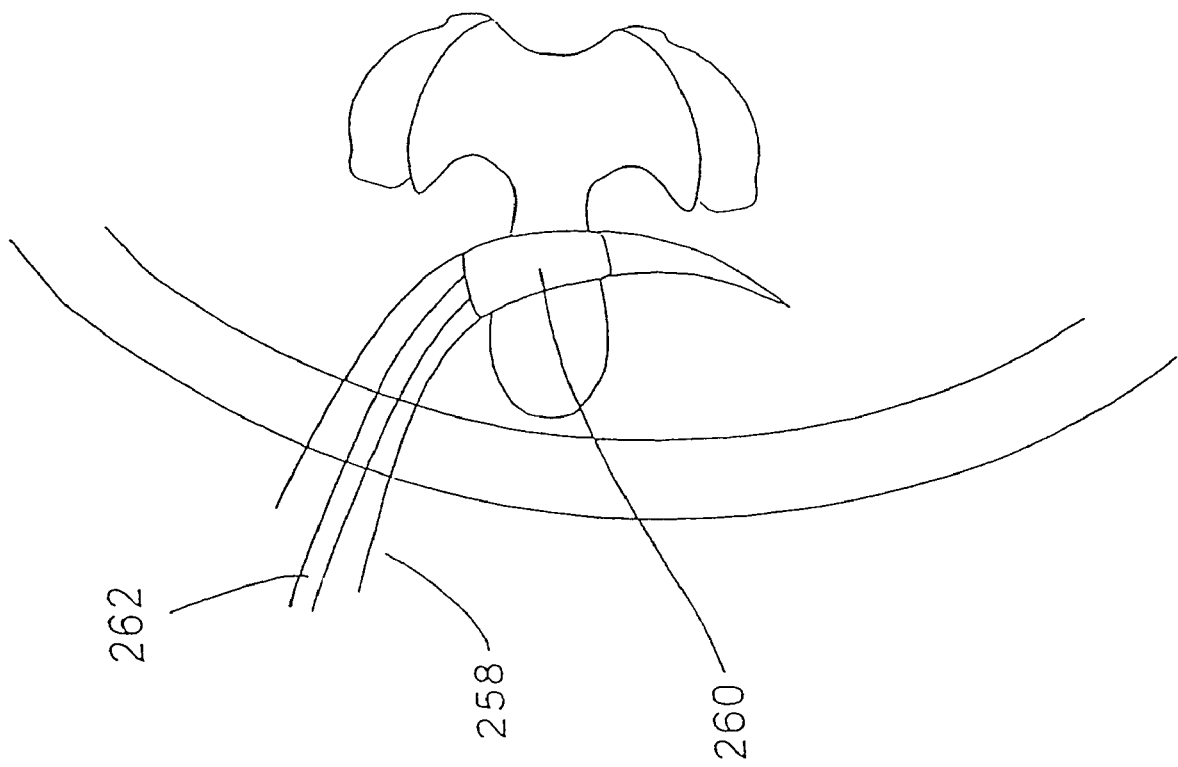

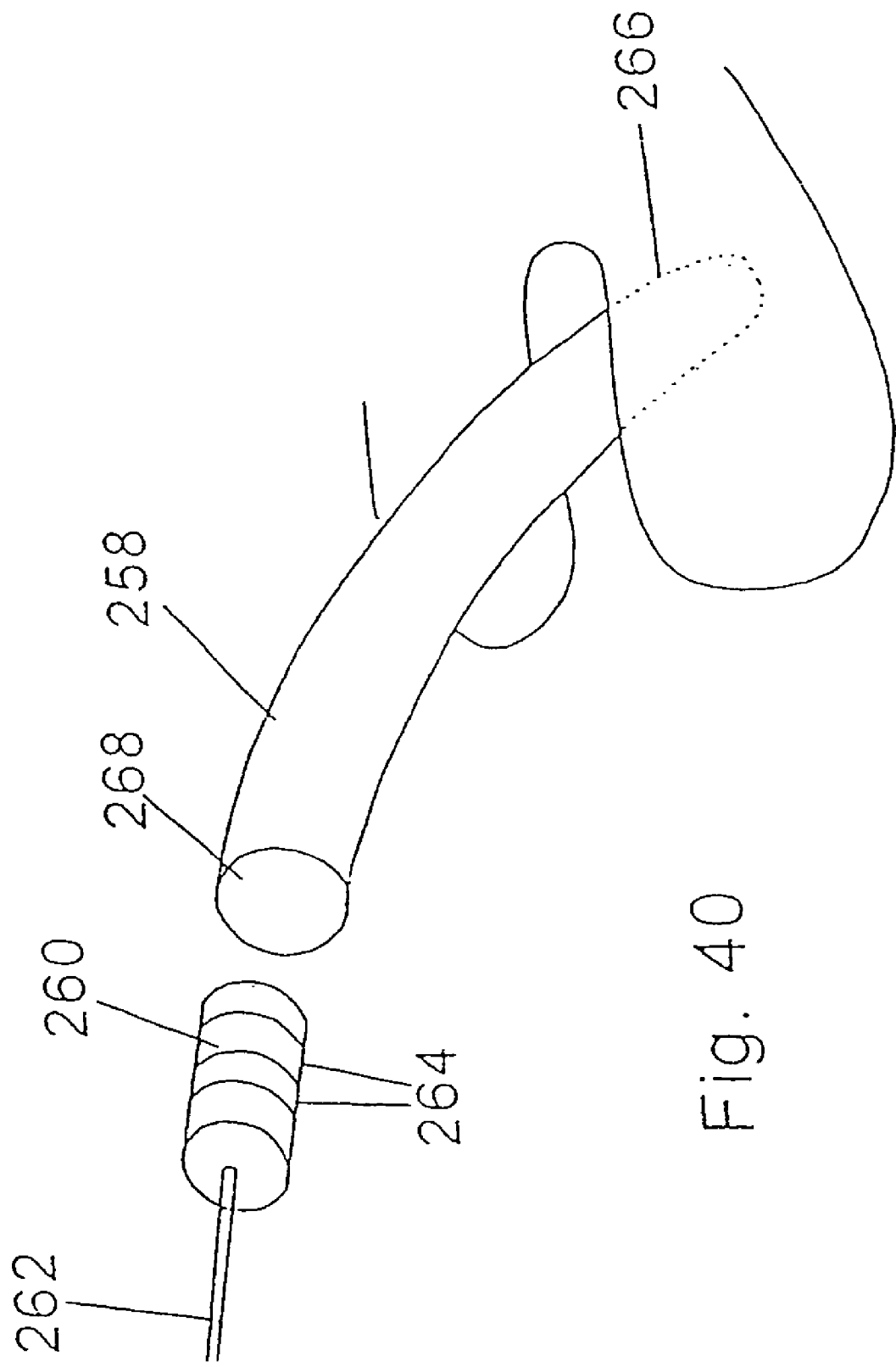

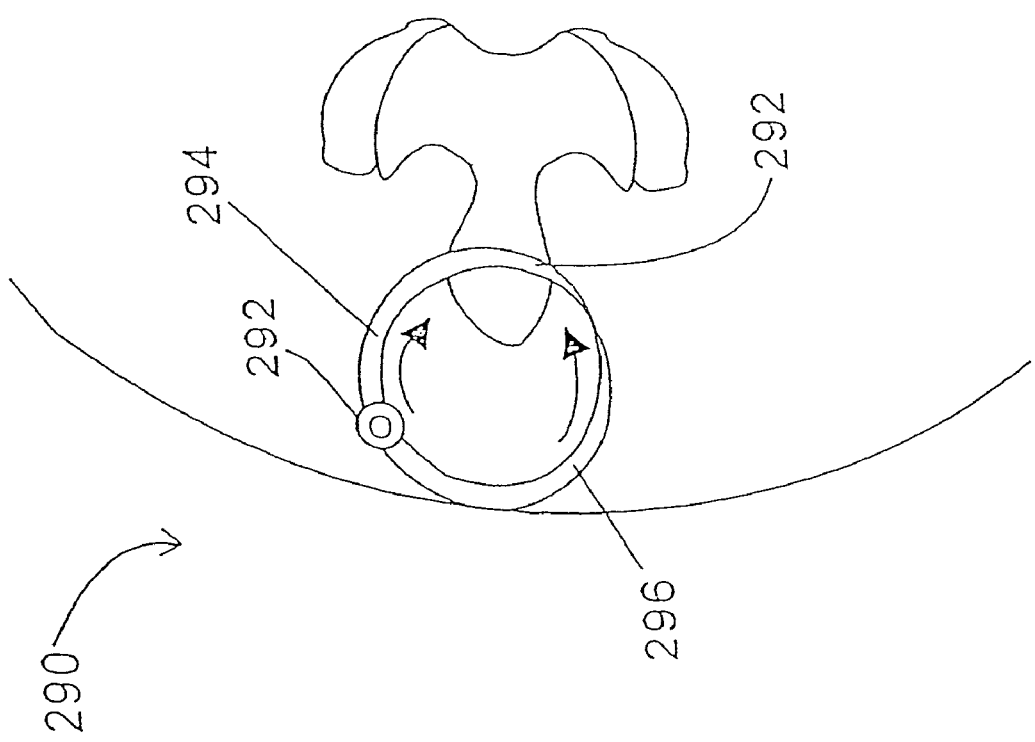

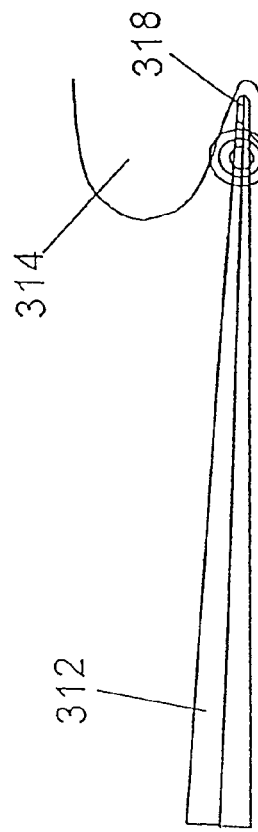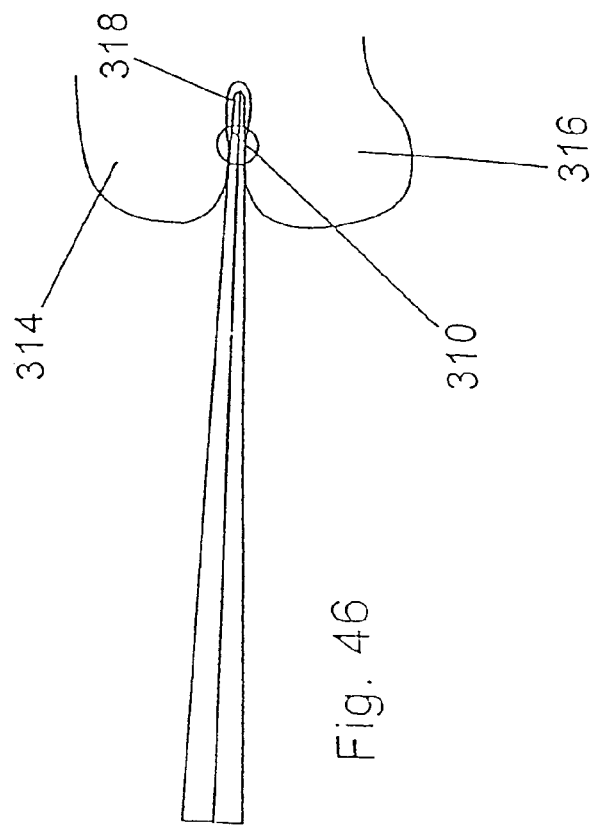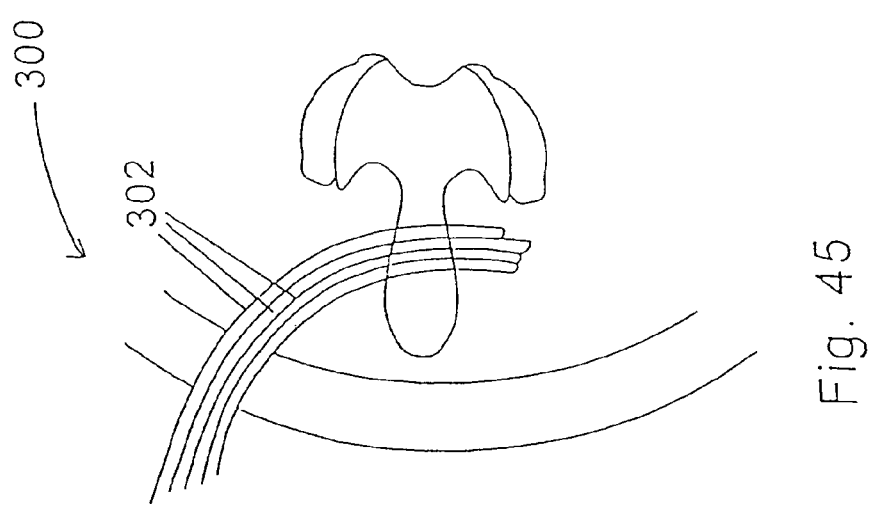

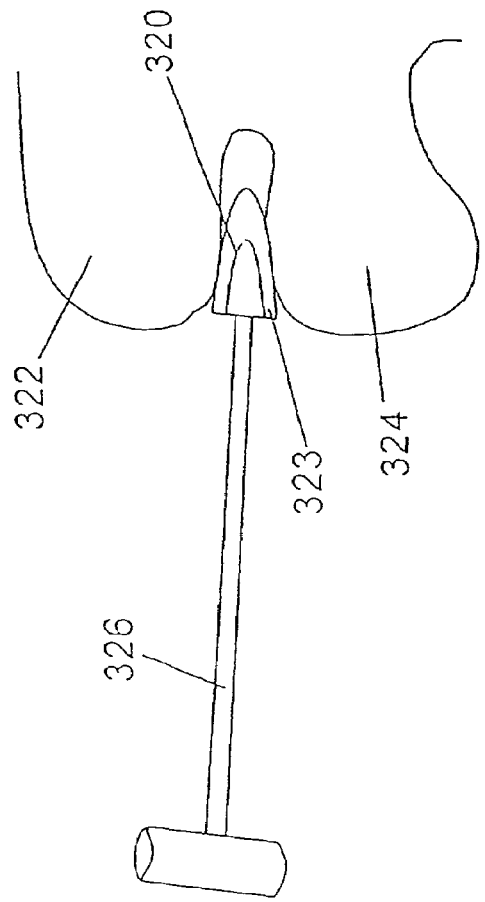
Fig. 48
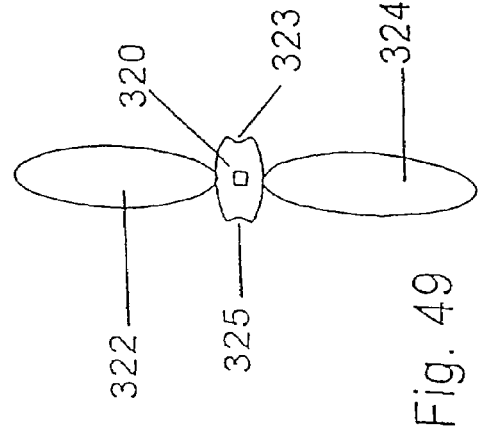
Fig. 49
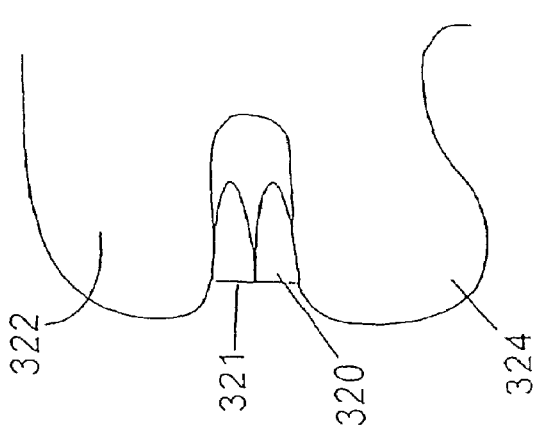
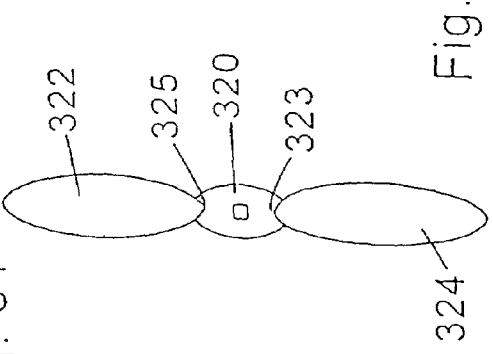
Fig. 51
Fig. 50

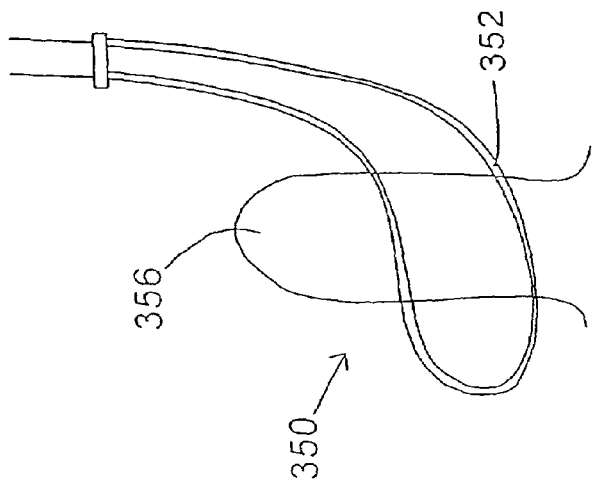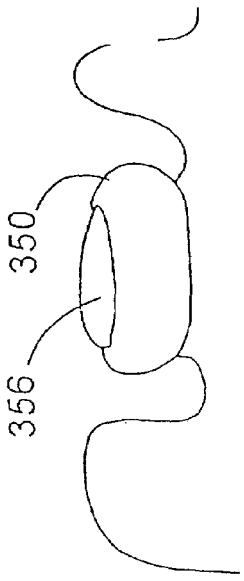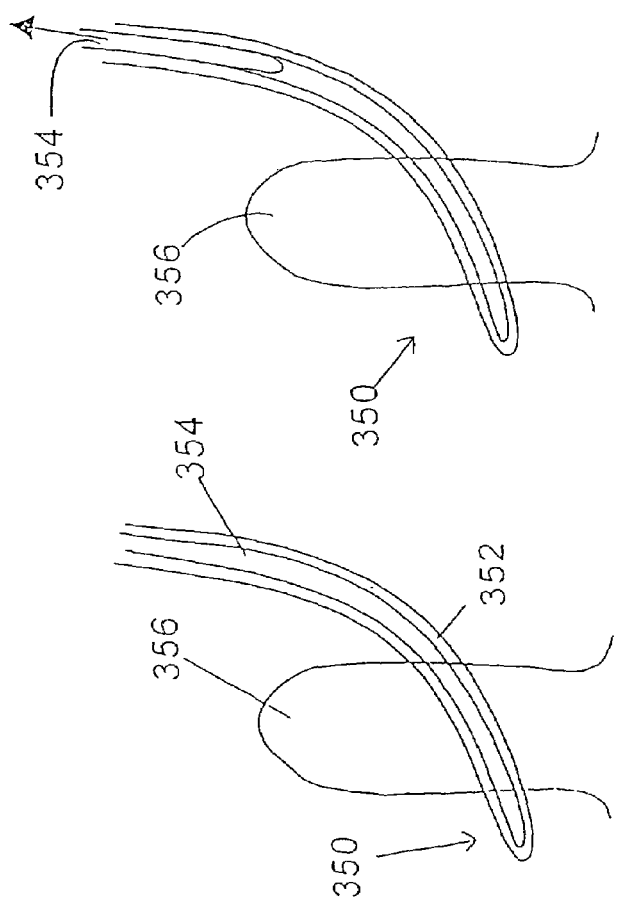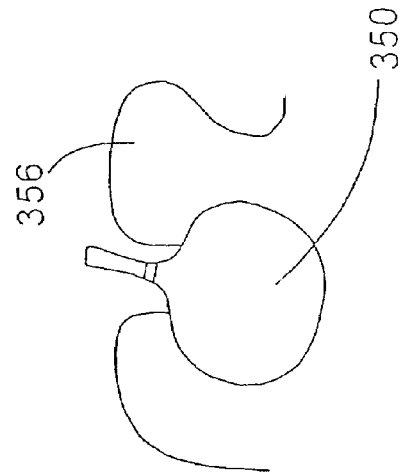

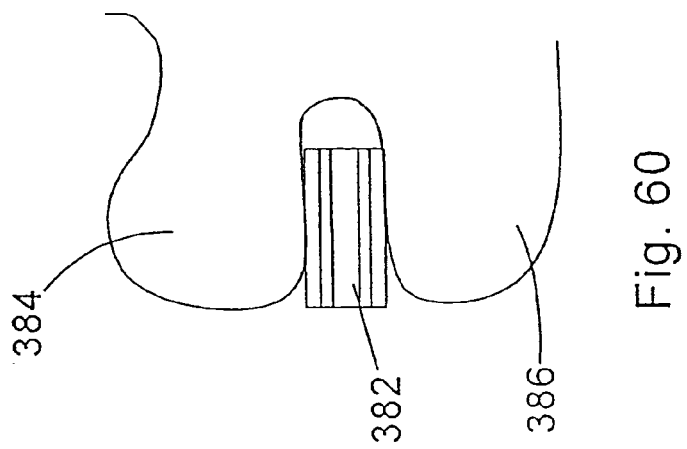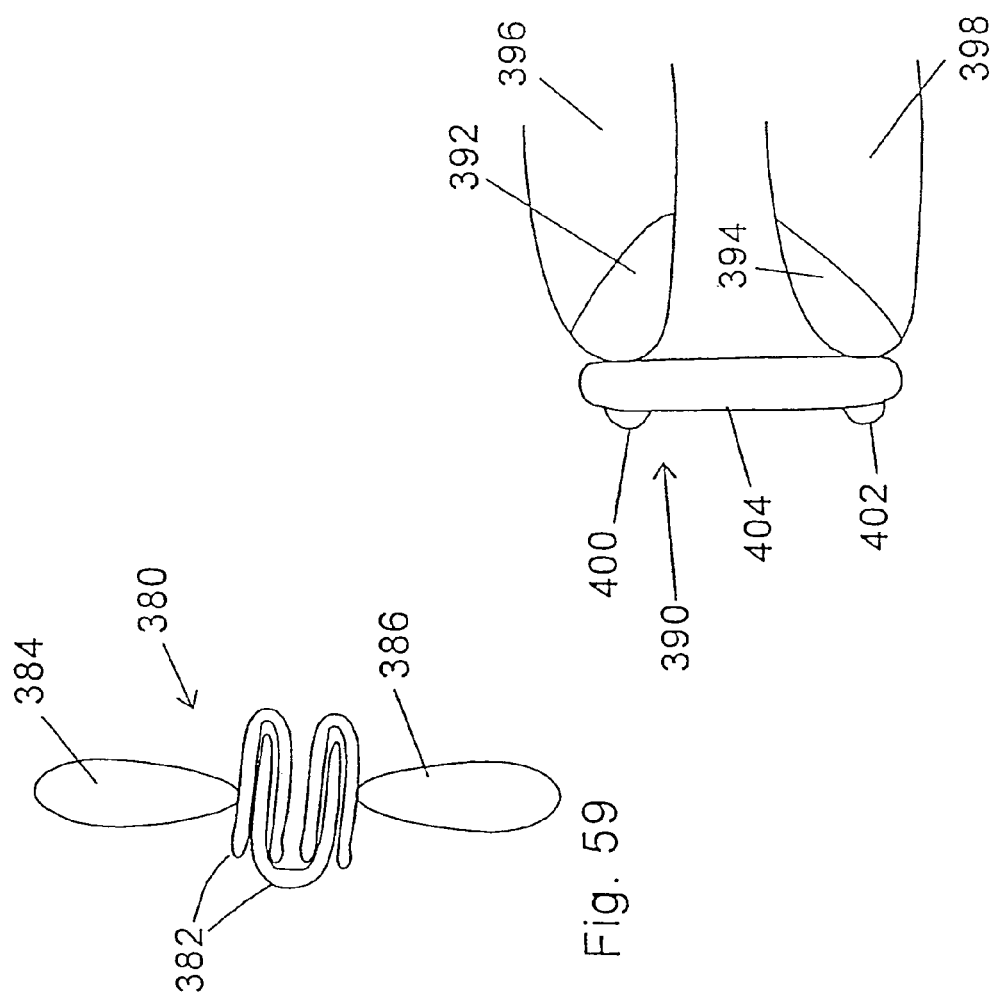

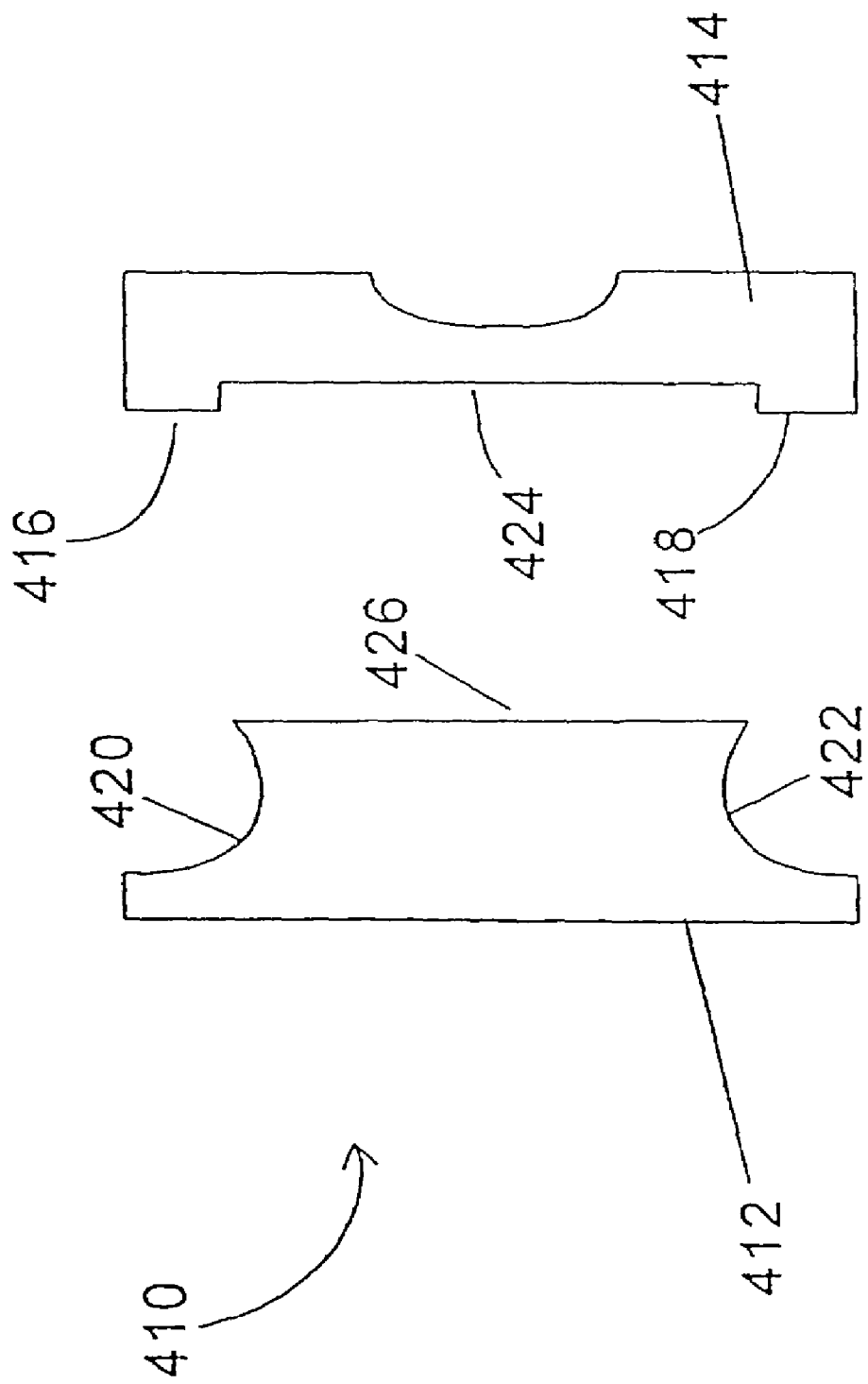

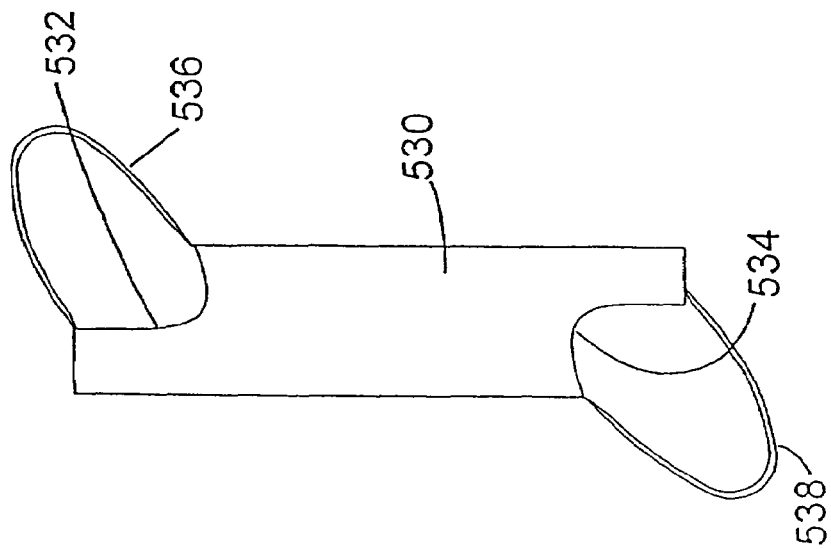
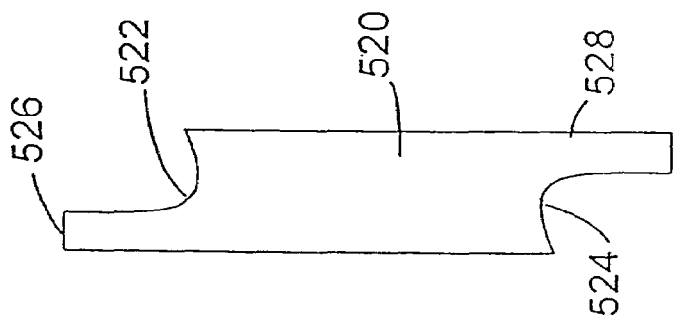

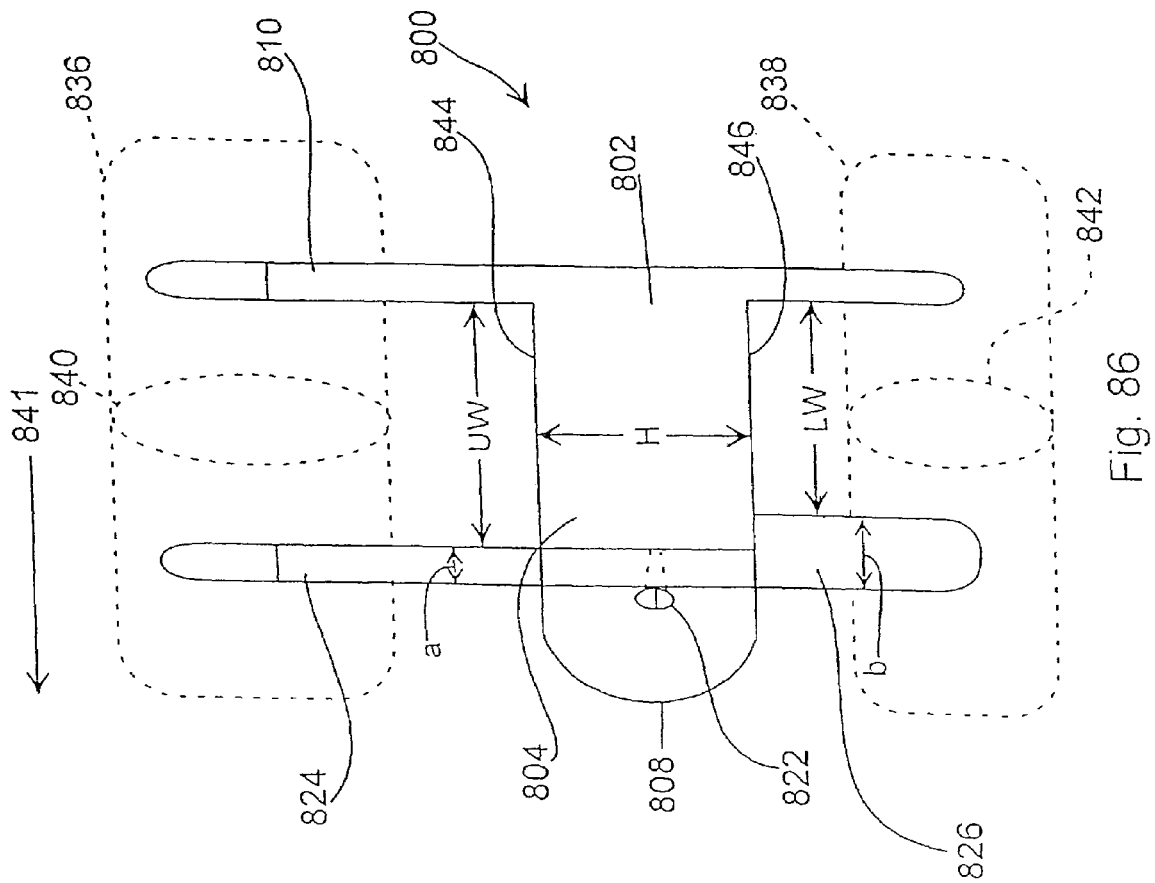
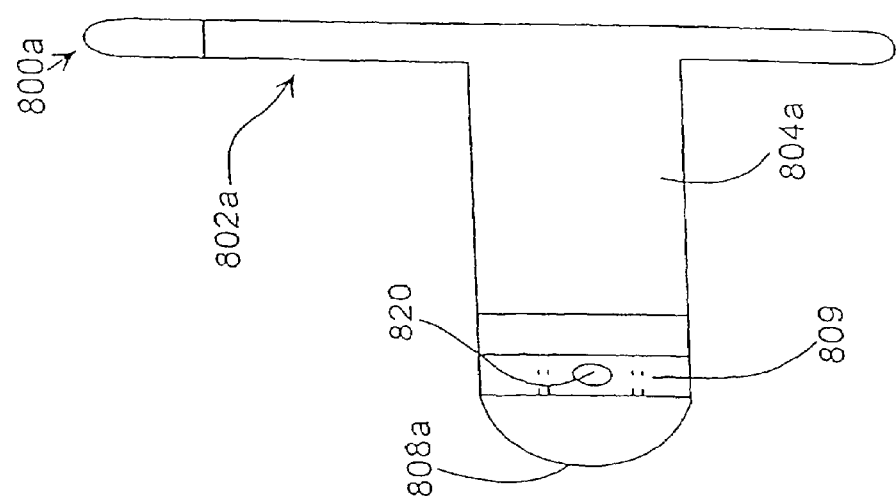

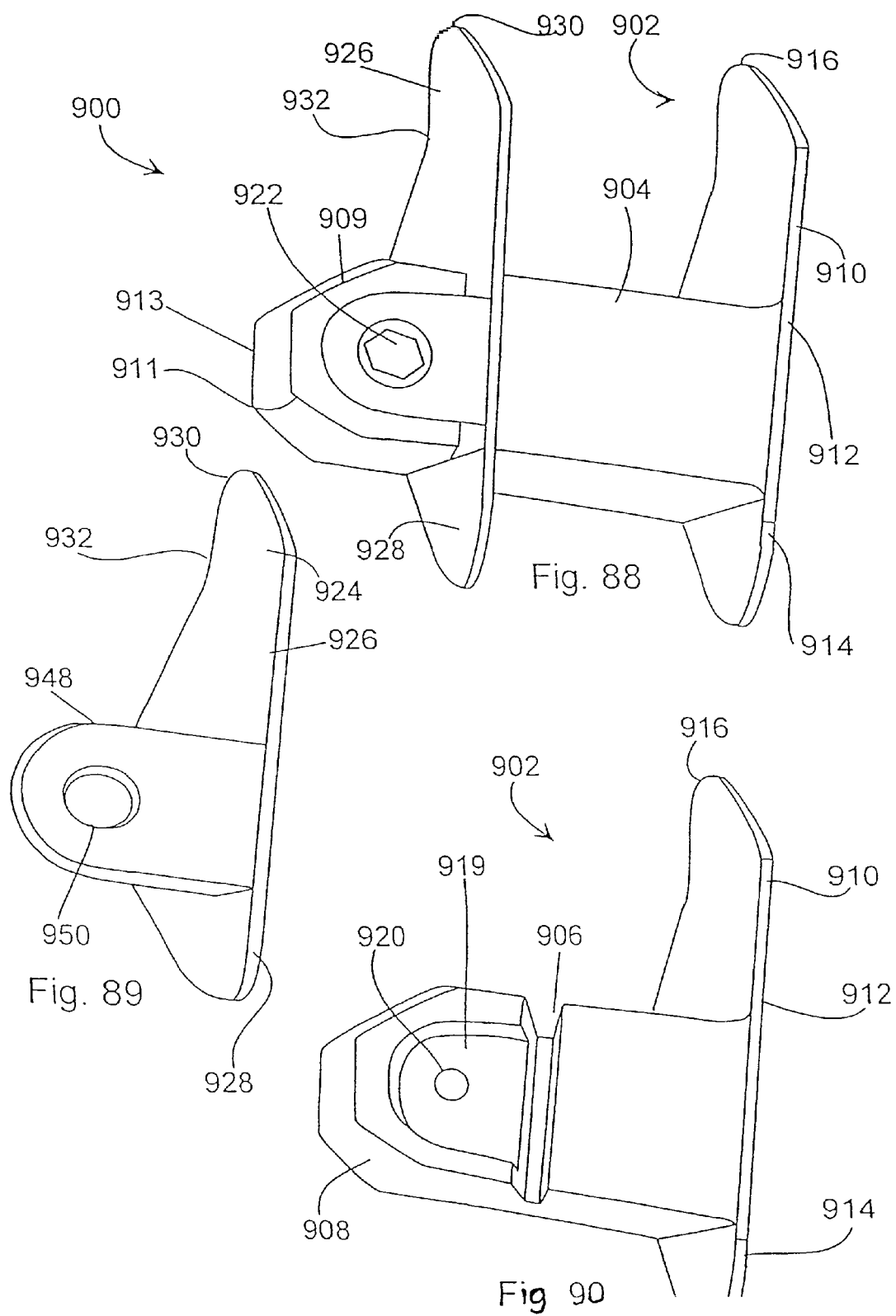

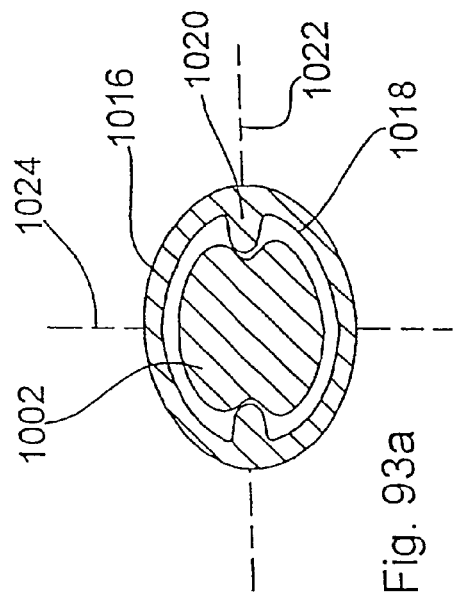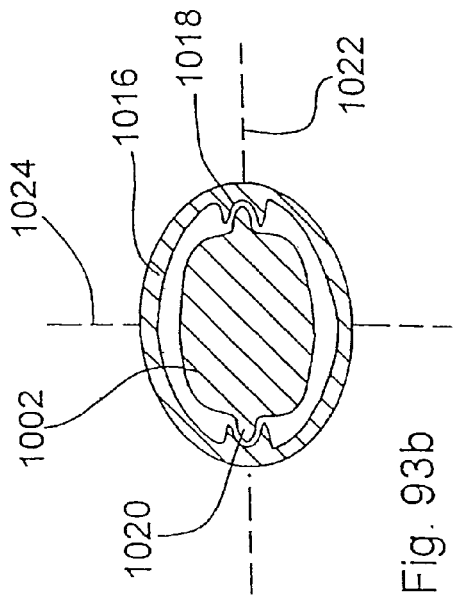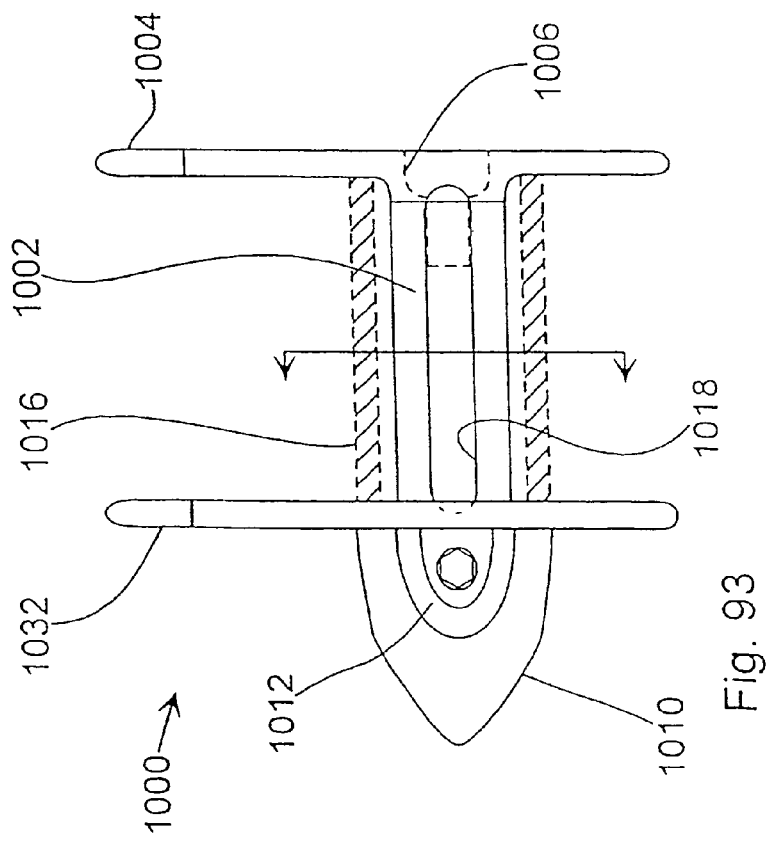

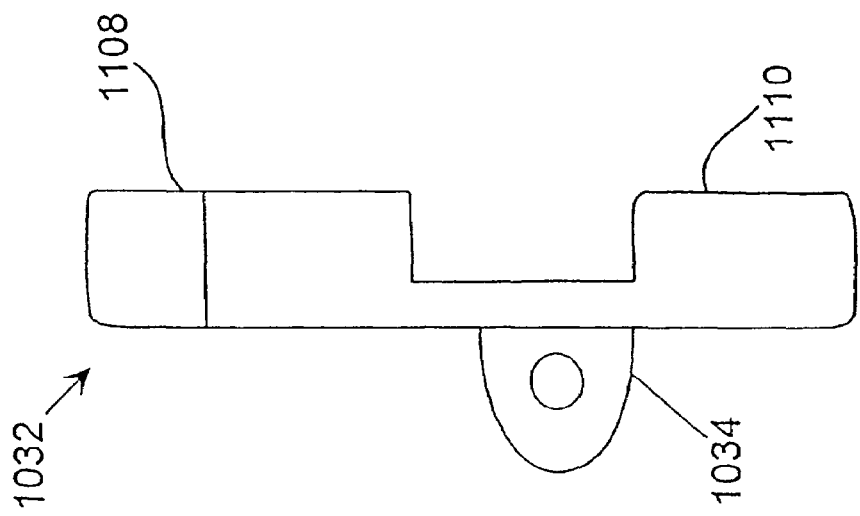
Fig. 105
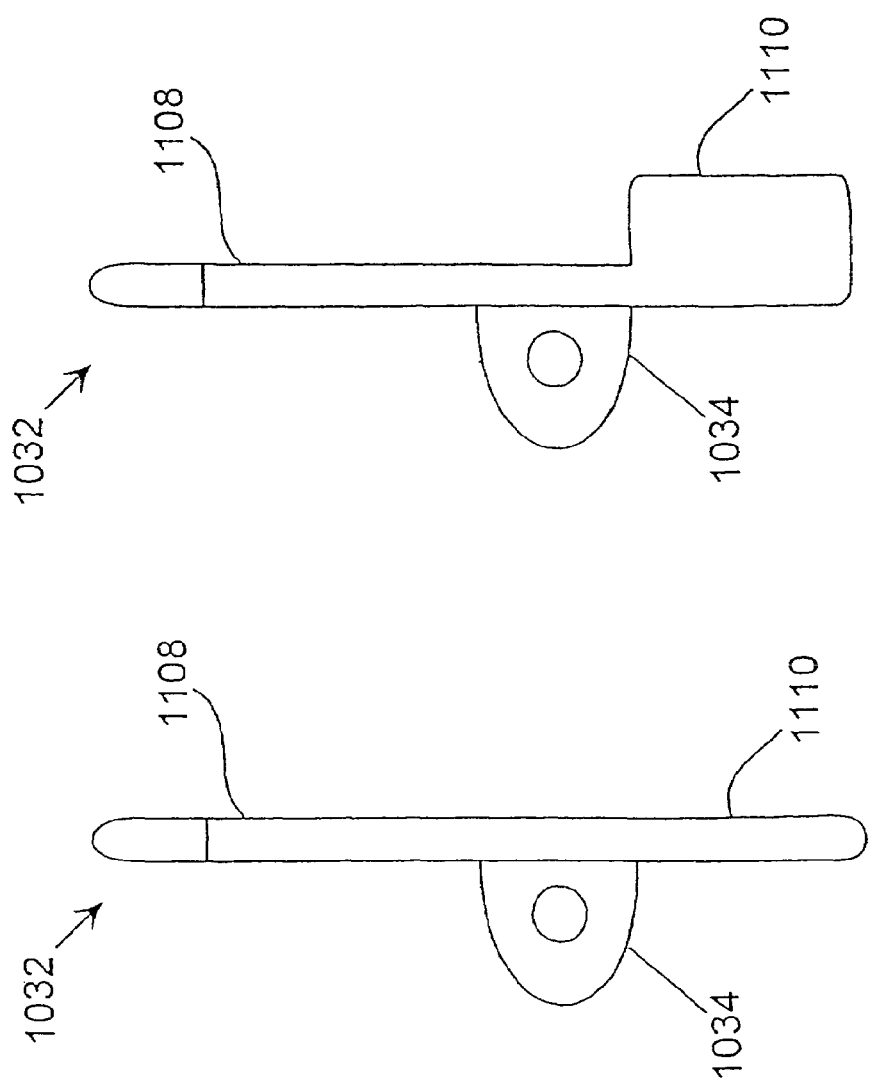
Fig. 104
Fig. 103

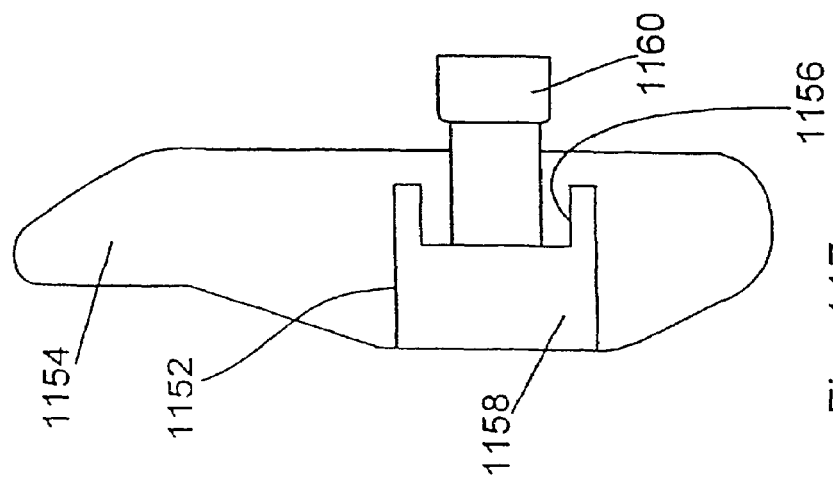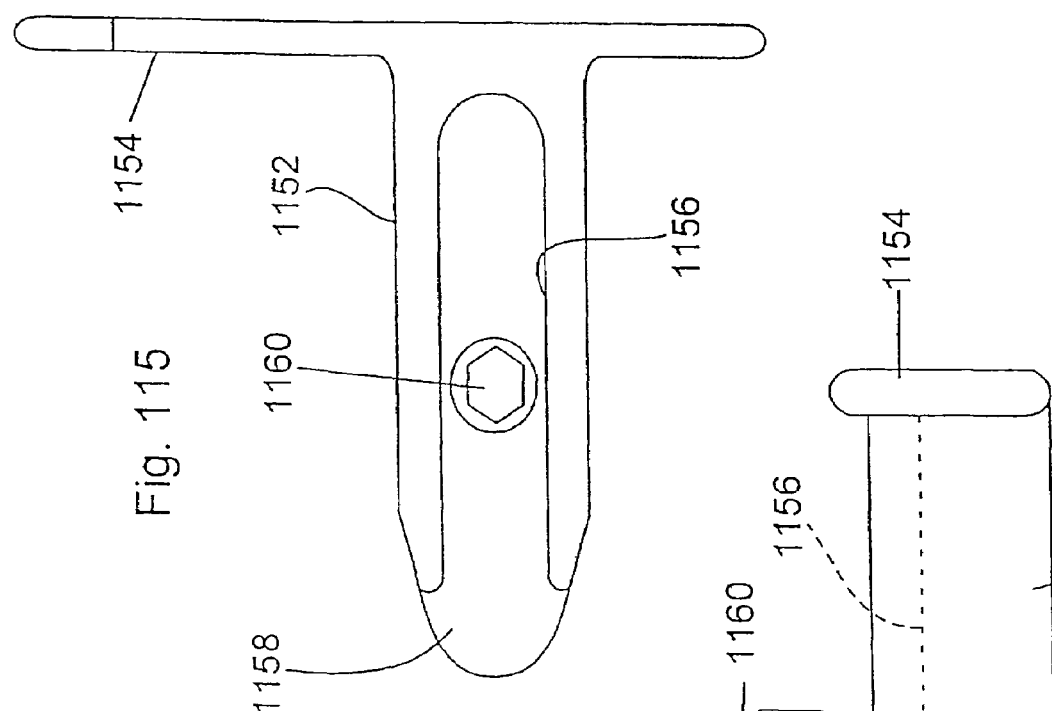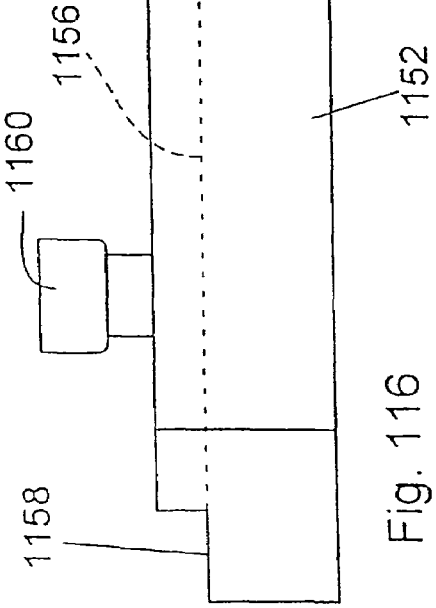

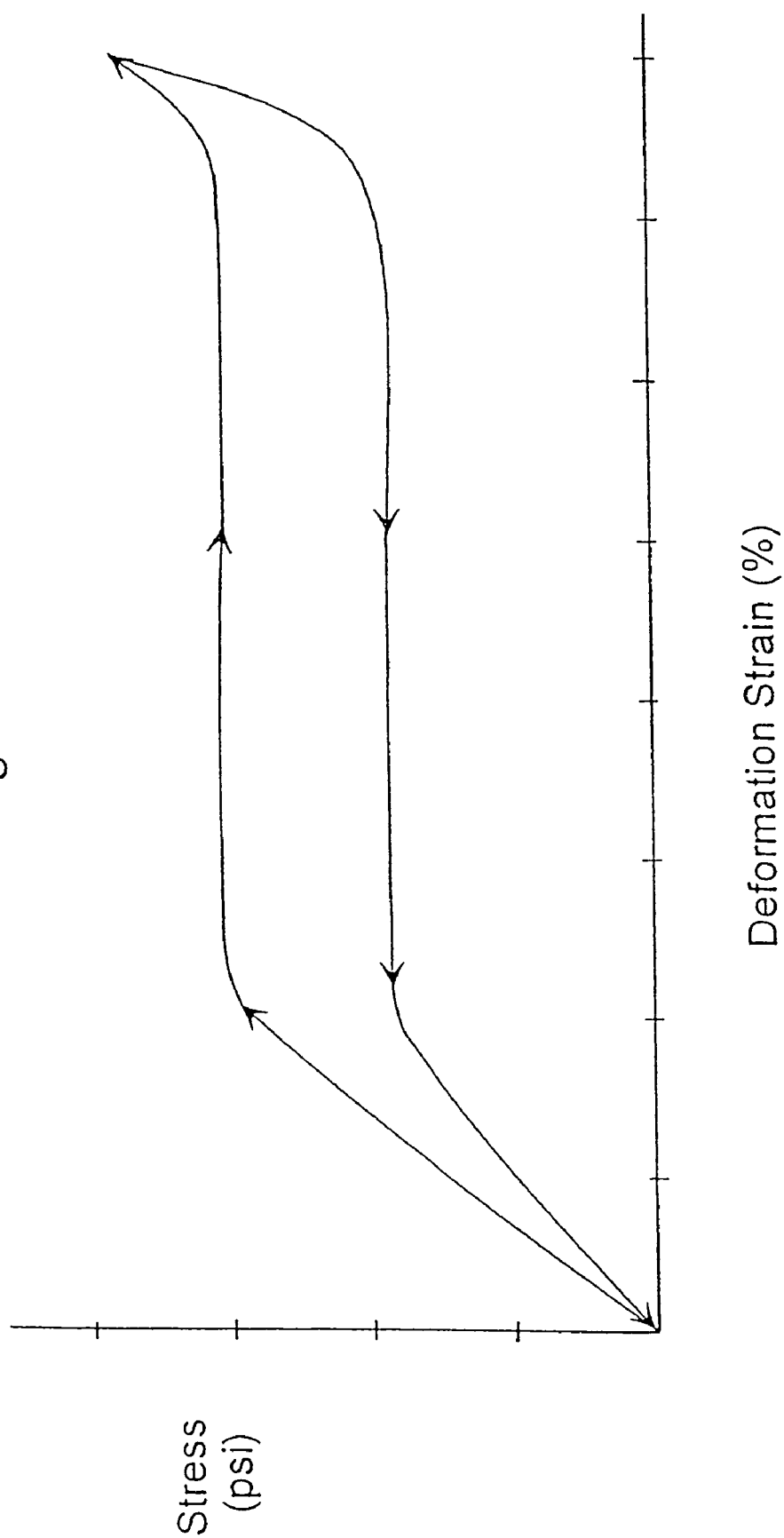

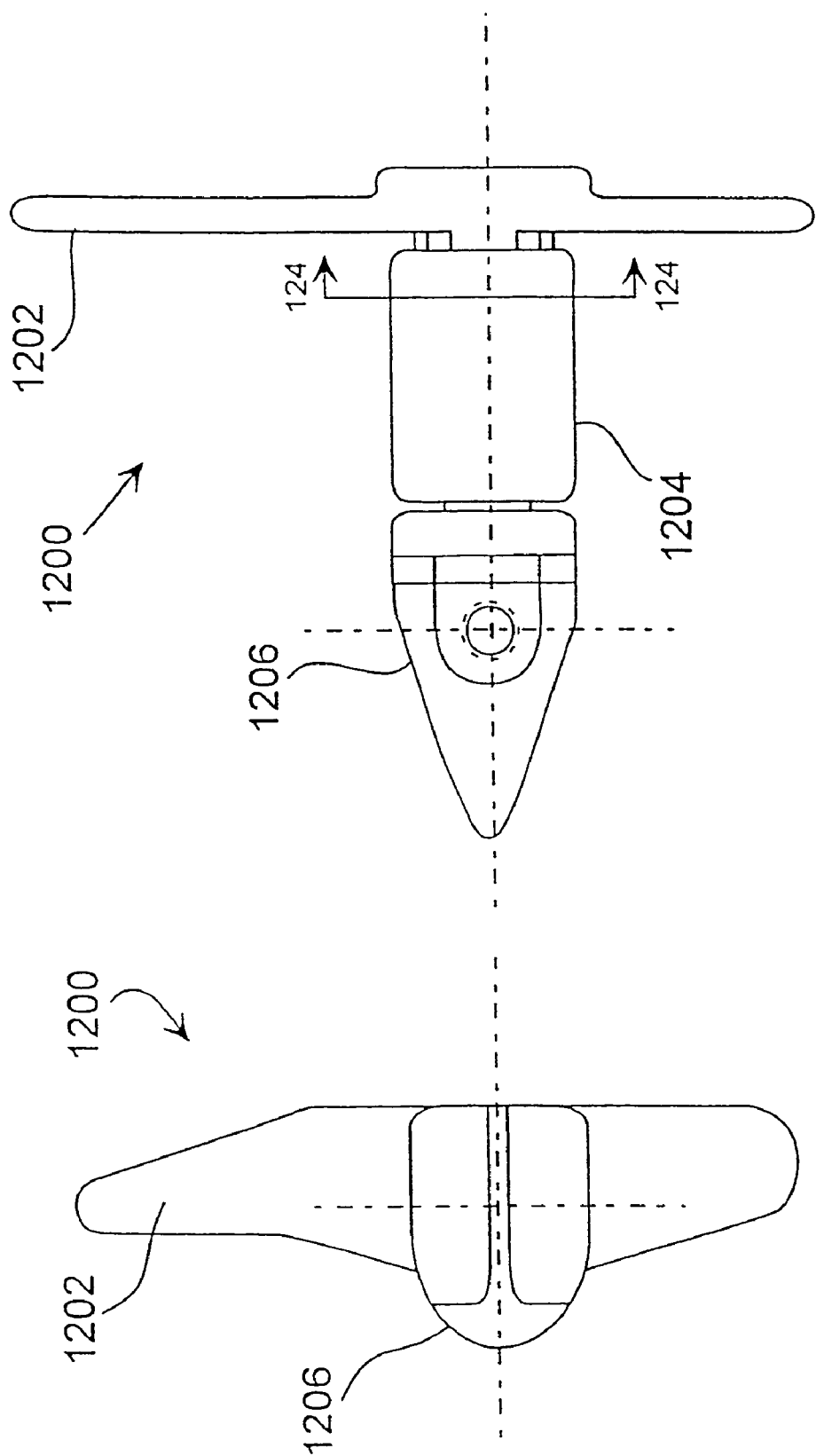

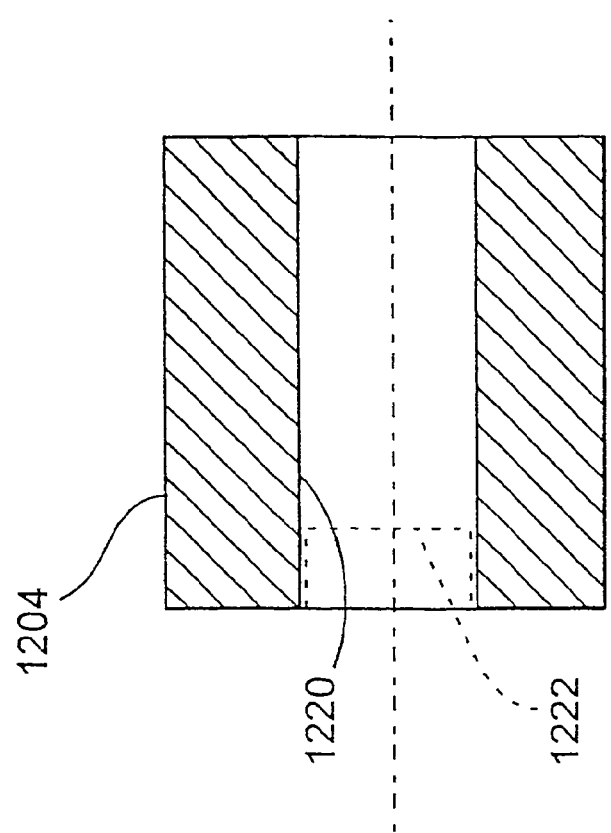
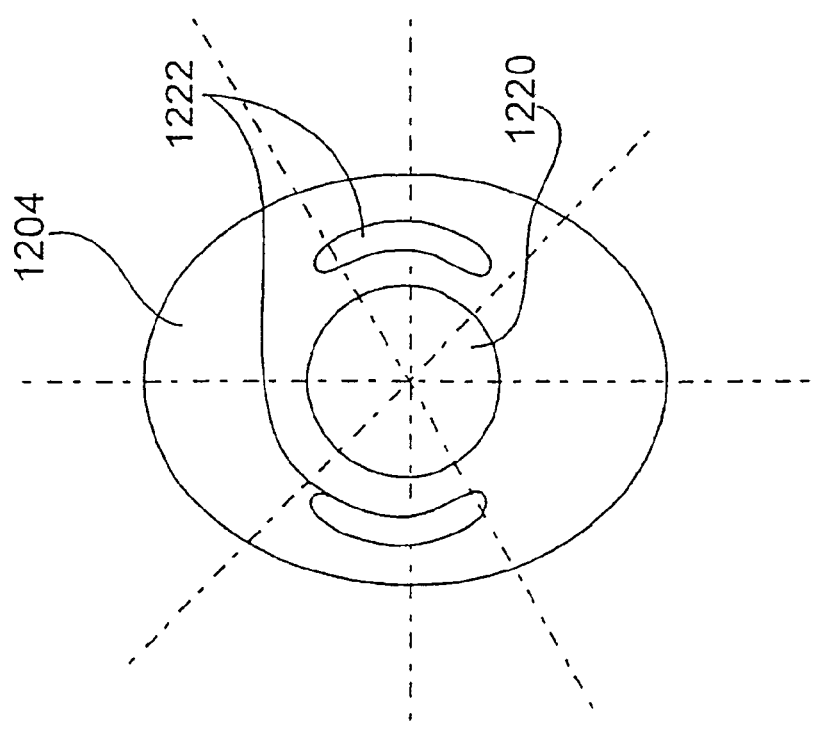
Fig. 123b
Fig. 123a

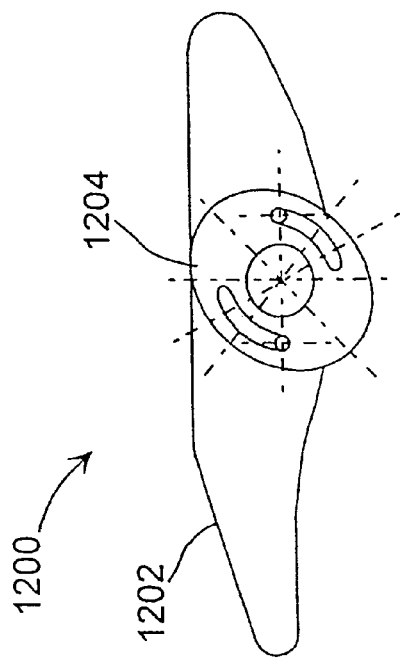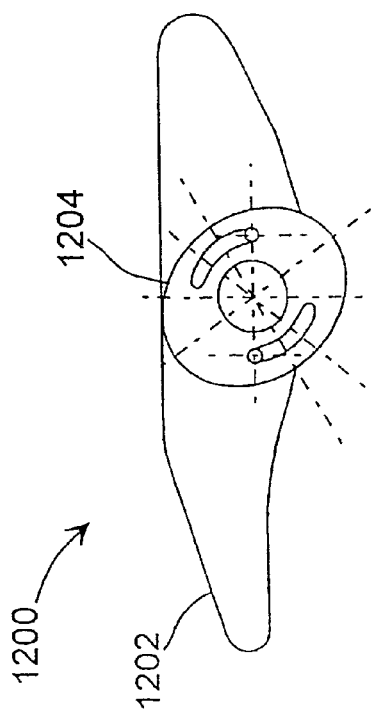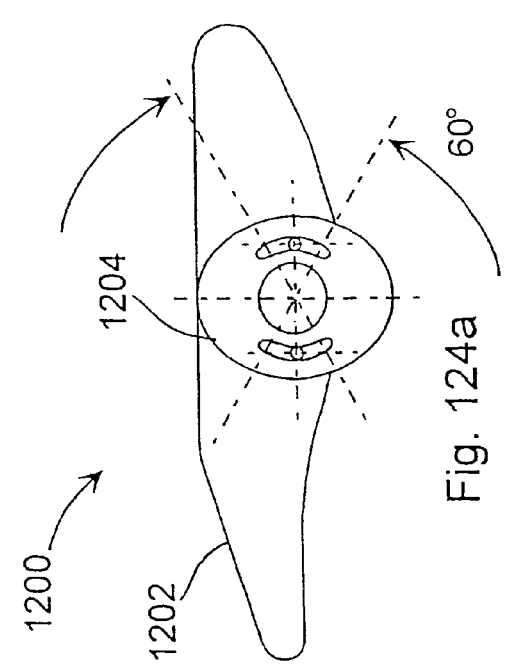

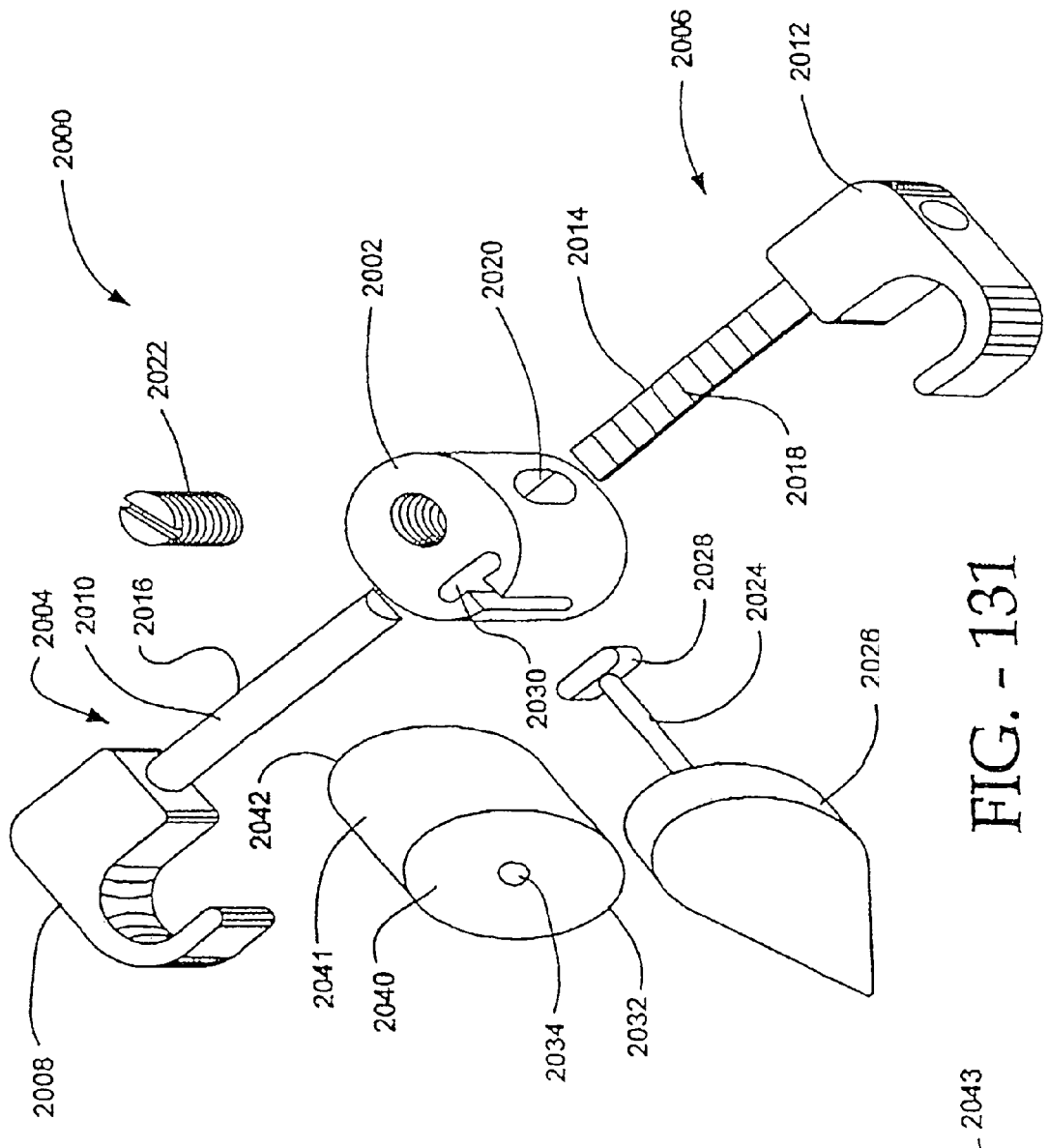
FIG. - 131
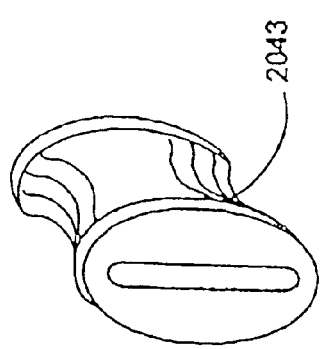
FIG. - 131a
FIG. - 131b

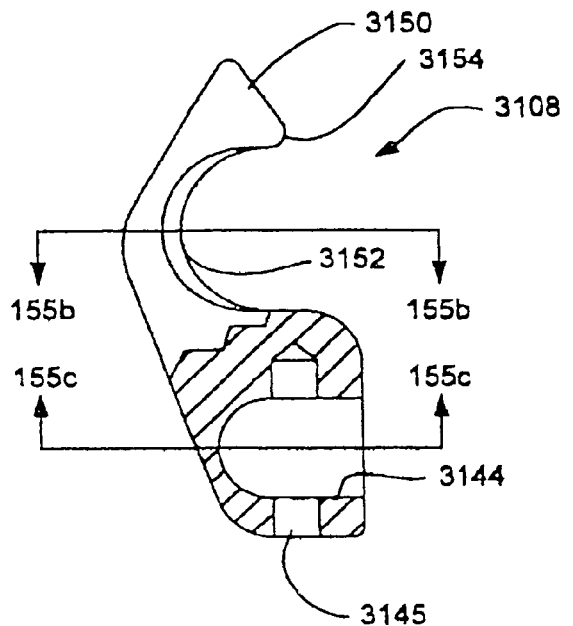
FIG. - 155a
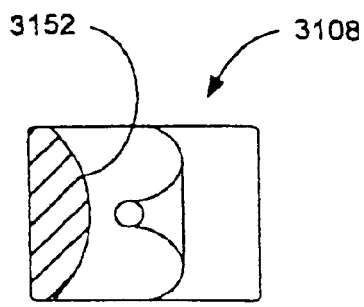
FIG. - 155b
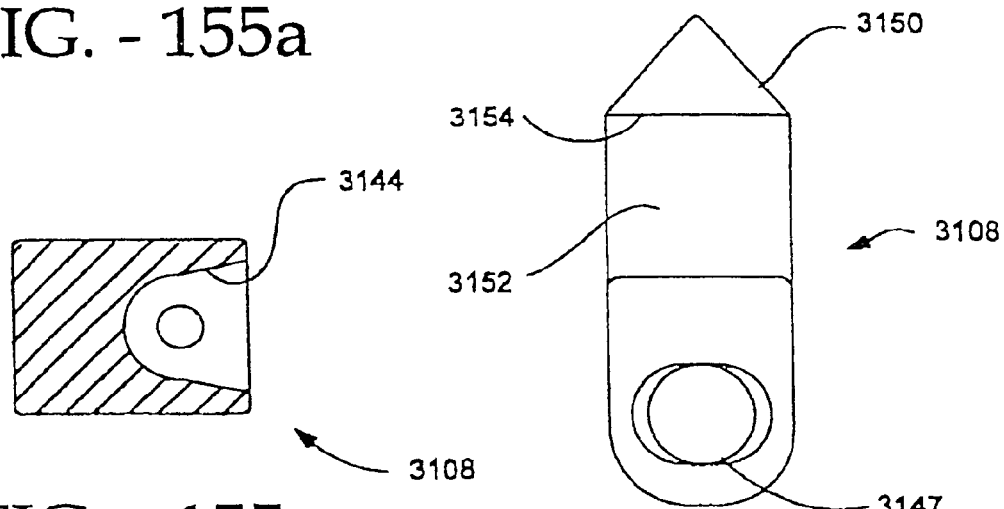
FIG. - 155c
FIG. - 155d
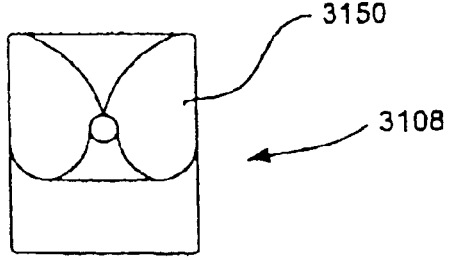
FIG. - 155e

SUPPLEMENTAL SPINE FIXATION DEVICE AND METHOD

PRIORITY CLAIM

This U.S. Patent Application is a divisional application of U.S. patent application Ser. No. 09/842,819, filed Apr. 26, 2001, entitled SUPPLEMENTAL SPINE FIXATION DEVICE AND METHOD, now U.S. Pat. No. 7,201,751 issued Apr. 10, 2007; U.S. patent application Ser. No. 09/842,819 claims priority from U.S. Provisional Patent Application, 60/219,985, filed Jul. 21, 2000, and is a continuation-in-part of U.S. patent application Ser. No. 09/579,039, filed on May 26, 2000 and entitled SUPPLEMENTAL SPINE FIXATION DEVICE AND METHOD, now U.S. Pat. No. 6,451,019 issued Sep. 17, 2002, which is a continuation-in-part of U.S. patent application Ser. No. 09/473,173 filed on Dec. 28, 1999 and entitled SPINE DISTRACTION IMPLANT, now U.S. Pat. No. 6,235,030 issued May 22, 2001, which is a continuation of U.S. patent application Ser. No. 09/179,570 filed on Oct. 27, 1998 and entitled SPINE DISTRACTION IMPLANT, now U.S. Pat. No. 6,048,342 issued Apr. 11, 2000, which is a continuation-in-part of U.S. patent application Ser. No. 09/175,645 filed on Oct. 20, 1998 and entitled SPINE DISTRACTION IMPLANT, now U.S. Pat. No. 6,068,630 issued May 30, 2000, which is a continuation-in-part of U.S. patent application Ser. No. 08/958,281 filed on Oct. 27, 1997 and entitled SPINE DISTRACTION IMPLANT AND METHOD, now U.S. Pat. No. 5,860,977 issued Jan. 19, 1999, which is a continuation-in-part of U.S. patent application Ser. No. 08/778,093 filed Jan. 2, 1997 entitled SPINE DISTRACTION IMPLANT AND METHOD, now U.S. Pat. No. 5,836,948 issued Nov. 17, 1998. All of the above applications and patents are incorporated herein by reference.

FIELD OF THE INVENTION

The present invention is directed to supplemental spine fixation devices and methods which are used as an adjunct to a primary spine fusion device, such as by way of example only, an interbody fusion device.

BACKGROUND OF THE INVENTION

A common procedure for handling pain associated with degenerative spinal disk disease is the use of devices for fusing together two or more adjacent vertebral bodies. The procedure is known by a number of terms, one of which is interbody fusion. Interbody fusion can be accomplished through the use of a number of devices and methods known in the art. These include screw arrangements, solid bone implant methodologies, and fusion devices which include a cage or other mechanism which is packed with bone and/or bone growth inducing substances. All of the above are implanted between adjacent vertebral bodies in order to fuse the vertebral bodies together, alleviating associated pain.

Associated with such primary fusion devices and methods are supplemental devices which assist in the fusion process. These supplemental devices assist during the several month period when bone from the adjacent vertebral bodies is growing together through the primary fusion device in order to fuse the adjacent vertebral bodies. During this period it is advantageous to have the vertebral bodies held immobile with respect to each other so that sufficient bone growth can be established.

Such supplemental devices can include hook and rod arrangements, screw arrangements, and a number of other devices which include straps, wires, and bands, all of which are used to immobilize one portion of the spine relative to another.

All of these devices generally require extensive surgical procedures in addition to the extensive procedure surrounding the primary fusion implant.

It would be advantageous if the device and procedure for supplemental spine fixation were as simple and easy to perform as possible, and would leave intact all bone, ligament, and other tissue which comprise and surround the spine.

Accordingly, there needs to be developed procedures and implants which are minimally invasive and are supplemental to spine fixation devices and methods.

SUMMARY OF THE INVENTION

The present invention is directed to providing a minimally invasive supplemental spine fixation implant and method for alleviating discomfort associated with the spine.

The present invention provides for a method and apparatus for assisting in the fusing together of vertebral bodies of the spine. One of the features and purposes of the invention is to immobilize the vertebral bodies while spine fusion is accomplished. Generally fusion requires upwards of six months for bone cells from the upper and lower vertebral bodies to grow towards each other, generally through a primary fusion device.

In order to assist in the fusing process, the supplemental spinal fixation device and method of the invention immobilizes the vertebral bodies by immobilizing the respective spinous processes extending therefrom. In addition, the present invention and method can be used to distract apart the posterior sides of the vertebral bodies in order to put additional force and compression on the anterior sides of the vertebral bodies, further assisting in the interbody fusion process.

The present invention and method is minimally invasive such that it does not add to the trauma of the primary fusion procedure, especially if the fusion procedure is from a posterior approach. With an anterior fusion approach additional posterior incisions are required. However, these are minimal when compared to other devices and methods.

Accordingly an object of the present invention is to increase the rigidity and stability with respect to the adjacent spinous process and vertebral bodies in order to promote interbody fusion between the vertebral bodies. It is further an object of the present invention to be as minimally invasive as possible.

It is yet a further object of the present invention to provide for an implant and method which does not require modification of the bone, ligaments, or adjoining tissues. In other words, it is an object of the present invention to provide for an implant and method which does not require that the bone be reshaped, notched, or in anyway modified. Further it is an object of the present invention to provide for an implant and method which does not require that any of the ligaments associated with the spinous processes be altered.

It is a further object of the present invention to provide for an implant and method which can be inserted from one side of adjacent spinous processes, in order to immobilize the spinous processes and resultingly immobilize the adjacent vertebral bodies. By addressing the spinous processes from one side, the objects and advantages of a minimally invasive procedure, with reduced trauma, can be accomplished.

It is another object of the present invention to provide for a device and method which provides for distraction of the spinous processes in order to place pressure on at least the anterior portion of the vertebral bodies in order to assist in the primary fusion.

It is still a further object of the present invention to provide for an implant and method which can increase the space between spinous processes in order to adjust the height between vertebral bodies.

It is yet a further object of the present invention to provide for a device which has securing and/or hook elements which can easily and conveniently be secured about the spinous processes, which hook devices are preferably designed in order to accommodate the shape of the spinous processes and are preferably swivelable or pivotable in order to accommodate the position and shape of one spinous processes relative to another.

It is another object of the invention to provide for a device which has several degrees of freedom in order to allow a portion of the device to be positioned between spinous processes in order to distract apart the spinous processes and other portions of the device to engage the spinous processes in order to rigidly immobilize the spinous processes. These degrees of freedom allow the device to conform to the bones, ligaments, and tissues of each individual patient. Thus, the present device allows for adjustments along two and three axises in order to successfully distract and immobilize spinous processes.

It is yet a further object of the present invention to have at least one portion of the device selectably positionable with respect to other portions of the device in order to accommodate the anatomy of the spine and in particular of the spinous processes.

It is still a further object of the present invention to provide for a device and method which can be used with both primary anterior or posterior interbody fusion.

Accordingly, it is an object and aspect of the invention to provide a device and method for augmentation of single or multiple level lumbar spinal fusion. Ideally the fusion and the device and method of this invention are addressed at the L4/L5 vertebral bodies and above, and also at the L5/S1 vertebral bodies. The device and method can also be used with other vertebral bodies located along the spine.

The present invention provides for rigidity without risk to the neural elements. The present invention is cost effective and minimally invasive.

Accordingly, an aspect of the present invention includes an implant for rigidly positioning spinous processes, which implant includes a first means adapted for engaging the first spinous process and a second means adapted for engaging the second spinous process. The implant includes a body means adapted for positioning between the first spinous process and the second spinous process and a hub means for engaging the first means, the second means, and the body means.

Further, the invention includes at least one of the hub means and the body means allowing for the body means to move relative to at least one of the first and second means.

In a further aspect and object of the present invention, an implant includes a first hook adapted to engage a first spinous process and a second hook adapted to engage a second spinous process. The implant has a body adapted to the position between the spinous processes and a hub to which mounts the first and second hooks and the body. The body is moveable relative to at least one of the first and second hooks.

It is further an aspect and object of the present invention to provide an implant for rigidly positioning spinous processes as an adjunct to spine fusion, where the improvement includes a sleeve position between adjacent spinous processes.

It is a further aspect of the present invention to provide an implant for rigidly positioning spinous processes as an adjunct to spine fusion wherein the improvement comprises a sleeve or spacer positioned between adjacent spinous processes and a first hook which is adapted to engage a first spinous process and a second hook which is adapted to engage a second spinous process.

The method of the present invention is for rigidly positioning a first spinous process relative to a second spinous process and includes the steps in any desired order of placing a first hook around a first spinous process and a second hook around a second spinous process. The steps include placing a sleeve or spacer between the first and second spinous processes, which spacer mounts to a hub. The hub is used to interlock the first hook relative to the second hook.

It is a further object of the present invention to provide a supplemental spine fixation device and method which has additional freedom in the placement of the hooks and the spacer relative to the hub. In one aspect of the invention, the spacer is mounted on a shaft relative to hub and is pivotable about a pivot point relative to the hub. This is in addition to the spacer being rotatable about the shaft relative to the hub in a particular embodiment.

The hook themselves have a lead-in nose which is adapted to separate tissues between the spinous process in order to allow the hook to be urged into engagement with a spinous process.

In another aspect of the invention, the hub is designed in order to on assembly, lock in the spacer and the hooks by locking in the shafts upon which they are mounted.

In still a further aspect of the invention, the spacer is egg-shaped in order to accommodate the shape of the spinous process and the space there between. In a further aspect of the invention, in particular with respect to the egg-shaped spacer, the spacer has a bore therethrough on which the spacer can rotate, which bore is offset, being closer to the blunt end of the shape spacer than the pointed end. This allows the spacer to have the pointed end positioned closer to the spine. According, more surface area of the spacer supports the spinous processes in areas where the spinous processes are stronger.

Other embodiments of the implants and methods, within the spirit and scope of the invention, can be understood by a review of the specification, the claims, and the figures.

BRIEF DESCRIPTION OF THE FIGURES

FIG. 1 depicts the implant in a more extended configuration than does FIG. 2.

FIGS. 6, 7, 8, 9 and 10 depict apparatus and method for another embodiment of the present invention for creating distraction between adjacent spinous processes.

FIGS. 16, 16*a*, and 17 depict yet another embodiment of the present invention.

FIGS. 34 and 35 depict yet another apparatus and method of the present invention.

FIGS. 36, 37 and 38 depict three different embodiments of the present invention.

FIGS. 39 and 40 depict yet another apparatus and method of an embodiment of the present invention.

FIG. 44 is still a further embodiment of an implant of the invention.

FIG. 45 is yet another depiction of an apparatus and method of the invention.

FIGS. 46 and 47 depict still a further apparatus and method of an embodiment of the invention.

FIGS. 48, 49, 50 and 51 depict yet a further apparatus and method of the invention.

FIGS. 52, 53, 54, 55*a* and 55*b* depict another apparatus and method of the invention.

FIGS. 59 and 60 depict still a further embodiment of the invention.

FIG. 61 depict another embodiment of the invention.

FIGS. 62 and 63 depict yet another embodiment of the present invention.

FIGS. 64 and 65 depict still a further embodiment of the present invention.

FIG. 66 depicts another embodiment of the invention.

FIGS. 79, 80, 80*a*, 81, 82, 83, 83*a*, 84, 85, 86 and 87 depict still a further embodiment of the present invention.

FIGS. 88, 89, 90 and 91 depict yet another embodiment of the present invention.

FIGS. 92, 92*a*, 92*b*, 93, 93*a*, 93*b*, 93*c*, 93*d*, 94, 94*a*, 94*b*, 95, 95*a*, and 96, depict still a further embodiment of the present invention wherein a sleeve is provided which is capable of deflecting response to relative motion between the spinous processes.

FIGS. 101, 102, 102*a*, 103, 104, 105, 106, and 107 depict still a further embodiment of the present invention.

FIGS. 111, 112, 113, 114, 115, 116, and 117 depict yet another embodiment of the present invention.

FIG. 118 depicts a graph showing characteristics of a preferred material usable with several of the embodiments of the present invention.

FIGS. 119*a* and 119*b* depict side and plan views of still a further embodiment of the present invention.

FIGS. 123*a* and 123*b* depict an end view and a cross-sectioned view respectfully of the sleeve of the embodiment of the invention of FIGS. 119*a* and 119*b*.

FIGS. 124*a*, 124*b* and 124*c* depict a view of the embodiment of the invention of FIGS. 119*a* and 119*b* taken through line 124-124 in FIG. 119*b* shown in with the sleeve in various positions relative to a first wing.

FIG. 131 is an exploded view of the embodiment of the invention of FIG. 130. FIGS. 131*a* and 131*b* are alternative components of the embodiment of FIG. 131.

FIG. 138*a* is an alternative component of the embodiment of FIG. 137.

FIG. 138*b* is an upside down perspective view of a component of the embodiment of FIG. 138.

FIG. 141a is an upside down perspective view of a component of the embodiment of FIG. 141.

FIG. 154a is a sectioned view of the spacer and lead-in nose tissue expander of the invention.

FIG. 154b is an end view of a spacer of FIG. 154a.

FIG. 154c is an exploded view of several of the components of FIG. 154a.

FIG. 155a is a plan, partially sectioned view of an embodiment of a hook of the invention.

FIG. 155b is a sectioned view taken through line 155b-155b of FIG. 155a.

FIG. 155c is a sectioned view taken through line 155c-155c of FIG. 155a.

FIG. 155d is a bottom view of the embodiment of the hook of the invention of 155a.

FIG. 155e is an end view of FIG. 155d.

DETAILED DESCRIPTION OF THE EMBODIMENT

Figure 1:
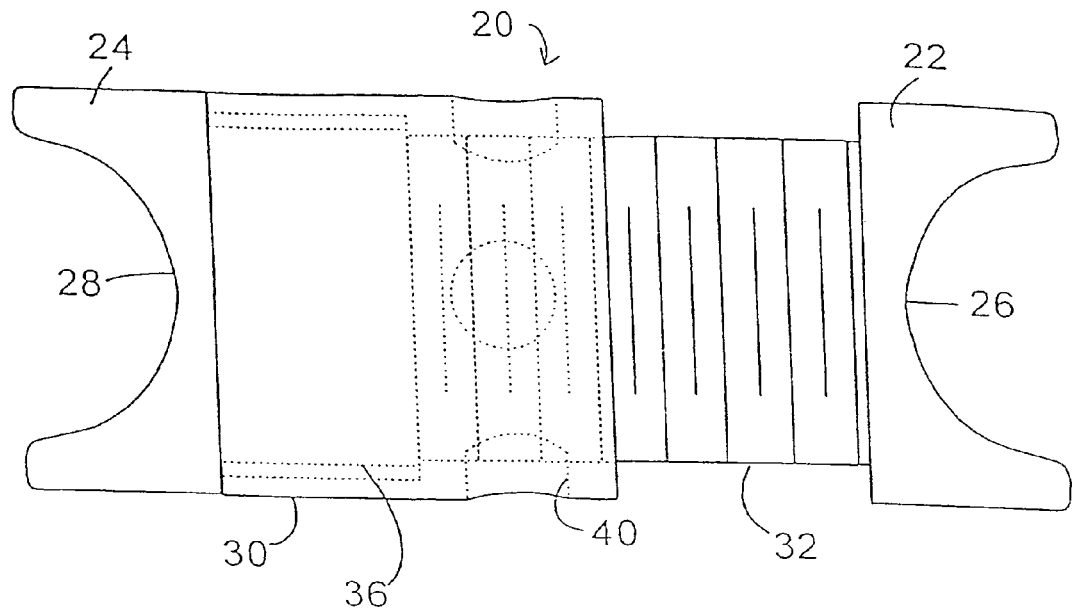
FIGS. 1 and 2 depict an embodiment of an implant of the invention which is adjustable in order to select the amount of distraction required.
Figure 129:
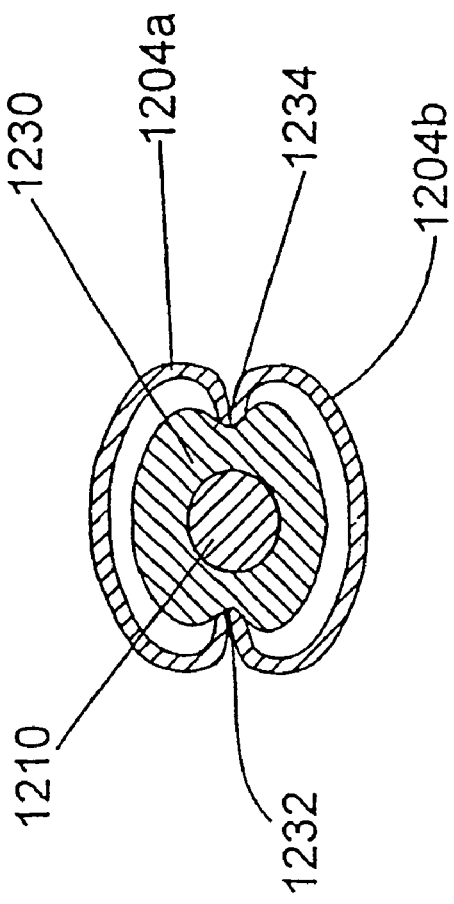
FIG. 129 depicts still a further embodiment of the invention as depicted in FIGS. 119*a* and 119*b*.

The present invention, although directed to embodiments for providing supplemental spine fixation devices and methodologies depicted in FIGS. 130 to 160, have some of the same functionalities, features, design characteristics, and materials as previously described in the embodiments depicted and described in FIGS. 1 to 129. FIGS. 1 to 129 are directed to spine distraction implant and method used in distracting apart spinous processes in order to relieve pain associated with the spine such as, by way of example only, the pain associated with spinal stenosis. Accordingly, as appropriate, and even if not specifically mentioned in each inventive description of FIGS. 130 to 160, many of the design characteristics, features, functionalities, materials, measurements, dimensions, purposes, aspects, and objects of the devices in FIGS. 1 to 129 are applicable to the present invention.

Embodiment of FIGS. 1-5a, 5b

A first embodiment of the invention is shown in FIGS. 1-5a, 5b. Implant 20 includes first and second forked ends 22 and 24, each defining a saddle 26, 28 respectively. The forked ends 22, 24 are mated using an interbody piece 30. As can be seen in FIGS. 3a, 3b, the first forked end 22 includes a threaded shaft 32 which projects rearwardly from the saddle 26. The threaded shaft 32 fits into the threaded bore 34 (FIG. 4a) of the interbody piece 30.

The second forked end 24 (FIGS. 5a, 5b) includes a smooth cylindrical shaft 36 which can fit into the smooth bore 38 of the interbody piece 30.

Figure 2:
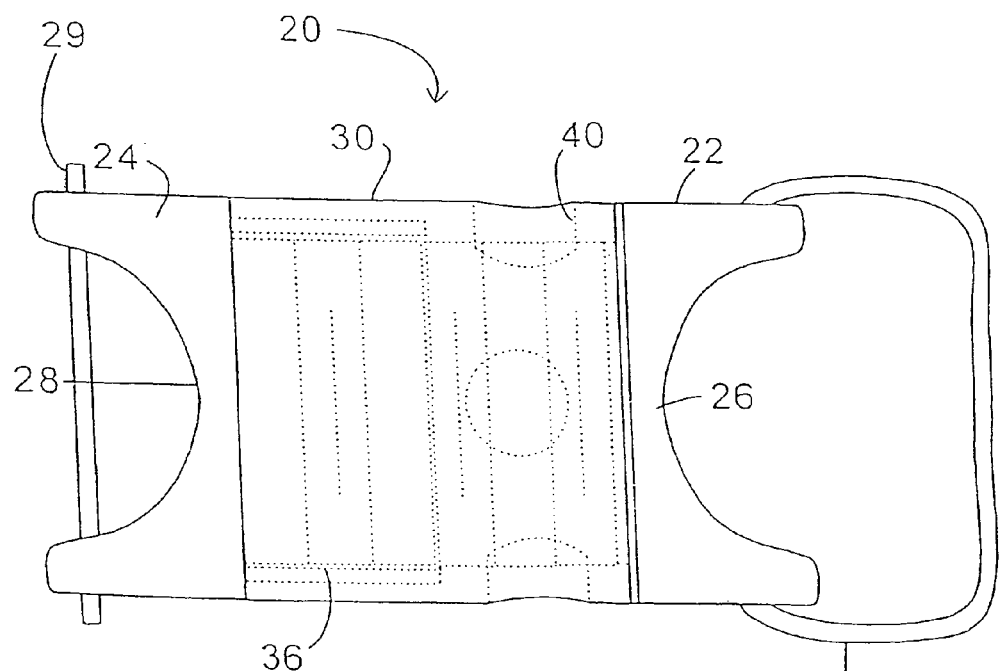
Figure 3A:
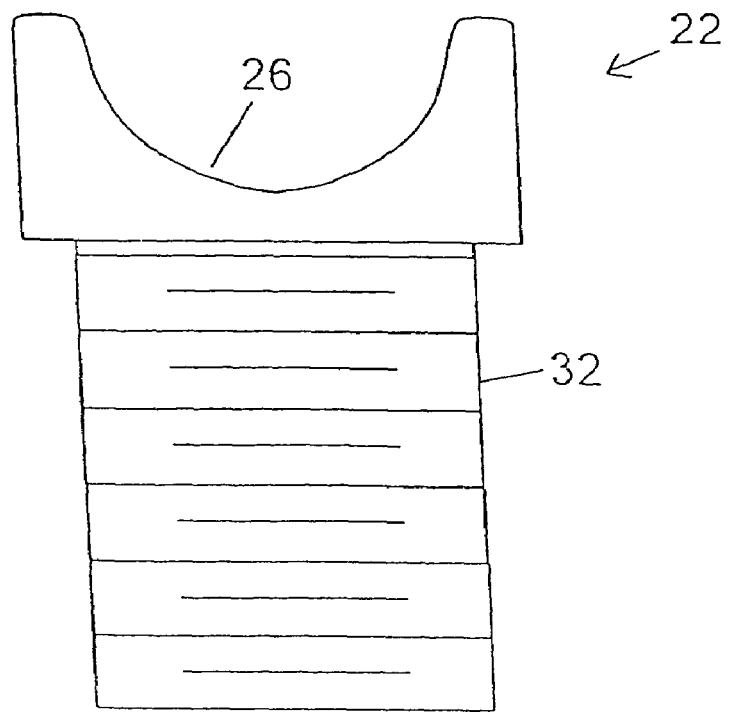
FIGS. 3a and 3b depict side and end views of a first forked and of the embodiment of FIG. 1.
Figure 3B:
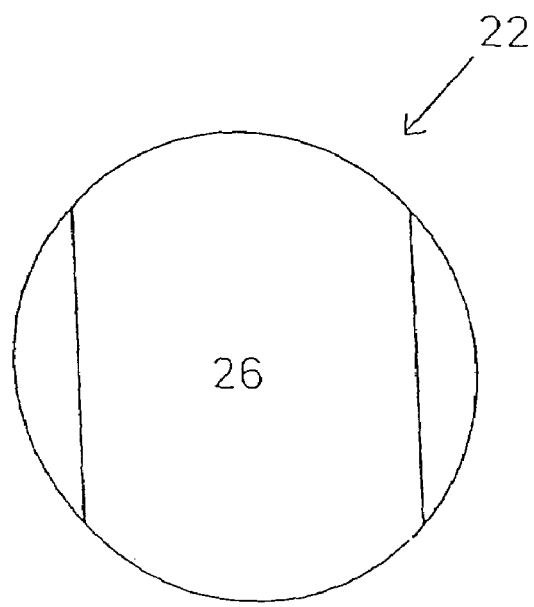
Figure 4A:
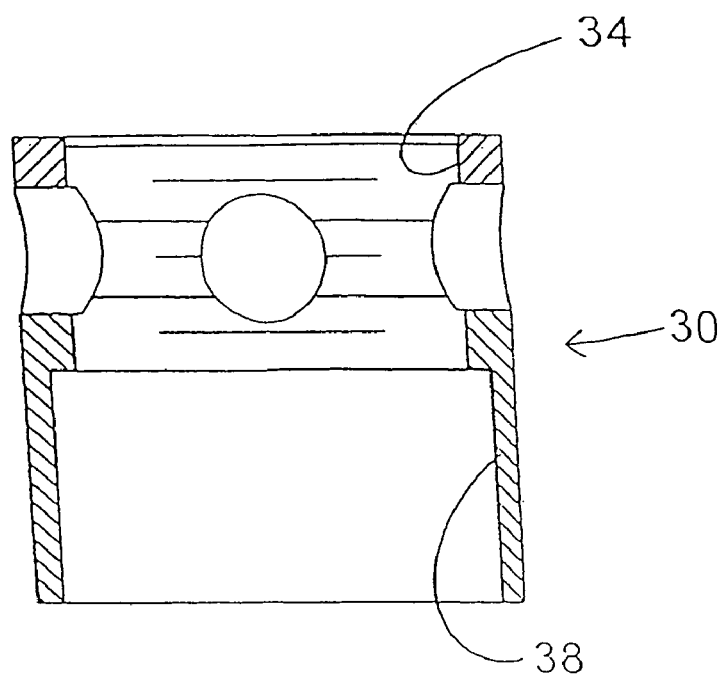
FIGS. 4a and 4b depict side sectioned and end views of an interbody piece of the implant of FIG. 1.
Figure 4B:
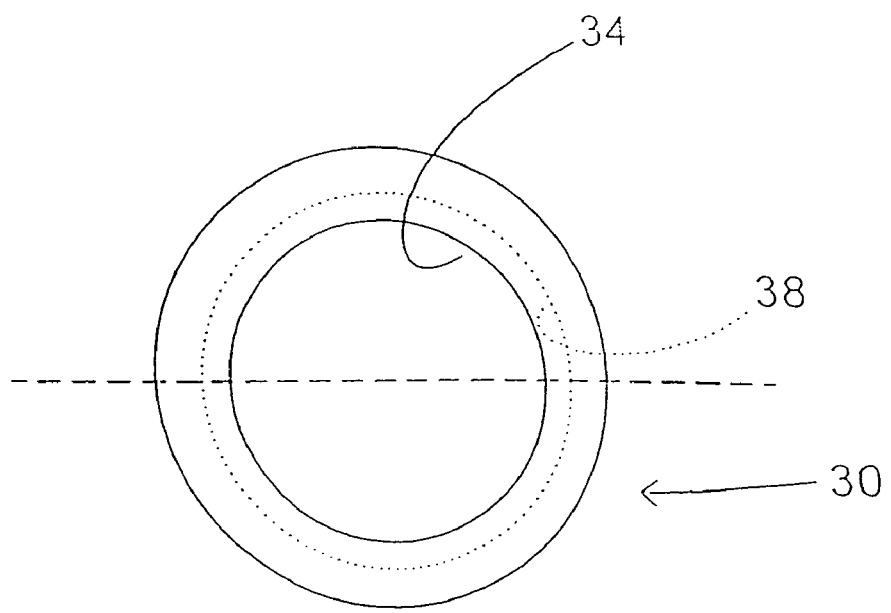
Figure 5A:
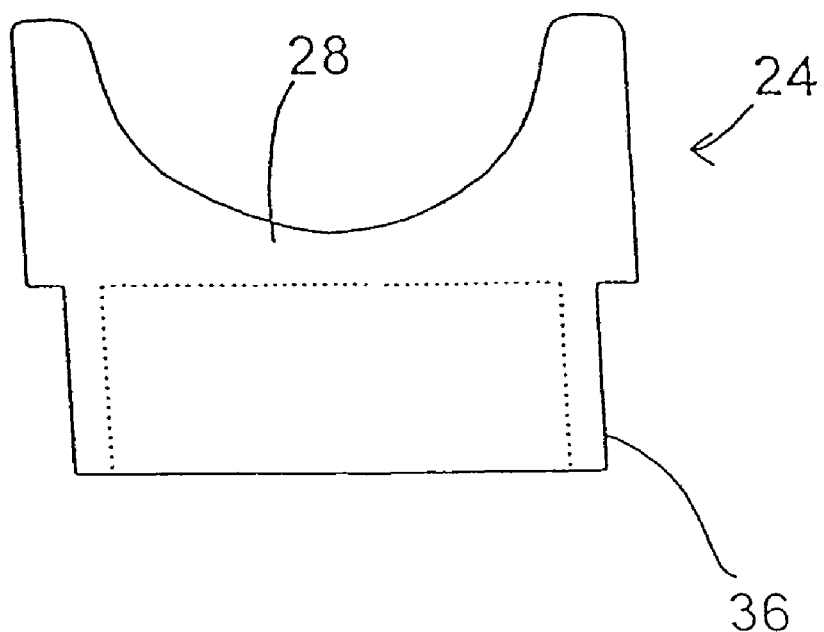
FIGS. 5a and 5b depict side and end views of a second forked end of the embodiment of FIG. 1.
Figure 5B:
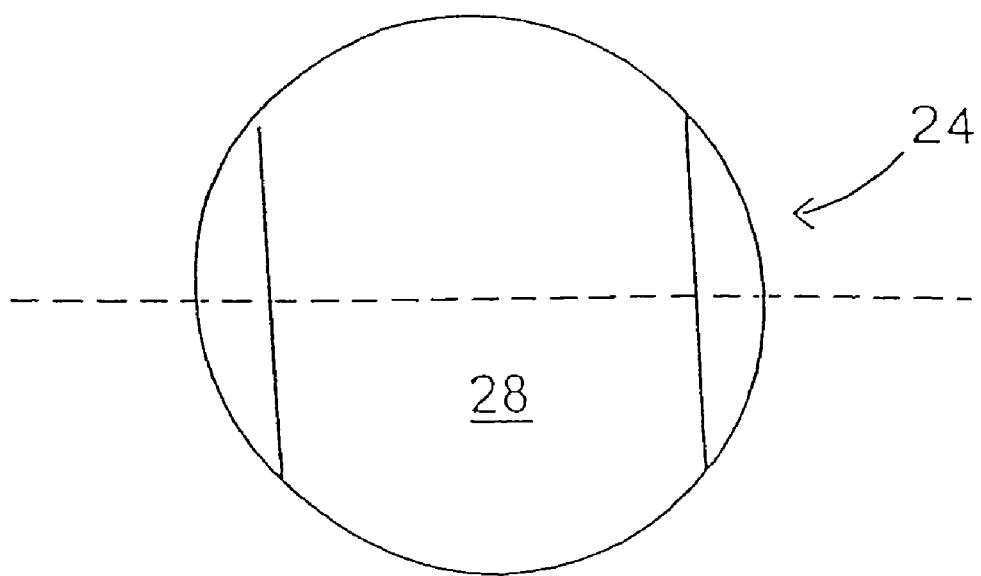

FIG. 1 shows the implant 20 in a fully extended position, while FIG. 2 shows the implant in an unextended position. In the unextended position, it can be seen that the threaded shaft 32 of the first forked end 22 fits inside the hollow cylindrical shaft 36 of the second forked end 24.

For purposes of implantation between adjacent first and second spinous processes of the spinal column, the implant 20 is configured as shown in FIG. 2. The first and second spinous processes are exposed using appropriate surgical techniques and thereafter, the implant 20 is positioned so that saddle 26 engages the first spinous process, and saddle 28 engages the second spinous process. At this point, the interbody piece 30 can be rotated by placing an appropriate tool or pin into the cross holes 40 and upon rotation, the saddle 26 is moved relative to the saddle 28. Such rotation spreads apart or distracts the spinous processes with the resultant and beneficial effect of enlarging the volume of the spinal canal in order to alleviate any restrictions on blood vessels and nerves.

It is noted that this implant as well as the several other implants described herein act as an extension stop. That means that as the back is bent backwardly and thereby placed in extension the spacing between adjacent spinous processes cannot be reduced to a distance less than the distance between the lowest point of saddle 26 and the lowest point of saddle 28. This implant, however, does not inhibit or in anyway limit the flexion of the spinal column, wherein the spinal column is bent forward.

Preferably, such a device provides for distraction in the range of about 5 mm to about 15 mm. However, devices which can distract up to and above 22 mm may be used depending on the characteristics of the individual patient.

With all the ligaments (such as the superspinous ligament) and tissues associated with the spinous processes left intact, the implant 20 can be implanted essentially floating in position in order to gain the benefits of the aforementioned extension stop and flexion non-inhibitor. If desired, one of the saddles 26 can be laterally pinned with pin 29 to one of the spinous processes and the other saddle can be loosely associated with the other spinous processes by using a tether 31 which either pierces or surrounds the other spinous process and then is attached to the saddle in order to position the saddle relative to the spinous process. Alternatively, both saddles can be loosely tethered to the adjacent spinous process in order to allow the saddles to move relative to the spinous processes.

The shape of the saddles, being concave, gives the advantage of distributing the forces between the saddle and the respective spinous process. This ensures that the bone is not resorbed due to the placement of the implant 20 and that the structural integrity of the bone is maintained.

The implant 20 in this embodiment can be made of a number of materials, including but not limited to, stainless steel, titanium, ceramics, plastics, elastics, composite materials or any combination of the above. In addition, the modulus of elasticity of the implant can be matched to that of bone, so that the implant 20 is not too rigid. The flexibility of the implant can further be enhanced by providing additional apertures or perforations throughout the implant in addition to the holes 40 which also have the above stated purpose of allowing the interbody piece 30 to be rotated in order to expand the distance between the saddle 26, 28.

In the present embodiment, it is understood that the spinous processes can be accessed and distracted initially using appropriate instrumentation, and that the implant 20 can be inserted and adjusted in order to maintain and achieve the desired distraction. Alternatively, the spinous process can be accessed and the implant 20 appropriately positioned. Once positioned, the length of the implant can be adjusted in order to distract the spinous processes or extend the distraction of already distracted spinous processes. Thus, the implant can be used to create a distraction or to maintain a distraction which has already been created.

The placement of implants such as implant 20 relative to the spinous process will be discussed hereinbelow with other embodiments. However, it is to be noted that ideally, the implant 20 would be placed close to the instantaneous axis of rotation of the spinal column so that the forces placed on the implant 20 and the forces that the implant 20 places on the spinal column are minimized.

Further, it is noted that during the actual process of installing or implanting the implant 20, that the method uses the approach of extending the length of the implant 20 a first amount and then allowing the spine to creep or adjust to this distraction. Thereafter, implant 20 would be lengthened another amount, followed by a period where the spine is allowed to creep or adjust to this new level of distraction. This process could be repeated until the desired amount of distraction has been accomplished. This same method can be used with insertion tools prior to the installation of an implant. The tools can be used to obtain the desired distraction using a series of spinal distraction and spine creep periods before an implant is installed.

Embodiment of FIGS. 6, 7, 8, 9 and 10

Figure 10:
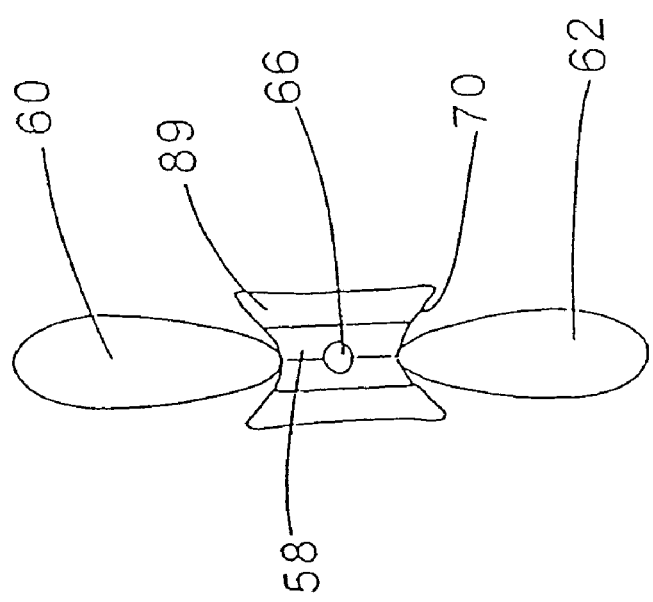

The embodiment of the invention shown in the above FIGS. 6, 7, 8, 9 and 10 includes distraction or spreader tool 50 which has first and second arms 52, 54. Arms 52, 54 are pivotal about pivot point 56 and releaseable from pivot point 56 in order to effect the implantation of implant 58. As can be seen in FIG. 6, in cross-section, the arms 52, 54 are somewhat concave in order to cradle and securely hold the first spinous process 60 relative to arm 52 and the second spinous process 62 relative to arm 54. The distraction tool 50 can be inserted through a small incision in the back of the patient in order to address the space between the first spinous process 60 and the second spinous process 62. Once the tool 50 is appropriately positioned, the arms 52, 54 can be spread apart in order to distract the spinous processes. After this has occurred, an implant 58 as shown in FIGS. 8 and 9, or of a design shown in other of the embodiments of this invention, can be urged between the arms 52, 54 and into position between the spinous processes. After this occurs, the arms 52, 54 can be withdrawn from the spinous processes leaving the implant 58 in place. The implant 58 is urged into place using a tool 64 which can be secured to the implant 58 through a threaded bore 66 in the back of the implant. As can be seen in FIG. 10, the implant 58 includes saddles 68 and 70 which cradle the upper and lower spinous processes 60, 62 in much the same manner as the above first embodiment and also in much the same manner as the individual arms of the tool 50. The saddles as described above tend to distribute the load between the implant and the spinous processes and also assure that the spinous process is stably seated at the lowest point of the respective saddles.

Figure 11:
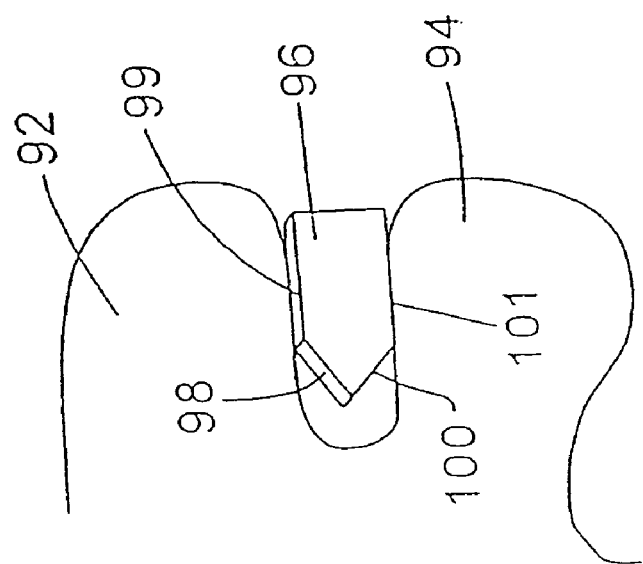
FIGS. 11, 12 and 13 depict yet a further embodiment of the invention for creating distraction between adjacent spinous processes.
Figure 12:
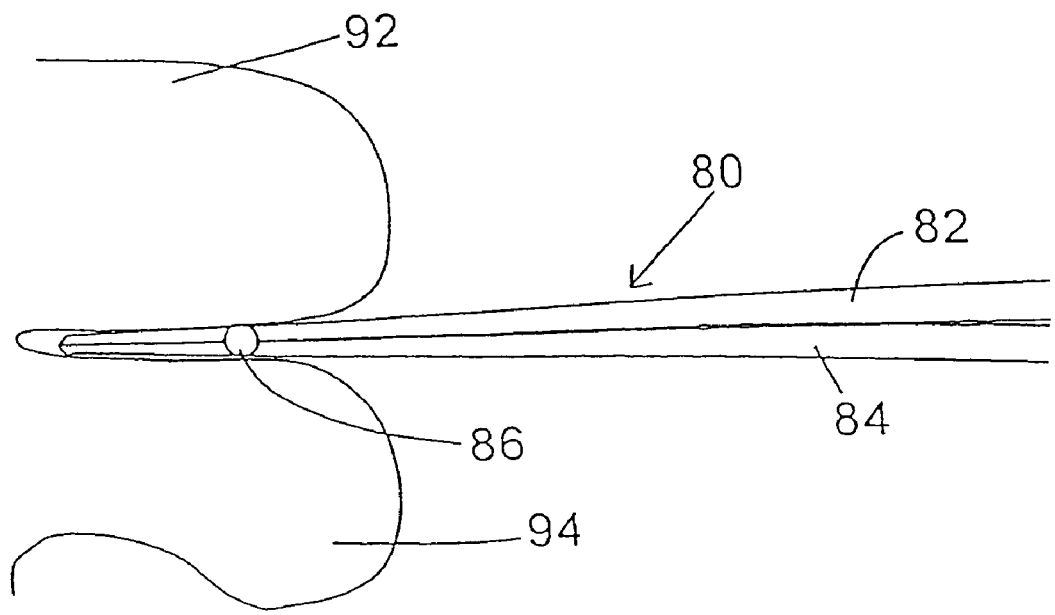
Figure 13:
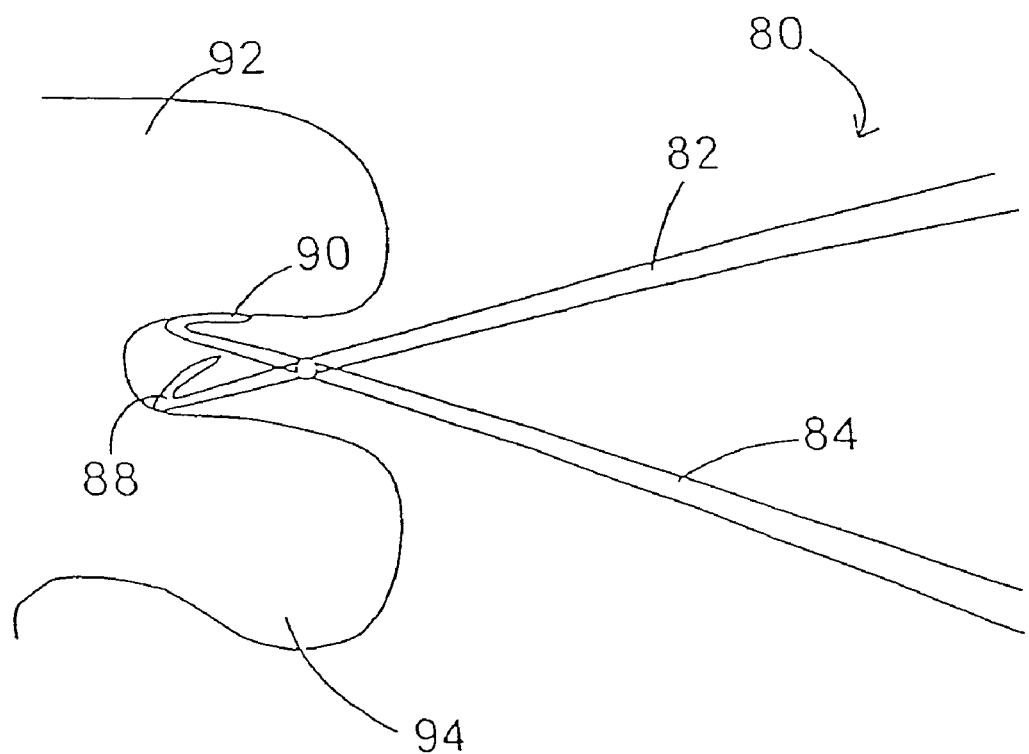

Embodiment of FIGS. 11, 12 and 13

Another embodiment of the apparatus and method of the invention is shown in FIGS. 11, 12 and 13. In this embodiment, the spreader or distraction tool 80 includes first and second arms 82, 84 which are permanently pivoted at pivot point 86. The arms include L-shaped ends 88, 90. Through a small incision, the L-shaped ends 88, 90 can be inserted between the first and second spinous processes 92, 94. Once positioned, the arms 82, 84 can be spread apart in order to distract the spinous processes. The implant 96 can then be urged between the spinous processes in order to maintain the distraction. It is noted that implant 96 includes wedged surfaces or ramps 98, 100. As the implant 96 is being urged between the spinous processes, the ramps further cause the spinous processes to be distracted. Once the implant 96 is fully implanted, the full distraction is maintained by the planar surfaces 99, 101 located rearwardly of the ramps. It is to be understood that the cross-section of the implant 96 can be similar to that shown for implant 58 or similar to other implants in order to gain the advantages of load distribution and stability.

Embodiments of FIGS. 14, 15, 16, 16a, and 17

Figure 14:
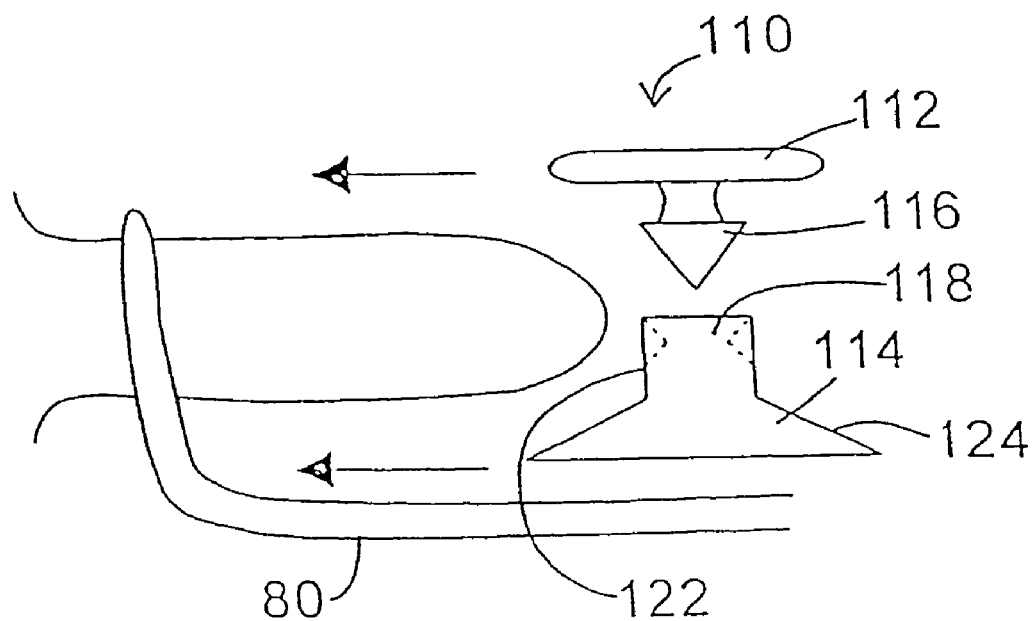
FIGS. 14 and 15 depict a further apparatus and method of an embodiment of the invention for creating distraction.
Figure 15:
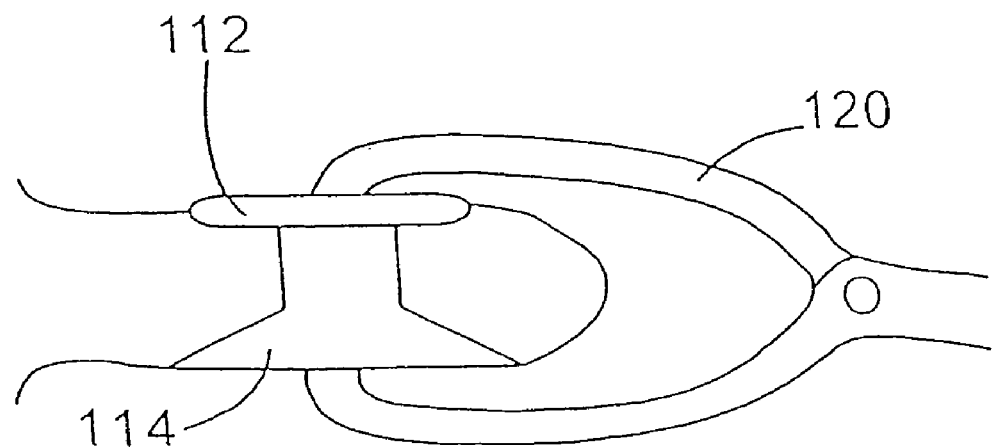

In FIGS. 14 and 15, yet another embodiment of the invention is depicted. In this embodiment, the implant 110 includes first and second conically shaped members 112, 114. Member 112 includes a male snap connector 116 and member 114 includes a female snap connector 118. With male snap connector 116 urged into female snap connector 118, the first member 112 is locked to the second member 114. In this embodiment, a distraction or spreader tool 80 could be used. Once the spinous process has been spread apart, an implantation tool 120 can be used to position and snap together the implant 110. The first member 112 of implant 110 is mounted on one arm and second member 114 is mounted on the other arm of tool 120. The member 112, 114 are placed on opposite sides of the space between adjacent spinous processes. The members 112, 114 are urged together so that the implant 110 is locked in place between the spinous processes as shown in FIG. 15. It is to be noted that the implant 110 can also be made more self-distracting by causing the cylindrical surface 122 to be more conical, much as surface 124 is conical, in order to hold implant 110 in place relative to the spinous processes and also to create additional distraction.

An alternative embodiment of the implant can be seen in FIGS. 16 and 17. This implant 130 includes first and second members 132, 134. In this particular embodiment, the implants are held together using a screw (not shown) which is inserted through countersunk bore 136 and engages a threaded bore 138 of the second member 134. Surfaces 139 are flattened (FIG. 17) in order to carry and spread the load applied thereto by the spinous processes.

The embodiment of implant 130 is not circular in overall outside appearance, as is the embodiment 110 of FIGS. 14 and 15. In particular, with respect to the embodiment of implant 130 of FIGS. 16 and 17, this embodiment is truncated so that the lateral side 140, 142 are flattened with the upper and lower sides 144, 146 being elongated in order to capture and create a saddle for the upper and lower spinous processes. The upper and lower sides, 144, 146 are rounded to provide a more anatomical implant which is compatible with the spinous processes.

If it is desired, and in order to assure that the first member 132 and the second member 134 are aligned, key 148 and keyway 150 are designed to mate in a particular manner. Key 148 includes at least one flattened surface, such as flattened surface 152, which mates to an appropriately flattened surface 154 of the keyway 150. In this manner, the first member is appropriately mated to the second member in order to form appropriate upper and lower saddles holding the implant 130 relative to the upper and lower spinous processes.

Figure 16A:
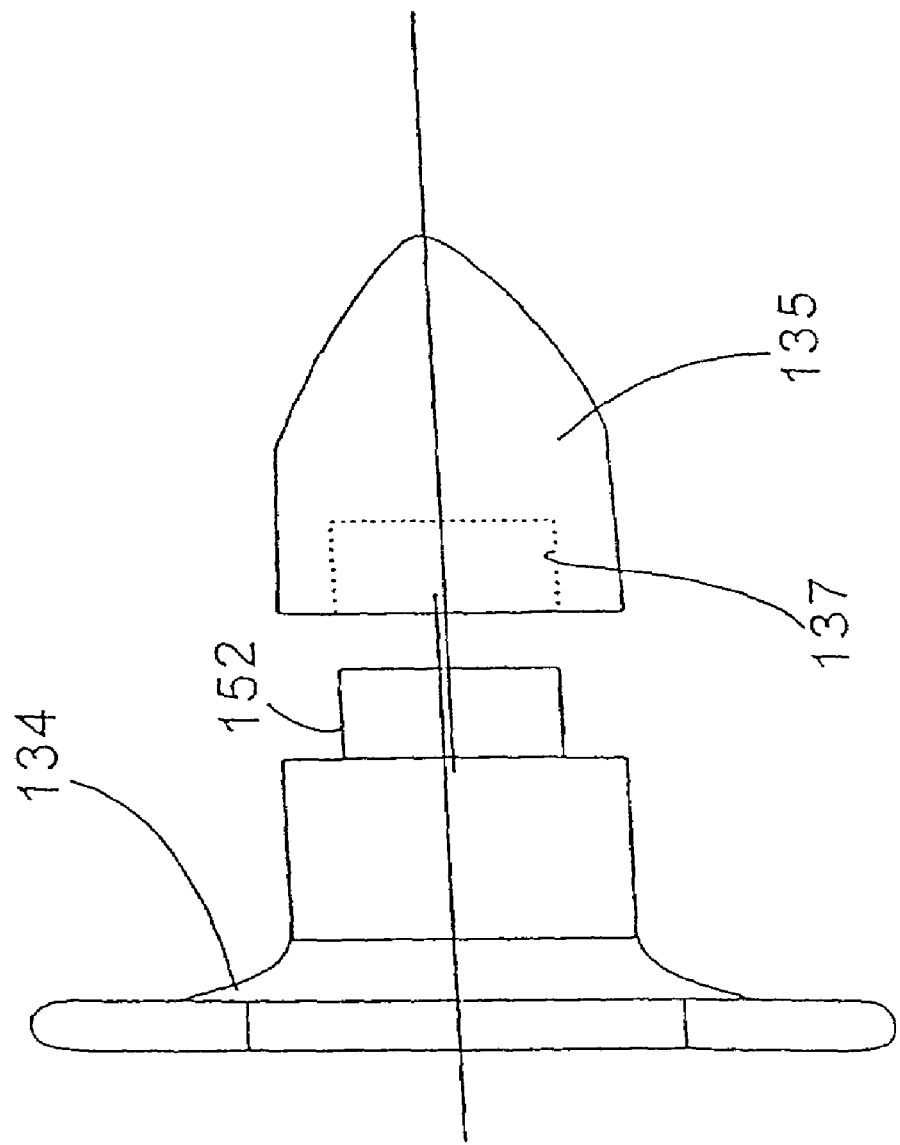

FIG. 16a depicts second member 134 in combination with a rounded nose lead-in plug 135. Lead-in plug 135 includes a bore 137 which can fit snugly over key 148. In this configuration, the lead-in plug 135 can be used to assist in the placement of the second member 134 between spinous processes. Once the second member 134 is appropriately positioned, the lead-in plug 135 can be removed. It is to be understood that the lead-in plug 135 can have other shapes such as pyramids and cones to assist in urging apart the spinous processes and soft tissues in order to position the second member 134.

Figure 18:
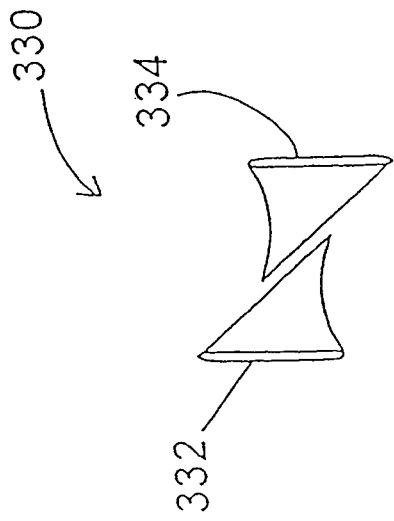
FIGS. 18, 19 and 20 depict yet a further apparatus and method of the present embodiment.
Figure 19:
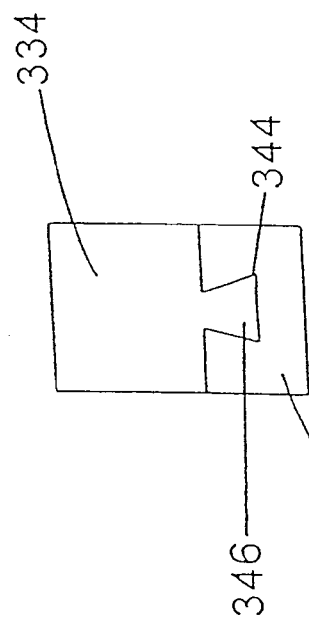
Figure 20:
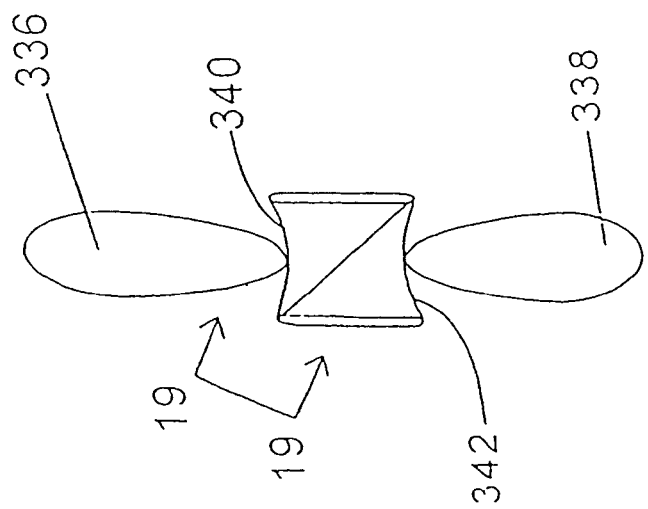

Embodiment of FIGS. 18, 19 and 20

The implant 330 as shown in FIG. 18 is comprised of first and second mating wedges 332 and 334. In order to implant these wedges 332, 334, the spinous processes are accessed from both sides and then a tool is used to push the wedges towards each other. As the wedges are urged towards each other, the wedges move relative to each other so that the combined dimension of the implant 330 located between the upper and lower spinous processes 336, 338 (FIG. 20), increases, thereby distracting the spinous processes. It is noted that the wedges 332, 334 include saddle 340, 342, which receiving the spinous processes 336, 338. These saddles have the advantages as described hereinabove.

The first or second wedges 332, 334 have a mating arrangement which includes a channel 344 and a projection of 346 which can be urged into the channel in order to lock the wedges 332, 334 together. The channel 334 is undercut in order to keep the projection from separating therefrom. Further, as in other devices described herein, a detent can be located in one of the channel and the projection, with a complimentary recess in the other of the channel and the projection. Once these two snap together, the wedges are prevented from sliding relative to the other in the channel 344.

While the above embodiment was described with respect to wedges, the wedges could also have been designed substantially as cones with all the same features and advantages.

Figure 22:
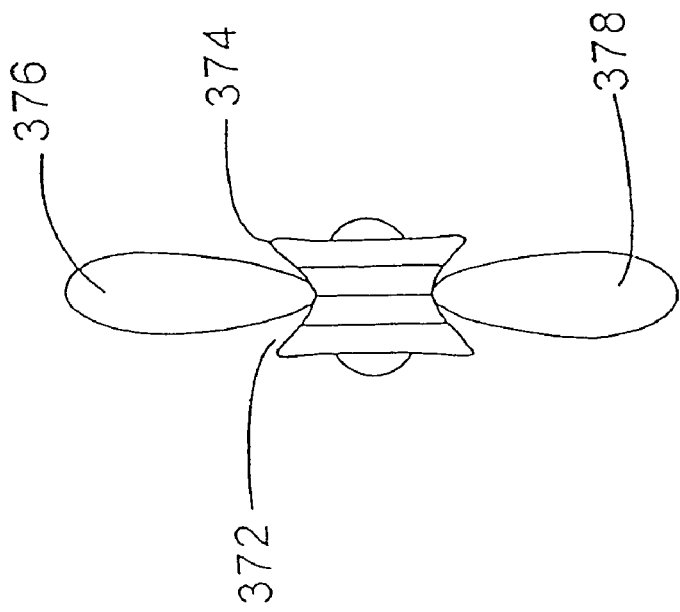
FIGS. 21 and 22 depict still a further embodiment of the present invention.
Figure 21:
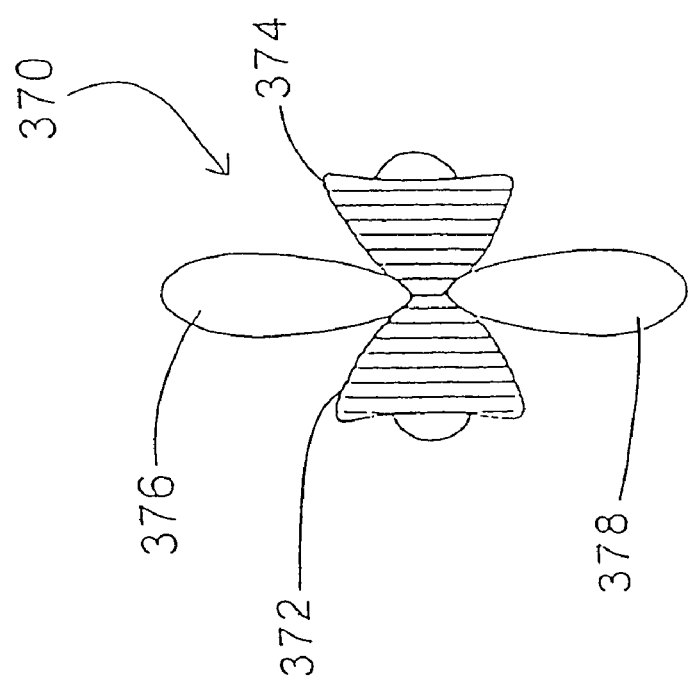

Embodiments of FIGS. 21 and 22

The implant 370 is comprised of first and second distraction cone 372, 374. These cones are made of a flexible material. The cones are positioned on either side of the spinous processes 376, 378 as shown in FIG. 21. Using appropriate tool as shown hereinabove, the distraction cones 372, 374 are urged together. As they are urged together, the cones distract the spinous processes as shown in FIG. 22. Once this has occurred, an appropriate screw or other type of fastening mechanism 380 can be used to maintain the position of the distraction cones 372, 374. The advantage of this arrangement is that the implant 370 is self-distracting and also that the implant, being flexible, molds about the spinous processes as shown in FIG. 22.

Figure 24:
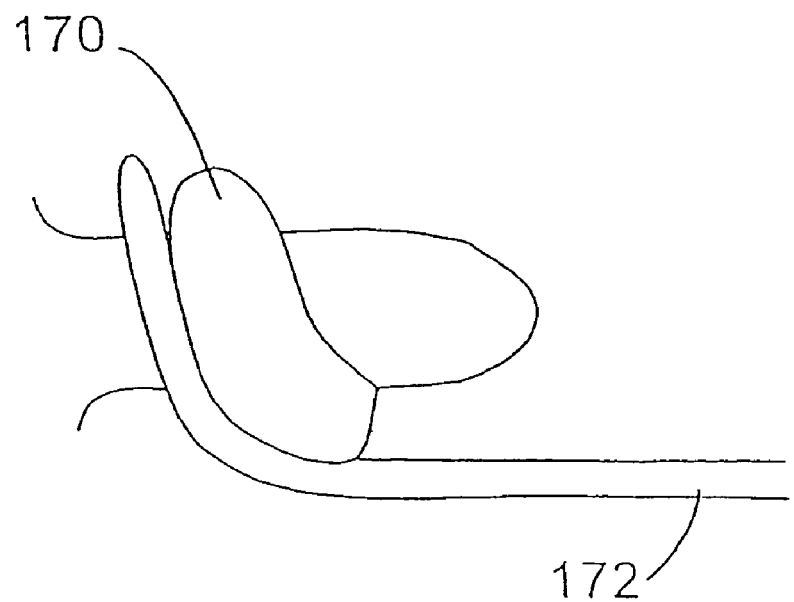
FIGS. 23, 24 and 25 depict another embodiment of the present invention.
Figure 23:
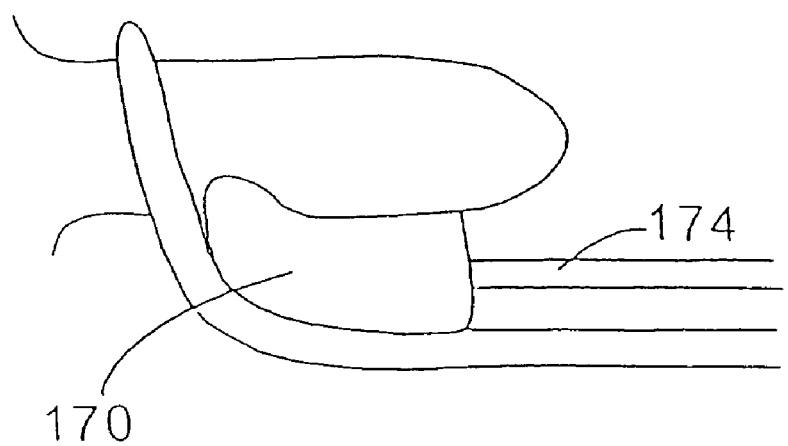
Figure 25:
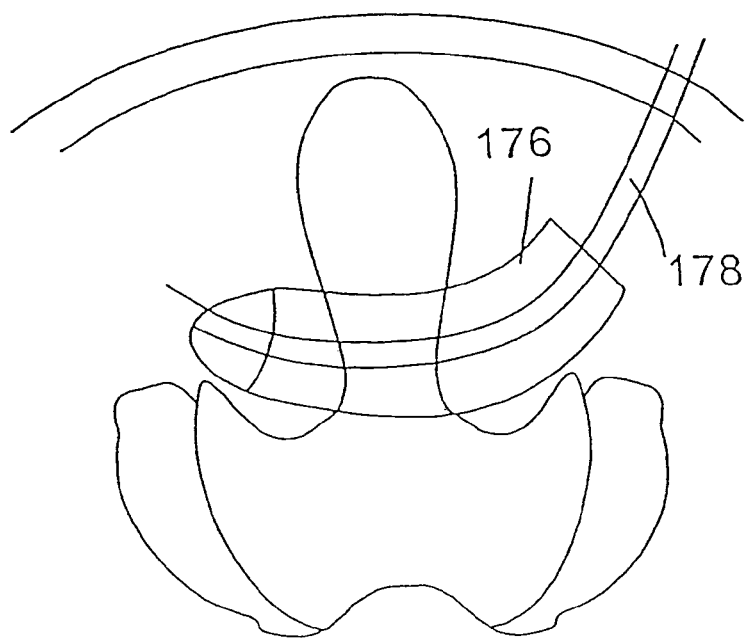

Embodiments of FIGS. 23, 24 and 25

In FIGS. 23 and 24, another embodiment of the implant 170 is depicted. This implant is guided in place using an L-shaped guide 172 which can have a concave cross-section such as the cross-section 52 of retraction tool 50 in FIG. 6 in order to cradle and guide the implant 170 in position. Preferably a small incision would be made into the back of the patient and the L-shaped guide tool 172 inserted between the adjacent spinous processes. The implant 170 would be mounted on the end of insertion tool 174 and urged into position between the spinous processes. The act of urging the implant into position could cause the spinous processes to be further distracted if that is required. Prior to the insertion of the L-shaped guide tool 172, a distraction tool such as shown in FIG. 13 could be used to initially distract the spinous processes.

Implant 170 can be made of a deformable material so that it can be urged into place and so that it can somewhat conform to the shape of the upper and lower spinous processes. This deformable material would be preferably an elastic material. The advantage of such a material would be that the load forces between the implant and the spinous processes would be distributed over a much broader surface area. Further, the implant would mold itself to an irregular spinous process shape in order to locate the implant relative to spinous processes.

With respect to FIG. 25, this implant 176 can be inserted over a guide wire, guide tool or stylet 178. Initially, the guide wire 178 is positioned through a small incision to the back of the patient to a position between the adjacent spinous processes. After this has occurred, the implant is threaded over the guide wire 178 and urged into position between the spinous processes. This urging can further distract the spinous processes if further distraction is required. Once the implant is in place, the guide tool 178 is removed and the incision closed. The insertion tools of FIGS. 23 and 24 can also be used if desired.

Figure 26:
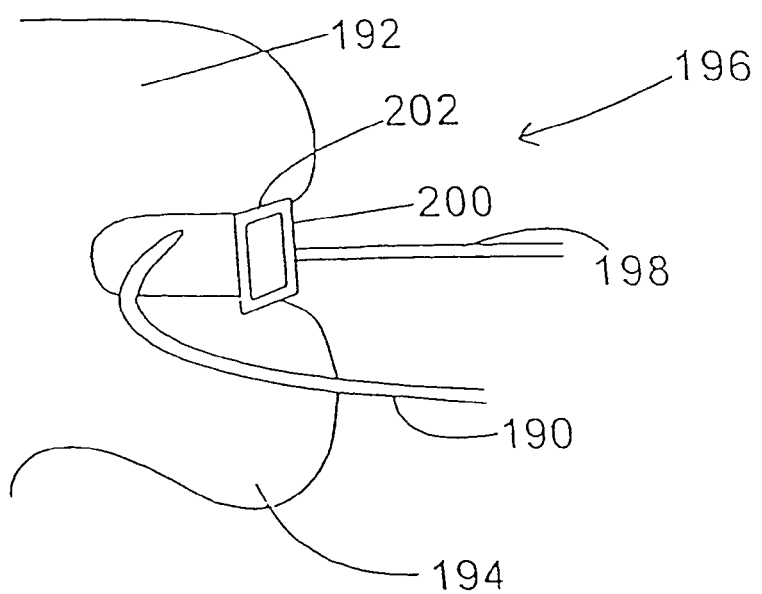
FIGS. 26, 27 and 28 depict another embodiment of the invention.
Figure 28:
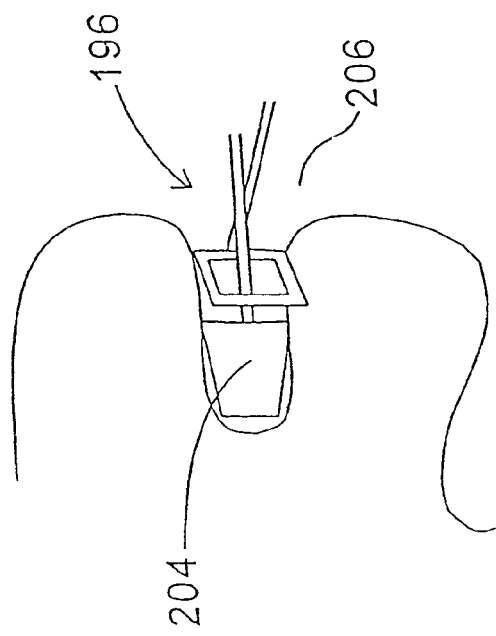
Figure 27:
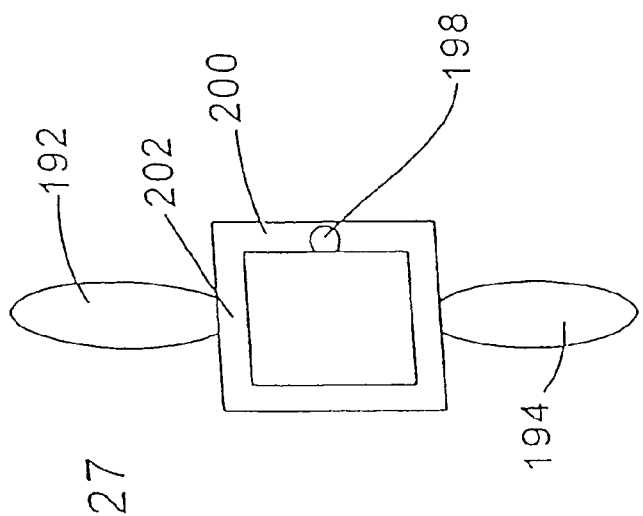

Embodiment of FIGS. 26, 27 and 28

The embodiment shown in FIGS. 26, 27 and 28 uses an implant similar to that depicted in FIGS. 8 and 9 with different insertion tools. As can be seen in FIG. 26, an L-shaped distraction tool 190 is similar to L-shaped distraction tool 80 (FIG. 12), is used to distract the first and second spinous processes 192, 194. After this has occurred, an insertion tool 196 is placed between the spinous processes 192, 194. Insertion tool 196 includes a handle 198 to which is mounted a square-shaped ring 200.

The distraction tool 190 can be inserted through a small incision in the back in order to spread apart the spinous processes. Through the same incision which has been slightly enlarged laterally, an upper end 202 of ring 200 can be initially inserted followed by the remainder of the ring 200.

Once the ring is inserted, the ring can be rotated slightly by moving handle 198 downwardly in order to further wedge the spinous processes apart. Once this has been accomplished, an implant such as implant 204 can be inserted through the ring and properly positioned using implant handle 206. Thereafter, the implant handle 206 and the insertion tool 196 can be removed.

Embodiments of FIGS. 29, 30, 31, 32 and 33

Figure 30:
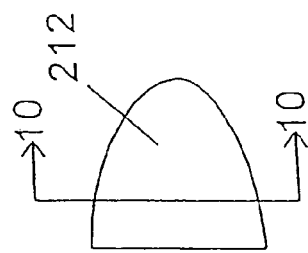
FIGS. 29 and 30 depict side elevational views of differently shaped implants of embodiments of the present invention.
Figure 29:
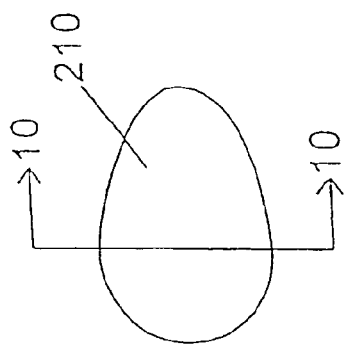

As can be seen in FIGS. 29 and 30, the implants 210, 212, can have different shapes when viewed from the side. These implants are similar to the above-referenced implants 58 (FIG. 8) and 204 (FIG. 28). These implants have cross-sections similar to that shown in FIG. 10 which includes saddles in order to receive and hold the adjacent spinous processes.

Figure 33:
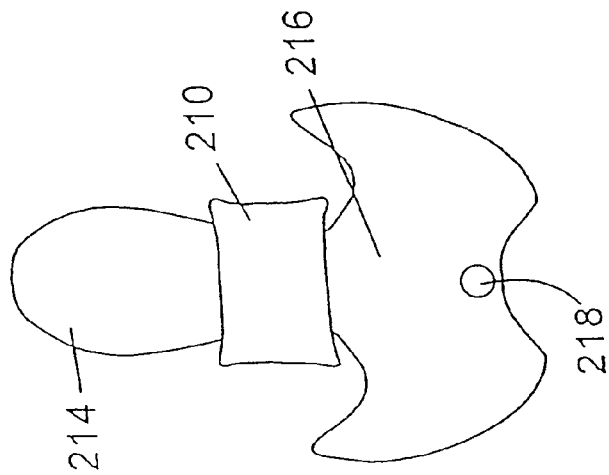
FIGS. 31, 32 and 33 depict various implant positions of an apparatus of the present invention.
Figure 32:
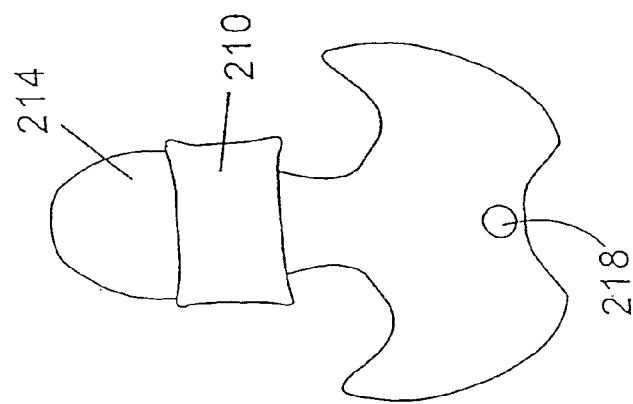
Figure 31:
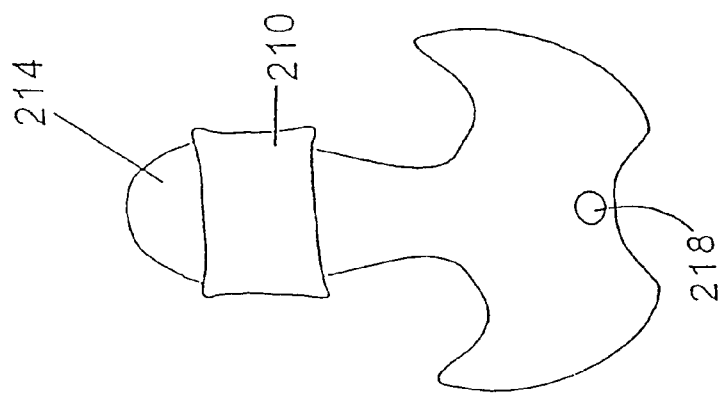

As can be seen in FIGS. 31, 32 and 33, these implants can be placed in different positions with respect to the spinous process 214. Preferably as shown in FIG. 33, the implant 210 is placed closest to the lamina 216. Being so positioned, the implant 210 is close to the instantaneous axis of rotation 218 of the spinal column, and the implant would experience least forces caused by movement of the spine. Thus, theoretically, this is the optimal location for the implant.

As can be seen in FIGS. 31 and 32, the implant can be placed midway along the spinous process (FIG. 32) and towards the posterior aspect of the spinous process (FIG. 31). As positioned shown in FIG. 31, the greatest force would be placed on the implant 210 due to a combination of compression and extension of the spinal column.

Embodiment of FIGS. 34 and 35

Another embodiment of the invention is shown in FIGS. 34 and 35. In these figures, implant 220 is comprised of a plurality of individual leaves 222 which are substantially V-shaped. The leaves include interlocking indentations or detents 224. That is, each leaf includes an indentation with a corresponding protrusion such that a protrusion of one leaf mates with an indentation of an adjacent leaf. Also associated with this embodiment is an insertion tool 226 which has a blunt end 228 which conforms to the shape of an individual leaf 222. For insertion of this implant into the space between the spinous processes as shown in FIG. 29, the insertion tool 226 first insert a single leaf 220. After that has occurred, the insertion tool then inserts a second leaf with the protrusion 224 of the second leaf snapping into corresponding indentation made by the protrusion 224 of the first leaf. This process would reoccur with third and subsequent leaves until the appropriate spacing between the spinous processes was built up. As can be seen in FIG. 29, the lateral edges 229 of the individual leaves 222 are slightly curved upwardly in order to form a saddle for receiving the upper and lower spinous processes.

Embodiments of FIGS. 36, 37 and 38

The embodiments of FIGS. 36, 37 and 38 which include implants 230, 232, and 234 respectively, are designed in such a manner so the implant locks itself into position once it is properly positioned between the spinous processes. Implant 220 is essentially a series of truncated cones and includes a plurality of ever expanding steps 236. These steps are formed by the conical bodies starting with the nose body 238 followed there behind by conical body 240. Essentially, the implant 234 looks like a fir tree placed on its side.

The implant 230 is inserted laterally throughout the opening between upper and lower spinous processes. The first body 238 causes the initial distraction. Each successive conical body distracts the spinous processes a further incremental amount. When the desired distraction has been reached, the spinous processes are locked into position by steps 236. At this point, if desired, the initial nose body 238 of the implant and other bodies 240 can be broken, snapped or sawed off if desired in order to minimize the size of the implant 230. In order for a portion of the implant 230 to be broken or snapped off, the intersection between bodies such as body 238 and 240, which is intersection line 242, would be somewhat weaken with the appropriate removal of material. It is noted that only the intersection lines of the initial conical bodies need to be so weakened. Thus, intersection line 244 between the bodies which remain between the spinous processes would not need to be weaker, as there would be no intention that the implant would be broken off at this point.

FIG. 37 shows implant 232 positioned between upper and lower spinous processes. This implant is wedge-shaped or triangular shaped in cross-sectioned and includes bore pluralities 245 and 246. Through these bores can be placed locking pins 248 and 250. The triangular or wedged-shaped implant can be urged laterally between and thus distract the upper and lower spinous processes. Once the appropriate distraction is reached, pins 248, 250 can be inserted through the appropriate bores of the bore pluralities 245 and 246 in order to lock the spinous processes in a V-shaped valley formed by pins 248, 250 on the one hand and the ramped surface 233, 235 on the other hand.

Turning to FIG. 38, the implant 234 has a triangular-shaped or wedge-shaped body similar to that shown in FIG. 32. In this embodiment, tab 252, 254 are pivotally mounted to the triangular shaped body 234. Once the implant 234 is appropriately positioned in order to distract the spinous processes to the desired amount, the tabs 252, 254 rotate into position in order to hold the implant 234 in the appropriate position.

Embodiment of FIGS. 39 and 40

In the embodiment of FIGS. 39 and 40, cannula 258 is inserted through a small incision to a position between upper and lower spinous processes. Once the cannula is properly inserted, an implant 260 is pushed through the cannula 258 using an insertion tool 262. The implant 260 includes a plurality of ribs or indentation 264 that assist in positioning the implant 260 relative to the upper and lower spinal processes. Once the implant 260 is in position, the cannula 258 is withdrawn so that the implant 260 comes in contact with and wedges between the spinous processes. The cannula 258 is somewhat conical in shape with the nose end 266 being somewhat smaller than the distal end 268 in order to effect the insertion of the cannula into the space between the spinous processes.

Further, a plurality of cannula can be used instead of one, with each cannula being slightly bigger than one before. In the method of the invention, the first smaller cannula would be inserted followed by successively larger cannula being placed over the previous smaller cannula. The smaller cannula would then be withdrawn from the center of the larger cannula. Once the largest cannula is in place, and the opening of the skin accordingly expanded, the implant, which is accommodated by only the larger cannula, is inserted through the larger cannula and into position.

Figure 43:
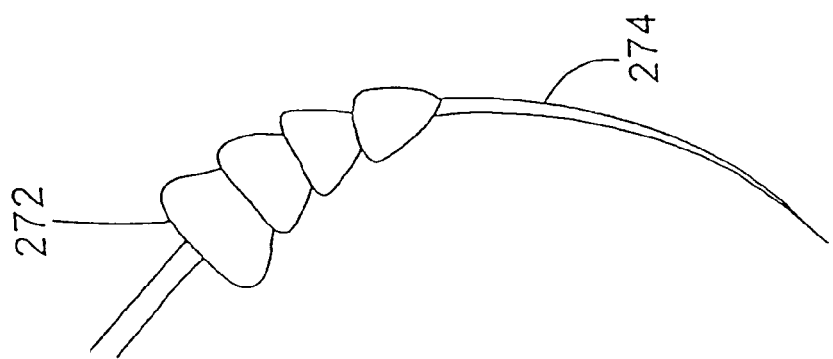
FIGS. 41, 42 and 43 depict yet further embodiments of an apparatus and method of the present invention.
Figure 42:
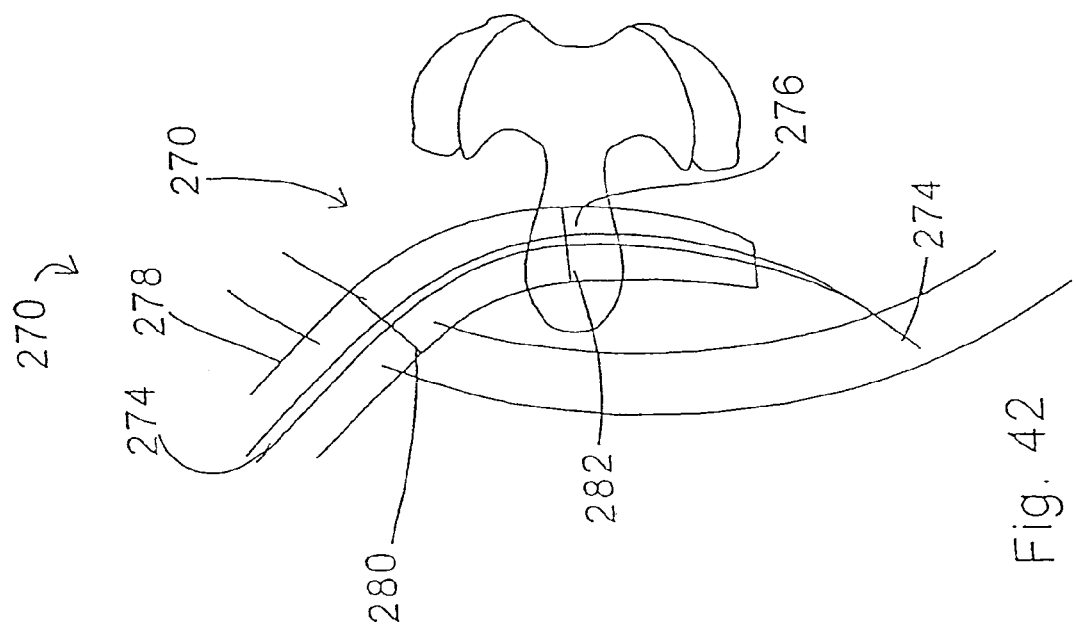
Figure 41:
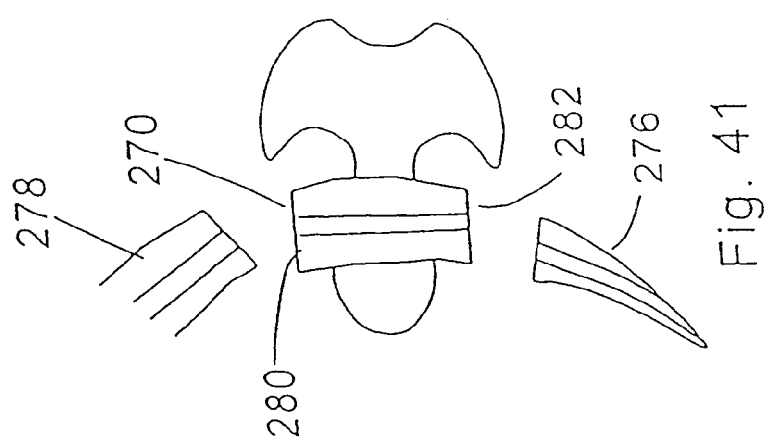

Embodiments of FIGS. 41, 42 and 43

The precurved implant 270 in FIGS. 41 and 42, and precurved implant 272 in FIG. 43 have common introduction techniques which includes a guide wire, guide tool, or stylet 274. For both embodiments, the guide wire 274 is appropriately positioned through the skin of the patient and into the space between the spinous processes. After this is accomplished, the implant is directed over the guide wire and into position between the spinous processes. The precurved nature of the implant assist in (1) positioning the implant through a first small incision in the patient's skin on one side of the space between two spinous processes and (2) guiding the implant toward a second small incision in the patient's skin on the other side of the space between the two spinous processes. With respect to the implant 270, the implant includes a conical introduction nose 276 and a distal portion 278. As the nose 276 is inserted between the spinous processes, this causes distraction of the spinous processes. Break lines 280, 282 are established at opposite sides of the implant 270. Once the implant is properly positioned over the guide wire between the spinous processes, the nose portion 276 and the distal portion 278 can be broken off along the break lines, through the above two incisions, in order to leave the implant 270 in position.

Although only two break lines 280, 282 are depicted, multiple break lines can be provided on implant 270 so that the implant can continue to be fed over the guide wire 278 until the appropriate width of the implant 270 creates the desired amount of distraction. As described hereinabove, the break lines can be created by perforating or otherwise weakening the implant 270 so that the appropriate portions can be snapped or sawed off.

With respect to the precurved implant 272, this implant is similar in design to the implant 230 shown in FIG. 36. This implant 272 in FIG. 47, however, is precurved and inserted over a guide wire 274 to a position between the spinous processes. As with implant 230 in FIG. 43, once the appropriate level of this distraction has been reached and if desired, sections of the implant 272 can be broken, snapped or sawed off as described hereinabove in order to leave a portion of the implant wedged between the upper and lower spinous processes.

Embodiment of FIG. 44

A further embodiment of the invention is shown in FIG. 44. This embodiment includes a combination insertion tool and implant 290. The insertion tool and implant 290 is in the shape of a ring which is hinged at point 292. The ring is formed by a first elongated and conically shaped member 294 and a second elongated and conically shaped member 296. Members 294 and 296 terminate in points and through the use of hinge 292 are aligned and meet. Through similar incisions on both sides of the spinous processes, first member and second member are inserted through the skins of the patient and are mated together between the spinous processes. After this has occurred, the implant 290 is rotated, for example clockwise, so that increasingly widening portions of the first member 292 are used to distract the first and second spinous processes. When the appropriate level of distraction has occurred, the remainder of the ring before and after the section which is located between the spinous processes can be broken off as taught hereinabove in order to maintain the desired distraction. Alternatively, with a small enough ring, the entire ring can be left in place with the spinous processes distracted.

Embodiment of FIG. 45

In FIG. 45, the implant 300 is comprised of a plurality of rods or stylets 302 which are inserted between the upper and lower spinous processes. The rods are designed much as described hereinabove so that they may be broken, snapped or cut off. Once these are inserted and the appropriate distraction has been reached, the stylets are broken off and a segment of each stylet remains in order to maintain distraction of the spinous process.

Embodiment of FIGS. 46 and 47

Implant 310 of FIGS. 46 and 47 is comprised of a shape memory material which coils upon being released. The material is straightened out in a delivery tool 312. The delivery tool is in position between upper and lower spinous processes 314, 316. The material is then pushed through the delivery tool. As it is released from the delivery end 318 of the delivery tool, the material coils, distracting the spinous processes to the desired amount. Once this distraction has been achieved, the material is cut and the delivery tool removed.

Embodiments of FIGS. 48, 49, 50 and 51

As can be seen in FIG. 48, the implant 320 is delivered between upper and lower spinous processes 322 and 324, by delivery tool 326. Once the implant 320 is in place between the spinous processes, the delivery tool is given a 90° twist so that the implant goes from the orientation as shown in FIG. 49, with longest dimension substantially perpendicular to the spinous processes, to the orientation shown in FIG. 50 where the longest dimension is in line with and parallel to the spinous processes. This rotation causes the desired distraction between the spinous processes. Implant 320 includes opposed recesses 321 and 323 located at the ends thereof. Rotation of the implant 320 causes the spinous processes to become lodged in these recesses.

Alternatively, the insertion tool 326 can be used to insert multiple implants 320, 321 into the space between the spinous processes 322, 324 (FIG. 51). Multiple implants 320, 321 can be inserted until the appropriate amount of distraction is built up. It is to be understood in this situation that one implant would lock to another implant by use of, for example, a channel arrangement wherein a projection from one of the implants would be received into and locked into a channel of the other implant. Such a channel arrangement is depicted with respect to the other embodiment.

Embodiment of FIGS. 52, 53, 54, 55a and 55b

The embodiment of FIGS. 52 through 55b is comprised of a fluid-filled dynamic distraction implant 350. This implant includes a membrane 352 which is placed over pre-bent insertion rod 354 and then inserted through an incision on one side of the spinous process 356. The bent insertion rod, with the implant 350 thereover, is guided between appropriate spinous processes. After this occurs, the insertion rod 354 is removed leaving the flexible implant in place. The implant 350 is then connected to a source of fluid (gas, liquid, gel and the like) and the fluid is forced into the implant causing it to expand as shown in FIG. 54, distracting the spinal processes to the desired amount. Once the desired amount of distraction has occurred, the implant 350 is closed off as is shown in FIG.

55a. The implant 350 being flexible, can mold to the spinous processes which may be of irregular shape, thus assuring positioning. Further, implant 350 acts as a shock absorber, damping forces and stresses between the implant and the spinous processes.

A variety of materials can be used to make the implant and the fluid which is forced into the implant. By way of example only, viscoelastic substances such as methylcellulose, or hyaluronic acid can be used to fill the implant. Further, materials which are initially a fluid, but later solidify, can be inserted in order to cause the necessary distraction. As the materials solidify, they mold into a custom shape about the spinous processes and accordingly are held in position at least with respect to one of two adjacent spinous processes. Thus, it can be appreciated that using this embodiment and appropriate insertion tools the implant can be formed about one spinous process in such a manner that the implant stays positioned with respect to that spinous process (FIG. 55b). With such an embodiment, a single implant can be used as an extension stop for spinous process located on either side, without restricting flexion of the spinal column.

It is to be understood that many of the other implants disclosed herein can be modified so that they receive a fluid in order to establish and maintain a desired distraction much in the manner as implant 350 receives a fluid.

Figure 58:
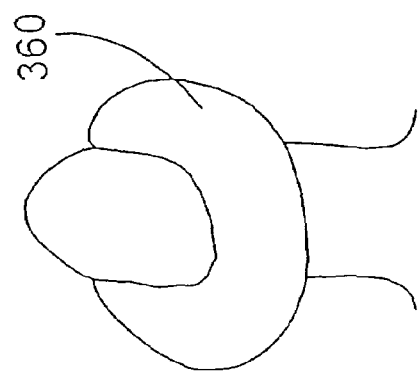
FIGS. 56, 57 and 58 depict yet a further apparatus and method of the invention.
Figure 57:
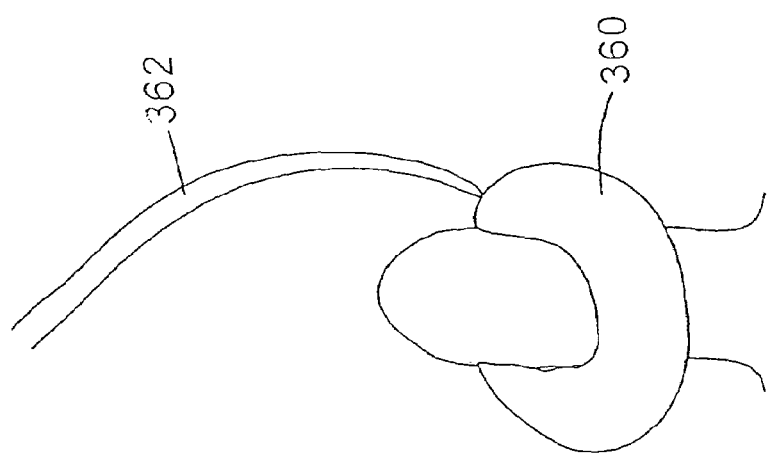
Figure 56:
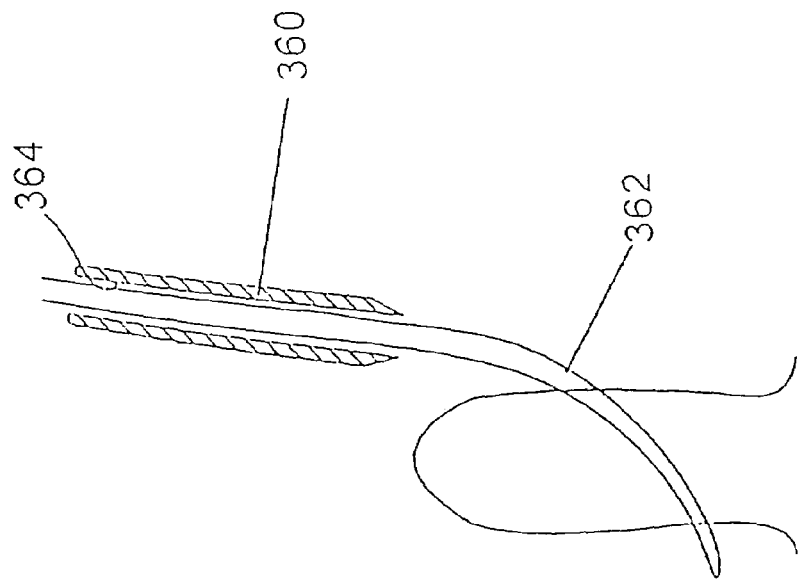

Embodiment of FIGS. 56, 57 and 58

The implant 360 as shown in FIG. 56 is comprised of a shape memory material such as a plastic or a metal. A curved introductory tool 362 is positioned between the appropriate spinous processes as described hereinabove. Once this has occurred, bore 364 of the implant is received over the tool. This act can cause the implant to straighten out. The implant is then urged into position and thereby distracts the spinous processes. When this has occurred, the insertion tool 362 is removed, allowing the implant to assume its pre-straightened configuration and is thereby secured about one of the spinous processes. Such an arrangement allows for an implant that is an extension stop and does not inhibit flexion of the spinous column. Alternatively, the implant can be temperature sensitive. That is to say that the implant would be more straightened initially, but become more curved when it was warmed by the temperature of the patient's body.

Embodiments of FIGS. 59 and 60

In this embodiment, the implant 380 is comprised of a plurality of interlocking leaves 382. Initially, a first leaf is positioned between opposed spinous processes 384, 386. Then subsequently, leafs 382 are interposed between the spinous processes until the desired distraction has been built up. The leaves are somewhat spring-like in order to absorb the shock and can somewhat conform to the spinous processes.

Embodiment of FIG. 61

The implant 390 of FIG. 61 includes the placement of shields 392, 394 over adjacent spinous processes 396, 398. The shields are used to prevent damage to the spinous processes. These shields include apertures which receives a self-tapping screw 400, 402. In practice, the shields are affixed to the spinous processes and the spinous processes are distracted in the appropriate amount. Once this has occurred, a rod 404 is used to hold the distracted position by being screwed into each of the spinous processes through the aperture in the shields using the screws as depicted in FIG. 61.

Figure 63:
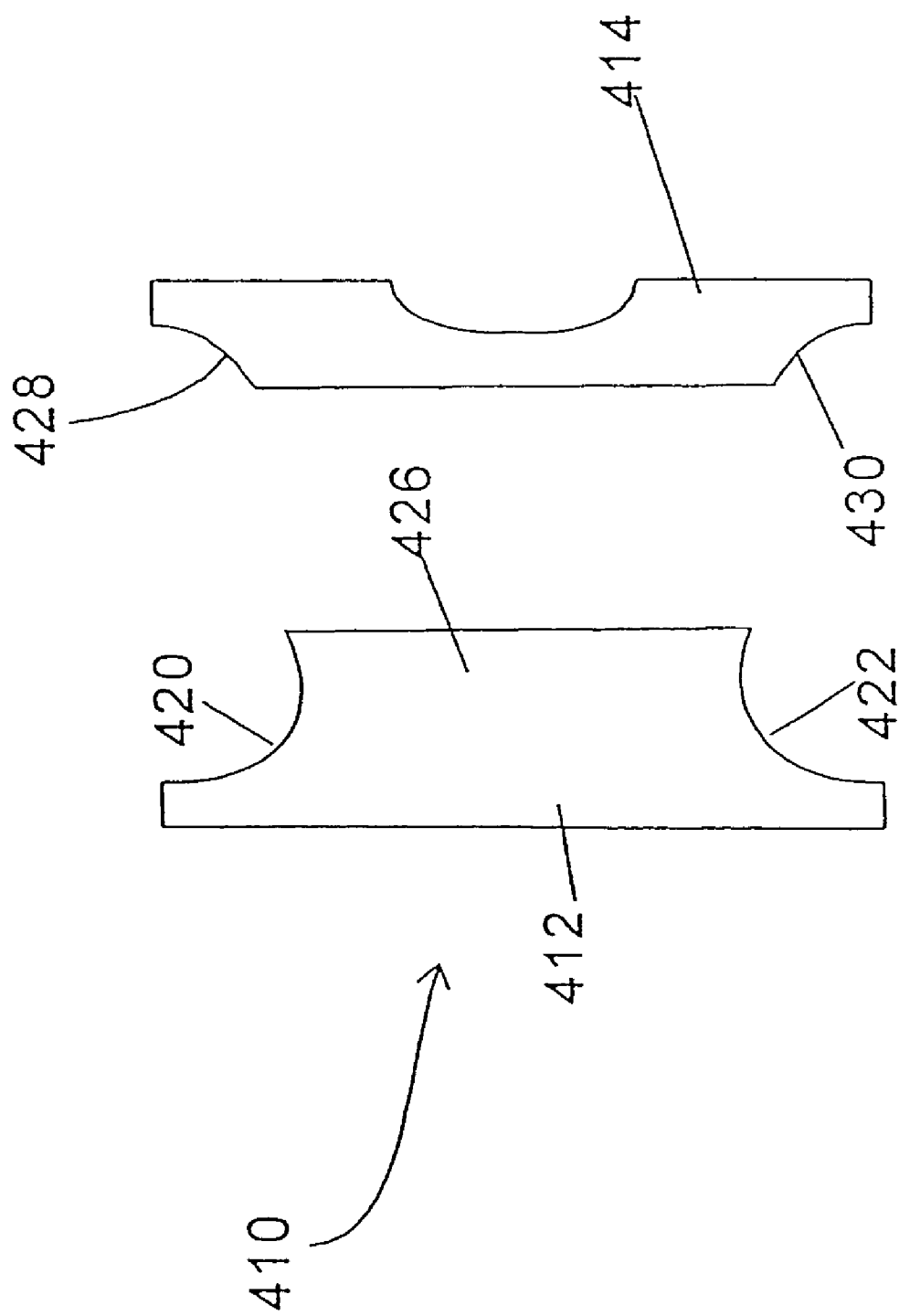

Embodiment of FIGS. 62 and 63

Implant 410 of FIGS. 62, 63 is comprised of first and second members 412, 414 which can be mated together using an appropriate screw and threaded bore arrangement to form the implant 410. Main member 412 and mating member 414 form implant 410. Accordingly, the implant 410 would have a plurality of members 414 for use with a standardized first member 412. FIGS. 62 and 64 show different types of mating members 414. In FIG. 62, the mating member 414 includes projections 416 and 418 which act like shims. These projections are used to project into the space of saddles 420, 422 of the first member 412. These projections 416, 418 can be of varying lengths in order to accommodate different sizes of spinous processes. A groove 424 is placed between the projections 416, 418 and mates with an extension 426 of the first member 412.

As shown in FIG. 63, the projections of the embodiment shown in FIG. 62 are removed and recesses 428, 430 are substituted therefor. These recesses expand the area of the saddles 420, 422 in order to accommodate larger spinous processes.

Embodiment of FIGS. 64, 65 and 66

The embodiments of FIGS. 64, 65 and 66 are similar in design and concept to the embodiment of FIGS. 62 and 63. In FIG. 64, the implant 500 includes the first and second members 502, 504. These members can be secured together with appropriate screws or other fastening means as taught in other embodiments. Implant 500 includes first and second saddles 506, 508 which are formed between the ends of first and second members 502, 504. These saddles 506, 508 are used to receive and cradle the adjacent spinous processes. As can be seen in FIG. 64, each saddle 506, 508 is defined by a single projection or leg 510, 512, which extends from the appropriate first and second members 502, 504. Unlike the embodiment found in FIGS. 62 and 63, each of the saddles is defined by only a single leg as the ligaments and other tissues associated with the spinous processes can be used to ensure that the implant is held in an appropriate position. With the configuration of FIG. 64, it is easier to position the implant relative to the spinous processes as each saddle is defined by only a single leg and thus the first and second members can be more easily worked into position between the various tissues.

In the embodiment of FIG. 65, the implant 520 is comprised of a single piece having saddles 522 and 524. The saddles are defined by a single leg 526, 528 respectively. In order for this implant 520 to be positioned between the spinous processes, an incision is made between lateral sides of adjacent spinous processes. The single leg 526 is directed through the incision to a position adjacent to an opposite lateral side of the spinous process with the spinous process cradled in the saddle 522. The spinous processes are then urged apart until saddle 524 can be pivoted into position into engagement with the other spinous process in order to maintain the distraction between the two adjacent spinous processes.

The embodiment of FIG. 66 is similar to that of FIG. 65 with an implant 530 and first and second saddles 532 and 534. Associated with each saddle is a tether 536, 538 respectively. The tethers are made of flexible materials known in the trade and industry and are positioned through bores in the implant 530. Once appropriately positioned, the tethers can be tied off. It is to be understood that the tethers are not meant to be used to immobilize one spinous process relative to the other, but are used to guide motion of the spinous processes relative to each other so that the implant 530 can be used as an extension stop and a flexion non-inhibitor. In other words, the saddles 532, 534 are used to stop spinal column backward bending and extension. However, the tethers do not inhibit forward bending and spinal column flexion.

Figure 68:
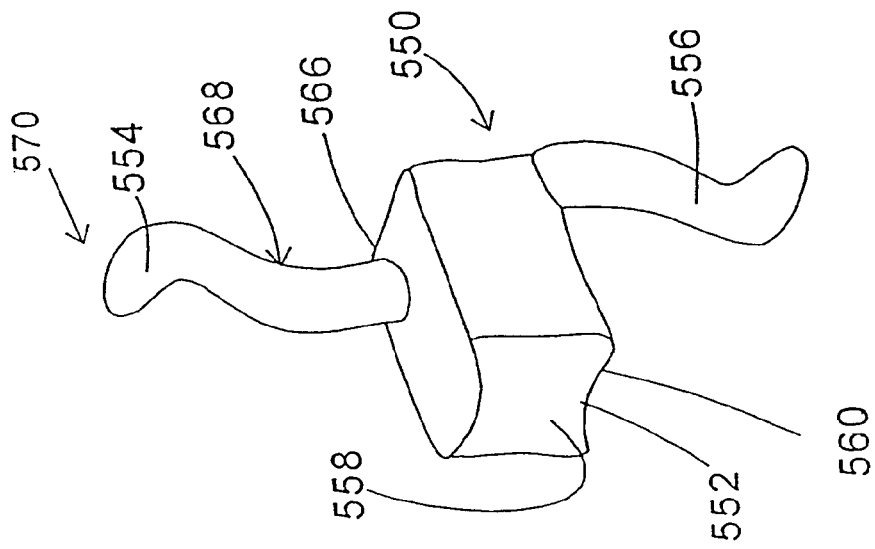
FIGS. 67 and 68 depict yet another embodiment of the present invention.
Figure 67:
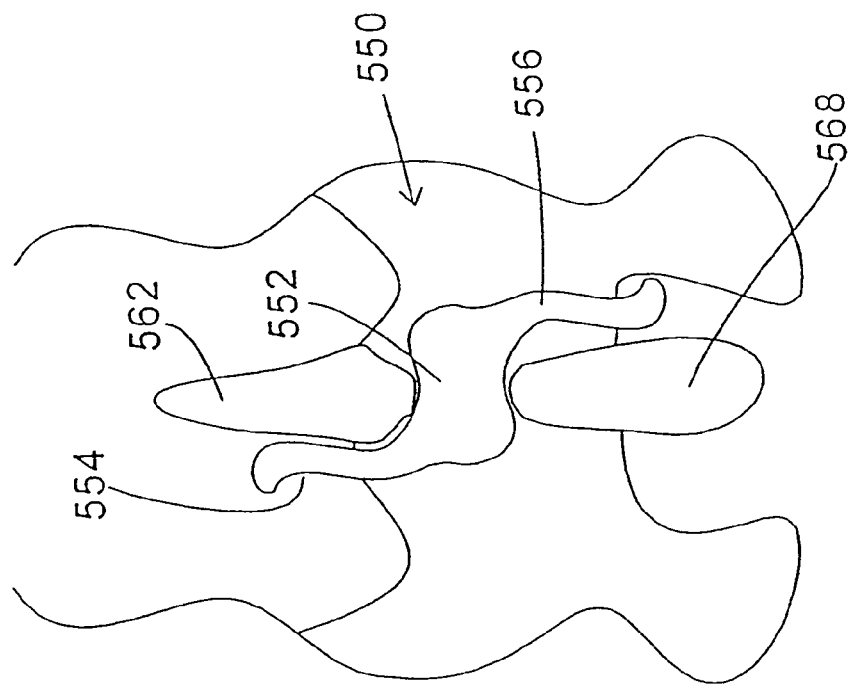

Embodiments of FIGS. 67, 68

The implant 550 is Z-shaped and includes a central body 552 and first and second arms 554, 556, extending in opposite directions therefrom. The central body 552 of the implant 550 includes first and second saddles 558 and 560. The first and second saddles 558 and 560 would receive upper and lower spinous processes 562, 568. The arms 554, 556 are accordingly located adjacent the distal end 566 (FIG. 68) of the central body 552. The first and second arms 554, 556, act to inhibit forward movement, migration or slippage of the implant 550 toward the spinal canal and keep the implant in place relative to the first and second spinal processes. This prevents the implant from pressing down on the ligamentum flavum and the dura. In a preferred embodiment, the central body would have a height of about 10 mm with each of the arms 554, 556 have a height of also about 10 mm. Depending on the patient, the height of the body could vary from about less than 10 mm to about greater than 24 mm. As can be seen in FIGS. 67 and 68, the first and second arms 554, 556 are additionally contoured in order to accept the upper and lower spinous processes 556, 558. In particular, the arms 554, 556 as can be seen with respect to arm 554 have a slightly outwardly bowed portion 568 (FIG. 68) with a distal end 570 which is slightly inwardly bowed. This configuration allows the arm to fit about the spinous process with the distal end 570 somewhat urged against the spinous process in order to guide the motion of the spinous process relative to the implant. These arms 554, 556 could if desired to be made more flexible than the central body 552 by making arms 554, 556 thin and/or with perforations, and/or other material different than that of the central body 550. As with the last embodiment, this embodiment can be urged into position between adjacent spinous processes by directing an arm into a lateral incision so that the central body 552 can be finally positioned between spinous processes.

Embodiment of FIGS. 69, 70, 71 and 71a

Figure 71:
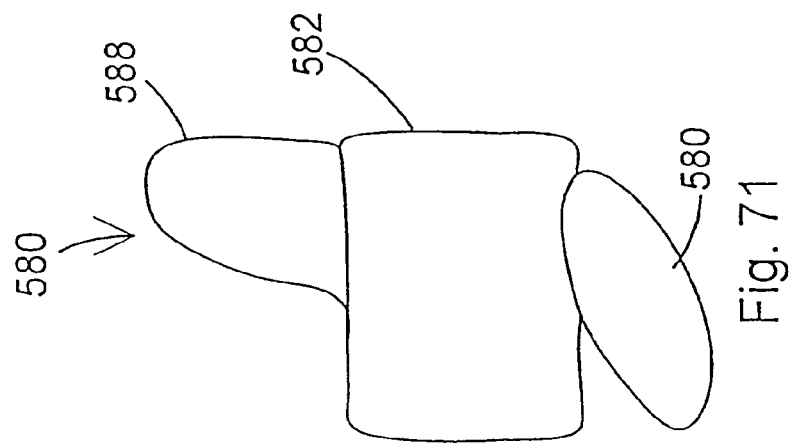
FIGS. 69, 70, 71 and 71*a* depict a further embodiment of the present invention.
Figure 70:
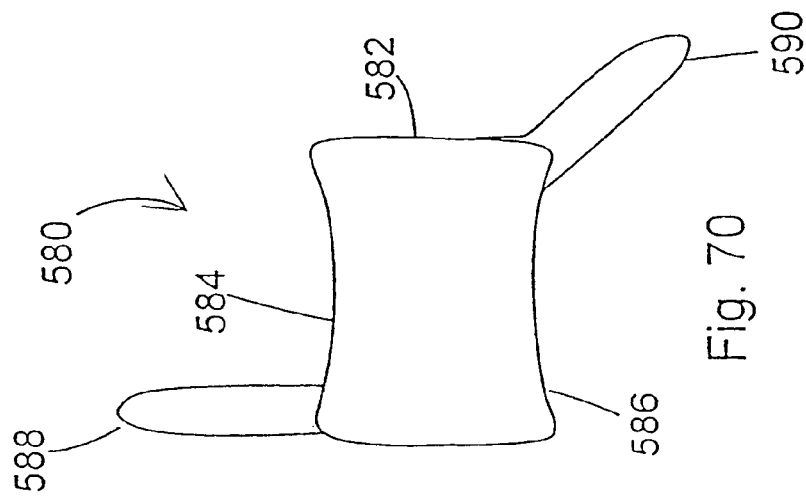
Figure 69:
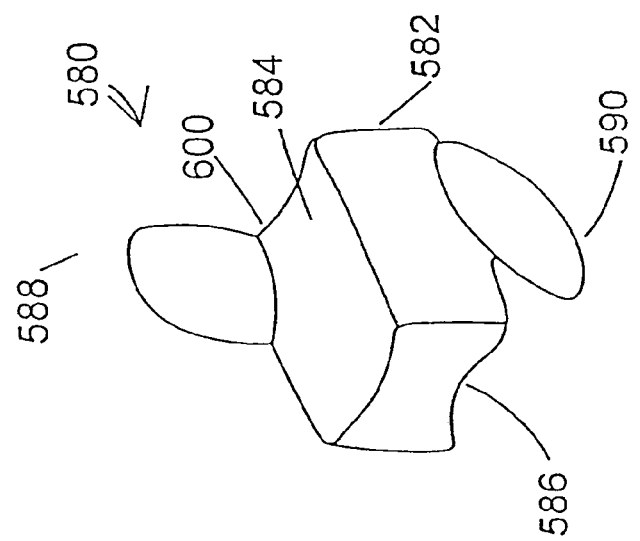

FIGS. 69, 70 and 71 are perspective front, end, and side views of implant 580 of the invention. This implant includes a central body 582 which has first and second saddles 584, 586 for receiving adjacent spinous processes. Additionally, the implant 580 includes first and second arms 588 and 590. The arms, as with the past embodiment, prevent forward migration or slippage of the implant toward the spinal canal. First arm 588 projects outwardly from the first saddle 584 and second arm 590 projects outwardly from the second saddle 586. In a preferred embodiment, the first arm 588 is located adjacent to the distal end 600 of the central body 582 and proceeds only partly along the length of the central body 582. The first arm 588 is substantially perpendicular to the central body as shown in FIG. 70. Further, the first arm 588, as well as the second arm 590, is anatomically rounded.

The second arm 590, projecting from second saddle 586, is located somewhat rearward of the distal end 600, and extends partially along the length of the central body 582. The second arm 590 projects at a compound angle from the central body 582. As can be seen in FIGS. 70 and 71, the second arm 590 is shown to be at about an angle of 45° from the saddle 586 (FIG. 70). Additionally, the second arm 590 is at an angle of about 45° relative to the length of the central body 580 as shown in FIG. 71. It is to be understood that other compound angles are within the spirit and scope of the invention as claimed.

In a preferred embodiment, the first and second arms 588, 590 have a length which is about the same as the width of the central body 582. Preferably, the length of each arm is about 10 mm and the width of the central body is about 10 mm. However, the bodies with the widths of 24 mm and greater are within the spirit and scope of the invention, along with first and second arms ranging from about 10 mm to greater than about 24 mm. Further, it is contemplated that the embodiment could include a central body having a width of about or greater than 24 mm with arms being at about 10 mm.

It is to be understood that the embodiment of FIGS. 69, 70 and 71 as well as the embodiment of FIGS. 67 and 68 are designed to preferably be positioned between the L4-L5 and the L5-S1 vertebral pairs. The embodiment of FIGS. 69, 70, 71 is particularly designed for the L5-S1 position with the arms being designed to conform to the sloping surfaces found therebetween. The first and second arms are thus contoured so that they lie flat against the lamina of the vertebra which has a slight angle.

The embodiment of FIGS. 69, 70, and 71 as with the embodiment of FIGS. 67 and 68 is Z-shaped in configuration so that it may be inserted from one lateral side to a position between adjacent spinous processes. A first arm, followed by the central body, is guided through the space between the spinous processes. Such an arrangement only requires that a incision on one side of the spinous process be made in order to successfully implant the device between the two spinous processes.

Figure 71A:
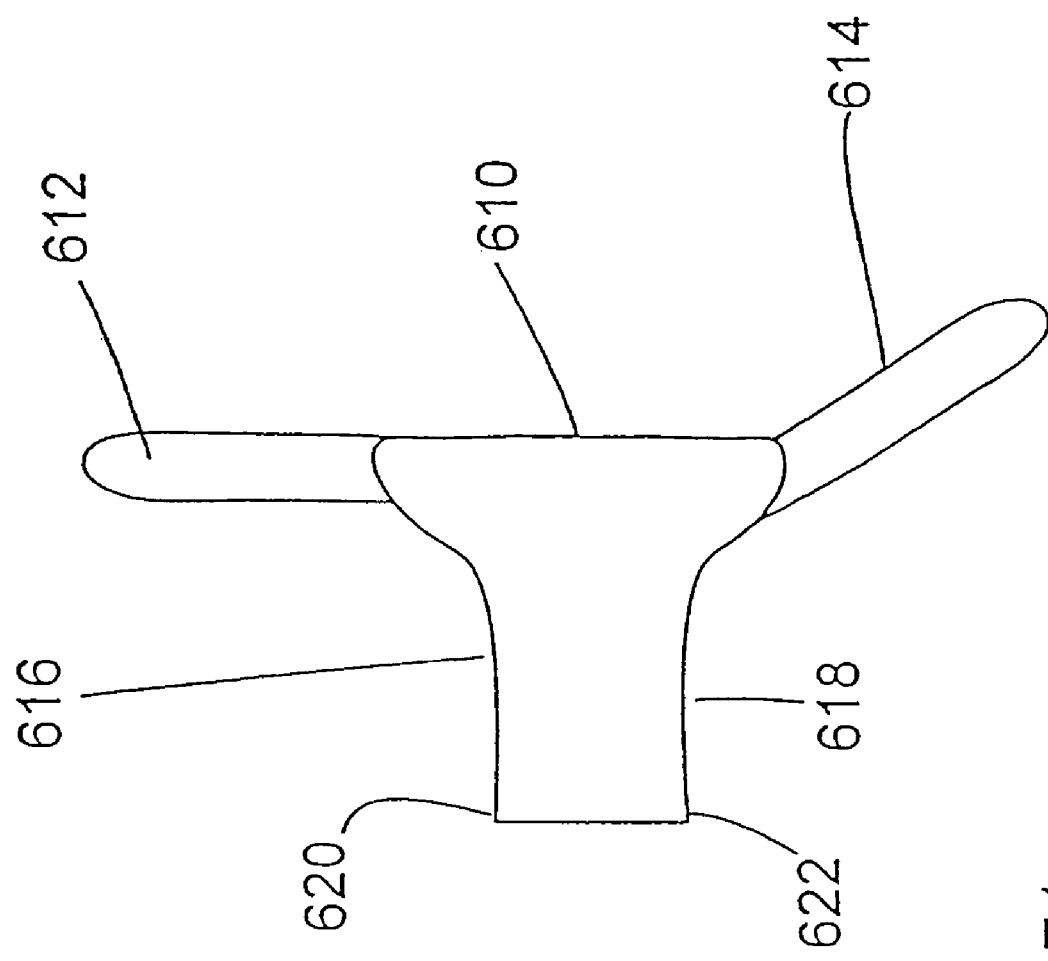

The implant 610 of FIG. 71a is similar to that immediately above with the first arm 612 located on the same side of the implant as the second arm 614. The first and second saddle 616, 618 are slightly modified in that distal portion 620, 622 are somewhat flattened from the normal saddle shape in order to allow the implant to be positioned between the spinous processes from one side. Once in position, the ligaments and tissues associated with the spinous processes would hold the implant into position. Tethers also could be used if desired.

Figure 72:
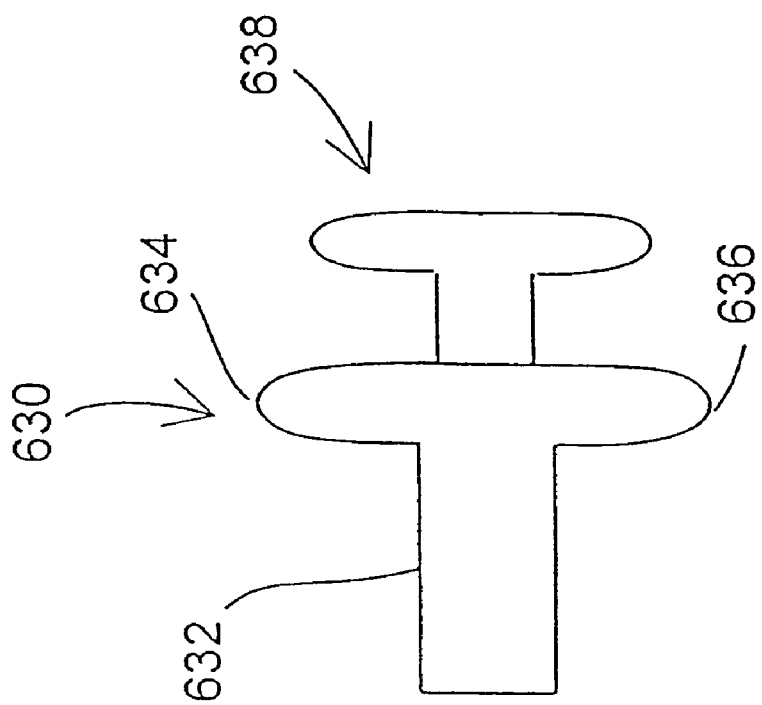
FIGS. 72 and 73 depict still another embodiment of the invention.
Figure 73:
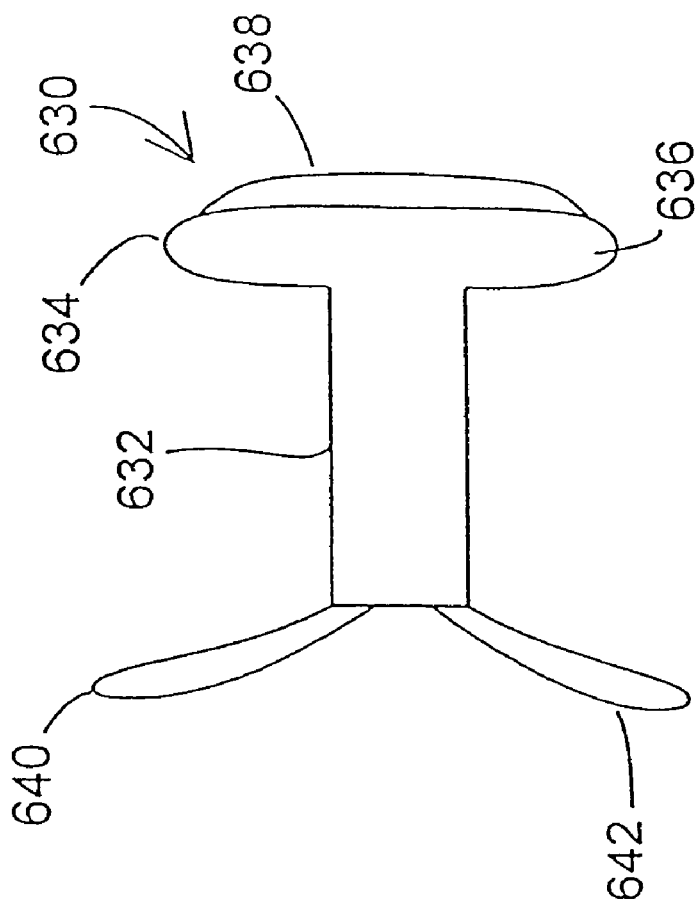

Embodiment of FIGS. 72, 73

Implant 630 is also designed so that it can be inserted from one side of adjacent spinous processes. This insert 630 includes a central body 632 with the first and second arms 634, 636 extending on either side thereof. As can be seen in FIG. 72, a plunger 638 is positioned to extend from an end of the central body 632. As shown in FIG. 72, the plunger 638 is fully extended and as shown in FIG. 73, the plunger 638 is received within the central body 632 of the implant 630. With the plunger received into the implant 632, the third and fourth arms or hooks 640, 642 can extend outwardly from the central body 632. The third and fourth arms or hooks 640, 642 can be comprised of a variety of materials, such as for example, shape memory metal materials or materials which have a springy quality.

For purposes of positioning the implant 630 between adjacent spinous processes, the plunger 638 is pulled outwardly as shown in FIG. 72. The central body 632 is then positioned between adjacent spinous processes and the plunger 638 is allowed to move to the position of FIG. 73 so that the third and fourth arms 640, 642 can project outwardly from the central body 632 in order to hold the implant 630 in position between the spinous processes.

Plunger 638 can be spring biased to the position as shown in FIG. 73 or can include detents or other mechanisms which lock it into that position. Further, the third and fourth arms themselves, as deployed, can keep the plunger in the position as shown in FIG. 73.

Embodiments of FIGS. 74, 75, 76, 77, and 78

Figure 74:
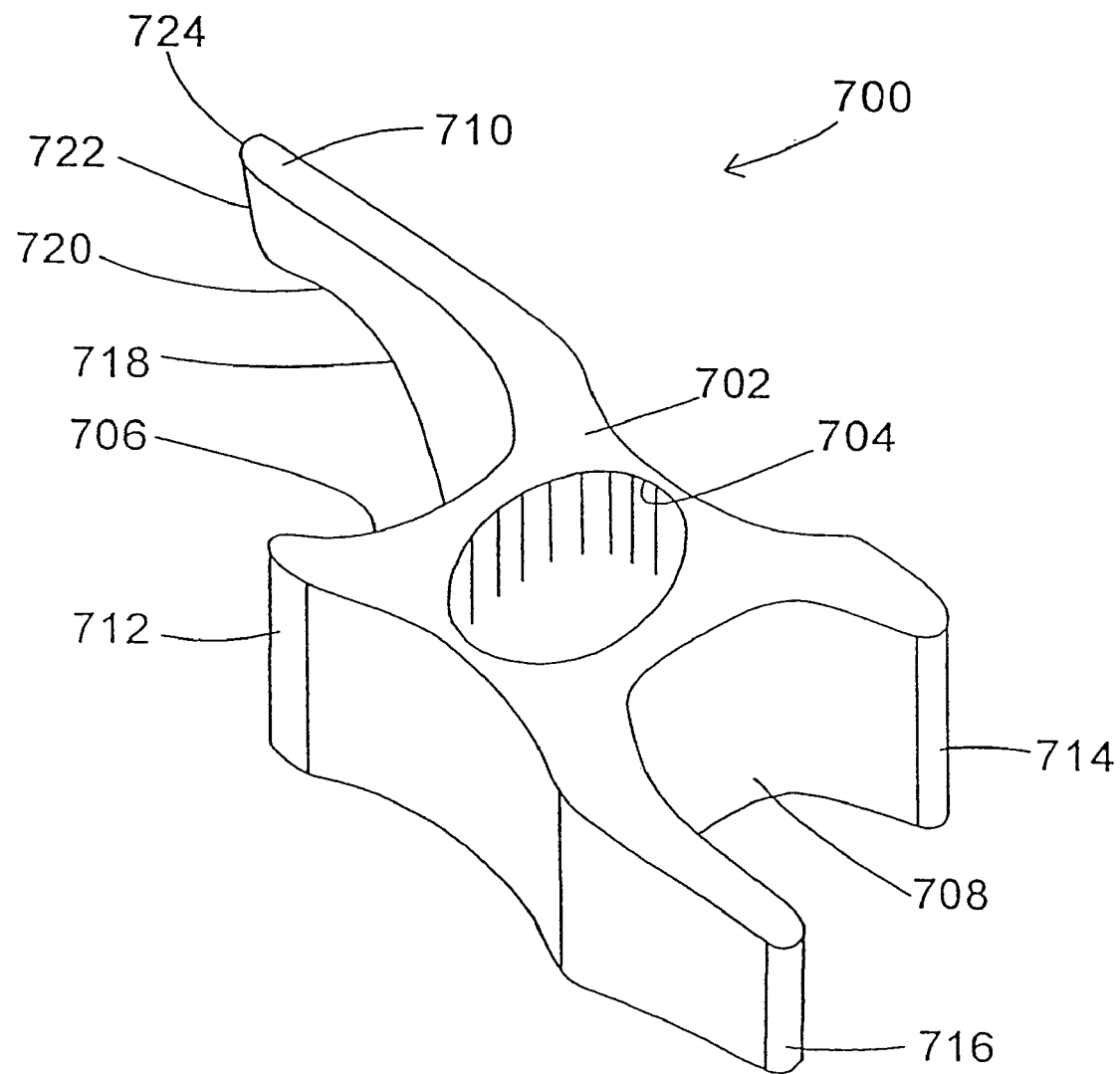
FIGS. 74, 75, 76, 77, and 78 depict still other embodiments of the invention.
Figure 75:
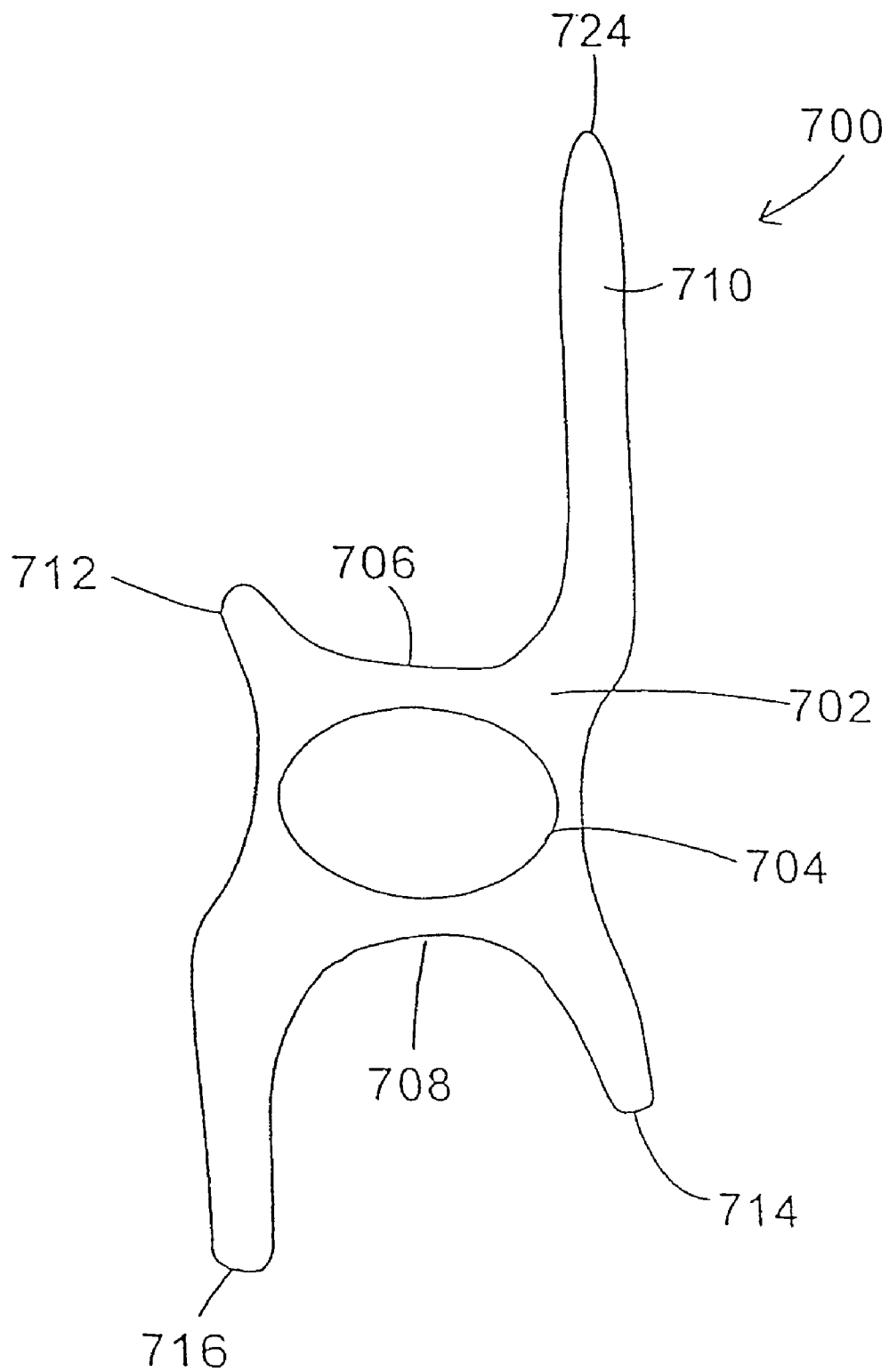
Figure 76:
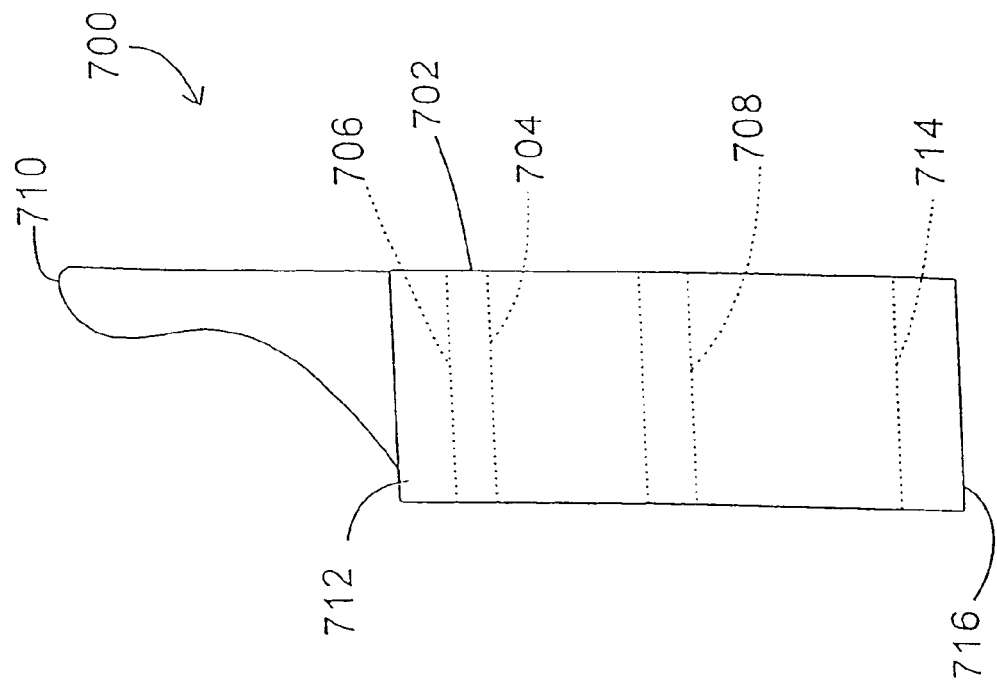

Other embodiments of the invention are shown in FIGS. 74 through 78. FIGS. 74, 75 and 76 disclose implant 700. Implant 700 is particularly suited for implantation between the L4-L5 and L5-S1 vertebra. As can be seen in FIG. 74, the implant 700 includes a central body 702 which has a bore 704 provided therein. Bore 704 is used in order to adjust the modulus of elasticity of the implant so that it is preferably approximately two times the anatomical load placed on the vertebra in extension. In other words, the implant 700 is approximately two times stiffer than the normal load placed on the implant. Such an arrangement is made in order to ensure that the implant is somewhat flexible in order to reduce potential resorption of the bone adjacent to the implant. Other modulus values can be used and be within the spirit of the invention.

Implant 700 includes first and second saddle 706, 708 which are used to receive and spread the load from the upper and lower spinous processes. The saddle 706 is defined by first and second arms 710 and 712. The second saddle 708 is defined by third and fourth arms 714 and 716. As can be seen in FIG. 74, the first arm 710, in a preferred embodiment, is approximately two times the length of the body 702 with the second arm being approximately less than a quarter length of the body. Third arm 714 is approximately one times the length of the body 702 with the fourth arm 716 being, in this preferred embodiment, approximately one and a half times the length of the body 702. The arms are designed in such a way that the implant (1) can be easily and conveniently inserted between the adjacent spinous processes, (2) will not migrate forwardly toward the spinal canal, and (3) will hold its position through flexion and extension as well as lateral bending of the spinal column.

Figure 77:
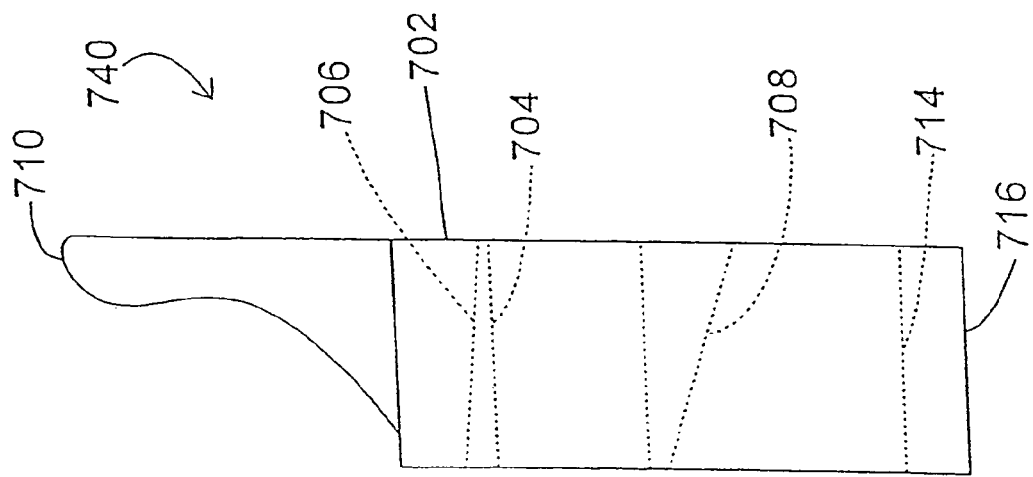
Figure 78:
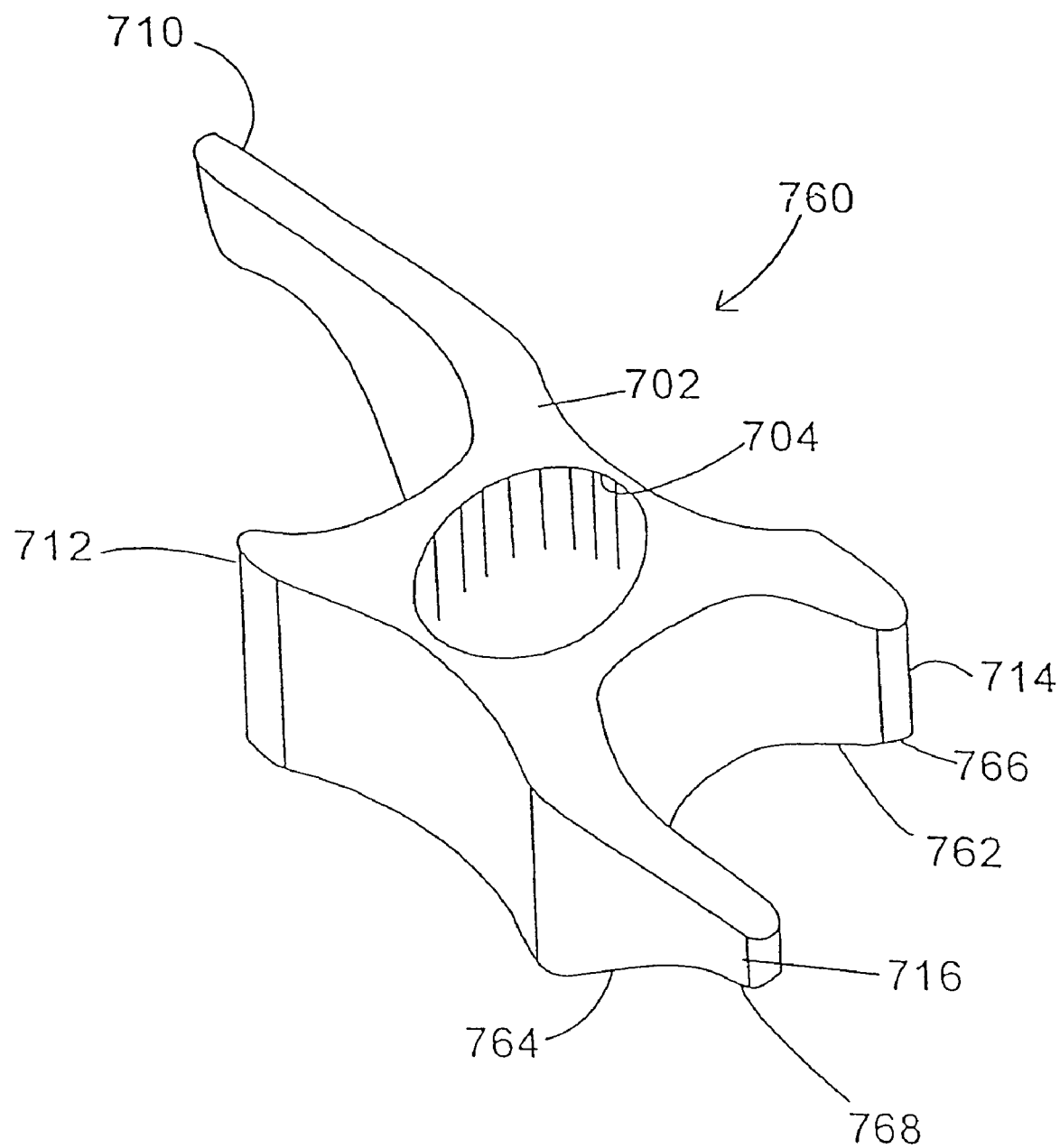
Figure 81:
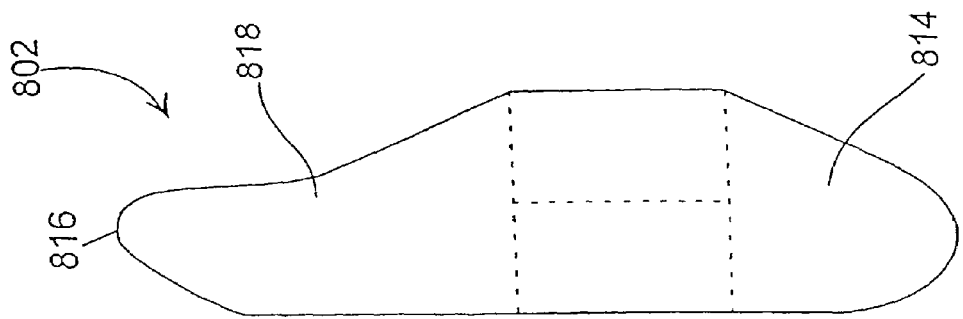

First arm 710 is in addition designed to accommodate the shape of the vertebra. As can be seen in FIG. 74, the first arm 710 becomes narrower as it extends away from the body 702. The first arm 710 includes a sloping portion 718 followed by a small recess 720 ending in a rounded portion 722 adjacent to the end 724. This design is provided to accommodate the anatomical form of for example the L4 vertebra. It is to be understood that these vertebra have a number of surfaces at roughly 30° angles and that the sloping surfaces of this embodiment and the embodiments shown in FIGS. 77 and 78 are designed to accommodate these surfaces. These embodiments can be further modified in order to accommodate other angles and shapes.

The second arm 712 is small so that it is easy to insert between the spinous processes, yet still define the saddle 706. The fourth arm 716 is larger than the third arm 714, both of which are smaller than the first arm 710. The third and fourth arms are designed so that they define the saddle 706, guide the spinous processes relative to the implant 700 during movement of the spinal column, and yet are of a size which makes the implant easy to position between the spinous processes.

The procedure, by way of example only, for implanting the implant 700 can be to make an incision laterally between two spinous processes and then initially insert first arm 710 between the spinous processes. The implant and/or appropriate tools would be used to distract the spinous processes allowing the third leg 714 and the central body 702 to fit through the space between the spinous processes. The third leg 714 would then come to rest adjacent the lower spinous processes on the opposite side with the spinous processes resting in the first and second saddle 706, 708. The longer fourth leg 716 would then assist in the positioning of the implant 700.

FIG. 77 includes an implant 740 which is similar to implant 700 and thus have similar numbering. The saddle 706, 708 of implant 740 have been cantered or sloped in order to accommodate the bone structure between, by way of example, the L4-L5 and the L5-S1 vertebra. As indicated above, the vertebra in this area have a number of sloping surfaces in the range of about 30°. Accordingly, saddle 706 is sloped at less than 30° and preferably about 20° while saddle 708 is sloped at about 30° and preferably more than 30°.

The implant 760 as shown in FIG. 78 is similar to implant 700 in FIG. 74 and is similarly numbered. Implant 760 includes third and fourth legs 714,716 which have sloping portions 762, 764 which slope toward ends 766, 768 of third and fourth arm 714, 716 respectively. The sloping portions accommodate the form of the lower vertebra against which they are positioned. In the preferred embodiment, the sloping portions are of about 30°. However, it is to be understood that sloping portions which are substantially greater and substantially less than 30° can be included and be within the spirit and scope of the invention.

Embodiment of FIGS. 79, 80, 80a, 81, 82, 83, 83a, 84, 85, 86 and 87

Figure 80:
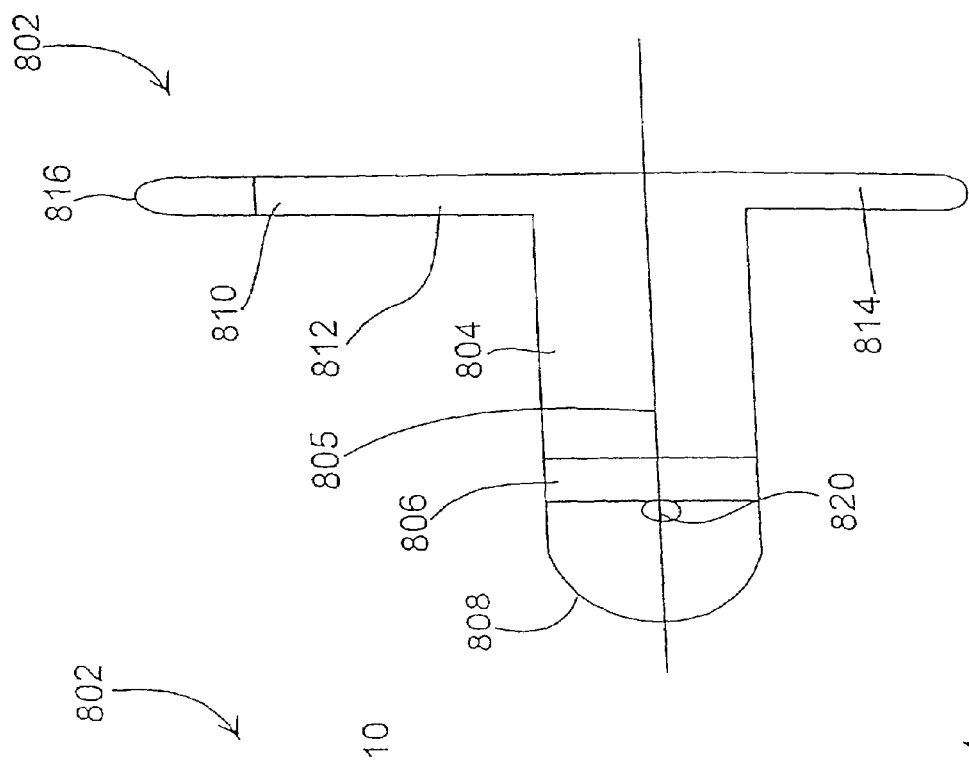
Figure 79:
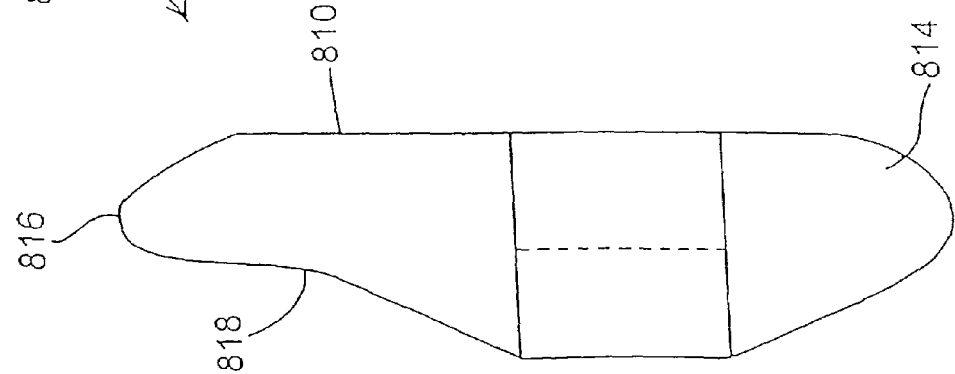
Figure 83A:
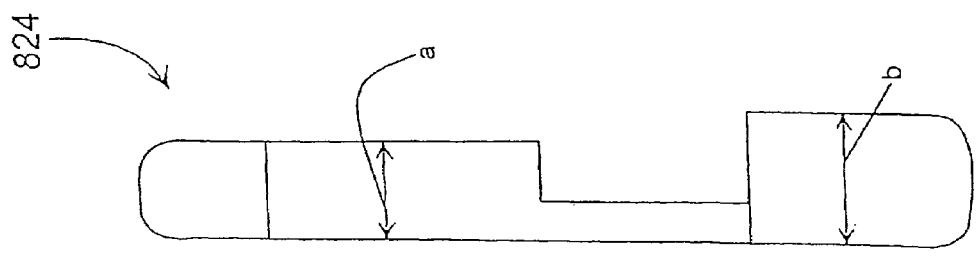
Figure 83:
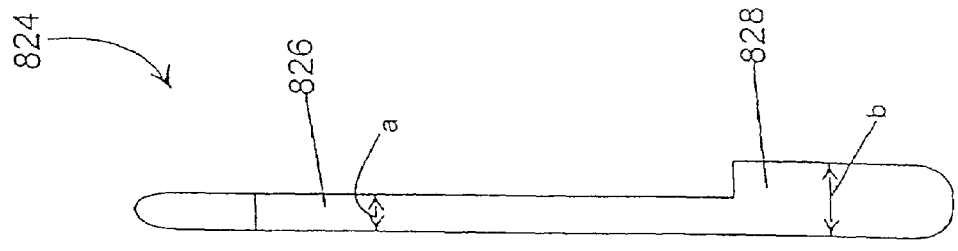
Figure 84:
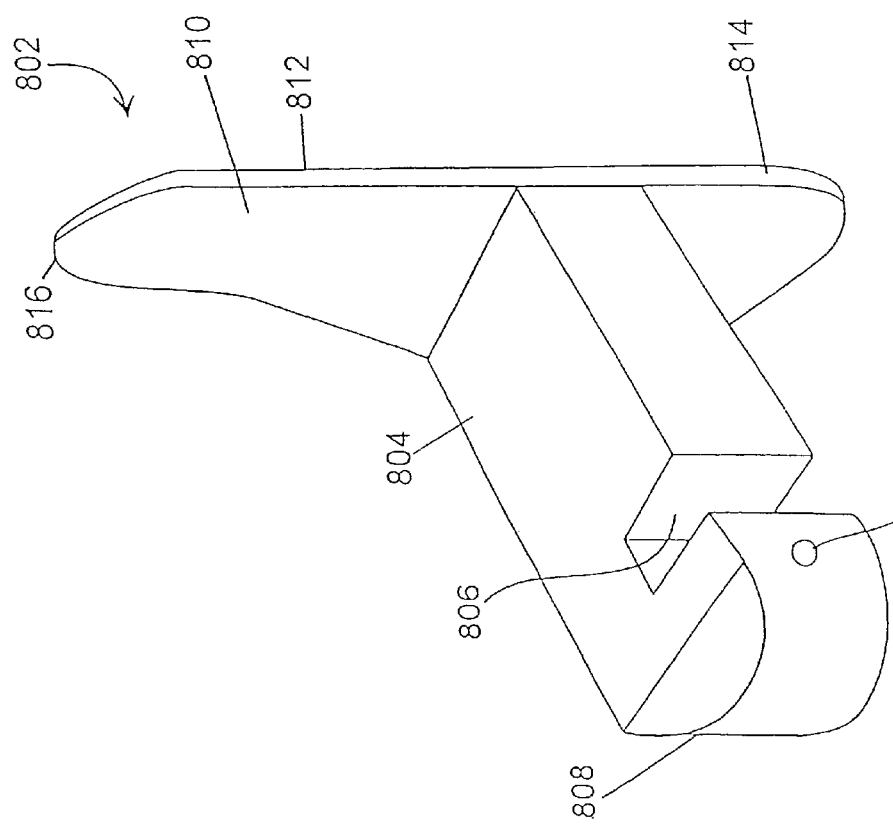

Another embodiment of the invention is shown in FIGS. 79-87 and includes implant 800 (FIG. 86). Implant 800 includes a distracting unit 802 which is shown in left side, plan, and right side views of FIGS. 79, 80 and 81. A perspective view of the distraction unit is shown in FIG. 84. The distracting unit as can be seen in FIG. 80 includes a distracting body 804, with longitudinal axis 805, which body 804 has a groove 806 and a rounded or bulbous end 808 which assist in the placement of the distracting body between adjacent spinous process so that an appropriate amount of distraction can be accomplished. Extending from the distracting body 804 is a first wing 810 which in FIG. 80 is substantially perpendicular to the distracting body 804. Such wings which are not perpendicular to the body are within the spirit and scope of the invention. First wing 810 includes a upper portion 812 and a lower portion 814. The upper portion 810 (FIGS. 79) includes a rounded end 816 and a small recess 818. The rounded end 816 and the small recess 818 in the preferred embodiment are designed to accommodate the anatomical form or contour of the L4 (for a L4-L5 placement) or L5 (for a L5-S1 placement) superior lamina of the vertebra. It is to be understood that the same shape or variations of this shape can be used to accommodate other lamina of any vertebra. The lower portion 814 is also rounded in order to accommodate in the preferred embodiment in order to accommodate the vertebrae. The distracting unit further includes a threaded bore 820 which in this embodiment accepts a set screw 822 (FIG. 86) in order to hold a second wing 824 (FIGS. 82, 83) in position as will be discussed hereinbelow.

The threaded bore 820 in this embodiment slopes at approximately 45° angle and intersects the slot 806. With the second wing 824 in position, the set screw 822 when it is positioned in the threaded bore 820 can engage and hold the second wing 824 in position in the slot 806.

Figure 82:
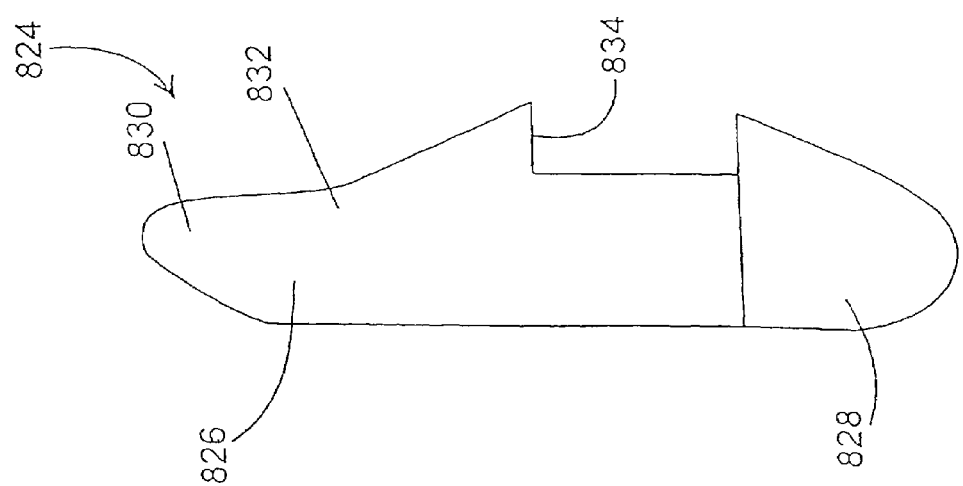
Figure 85:
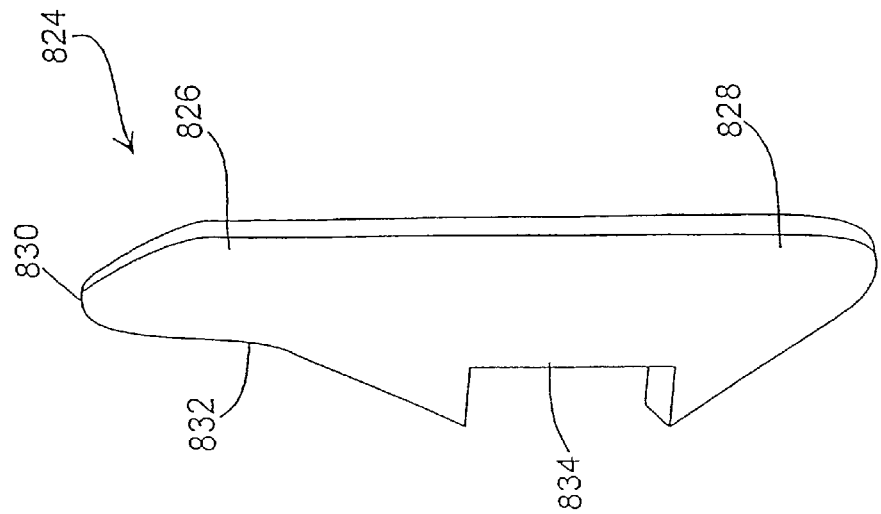

Turning to FIGS. 82, 83 and 85, left side, plan and perspective views of the second wing 824 are depicted. The second wing 824 is similar in design to the first wing. The second wing includes an upper portion 826 and a lower portion 828. The upper portion includes a rounded end 830 and a small recess 832. In addition, the second wing 824 includes a slot 834 which mates with the slot 806 of the distracting unit 802. The second wing 824 is the retaining unit of the present embodiment.

As can be seen in FIGS. 83 and 86, the second wing or retaining unit 824 includes the upper portion 826 having a first width "a" and the lower portion 828 having a second width "b". In the preferred embodiment, the second width "b" is larger than first width "a" due to the anatomical form or contour of the L4-L5 or L5-S1 laminae. As can be seen in FIG. 83a in second wing or retaining unit 824, the widths "a" and "b" would be increased in order to, as described hereinbelow, accommodate spinous processes and other anatomical forms or contours which are of different dimensions. Further, as appropriate, width "a" can be larger than width "b". Thus, as will be described more fully hereinbelow, the implant can include a universally-shaped distracting unit 802 with a plurality of retaining units 824, with each of the retaining units having different widths "a" and "b". During surgery, the appropriately sized retaining unit 824, width with the appropriate dimensions "a" and "b" can be selected to match to the anatomical form of the patient.

FIG. 86 depicts an assembled implant 800 positioned adjacent to upper and lower laminae 836, 838 (which are shown in dotted lines) of the upper and lower vertebrae. The vertebrae 836, 838 are essentially below the implant 800 as shown in FIG. 86. Extending upwardly from the vertebrae 836, 838, and between the first and second wings 810, 824, are the upper and lower spinous processes 840, 842. It is to be understood that in a preferred embodiment, the fit of the implant between the spinous processes can be such that the wings do not touch the spinous processes, as shown in FIG. 86, and be within the spirit and scope of the invention.

Figure 87:
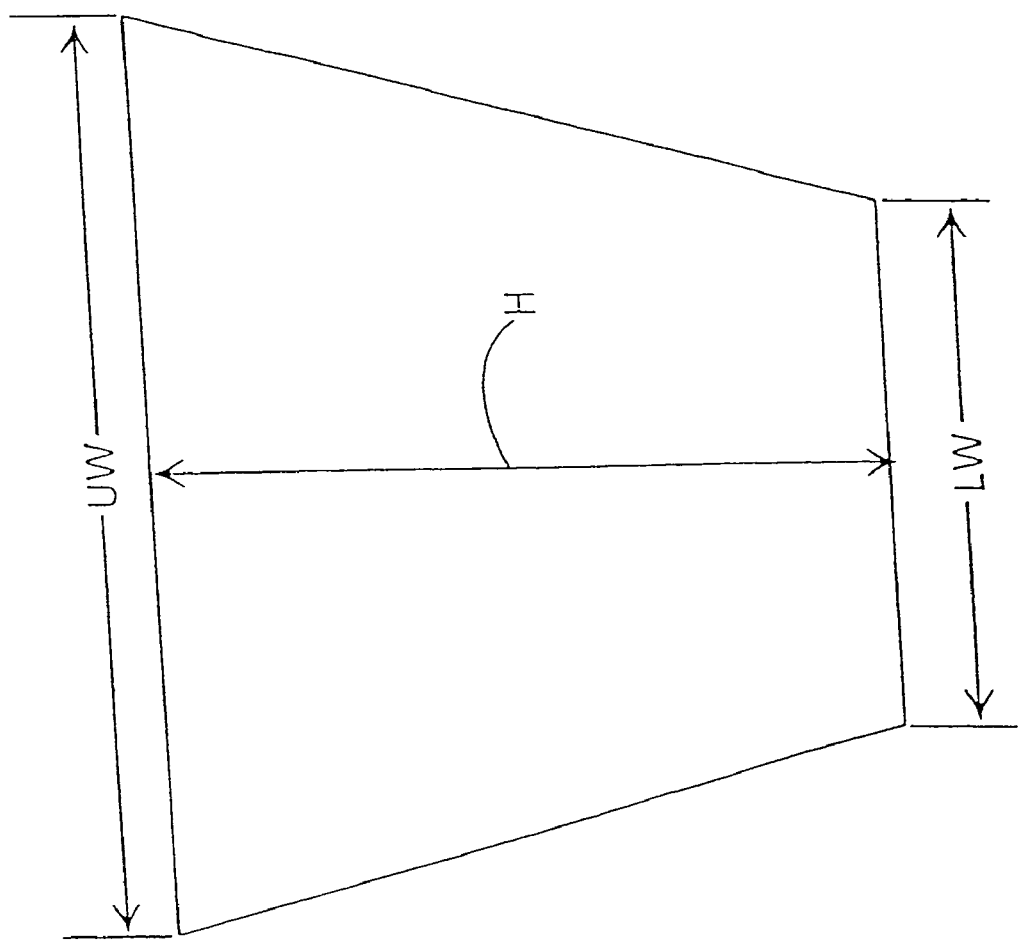
Figure 91:
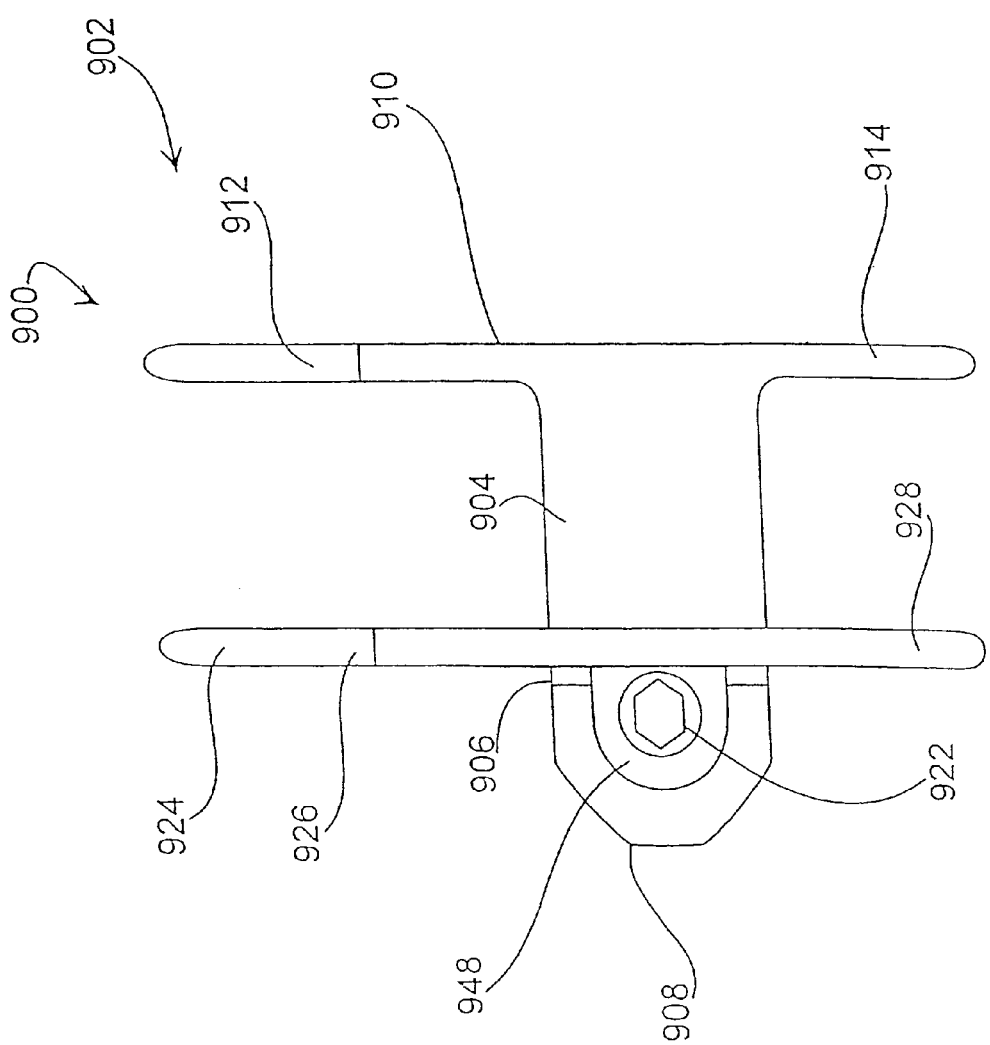

The implant 800 includes, as assembled, an upper saddle 844 and the lower saddle 846. The upper saddle 844 has an upper width identified by the dimension "UW". The lower saddle 846 has a lower width identified by the dimension "LW". In a preferred embodiment, the upper width is greater than the lower width. In other embodiments, the "UW"can be smaller than the "LW" depending on the anatomical requirements. The height between the upper and lower saddles 844, 846 is identified by the letter "h". These dimensions are carried over into FIG. 87 which is a schematic representation of the substantially trapezoidal shape which is formed between the upper and lower saddles. The table below gives sets of dimensions for the upper width, lower width, and height as shown in FIG. 87. This table includes dimensions for some variations of this embodiment.

TABLE

|  | Variation | | |
| --- | --- | --- | --- |
|  | 1 | 2 | 3 |
| Upper Width | 8 | 7 | 6 |
| Lower Width | 7 | 6 | 5 |
| Height | 10 | 9 | 8 |

For the above table, all dimensions are given in millimeters.

For the above table, all dimensions are given in millimeters.

For purposes of surgical implantation of the implant 800 into a patient, the patient is preferably positioned on his side (arrow 841 points up from an operating table) and placed in a flexed (tucked) position in order to distract the upper and lower vertebrae.

In a preferred procedure, a small incision is made on the midline of the spinous processes. The spinous processes are spread apart or distracted with a spreader. The incision is spread downwardly toward the table, and the distracting unit 802 is preferably inserted upwardly between the spinous processes 840 and 842 in a manner that maintains the distraction of spinous processes. The distracting unit 802 is urged upwardly until the distracting or bulbous end 808 and the slot 806 are visible on the other wide of the spinous process. Once this is visible, the incision is spread upwardly away from the table and the retaining unit or second wing 824 is inserted into the slot 806 and the screw 822 is used to secure the second wing in position. After this had occurred, the incisions can be closed.

An alternative surgical approach requires that small incisions be made on either side of the space located between the spinous processes. The spinous processes are spread apart or distracted using a spreader placed through the upper incision. From the lower incision, the distracting unit 802 is preferably inserted upwardly between the spinous processes 840 and 842 in a manner that urges the spinous processes apart. The distracting unit 802 is urged upwardly until the distracting or bulbous end 808 and the slot 806 are visible through the second small incision in the patient's back. Once this is visible, the retaining unit or second wing 824 is inserted into the slot 806 and the screw 822 is used to secure the second wing in position. After this has occurred, the incisions can be closed.

The advantage of either of the above present surgical procedures is that a surgeon is able to observe the entire operation, where he can look directly down onto the spinous processes as opposed to having to view the procedure from positions which are to the right and to the left of the spinous processes. Generally, the incision is as small as possible and the surgeon is working in a bloody and slippery environment. Thus, an implant that can be positioned directly in front of a surgeon is easier to insert and assemble than an implant which requires the surgeon to shift from side to side. Accordingly, a top-down approach, as an approach along a position to anterior line is preferred so that all aspects of the implantation procedure are fully visible to the surgeon at all times. This aides in the efficient location of (i) the distracting unit between the spinous processes, (ii) the retaining unit in the distracting unit, and (iii) finally the set screw in the distracting unit.

FIG. 80a shows an alternative embodiment of the distracting unit 802a. This distracting unit 802a is similar to distracting unit 802 in FIG. 80 with the exception that the bulbous end 808a is removable from the rest of the distracting body 804a as it is screwed into the threaded bore 809. The bulbous end 808a is removed once the distracting unit 802a is positioned in the patient in accordance with the description associated with FIG. 86. The bulbous end 808a can extend past the threaded bore 820 by about 1 cm in a preferred embodiment.

Embodiment of FIGS. 88, 89, 90 and 91

Another embodiment of the invention is shown in FIGS. 88, 89, 90 and 91. In this embodiment, the implant is identified by the number 900. Other elements of implant 900 which are similar to implant 800 are similarly numbered but in the 900 series. For example, the distracting unit is identified by the number 902 and this is in parallel with the distracting unit 802 of the implant 800. The distracting body is identified by the number 904 in parallel with the distracting body 804 of the implant 800. Focusing on FIG. 90, the distracting unit 902 is depicted in a perspective view. The distracting unit includes slot 906 which is wider at the top than at the bottom. The reason for this is that the wider upper portion of the slot 906, which is wider than the second wing 924 (FIG. 89), is used to allow the surgeon to easily place the second wing 924 into the slot 906 and allow the wedge-shaped slot 906 to guide the second wing 924 to its final resting position. As can be see in FIG. 91, in the final resting position, the largest portion of the slot 906 is not completely filled by the second wing 924.

The end 908 of implant 900 is different in that it is more pointed, having sides 909 and 911 which are provided at about 45° angles (other angles, such as by way of example only, from about 30° to about 60° are within the spirit of the invention), with a small flat tip 913 so that the body 904 can be more easily urged between the spinous processes.

The distracting unit 902 further includes a tongue-shaped recess 919 which extends from the slot 906. Located in the tongue-shaped recess is a threaded bore 920.

As can be seen in FIG. 89, a second wing 924 includes a tongue 948 which extends substantially perpendicular there to and between the upper and lower portions 926, 928. The tab 948 includes a bore 950. With the second wing 924 positioned in the slot 906 of the distracting unit 902 and tab 948 positioned in recess 919, a threaded set screw 922 can be positioned through the bore 950 and engage the threaded bore 920 in order to secure the second wing or retaining unit 924 to the distracting unit 902. The embodiment 900 is implanted in the same manner as embodiment 800 previously described. In addition, as the bore 922 is substantially perpendicular to the distracting body 904 (and not provided at an acute angle thereto), the surgeon can even more easily secure the screw in place from a position directly behind the spinous processes.

Embodiment of FIGS. 92, 92a, 92b, 93, 93a, 93b, 93c, 93d, 94, 94a, 94b, 95, 95a, and 96

Figure 92:
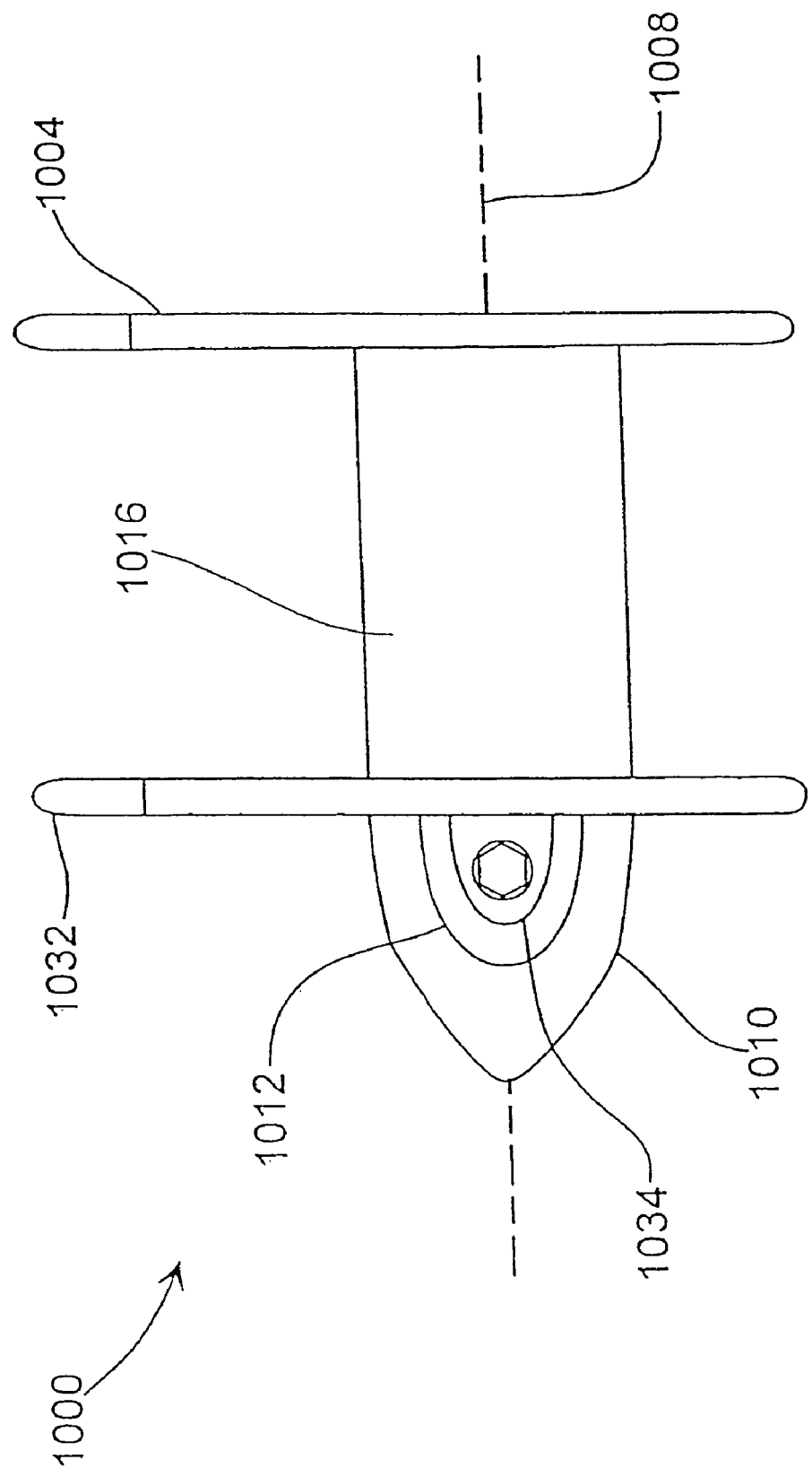
Figures 92A, 92B:
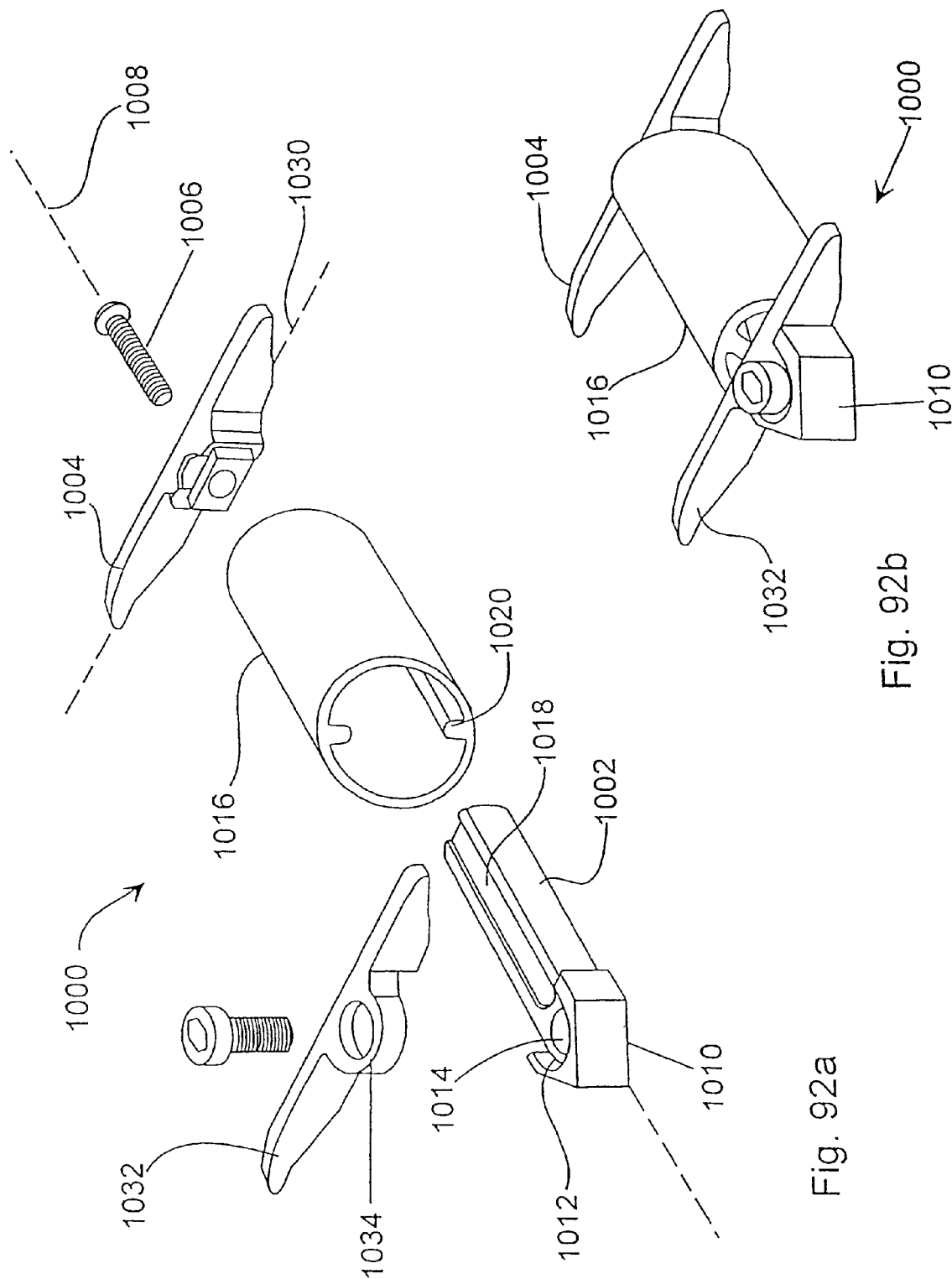

Still a further embodiment of the invention is depicted in FIGS. 92, and 92a. In this embodiment, the implant 1000 as can be seen in FIG. 92a includes a central elongated body 1002 which has positioned at one end thereof a first wing 1004. Wing 1004 is similar to the first wing previously described with respect to the embodiment of FIG. 88. Bolt 1006 secures wing 1004 to body 1002 in this embodiment. Bolt 1006 is received in a bore of the body 1002 which is along the longitudinal axis 1008 of body. It is to be understood that in this embodiment, the first unit is defined by the central body 1002, the first wing 1004, and the guide 1010.

Figure 93C:
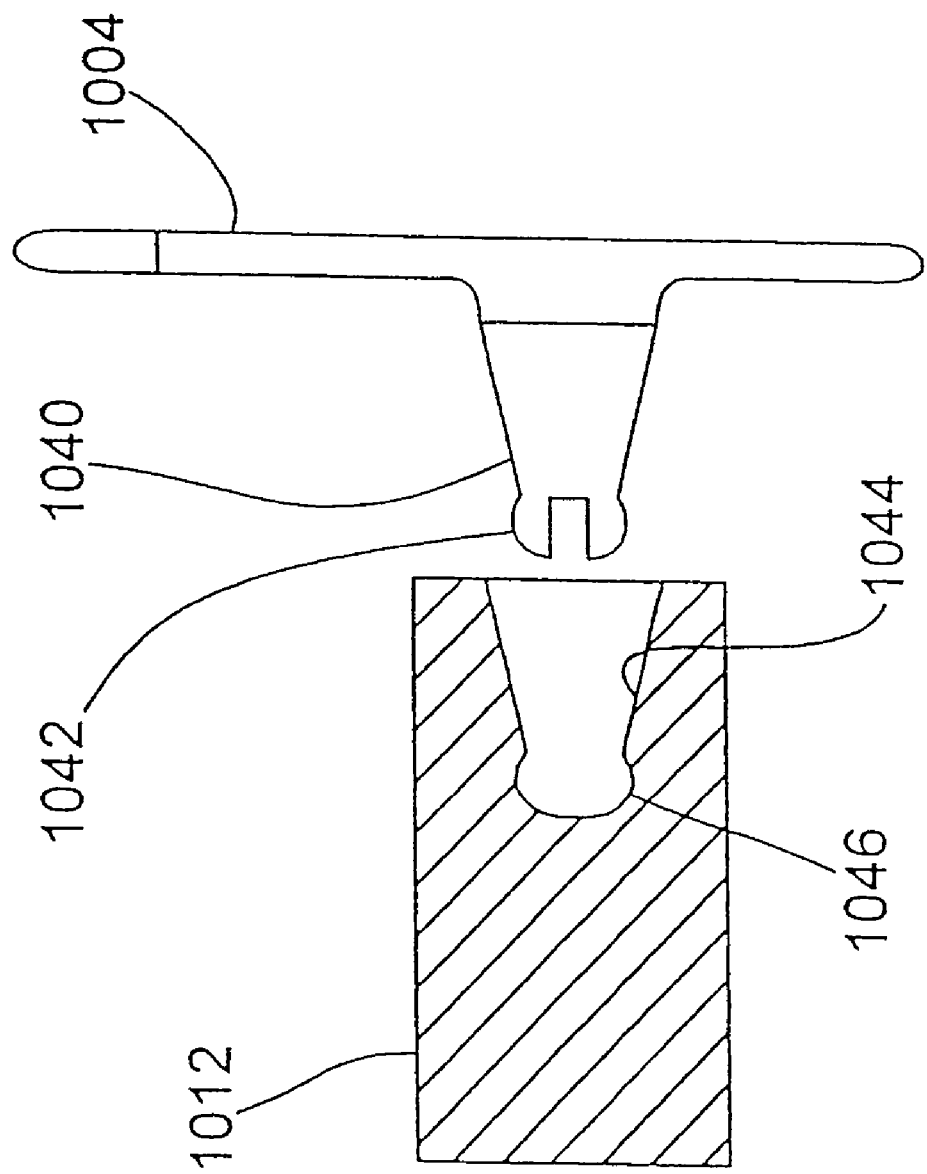

Alternatively, the first wing can be secured to the central body with a press fit and detent arrangement as seen in FIG. 93c. In this arrangement, the first wing has a protrusion 1040 extending preferably about perpendicularly from the first wing, with a flexible catch 1042. The protrusion and flexible catch are press fit into a bore 1044 of the central body with the catch received in a detent 1046.

Figure 93D:
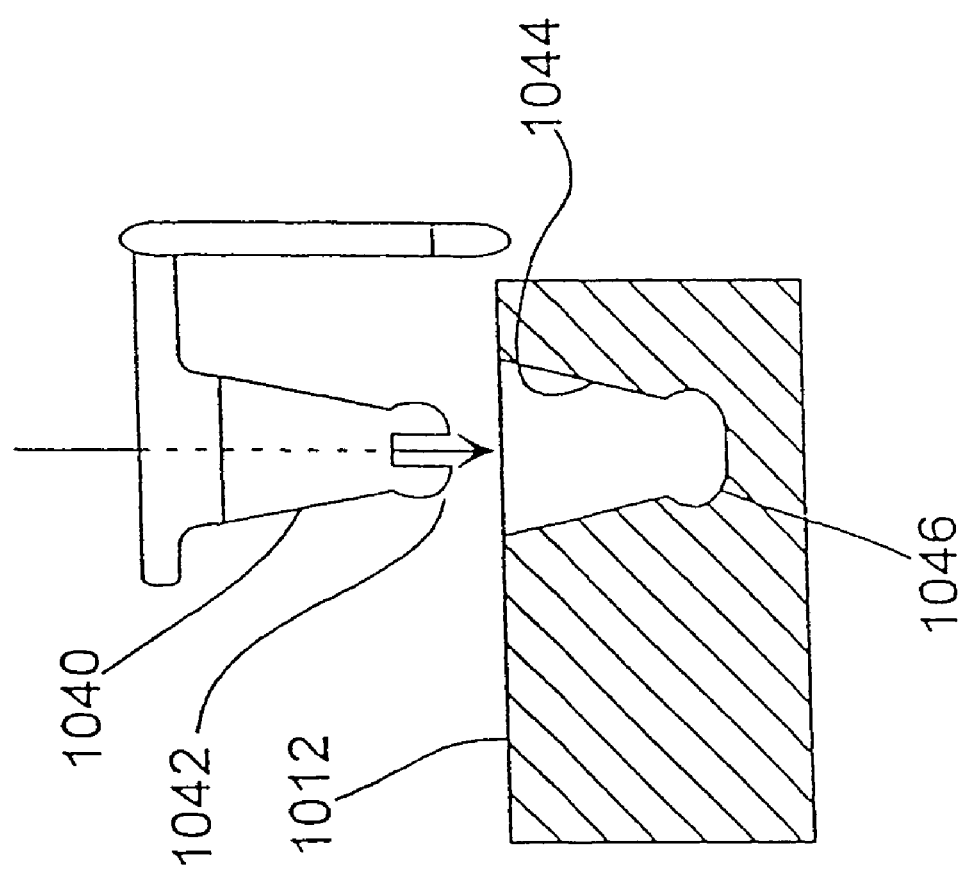

In yet another alternative embodiment, the first wing can be designed as shown in FIG. 93d with the protrusion directed substantially parallel to the first wing from a member that joins the first wing to the protrusion. Thus in this embodiment, the first wing is inserted into the body along the same direction as the second wing is inserted.

Positioned at the other end of the central body 1002 is a guide 1010. In this particular embodiment, guide 1010 is essentially triangularly-shaped so as to be a pointed and arrow-shaped guide. Alternatively, guide 1010 could be in the shape of a cone with lateral truncated sides along the longitudinal axis 1008. Guide 1010 includes a recess 1012 having a threaded bore 1014. Recess 1012 is for receiving a second wing 1032 as will be described hereinbelow.

Additionally, it is also to be understood that the guide 1010 can be bulbous, cone-shaped, pointed, arrow-shaped, and the like, in order to assist in the insertion of the implant 1000 between adjacent spinous processes. It is advantageous that the insertion technique disturb as little of the bone and surrounding tissue or ligaments as possible in order to (1) reduce trauma to the site and facilitate early healing, and (2) not destabilize the normal anatomy. It is to be noted that with the present embodiment, there is no requirement to remove any of the bone of the spinous processes and depending on the anatomy of the patient, there may be no requirement to remove or sever ligaments and tissues immediately associated with the spinous processes.

The implant 1000 further includes a sleeve 1016 which fits around and is at least partially spaced from the central body 1002. As will be explained in greater detail below, while the implant may be comprised of a bio-compatible material such as titanium, the sleeve is comprised preferably of a superelastic material which is by way of example only, a nickel titanium material (NiTi), which has properties which allow it to withstand repeated deflection without fatigue, while returning to its original shape. The sleeve could be made of other materials, such as for example titanium, but these materials do not have the advantages of a super-elastic material.

FIG. 93a is a cross-section through the implant 1000 depicting the central body 1002 and the sleeve 1016. As can be seen from the cross-section of FIG. 93a in a preferred embodiment, both the central body 1002 and the sleeve 1016 are substantially cylindrical and oval or ecliptically-shaped. An oval or elliptical shape allows more of the spinous process to be supported by the sleeve, thereby distributing the load between the bone and the sleeve more evenly. This reduces the possibility of fracture to the bone or bone resorption. Additionally, an oval or elliptical shape enhances the flexibility of the sleeve as the major axis of the sleeve, as described below, is parallel to the longitudinal direction of the spinous process. However, other shapes such as round cross-sections can come within the spirit and scope of the invention.

In this particular embodiment, the central body 1002 includes elongated grooves 1018, along axis 1008, which receives elongated spokes 1020 extending from the internal surface of the cylinder 1016.

In a preferred embodiment, both the cross-section of the central body and the sleeve have a major dimension along axis 1022 and a minor dimensional along axis 1024 (FIG. 93a). The spokes 1020 are along the major dimension so that along the minor dimension, the sleeve 1016 can have its maximum inflection relative to the central body 1002. It is to be understood that the central body along the minor dimension 1024 can have multiple sizes and can, for example, be reduced in thickness in order to increase the ability of the sleeve 1016 to be deflected in the direction of the central body 1002.

Alternatively as can be seen in FIG. 93b, the central body 1002 can include the spokes 1020 and the sleeve 1016 can be designed to include the grooves 1018 in order to appropriately space the sleeve 1016 from the central body 1002.

In other embodiments, the sleeve can have minor and major dimensions as follows:

| Minor Dimension | Major Dimension |
| --- | --- |
| 6 mm | 10 mm |
| 8 mm | 10.75 mm |
| 12 mm | 14 mm |
| 6 mm | 12.5 mm |
| 8 mm | 12.5 mm |
| 10 mm | 12.5 mm |

In one preferred embodiment, said sleeve has a cross-section with a major dimension and a minor dimension and said major dimension is greater than said minor dimension and less than about two times said minor dimension. In said embodiment, said guide has a cross-section which is adjacent to said sleeve with a guide major dimension about equal to said sleeve major dimension and a guide minor dimension about equal to said sleeve minor dimension. Further in said embodiment, said guide extends from said central body with a cross-section which reduces in size in a direction away from said central body.

In another preferred embodiment, said guide is cone-shaped with a base located adjacent to said sleeve. Further, said guide has a base cross-section about the same as the oval cross-section of said sleeve.

Thus, from the above, it is evident that preferably a major dimension of the sleeve correspond with a major dimension of the central body and a minor dimension of the sleeve corresponds with a minor dimension of the central body. Additionally, it is evident that the major dimension of the sleeve 1016 is substantially perpendicular to a major dimension of the first wing 1004 along longitudinal axis 1030 (FIG. 92*a*). This is so that as discussed above, when the implant 1000 is properly positioned between the spinous processes, a major portion of the sleeve comes in contact with both the upper and lower spinous processes in order to distribute the load of the spinous processes on the sleeve 1016 during spinal column extension.

As indicated above, the preferred material for the sleeve 1016 is a super-elastic material and more preferably one comprised of an alloy of nickel and titanium. Such materials are available under the trademark Nitinol. Other super-elastic materials can be used as long as they are bio-compatible and have the same general characteristics of super-elastic materials. In this particular embodiment, a preferred super-elastic material is made up of the following composition of nickel, titanium, carbon, and other materials as follows:

| | |
| --- | --- |
| Nickel | 55.80% by weight |
| Titanium | 44.07% by weight |
| Carbon | <0.5% by weight |
| Oxygen | <0.5% by weight |

In particular, this composition of materials is able to absorb about 8% recoverable strain. Of course, other materials which can absorb greater and less than 8% can come within the spirit and scope of the invention. This material can be repeatably deflected toward the central body and returned to about its original shape without fatigue. Preferably and additionally, this material can withstand the threshold stress with only a small amount of initial deforming strain and above the threshold stress exhibit substantial and about instantaneous deformation strain which is many times the small amount of initial deforming strain. Such a characteristic is demonstrated in FIG. 118 where it is shown that above a certain threshold stress level, deformation strain is substantially instantaneous up to about 8%. FIG. 118 shows a loading and unloading curve between stress and deformation strain for a typical type of super-elastic material as described above.

Preferably, the above super-elastic material is selected to allow deformation of up to about, by way of example only, 8%, at about 20 lbs. to 50 lbs. force applied between a spinous processes. This would cause a sleeve to deflect toward the central body absorbing a substantial amount of the force of the spinous processes in extension. Ideally, the sleeves are designed to absorb 20 lbs. to 100 lbs. before exhibiting the super-elastic effect (threshold stress level) described above. Further, it is possible, depending on the application of the sleeve and the anatomy of the spinal column and the pairs of spinous processes for a particular individual, that the sleeve can be designed for a preferable range of 20 lbs. to 500 lbs. of force before the threshold stress level is reached. Experimental results indicate that with spinous processes of an older individual, that at about 400 pounds force, the spinous process may fracture. Further, such experimental results also indicate that with at least 100 pounds force, the spinous process may experience some compression. Accordingly, ideally the super-elastic material is designed to deform or flex at less than 100 pounds force.

In a preferred embodiment, the wall thickness of the sleeve is about 1 mm or 40/1000 of an inch (0.040 in.). Preferably the sleeve is designed to experience a combined 1 mm deflection. The combined 1 mm deflection means that there is ½ mm of deflection at the top of the minor dimension and a ½ mm deflection at the bottom of the minor dimension. Both deflections are toward the central body.

In a particular embodiment where the sleeve is more circular in cross-section, with an outer dimension of 0.622 in. and a wall thickness of 0.034 in., a 20 lb. load causes a 0.005 in. deflection and a 60 lb. load causes a 0.020 in. deflection (approximately ½ mm). A 100 lb. load would cause a deflection of about 0.04 in. or approximately 1 mm.

Thus in summary, the above preferred super-elastic material means that the sleeve can be repeatedly deflected and returned to about its original shape without showing fatigue. The sleeve can withstand a threshold stress with a small amount of deforming strain and at about said threshold stress exhibit about substantially instantaneous deformation strain which is many times the small amount of the forming strain. In other words, such super-elastic qualities mean that the material experiences a plateau stress where the material supports a constant force (stress) over very large strain range as exhibited in FIG. 118.

It is to be understood that for this particular embodiment, bar stock of the super-elastic material is machined into the appropriate form and then heat treated to a final temperature to set the shape of the material by increasing the temperature of the material to 932° Fahrenheit and holding that temperature for five (5) minutes and then quickly quenching the sleeve in water. It is also to be understood that preferably the present nickel titanium super-elastic alloy is selected to have a transition temperature $A_f$ of about 59° Fahrenheit (15° C.). Generally for such devices the transition temperature can be between 15° C. to 65° C. (59° F. to 149 ° F.), and more preferably 10° C. to 40° C. (50° F. to 104° F.). Preferably, the material is maintained in the body above the transition temperature in order to exhibit optimal elasticity qualities.

Alternatively, and preferably, the sleeve can be fabricated by wire Electrical Discharge Machining (EDM) rather than machined. Additionally, the sleeve can be finished using a shot blast technique in order to increase the surface strength and elasticity of the sleeve.

Figure 94B:
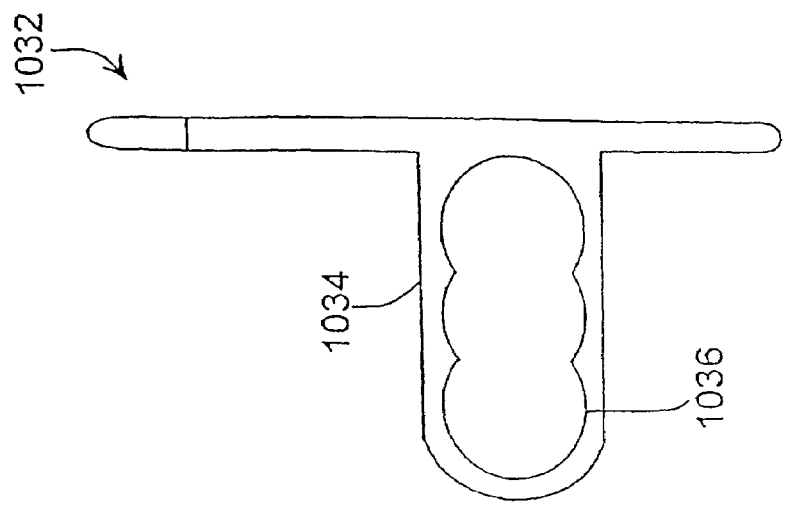
Figure 94A:
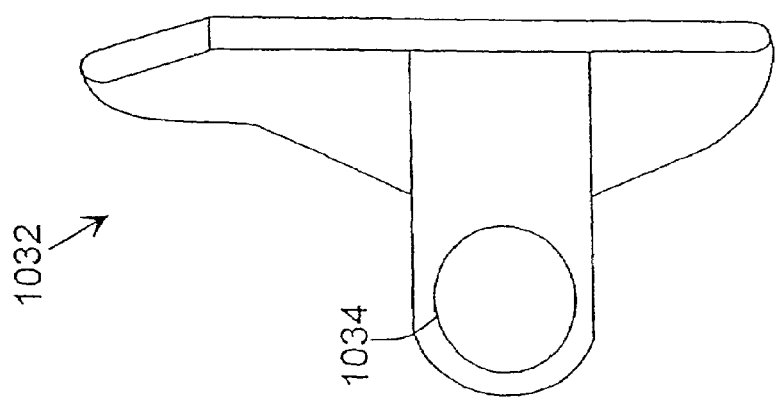
Figure 94:
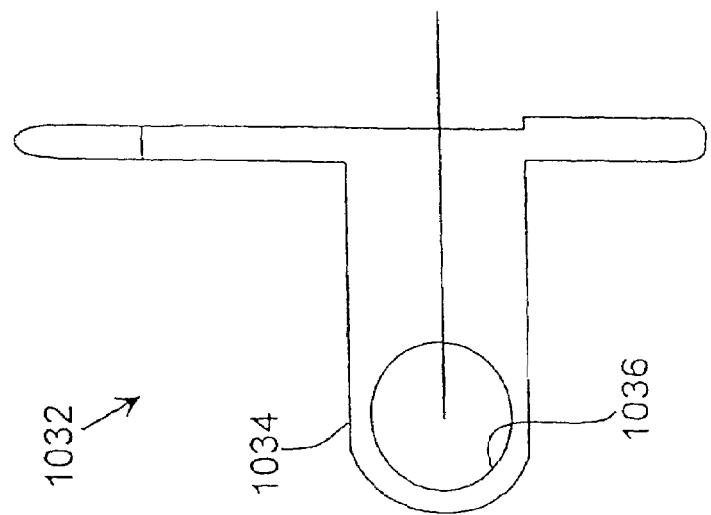
Figure 96:
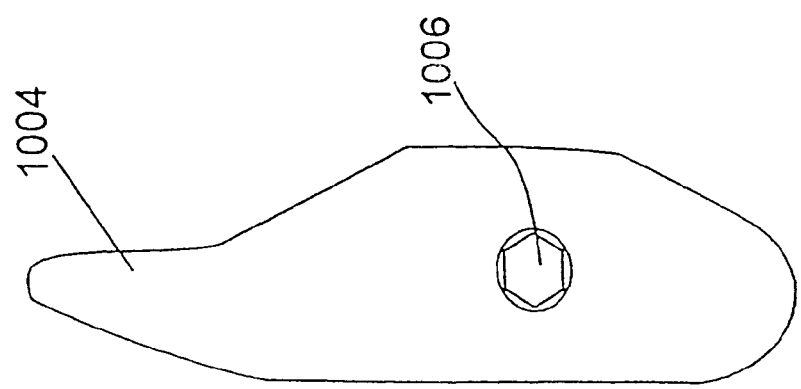
Figure 95A:
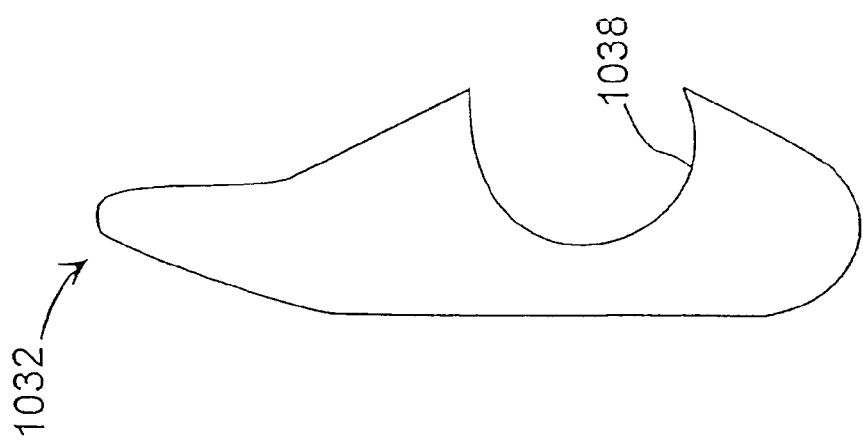
Figure 95:
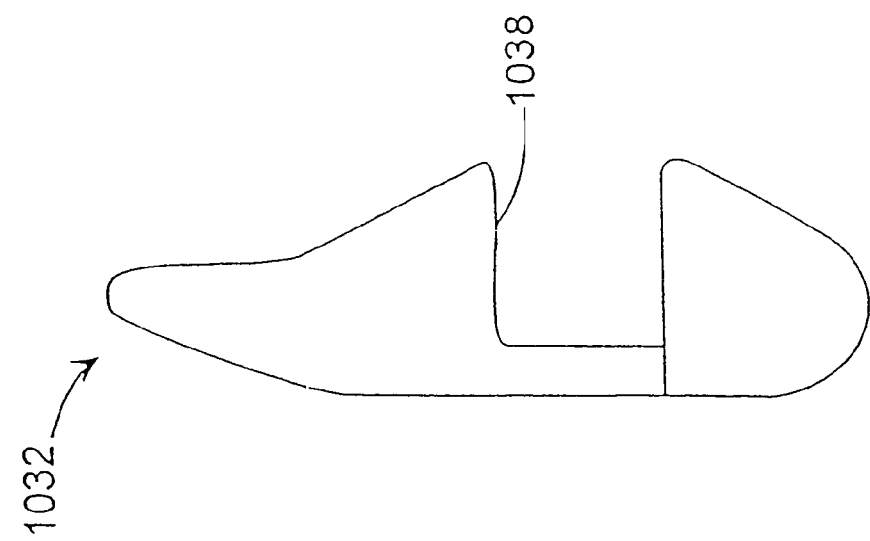

Top and side views of the second wing 1032 are shown in FIGS. 94 and 95. Second wing 1032 as in several past embodiments includes a tab 1034 with a bore 1036 which aligns with the bore 1014 of the guide 1010. In this particular embodiment, the second wing 1032 includes a cut-out 1038 which is sized to fit over the guide 1010, with the tab 1034 resting in the recess 1012 of the guide 1010.

An alternative configuration of the second wing 1032 is depicted in FIG. 94a. In this configuration, the second wing 1032 is held at acute angle with respect to the tab 1034. This is different from the situation in the embodiment of FIGS. 94 and 95 where the second wing is substantially perpendicular to the tab. For the embodiment of the second wing in FIG. 94a, such embodiment will be utilized as appropriate depending on the shape of the spinous processes.

With respect to the alternative second wing 1032 depicted in FIGS. 94b and 95a, elongated tab 1034 has a plurality of closely positioned bores 1036. The bores, so positioned, appear to form a scallop shape. Each individual scallop portion of the bore 1036 can selectively hold the bolt in order to effectively position the second wing 1032 in three different positions relative to the first wing 1004. The cut-out 1038 (FIG. 95a of this alternative embodiment) is enlarged over that of FIG. 95 as in a position closest to the first wing 1004, the second wing 1032 is immediately adjacent and must conform to the shape of the sleeve 1016.

Figure 97:
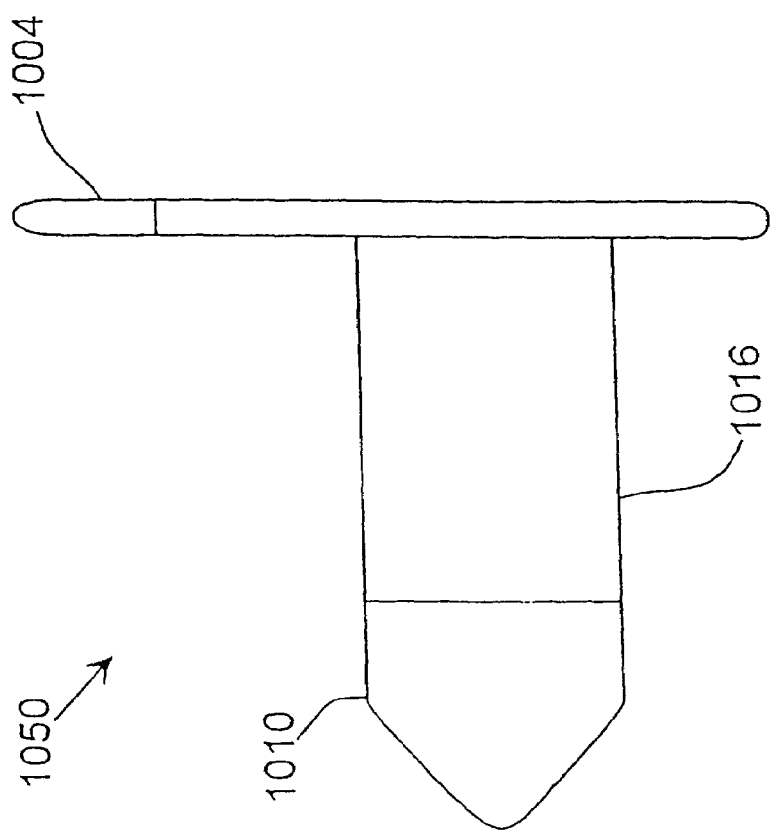
FIG. 97 depicts still another embodiment of the present invention.

Embodiment of FIG. 97

Implant 1050 of FIG. 97 is similar to the implant 1000 in FIG. 92 with the major difference being that a second wing is not required. The implant 1050 includes a central body as does implant 1000. The central body is surrounded by a sleeve 1016 which extends between a first wing 1004 and a guide 1010. The guide 1010 in this embodiment is substantially cone-shaped without any flats and with no bore as there is no need to receive a second wing. The sleeve and the central body as well as the first wing and guide act in a manner similar to those parts of the implant 1000 in FIG. 92. It is to be understood a cross-section of this implant 1050 through sleeve 1016 can preferably be like FIG. 93a. This particular embodiment would be utilized in a situation where it was deemed impractical or unnecessary to use a second wing. This embodiment has the significant advantages of the sleeve being comprised of super-elastic alloy materials as well as the guide being utilized to guide the implant between spinous processes while minimizing damage to the ligament and tissue structures found around the spinous processes.

Figure 98:
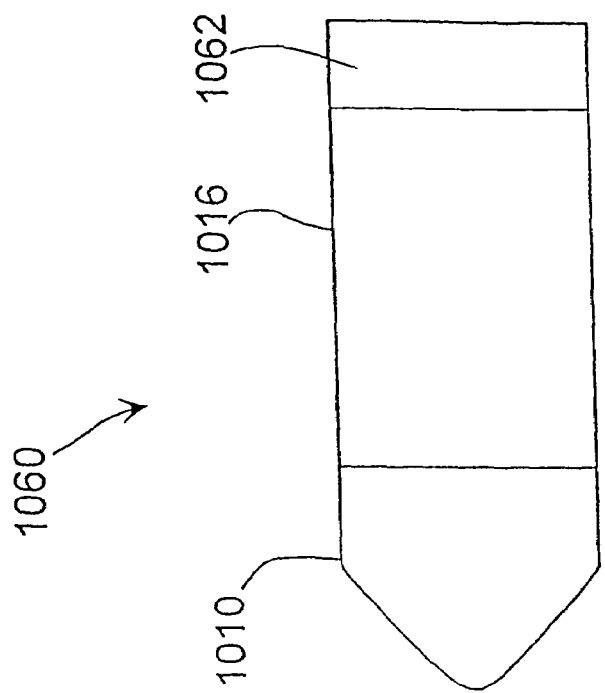
FIG. 98 depicts yet a further embodiment of the present invention.

Embodiment of FIG. 98

Implant 1060 is depicted in FIG. 98. This implant is similar to the implants 1000 of FIG. 92 and the implant 1050 of FIG. 97, except that this implant does not have either first or second wings. Implant 1060 includes a sleeve 1016 which surrounds a central body just as central body 1002 of implant 1000 in FIG. 93. It is to be understood that a cross-section of this implant 1060 through sleeve 1016 can preferably be like FIG. 93a. Implant 1060 includes a guide 1010 which in this preferred embodiment is cone-shaped. Guide 1010 is located at one end of the central body. At the other end is a stop 1062. Stop 1062 is used to contain the other end of the sleeve 1016 relative to the central body. This embodiment is held together with a bolt such as bolt 1006 of FIG. 93 that is used for the immediate above two implants. For the implant 1060 of FIG. 98, such a device would be appropriate where the anatomy between the spinous processes was such that it would be undesirable to use either a first or second wing. However, this embodiment affords all the advantageous described hereinabove (FIGS. 92 and 97) with respect to the guide and also with respect to the dynamics of the sleeve.

Figure 99:
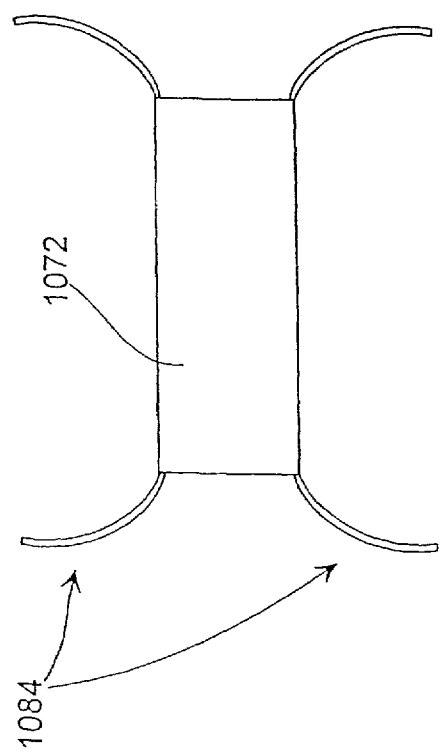
FIGS. 99 and 100 depict still another embodiment of the present invention including an insertion tool.
Figure 100:
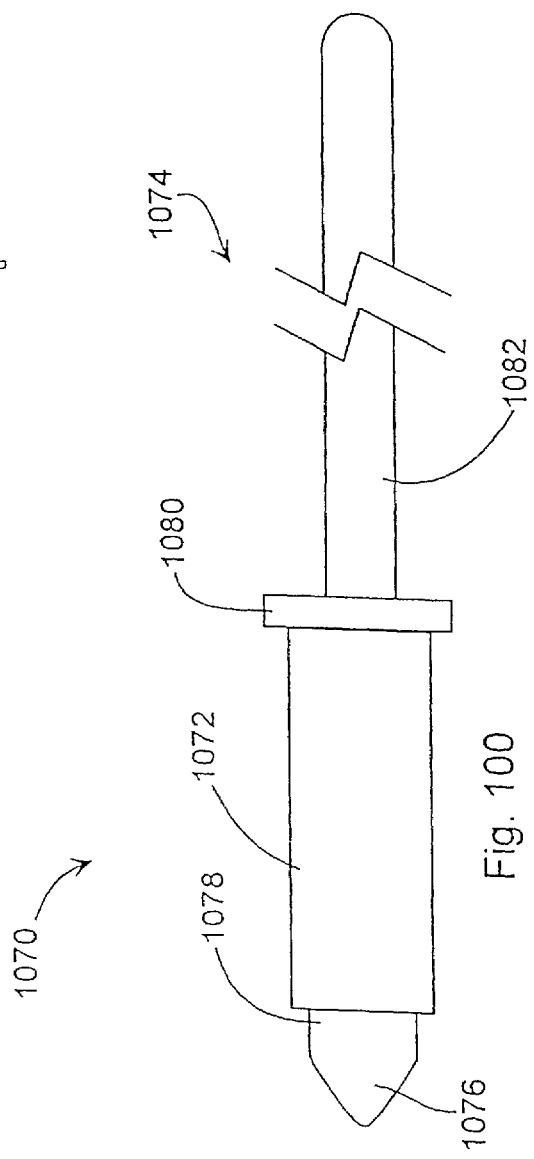

Embodiment of FIGS. 99 and 100

FIGS. 99 and 100 depict an implant system 1070. Implant system 1070 includes a sleeve 1072 which is similar to and has the advantageous of sleeve 1016 of the embodiment in FIG. 92. Sleeve 1072 does not, however, have any spokes. Additionally, implant system 1070 includes an insertion tool 1074. Insertion tool 1074 includes a guide 1076 which in a preferred embodiment is substantially cone-shaped. Guide 1076 guides the insertion of the sleeve 1072 and the insertion tool 1074 between adjacent spinous processes. The insertion tool 1074 further includes a central body 1078, a stop 1080, and a handle 1082. The guide 1076 at its base has dimensions which are slightly less than the internal dimensions of the sleeve 1074 so that the sleeve can fit over the guide 1076 and rest against the stop 1080. The tool 1074 with the guide 1076 is used to separate tissues and ligaments and to urge the sleeve 1072 in the space between the spinous processes. Once positioned, the guide insertion tool 1074 can be removed leaving the sleeve 1072 in place. If desired, after the sleeve is positioned, position maintaining mechanisms such as springy wires 1084 made out of appropriate material such as the super-elastic alloys and other materials including titanium, can be inserted using a cannula through the center of the sleeve 1072. Once inserted, the ends of the retaining wires 1084 (FIG. 99) extend out of both ends of the sleeve 1072, and due to this springy nature, bent at an angle with respect to the longitudinal axis of the sleeve 1072. These wires help maintain the position of the sleeve relative to the spinous processes.

Embodiment of FIGS. 101, 102, 102a, 103, 104, 105, 106, and 107

Figure 101:
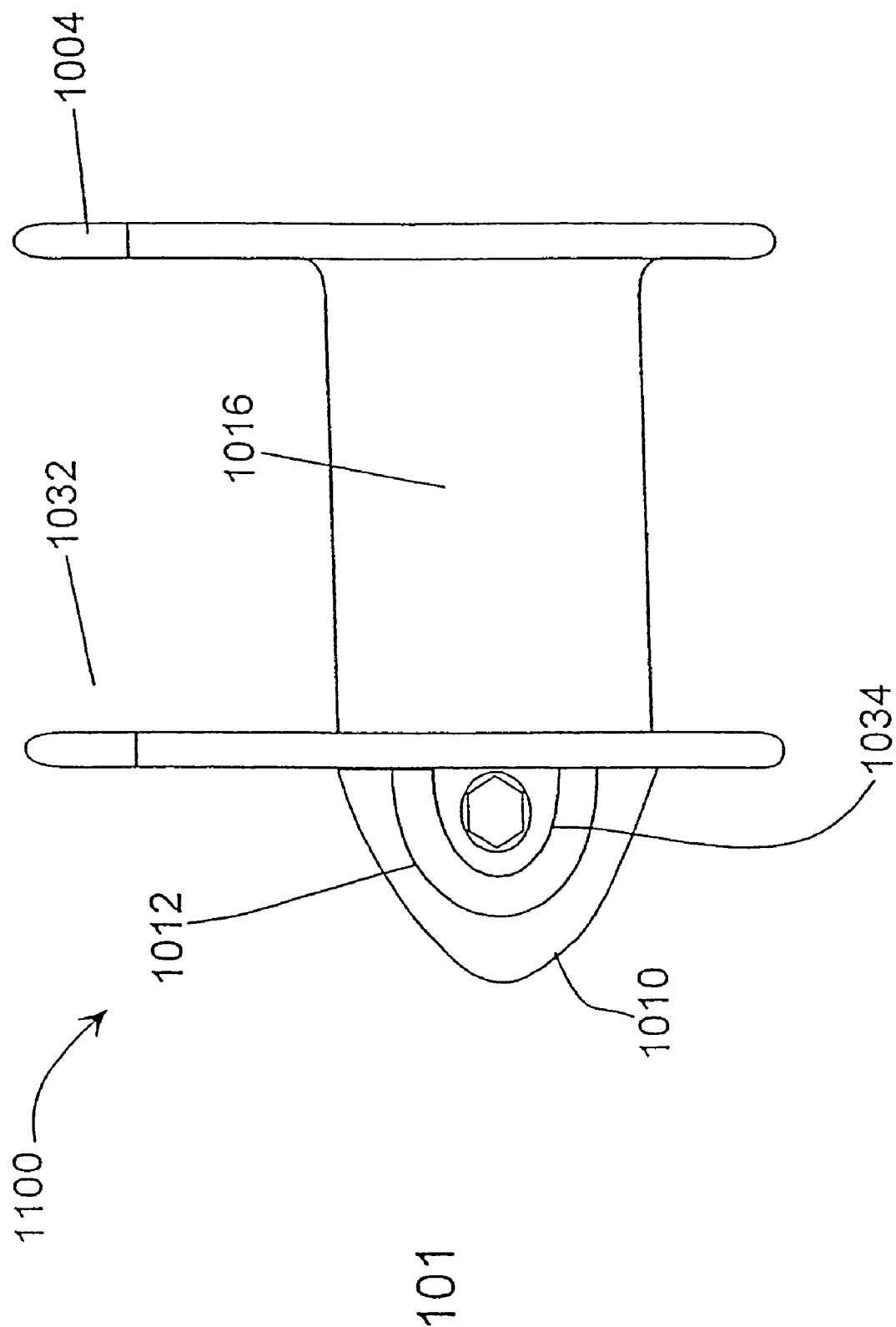

Another embodiment of the invention can be seen in FIG. 101 which includes implant 1100. Implant 1100 has many similar features that are exhibited with respect to implant 1000 in FIG. 92. Accordingly, elements with similar features and functions would be similarly numbered. Additionally, features that are different from implant 1100 can be, if desired, imported into and become a part of the implant 1000 of FIG. 92.

As with implant 1000, implant 1100 includes a central body 1002 (FIG. 102) with a first wing 1004 and a bolt 1006 which holds the first wing and the central body together. In this particular embodiment, the central body is made in two portions. The first portion 1102 is in the shape of a truncated cone with an oval or elliptical base and a second portion 1104 includes a cylindrical central portion with a distal end in the shape of a truncated cone 1103 with an oval or elliptical base. In addition, in this particular embodiment, formed with the central body is the guide 1010 which has an oval or elliptical base. Bolt 1006 is used to secure the first wing through the second portion 1104 with the first portion 1102 held in-between. In this particular embodiment, the guide 1010 in addition to including recess 1012 and bore 1014 includes a groove 1106 which receives a portion of the second wing 1032.

Figure 102A:
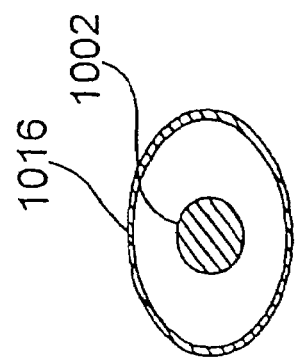
Figure 102:
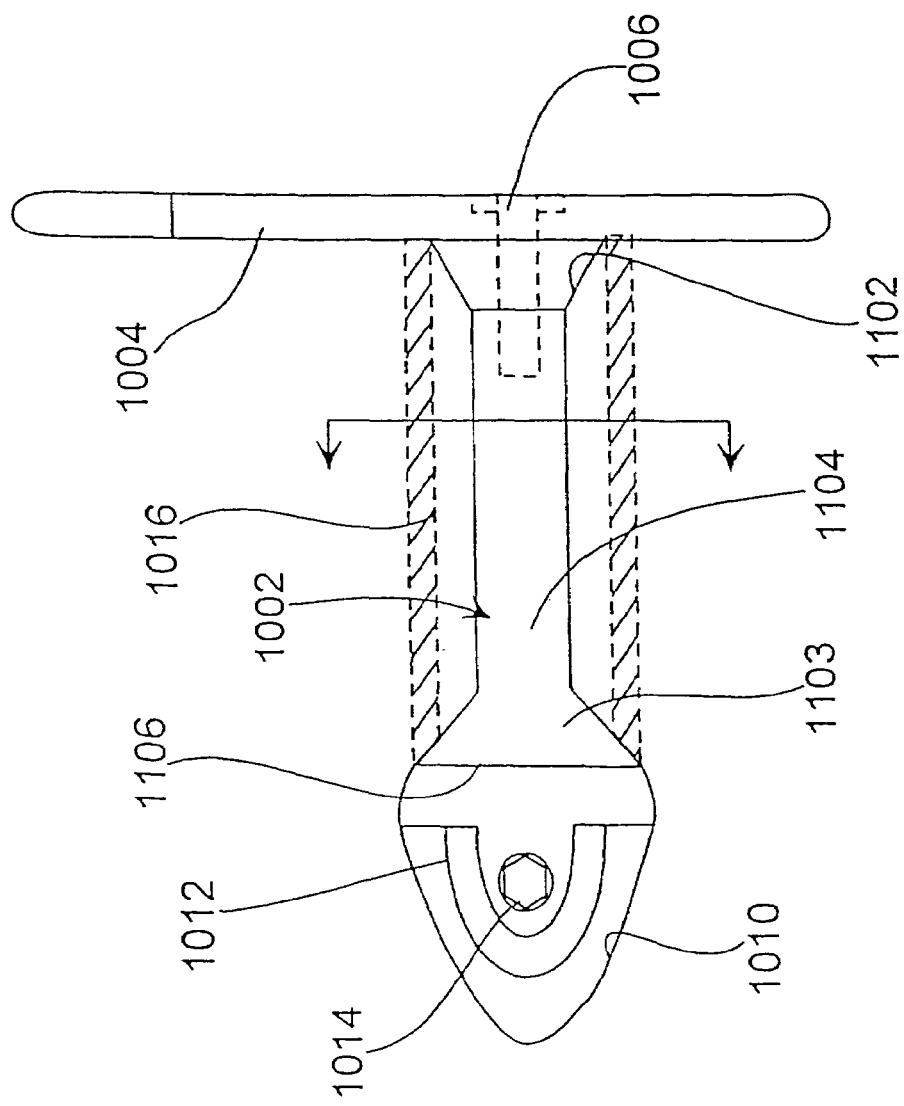

In this particular embodiment, the sleeve 1016 is preferably oval or elliptical in shape as can be seen in FIG. 102a. The central body can be oval, elliptical or circular in cross-section, although other shapes are within the spirit and scope of the invention. The sleeve 1016 held in position due to the fact that the truncated conical portion 1102 and the corresponding truncated conical portion 1103 each have a base that is elliptical or oval in shape. Thus, the sleeve is held in position so that preferably the major dimension of the elliptical sleeve is substantially perpendicular to the major dimension of the first wing. It is to be understood that if the first wing is meant to be put beside the vertebrae so that the first wing is set at an angle other than perpendicular with respect to the vertebrae and that the sleeve may be held in a position so that the major dimension of the sleeve is at an angle other than perpendicular to the major dimension of the first wing and be within the spirit and scope of the invention. This could be accomplished by tightening bolt 1006 with the first wing 1004 and sleeve 1016 so positioned. In such a configuration, the major dimension of the sleeve would be preferably positioned so that it is essentially parallel to the length of the adjacent spinous processes. So configured, the elliptical or oval shape sleeve would bear and distribute the load more evenly over more of its surface.

It is to be understood that the sleeve in this embodiment has all the characteristics and advantages described hereinabove with respect to the above-referenced super-elastic sleeves.

The second wing as discussed above, can come in a variety of shapes in order to provide for variations in the anatomical form of the spinous processes. Such shapes are depicted in FIGS. 103, 104, 105, 106, and 107. In each configuration, the second wing 1032 has a upper portion 1108 and a lower portion 1110. In FIG. 104, the lower portion is thicker than the upper portion in order to accommodate the spinous process, where the lower spinous process is thinner than the upper spinous process. In FIG. 105, both the upper and lower portions are enlarged over the upper and lower portions of FIG. 103 to accommodate both the upper and lower spinous processes being smaller. That is to say that the space between the upper and lower portions of the first and second wings are reduced due to the enlarged upper and lower portions of the second wing.

Figure 107:
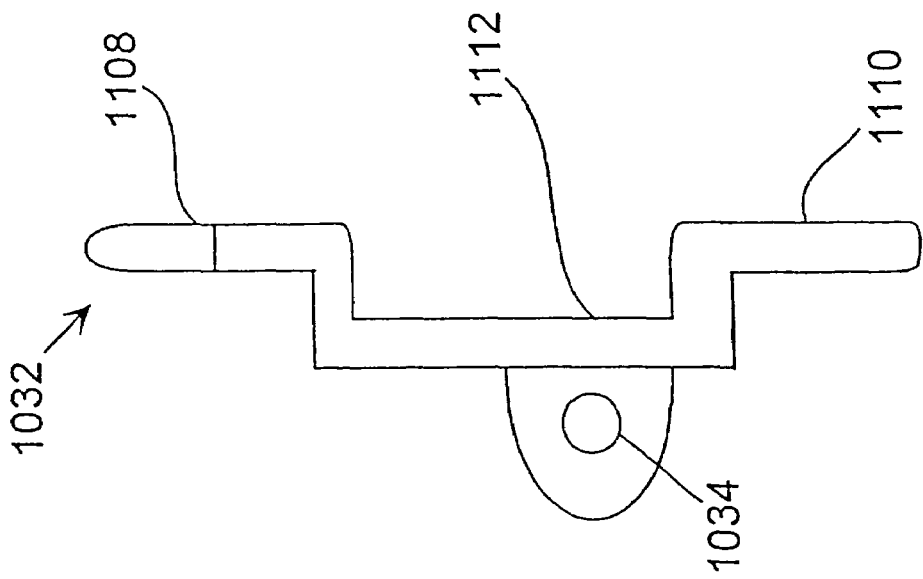
Figure 106:
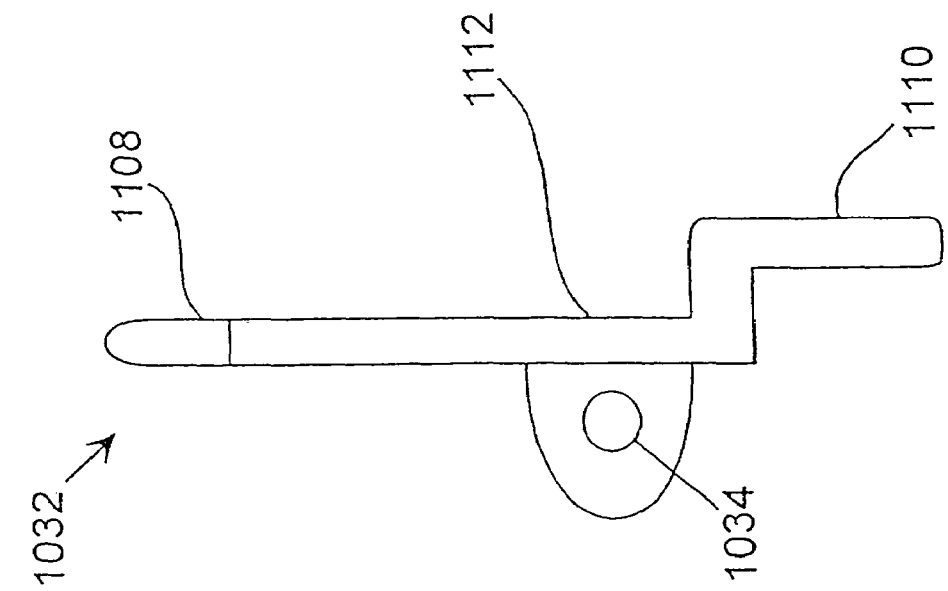

Alternative embodiments of second wings, as shown in FIGS. 104 and 105, are depicted in FIGS. 106 and 107. In these FIGS. 106 and 107, the second wing 1032 accommodates the same anatomical shape and size of the spinous processes as does the second wing in FIGS. 104 and 105 respectively. However, in the embodiments of the second wing 1032 of FIGS. 106 and 107, substantial masses have been removed from the wings. The upper and lower portions 1108 and 1110 are essentially formed or bent in order to extend from the central portion 1112 of the second wing 1032.

It is to be understood that in this embodiment, if desired, the second wing may not have to be used, depending on the anatomy of the spinal column of the body, and this embodiment still has the significant advantages attributable to the guide 1010 and the functionality of the sleeve 1016.

Figure 108:
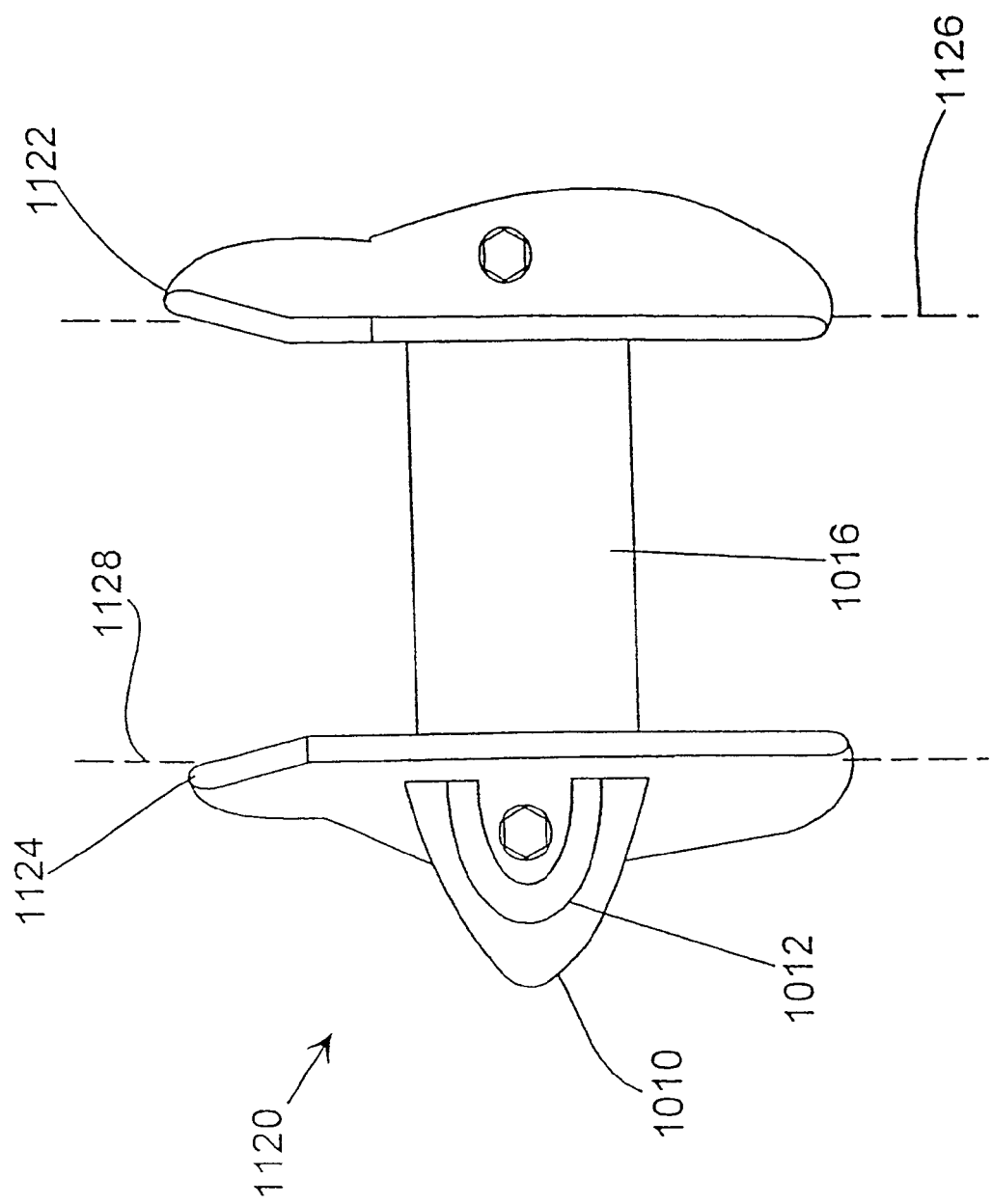
FIGS. 108, 109, and 110 depict still another embodiment of the present invention.
Figure 109:
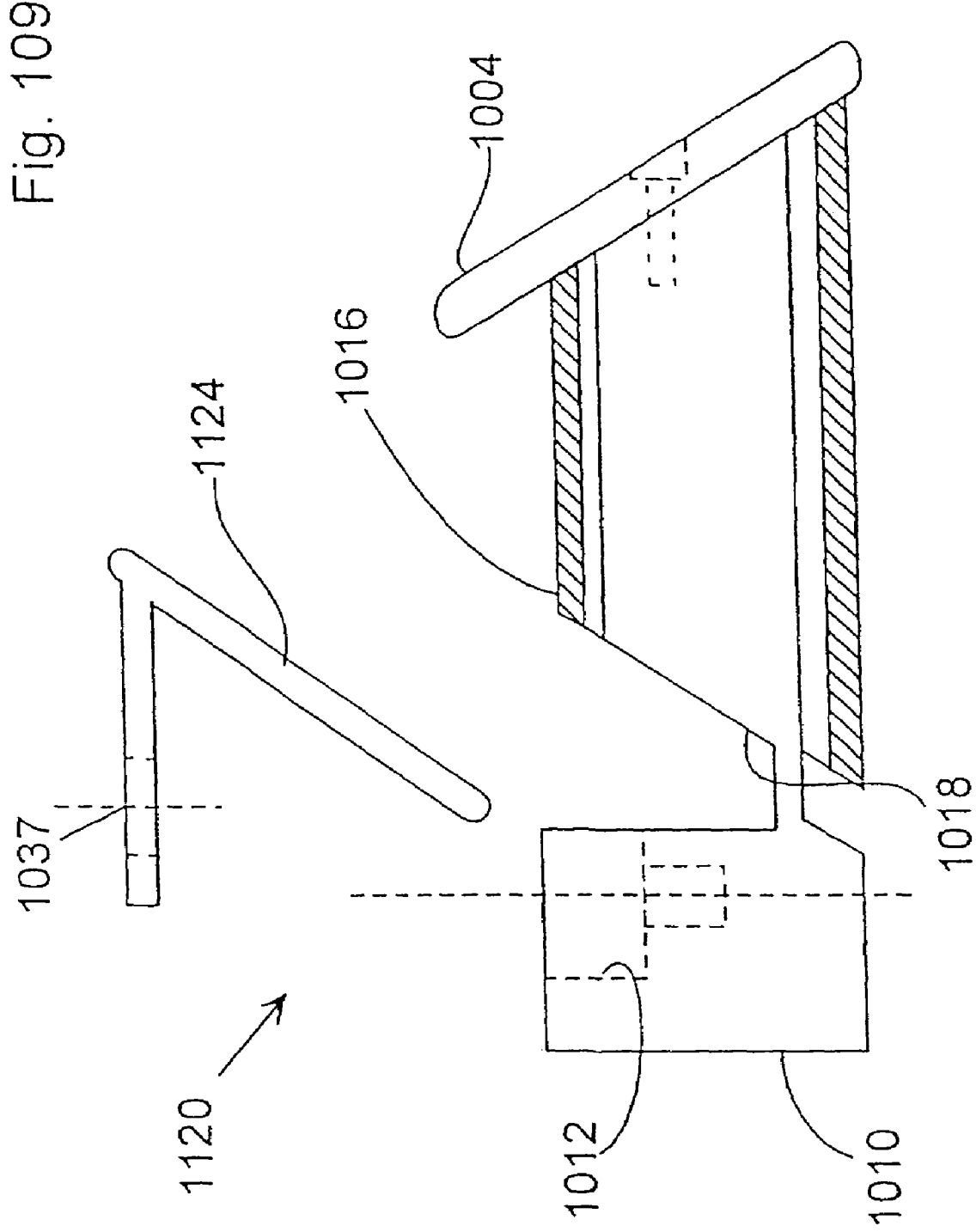
Figure 110:
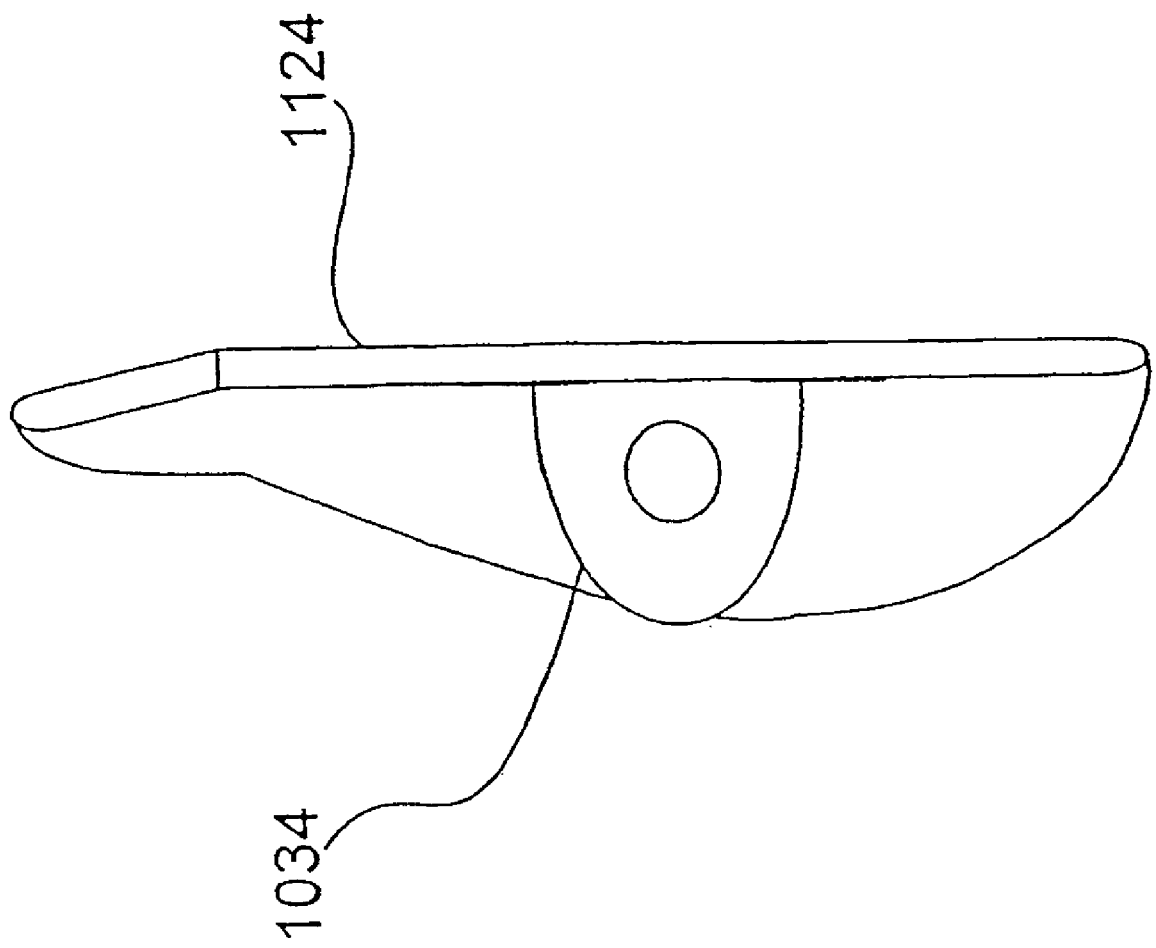

Embodiment of FIGS. 108, 109, and 110

The implant 1120 as shown in FIGS. 108 and 109, is similar to implant 1100 which is in turn similar to implant 1000. Such similar details have already been described above and reference here is made to the unique orientation of the first and second wings 1122 and 1124. These wings have longitudinal axis 1126 and 1128 respectfully. As can be seen in these figures, the first and second wings 1122, 1124 have been rotated so that they both slope inwardly and if they were to continue out of the page of the drawing of FIG. 108, they would meet to form an A-frame structure as is evident from the end view of FIG. 109. In this particular embodiment, as can be seen in FIGS. 109 and 110, the tab 1034 is provided an acute angle to the remainder of the second wing 1124. Further, the groove 1018 formed in the implant is sloped in order to accept the second wing 1124. Accordingly, this present implant 1120 is particularly suited for an application where the spinous process is wider adjacent to the vertebral body and then narrows in size at least some distance distally from the vertebral body. It is to be understood that a cross-section of this implant 1120 through sleeve 1016 can preferably be like FIG. 93*a*.

Embodiment of FIGS. 111, 112, 113, 114, 115, 116, and 117

Figure 111:
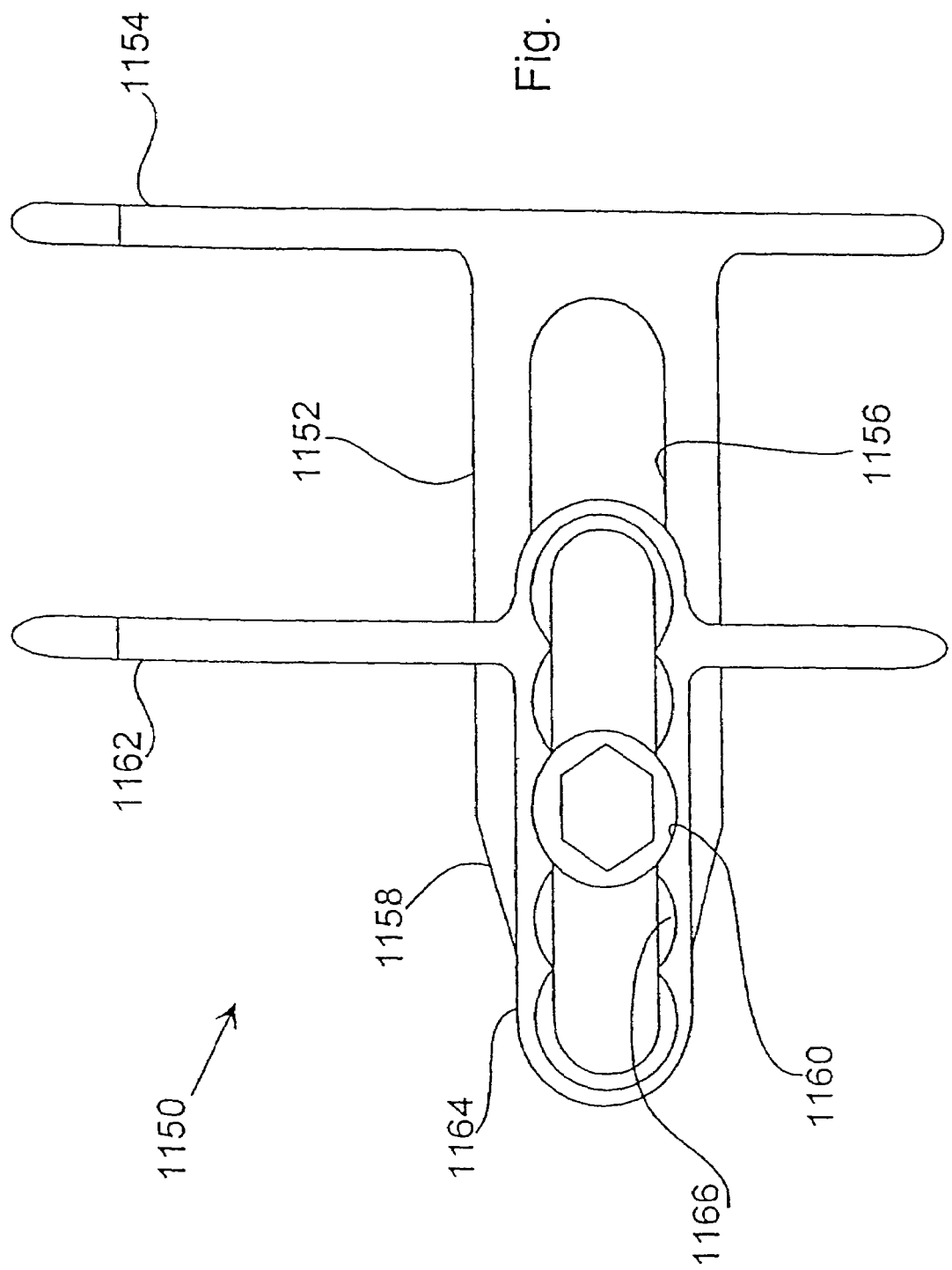

An additional embodiment of the implant 1150 is shown in FIG. 111. Implant 1150 has features similar to those described with respect to FIG. 94*b*.

Implant 1150 includes a central body 1152 with a first wing 1154, where central body 1152 includes elongated groove 1156 which extends to the guide 1158. A screw 1160 is received in a threaded bore located in the elongated groove 1156.

The second wing 1162 includes a central body 1164 which is substantially perpendicular to the second wing 1162.

Figure 112:
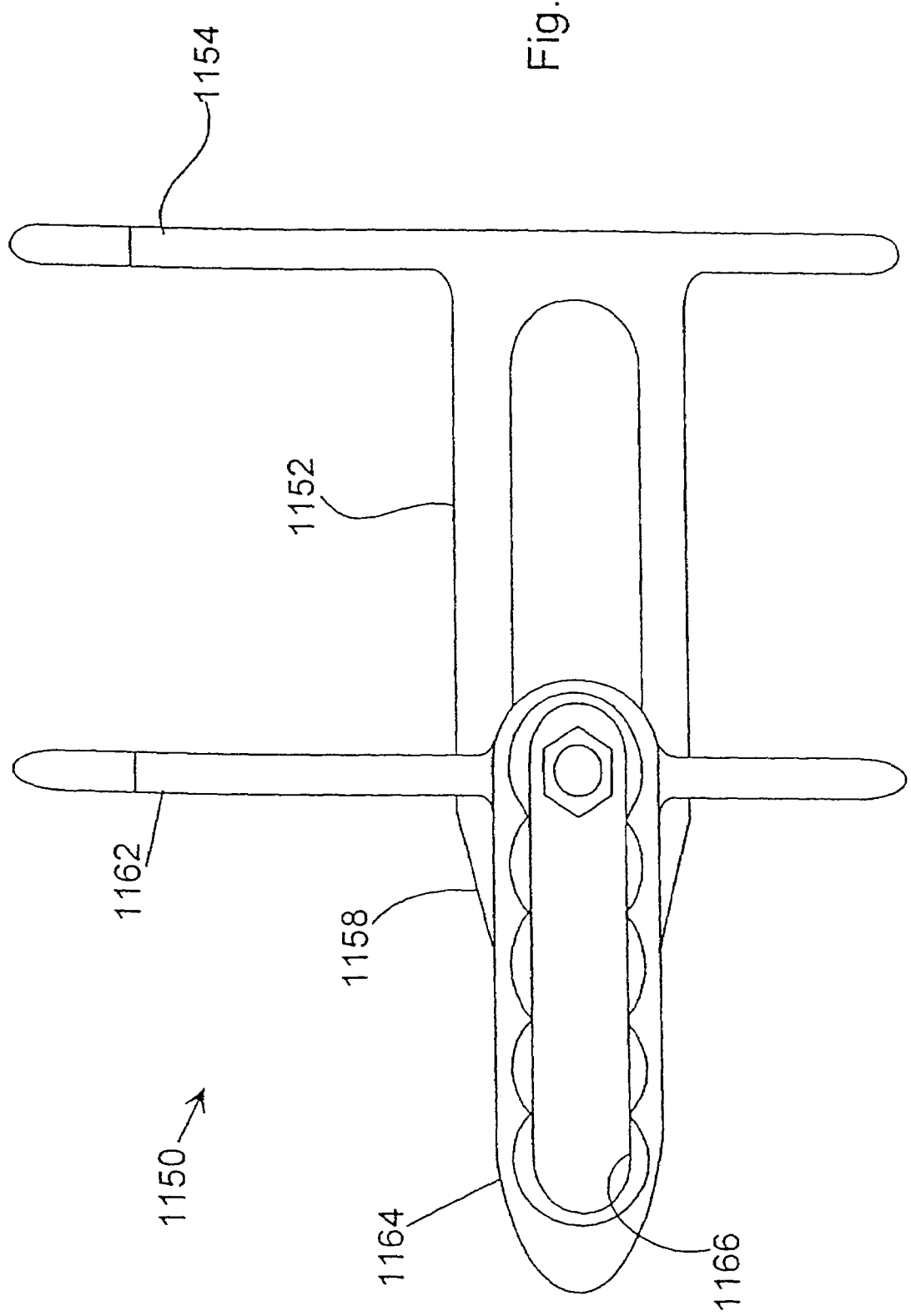
Figure 114:
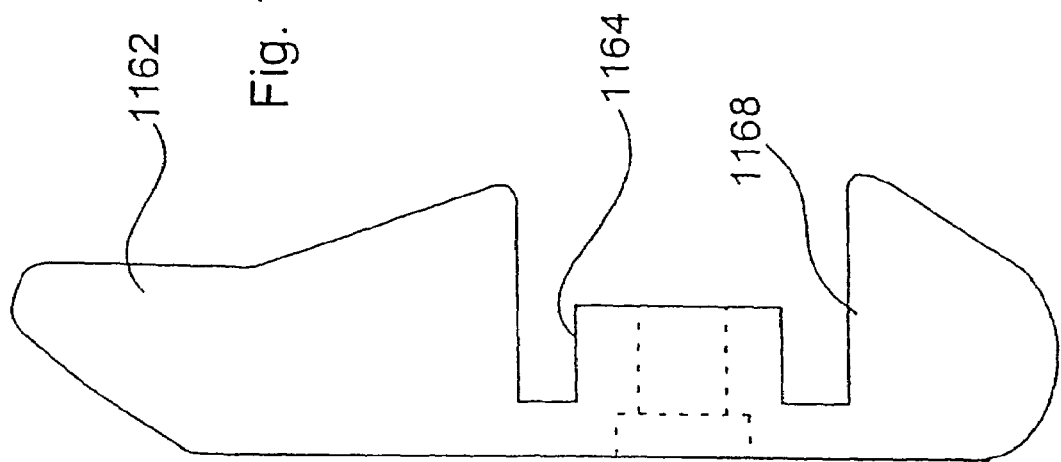
Figure 113:
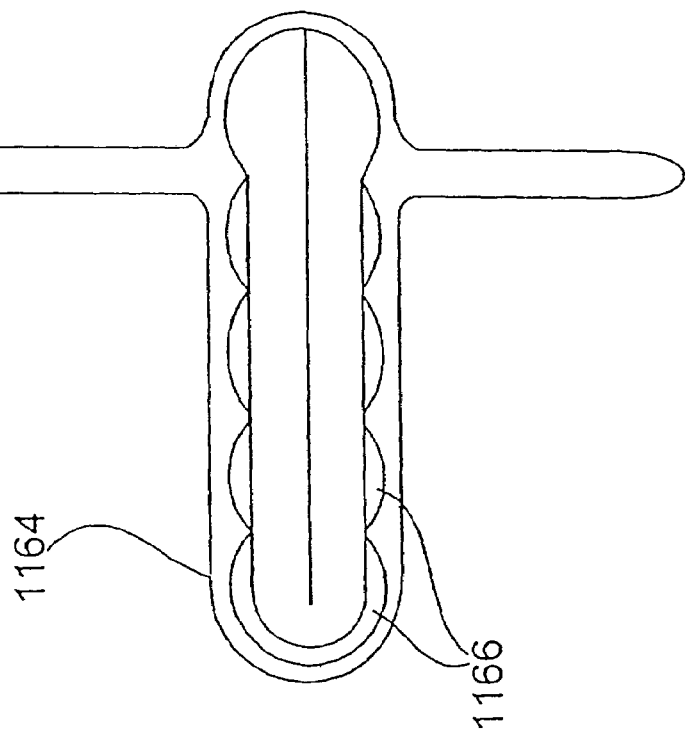

The central body 1164 includes a plurality of bores 1166 provided therein. These bores are formed adjacent to each other in order to define a plurality of scallops, each scallop capable of retaining bolt 1160 therein. As can be seen in FIG. 114, the second wing includes a cut-out 1168 such that with the central body 1164 of the second wing received in the groove 1156 of the central body associated with the first wing, the remainder of the second wing is received over the central body 1152 of the implant 1150. With this implant 1150, the distance between the first and second wings can be adjusted by selectively placing the bolt 1160 through one of the five specified bores defined by the scalloped plurality of bores 1166. Accordingly, FIG. 112 depicts the implant where the first and second wings are widest apart in order to accommodate spinous processes of greater thickness. FIG. 111 shows the middle position between the first and second wings in order to accommodate average size spinous processes.

It is to be understood that preferably during the surgical process, the central body 1152 is urged between spinous processes. After this has occurred, the second wing is guided by the other sides of the spinous processes from a path which causes the plane of the second wing to move substantially parallel to the plane of the first wing until the central body 1164 associated with the second wing 1162 is received in the groove of 1156 of the central body 1152 associated with the first wing 1154. After this has occurred, the bolt 1160 is positioned through aligned bores associated with the second wing 1162 and the central body 1152 in order to secure the second wing to the central body.

While embodiment 1150 does not depict a sleeve such as sleeve 1016, such a sleeve 1016 could be placed over body 1152 and be within the spirit of the invention.

Embodiments of FIGS. 119*a*, 119*b*, 120*a*, 120*b*, 121*a*, 121*b*, 122*a*, 122*b*, 122*c*, 123*a*, 123*b*, 124*a*, 124*b*, and 124*c*

Figure 120B:
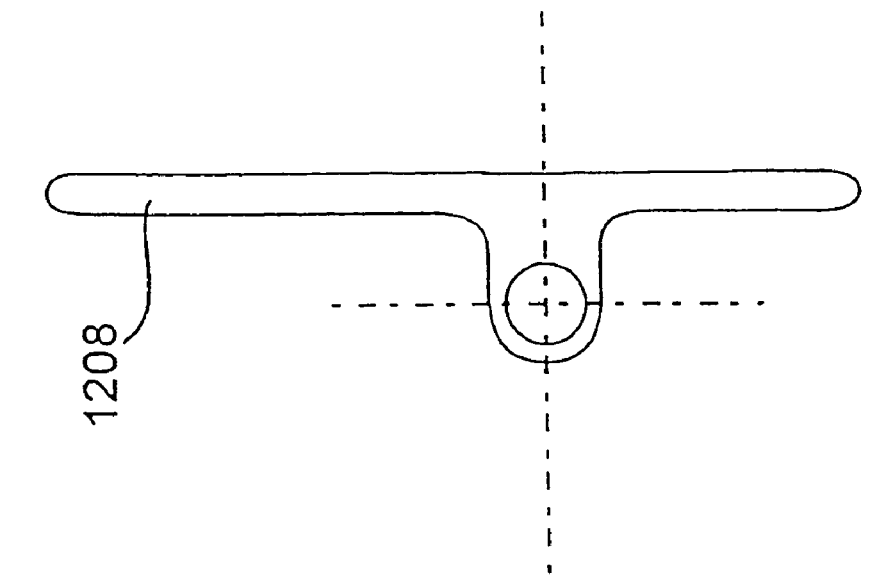
FIGS. 120*a* and 120*b* depict side and plan views of the second wing which can be used in conjunction with the embodiment of the invention of FIGS. 119*a* and 119*b*.
Figure 120A:
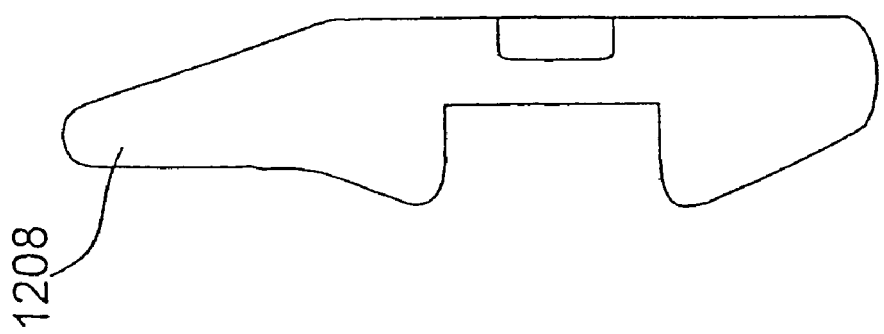

Implant 1200 of the invention is depicted in FIGS. 119*a* and 119*b*. This implant includes the first wing 1202 and sleeve 1204 and a guide 1206. An alternative to this embodiment further includes, as required, second wing 1208 as depicted in FIGS. 120*a* and 120*b*.

Figure 121B:
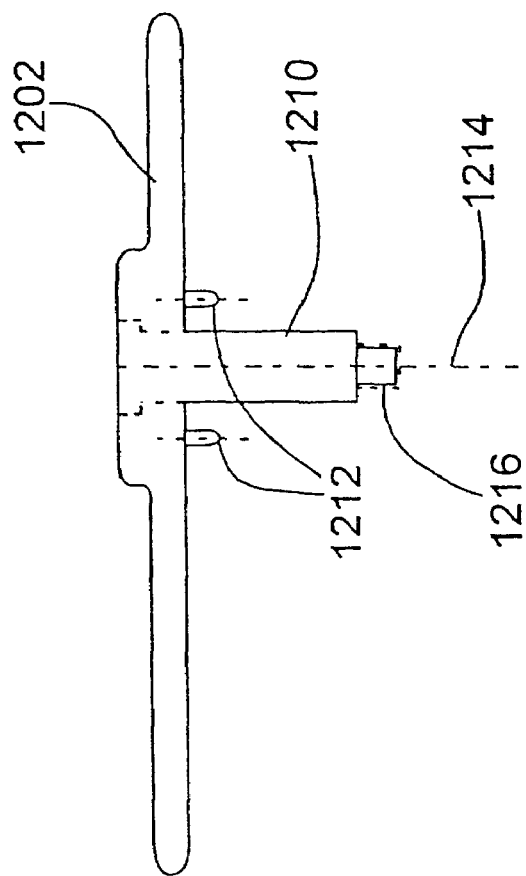
FIGS. 121*a* and 121*b* depict side and plan views of the first wing and central body of the embodiment of the invention depicted in FIGS. 119*a* and 119*b*.
Figure 121A:
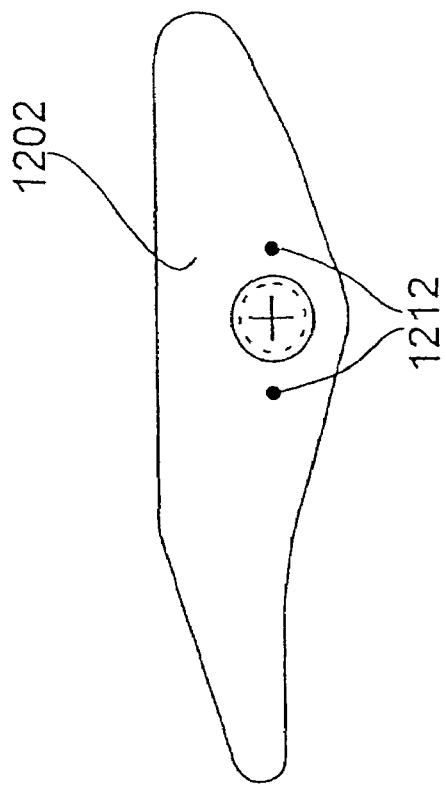

As can be seen in FIG. 121a and 121b, the first wing 1202 includes a bore which receives a central body 1210. Preferably, the central body is pressed fit through the bore of the first wing although it is to be understood that other securing mechanisms such as through the use of threads and still other mechanisms can be used to accomplish this task. Additionally, in this particular embodiment first and second pins 1212 extend from the first wing 1202, each along an axis which is substantially parallel to the longitudinal axis 1214 of the central body 1210. In this particular embodiment, the distal end 1216 of the central body 1210 is threaded in order to be coupled to the guide 1206.

Figure 122C:
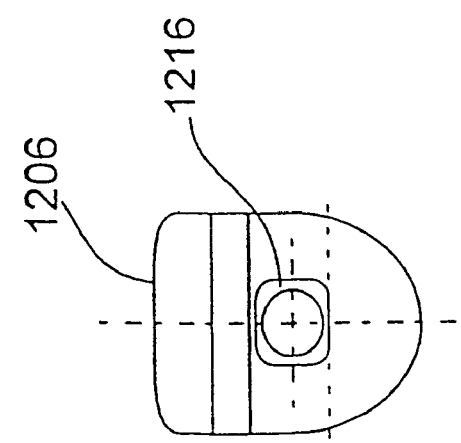
FIGS. 122*a*, 122*b*, and 122*c* depict top, side and end views of a guide which is a portion of the embodiment of the invention of FIGS. 119*a* and 119*b*.
Figure 122B:
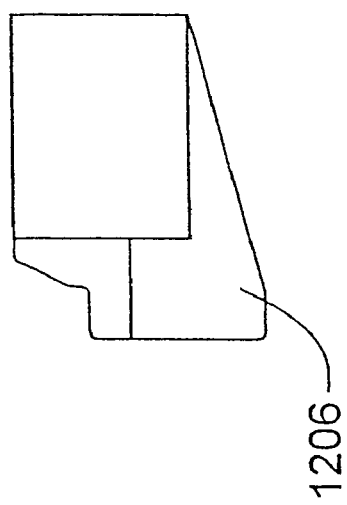
Figure 122A:
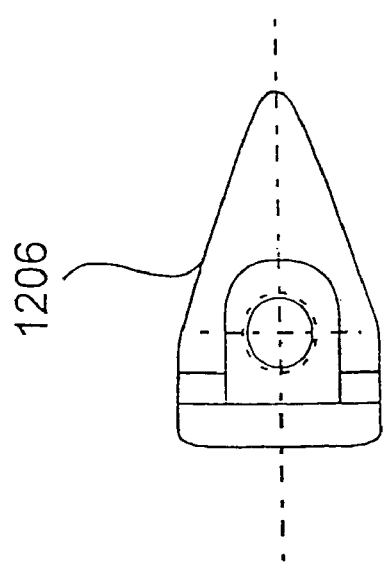

As can be seen in FIGS. 122a, 122b and 122c, the guide 1206 in this particular embodiment is pointed in order to allow the implant to be inserted between, and if necessary distract, adjacent spinous processes. The guide 206 includes a threaded bore 1218 which is designed to accept the threaded end 1216 of the central body 1210 in order to secure the guide to the central body and additionally for purposes of retaining the sleeve between the guide 1206 and the first wing 1202.

As can be seen in FIG. 123a the sleeve 1204 is preferably cylindrical, and oval or elliptical in shape in cross-section. It is to be understood that sleeve 1204 can have other shapes as described throughout the specification and be within the spirit and scope of the invention. In this particular embodiment, sleeve 1204 has at least one major diameter and one minor diameter in cross-section. Sleeve 1204 includes a central bore 1220 which extends the length of sleeve 1204 and curve grooves 1222 which are formed about central bore 1220 and extend only part way into the body of the sleeve. In this particular embodiment, the curved grooves 1222 describe an arc of about 60°. It is to be understood that in other embodiment, this arc can be less than 60° and extend past 120°.

The sleeve 1204 is received over the central body 1210 of the implant 1200 and can rotate thereon about the longitudinal axis 1214 of the central body 1210. When this particular embodiment is assembled, the grooves 1222 have received therein the pins 1212 that extend from the first wing 1202. Accordingly, the pins inserted in the grooves 1222 assist in the positioning of the sleeve relative to the remainder of the implant 1200. With the pins 1212 received in the curved grooves 1222, the pins limit the extent of the rotation of the sleeve about the central body and relative to the first wing.

As can be seen in FIGS. 124a, 124b, and 124c, the sleeve is free to rotate relative to the longitudinal axis of the central body 1210 and thus relative to the first wing 1202 of the embodiment shown in FIGS. 119a and 119b. The sleeve can rotate relative to a second wing 1208, when the second wing is utilized in conjunction with the embodiment of FIGS. 119a and 119b. The pins limit the rotation of the sleeve. In an alternative embodiment, the pins are eliminated so that the sleeve can rotate to any position relative to the first wing.

It is to be understood that the sleeve can be comprised of biologically acceptable material such as titanium. Additionally, it can be comprised of super-elastic material such as an alloy of nickel and titanium, much as described hereinabove with respect to other embodiments.

The great advantage of the use of the sleeve 1204 as depicted in the embodiment of FIGS. 119a and 119b is that the sleeve can be rotated and repositioned with respect to the first wing 1202, and/or the second wing 1208 should the second wing be used in the embodiment, in order to more optimally position the implant 1200 between spinous processes. It is to be understood that the cortical bone or the outer shell of the spinous processes is stronger at an anterior position adjacent to the vertebral bodies of the vertebra that at a posterior position distally located from the vertebral bodies.

Accordingly, there is some advantage of having the implant 1200 placed as close to the vertebral bodies as is possible. In order to facilitate this and to accommodate the anatomical form of the bone structures, as the implant is inserted between the vertebral bodies and urged toward the vertebral bodies, the sleeve 1204 can be rotated relative to the wings, such as wing 1202, so that the sleeve is optimally positioned between the spinous processes, and the wing 1202 is optimally positioned relative to the spinous processes. Without this capability, depending on the anatomical form of the bones, it is possible for the wings to become some what less than optimally positioned relative to the spinous processes.

Figure 127:
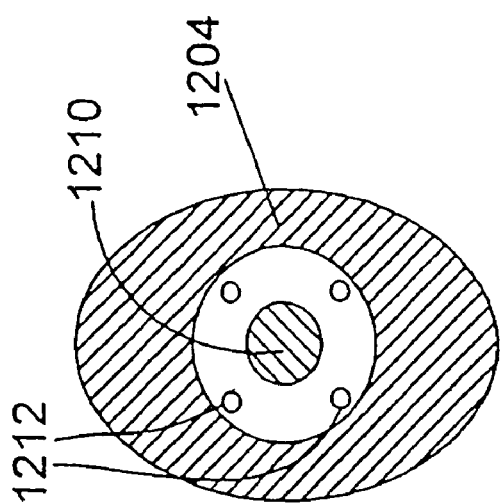
FIG. 127 depicts yet a further embodiment of the invention as depicted in FIGS. 119*a* and 119*b*.
Figure 126:
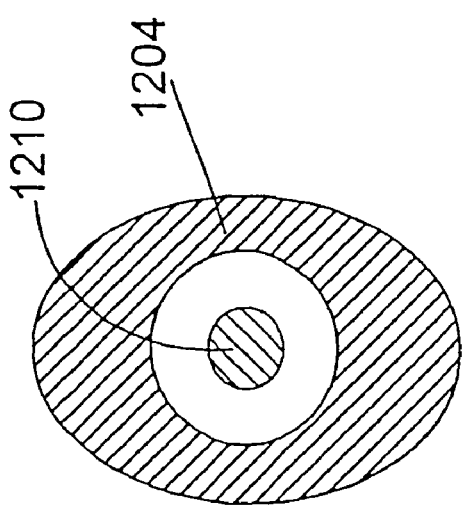
FIG. 126 depicts yet a further alternative embodiment of the invention depicted in FIGS. 119*a* and 119*b*.
Figure 125:
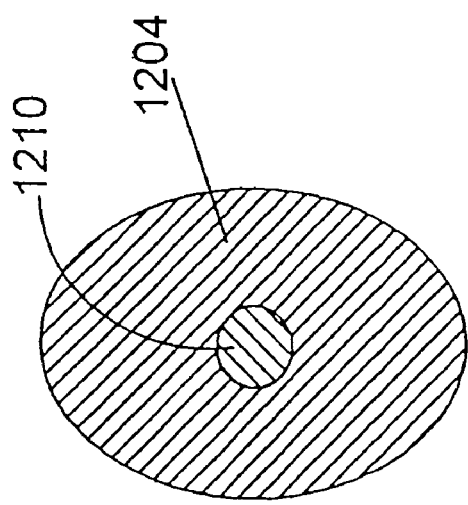
FIG. 125 depicts an alternative embodiment of the invention as depicted in FIGS. 119*a* and 119*b*.

Embodiments of FIGS. 125, 126, and 127

FIGS. 125, 126 and 127 depict three alternative embodiments of the invention as can be seen through a line parallel to line 124-124 of FIG. 119b.

In FIG. 125, the sleeve 1204 is rotatable about central body 1210. In this embodiment, however, the sleeve 1204 design does not include the grooves 1222 as previously depicted in the embodiment shown in FIG. 123a. Thus, without pins, the sleeve is completely free to rotate about the central body 1210.

An alternative embodiment is shown in FIG. 126. In this embodiment, the sleeve 1204 is essentially a thin wall cylinder which is spaced from the central body 1210. Sleeve 1204 is free to move relative to central body 1210. Sleeve 1204 can rotate relative to central body 1210. In addition, sleeve 1204 can take a somewhat cocked or skewed position relative to central body 1210.

A further embodiment, it is shown in FIG. 127. This embodiment is somewhat similar to the embodiment shown in FIG. 126 except that in this case, several pins project from the first wing in order to some what limit and restrict the motion of the sleeve 1204. As shown in FIG. 127, four pins are depicted. It is to be understood however that such an embodiment can include one, two, three, four or more pins and be within the spirit and scope of the invention. It is to be understood that if the embodiment is used with a second wing, that similar pins can extend from the second wing. However, in the embodiment using a second wing, the pins would preferably be somewhat flexible so that they could snap into the inside of the sleeve 1204 as the second wing is inserted relative to the central body and secured in place. In the embodiment shown in FIG. 127, the sleeve 1204 is free to rotate about the longitudinal axis of the central body 1210 and is somewhat restricted in this motion and its ability to become skewed relative to the longitudinal axis of the central body by the pins.

Figure 128:
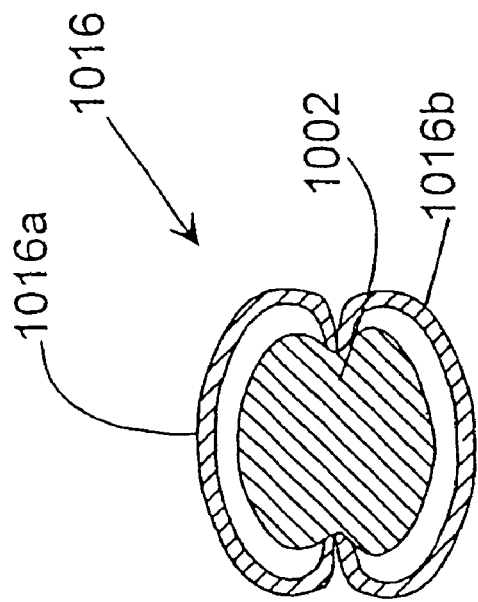
FIG. 128 is still a further embodiment of the invention as depicted in FIG. 93*a*.

Embodiments of FIGS. 128 and 129

The embodiments of FIG. 128 is an advantageous alternative to that of FIG. 93a. In this embodiment, the central body 1002 is similar to that as shown in FIG. 93a. The sleeve 116 is comprised of two sleeve portions 1016a and 1016b. The sleeve portions are preferably formed from flat stock material which is substantially easier to form than having the sleeve formed or machined from solid bar stock material. A further advantage of the sleeve 1016, if formed of super-elastic material, is that the sleeve can be formed in a manner which optimizes the super-elastic characteristics of such material in order to enhance its ability to repeatedly deflect under load. In this particular embodiment, the sleeve portions 1016a and 1016b are somewhat C-shaped and then after being formed, are snapped into the grooves of the central body 1002.

An alternative embodiment of the invention is shown in FIG. 128. This embodiment is most favorably used with the embodiment of FIGS. 119a and 119b. In this particular embodiment, the sleeve 1204 is designed to rotate about the central body 1210. Sleeve 1204 includes a central member 1230 which includes a bore that receives the central body 1210. The central member 1230 is rotatable about the central body 1210 of the implant 1200. The central member 1230 includes first and second grooves 1232 and 1234. These grooves can receive C-shaped sleeve members 1204a and 1204b. These C-shaped sleeve members are similar in construction and design to the C-shaped sleeve members shown above with respect to FIG. 128. These sleeve members can be snapped into position relative to the central member 1230 of the sleeve 1204. It is to be understood that other mechanisms can be used to secure the C-shaped sleeve member relative to the central member of the sleeve and be within the spirit and scope of the invention. Further, it is to be understood that the sleeve members 1204a and 1204b can be formed from a single flat stock material such that one of the grooves 1232 and 1234 receives continuous piece of flat material which has been appropriately bent and the other grooves receives two ends of the sleeve.

Embodiments of FIGS. 130-136

Figure 130:
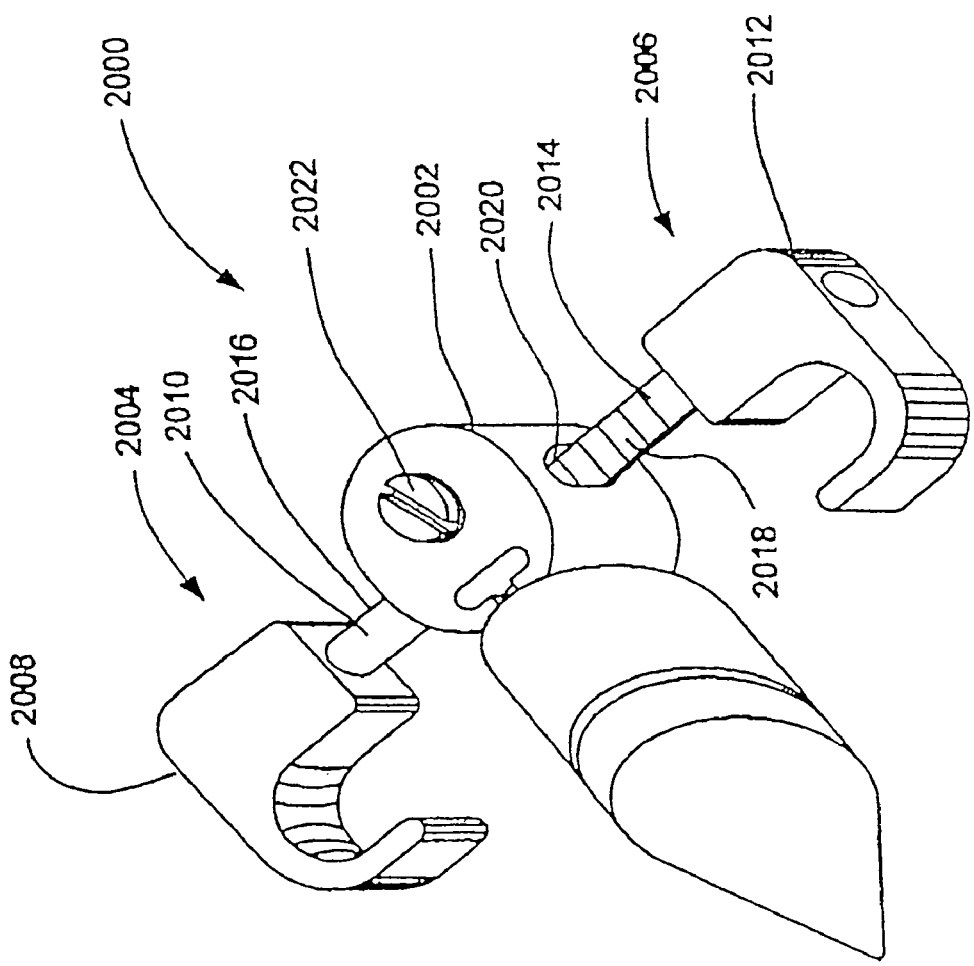
FIG. 130 is a perspective view of a first embodiment of the invention.
Figure 132:
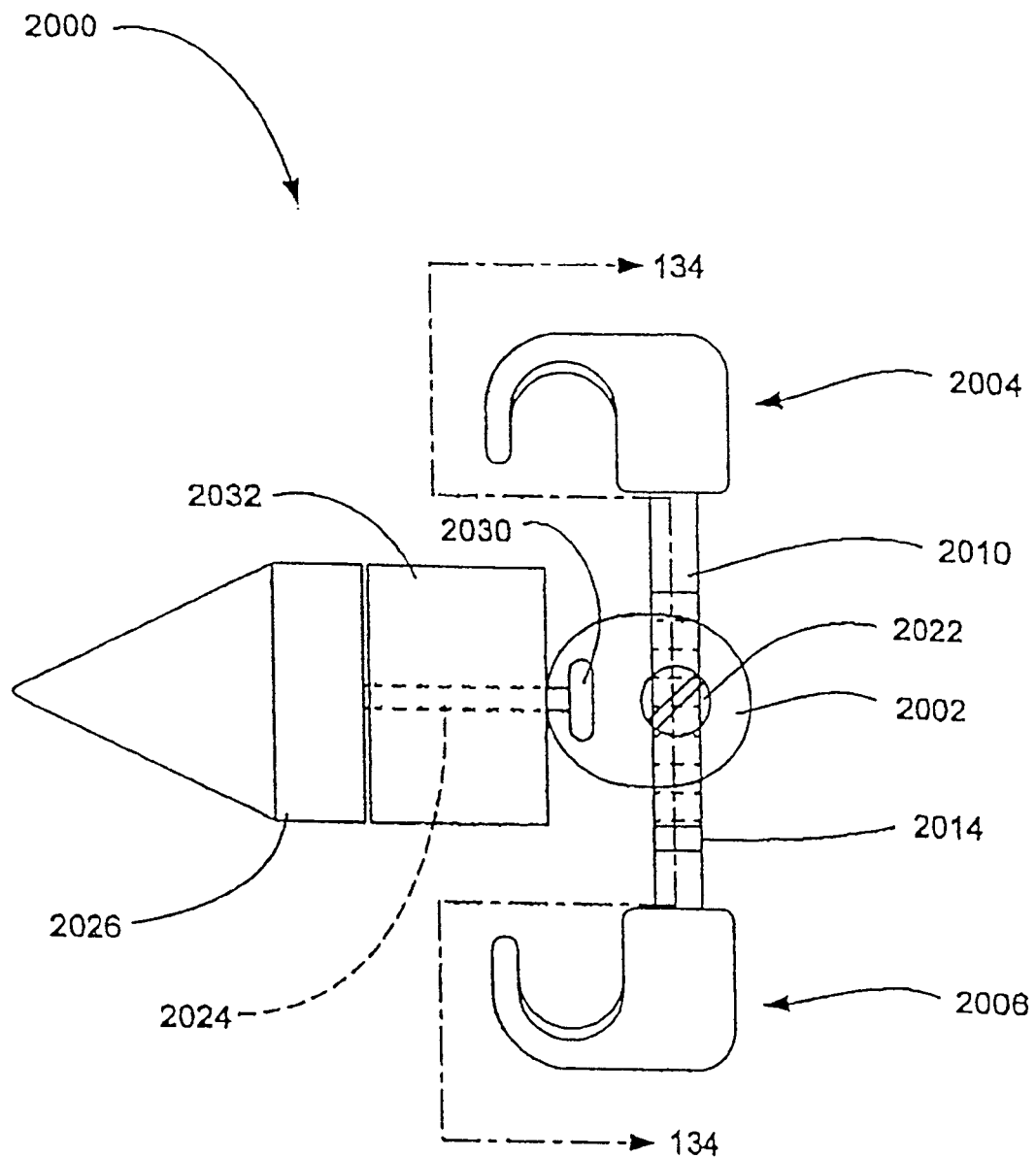
FIG. 132 is a plan view of the embodiment of the invention of FIG. 130.
Figure 133A:
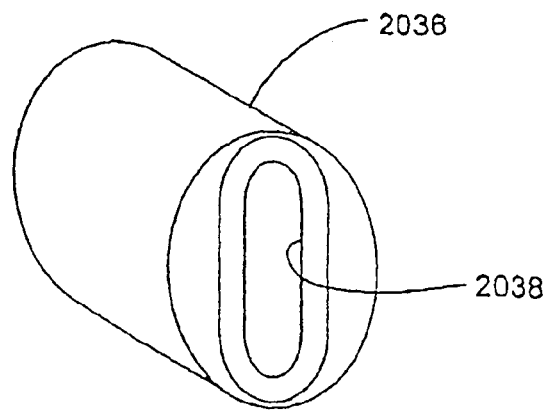
FIGS. 133*a*, 133*b*, 133*c*, and 133*d* are perspective, first end, second end, and sectional views of a spacer or sleeve of the embodiment of the invention depicted in FIG. 130.
Figures 133B, 133C:
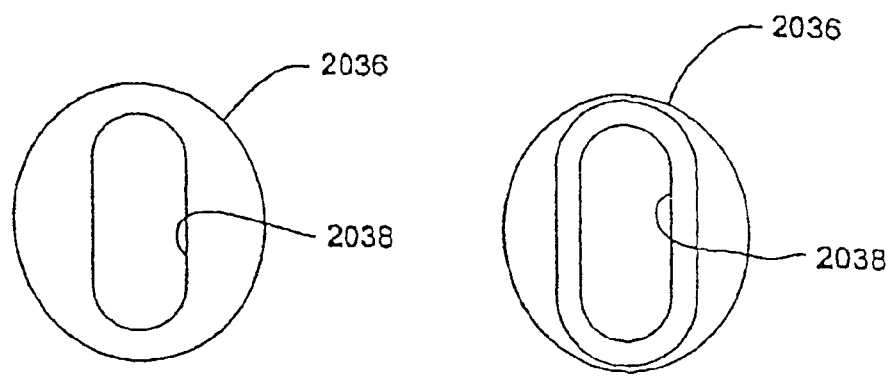
Figure 133D:
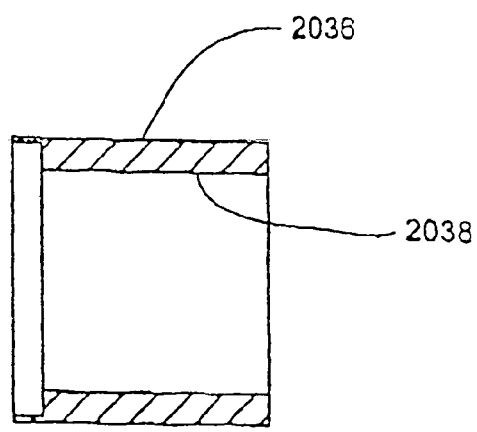
Figure 134:
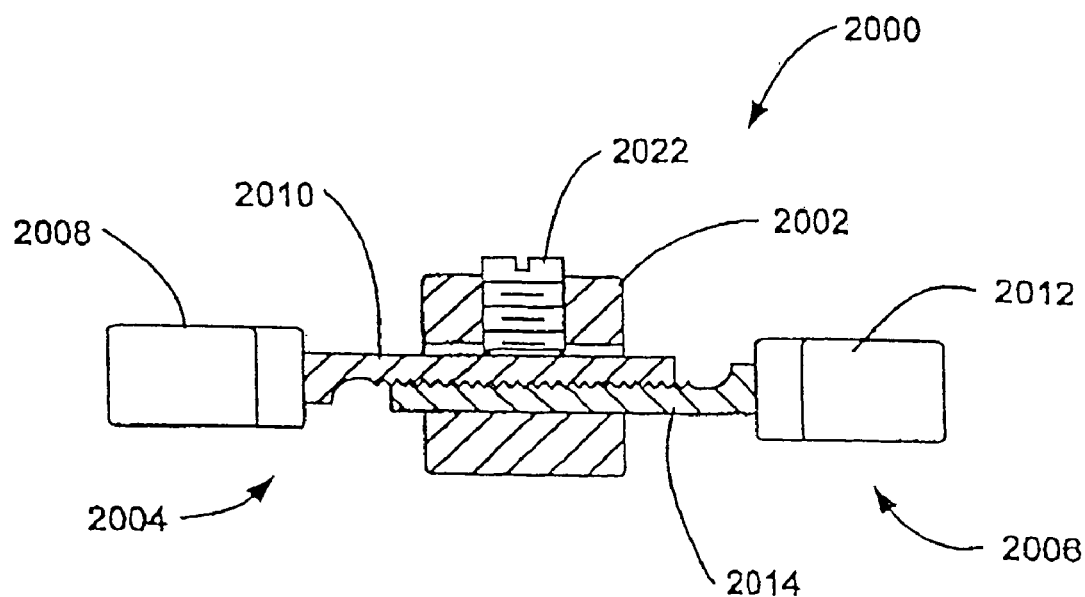
FIG. 134 is a cross sectional view of an embodiment of the invention taken through line 134-134 in FIG. 132.

Embodiment 2000 of the supplemental spine fixation device of the invention is depicted in FIG. 130. This embodiment 2000 includes a hub 2002 to which is adjustably secured a first hook member 2004 and a second hook member 2006. First hook member 2004 includes a hook 2008 which is more fully described hereinbelow, and a shaft 2010 extending therefrom. Similarly, second hook member 2006 includes a hook 2012 and a shaft 2014 extending therefrom. As described more fully hereinbelow, hook 2008 is swivelly or pivotably mounted to shaft 2010. It is to be understood that the description and functionality of first hook member 2004 applies equally well to that of second hook member 2006. The shaft 2010 in this embodiment includes a rack 2016 which can mate selectively with rack 2018 of hook member 2006. These two racks 2016 and 2018 interlock in a multitude of positions in order to adjust the position of first and second hook members 2004 and 2006, relative to each other and relative to the hub 2002. The shafts 2010 and 2014 are positioned through bore 2020 in the hub 2002, selectively interlocked together and are then lockingly positioned using a locking mechanism such as the screw 2022. As is described more fully below, the hooks 2008 and 2012 are designed and shaped to fit around spinous processes. Further, the hooks 2008 and 2012 are swivelly mounted to the shafts 2010 and 2014 in order to accommodate the various sizes, shapes, and positions of spinous processes of the human population.

Movably mounted to the hub 2002 is a shaft 2024 (FIG. 131) and extending from the shaft 2024 is an inter-spinous process guide 2026. The shaft 2024 at a proximal end includes a crossbar or tab 2028 which is slidingly or movingly received in a slot 2030 of the hub 2002. Once the tab 2028 is received in the slot 2030, the slot can be pinched off or slightly deformed at its open end using a punch or other mechanism in order to prevent the tab 2028, and thus the shaft 2024 and the guide 2026 from being removed from the hub 2002. With the tab 2028 located in the slot 2030, the shaft and also the guide 2026 extending from the distal end of the shaft 2024 are free to move relative to the hub and also relative to the first hook member 2004 and the second hook member 2006. This movement, as well as the ability of the hooks 2008 and 2012 to swivel on the shafts 2010 and 2014, allow the embodiment 2000 to conform to the spinous process anatomy.

Movably mounted on the shaft 2024 is a spacer or sleeve 2032. Spacer 2032 includes a central bore 2034 through which the shaft 2024 extends. The spacer 2032 is thus able to rotate about the shaft 2034. The spacer 2032 is cylindrical and in this particular embodiment is oval or elliptical in shape. In addition, the base of the guide 2026 is also somewhat elliptical in shape in order to make a smooth transition between the guide 2026 and the spacer 2032 as the guide and spacer are inserted between the spinous processes in order to distract apart the spinous processes during the insertion process. When the spacer 2032 is fully inserted between the spinous processes, the spacer 2032 extends through the sagittal plane defined by the adjacent spinous processes. As the spacer 2032 is rotatable on the shaft 2024, and as the spacer 2032 is elliptically shaped, it can be inserted in one position and then as the entire embodiment 2000 is positioned to the final securing position, the spacer 2032 can rotate about the shaft 2024 to accommodate the shape of the space between the spinous processes as the spacer is moved from a posterior position to an anterior position.

The spacer 2032 can include a second alternative spacer embodiment 2036 (FIG. 131a) in substitution for the spacer 2032. Spacer 2036 includes an elongated slot 2038 into which the shaft 2024 can be received. Elongated slot 2038 not only allows the spacer 2036 to rotate about the shaft 2024, it also allows it to translate relative to shaft 2024. Such translation in this embodiment is substantially perpendicular to the shaft, in any direction to which the spacer 2036 is rotated. Thus, in this embodiment the degrees of freedom which accommodate the anatomical shape of the spinous processes and the space therebetween, including the ligaments and tissues associated therewith, include (1) the ability of the hooks 2004, 2006 to swivel on the shafts, (2) the ability of the hooks 2004, 2006 to move relative to the hub 2002 and be locked to the hub, (3) the ability of the shaft 2024 to move in the slot 2030 of the hub, and (4) finally the ability of the spacer 2036 to both rotate and translate on the shaft 2024.

Before proceeding to more specific details of this embodiment 2000, it is to be understood that the same features of the spacer, the shaft, and the lead-in guide, which are found in other embodiments such as by way of example only, the embodiments of FIGS. 10, 16, 20, 22, 86, 88, 92, and 119b, and other figures, can be incorporated into this embodiment. By way of example only, the implant 2000 can be comprised of stainless steel, titanium or other biologically acceptable materials. The shape of the lead-in plug can be cone shaped, pyramid shaped, and other shapes with a small lead-in cross-section expanding into a larger cross-section which is similar to the cross-section of the spacer 2032, in order to gradually distract apart the spinous processes to a sufficient distance so that the spacer 2032 or the spacer 2036 can conveniently fit between the spinous processes. Further, the spacer, as shown in the other embodiments, can include a spacer made of stainless steel or titanium, or of a super-elastic material or of a silicone. The spacer besides being cylindrical can, from parallel planar end 2040 to parallel planar end 2042, be saddle-shaped along surface 2041 so that the ends are high and the center portions are low in order to more fully accommodate the shape of the spinous processes and also to spread the load across a broader contact surface between the spinous processes and the spacer. For example, the spacer 2032 could have a shape such as the saddle shape defined by the mated together components of the embodiment of FIG. 16. Further, the dimensions of this embodiment as applied to the guide 2006 and the spacer 2032 can be acquired from other embodiments presented herein.

The shape of the guide 2026 and the spacer 2032 is such that for purposes of insertion between spinous processes, the spinous processes to do not need to be altered or cut away in any manner in order to accommodate this implant. Further, the associated ligaments do not need to be cut away and there would be very little or no damage to the other adjacent and surrounding tissues. Similarly, the hook members 2004, 2006, are appropriately shaped and also pivotable so that alteration of the spinous process is not required.

Returning to FIGS. 135a-135f and FIG. 136, the design of the hook members 2004 and 2006 are more fully depicted and described. As indicated above, the description will be made with respect to first hook member 2004. This description applies equally to second hook member 2006. As can be seen in FIG. 135b, the first hook member 2004 includes a shaft 2010 which is received in a bore 2044 of the hook 2008. This bore receives a rounded ball end 2046 seated against a somewhat circular seat 2048. A screw 2050 (FIG. 135f) is received in the bore 2044 in order to retain the rounded ball end 2046. The other end of the bore 2044, end 2052, as can be seen in FIG. 135f is oval or elliptical in shape. This allows the hook 2008 to swivel side to side on the shaft 2010 in order to accommodate the spinous process while somewhat restricting the back and forth rocking of the hook 2008 relative to the shaft 2010. This freedom of motion can be seen in FIG. 136 with respect to the upper spinous processes 2054. The hook can swivel side to side in order to accommodate the shape of the upper spinous processes 2054. The lower hook 2006 additionally can move in order to accommodate the lower spinous processes 2056. As can be seen in FIGS. 135c and 135d, the hook 2008 can swivel about 15° on either side of a central longitudinal axis of the shaft 2010.

Figure 135A:
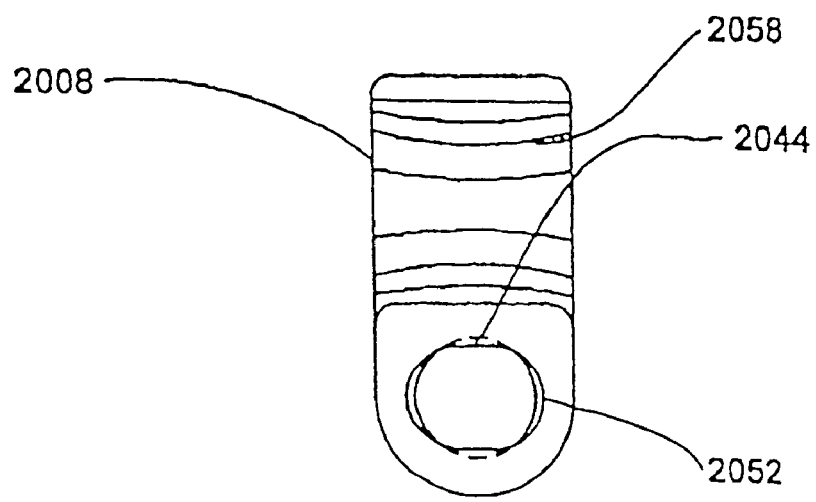
FIGS. 135*a*-135*f* are various views of an embodiment of the hook mechanism of the embodiment of the invention of FIG. 130.
Figure 135B:
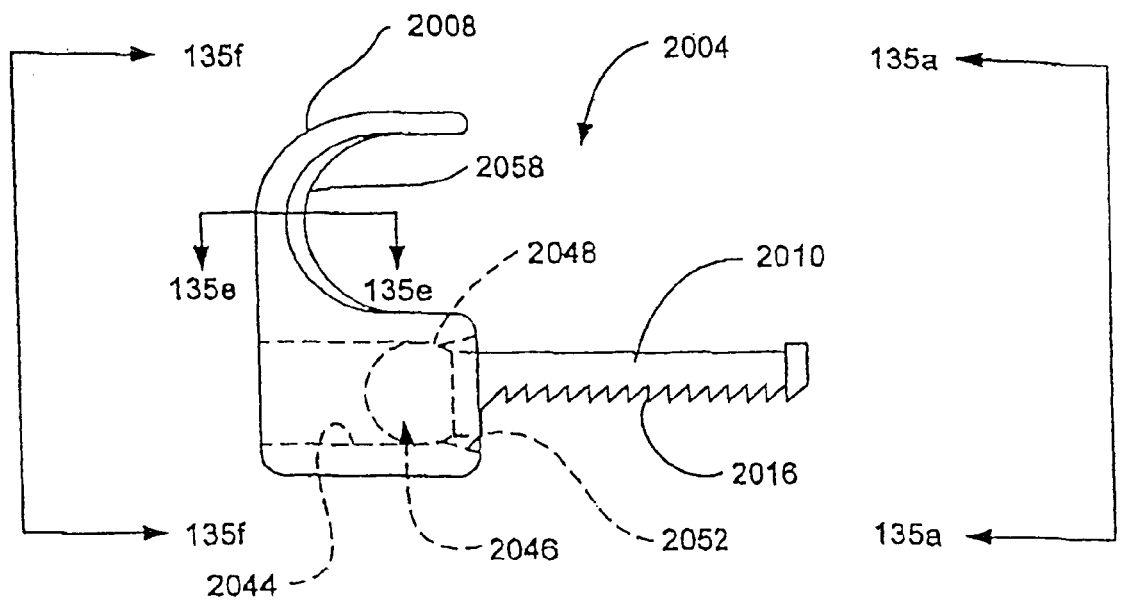
Figure 135C:
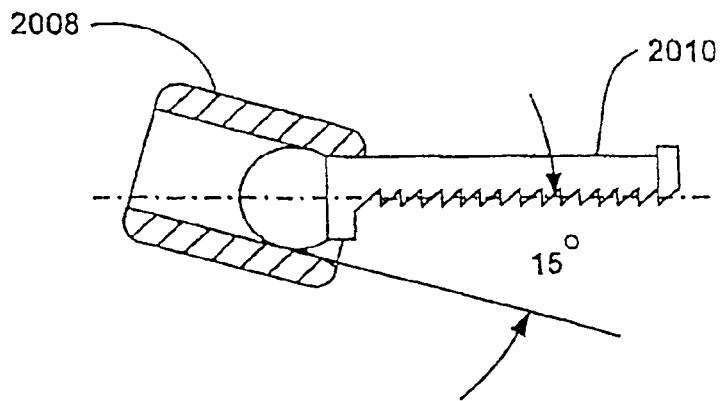
Figure 135D:
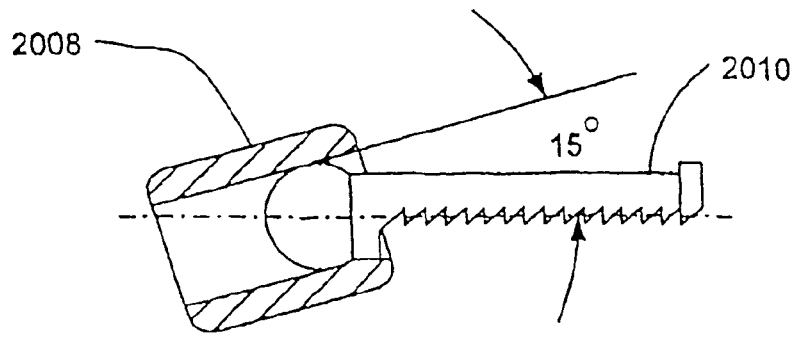
Figure 135E:
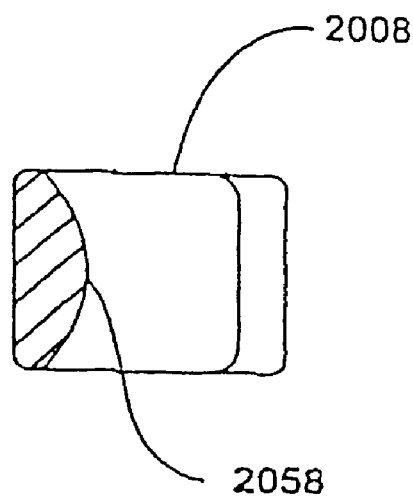
Figure 135F:
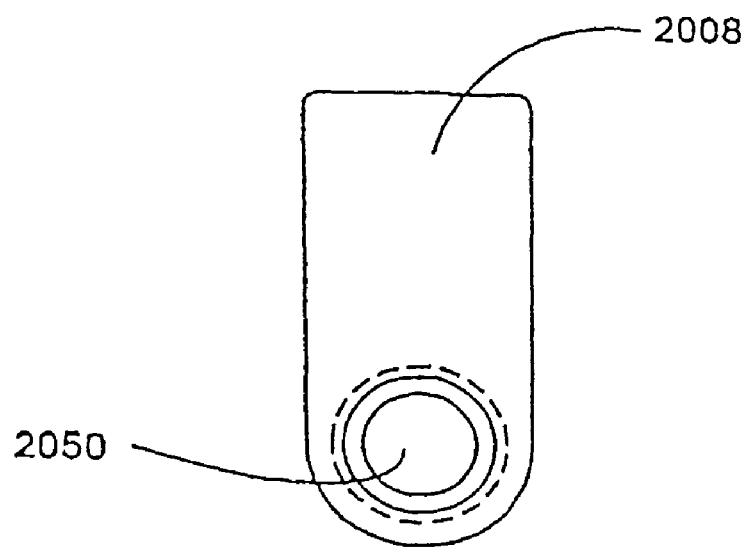

Additionally with respect to the hook 2008, as can be seen in FIGS. 135a, 135b, and 135e, the hook includes a convex inner surface 2058 in order to accommodate the varying surface shape of the spinous processes, and in order to even out the load transferred between the hook and the spinous processes.

Figure 136:
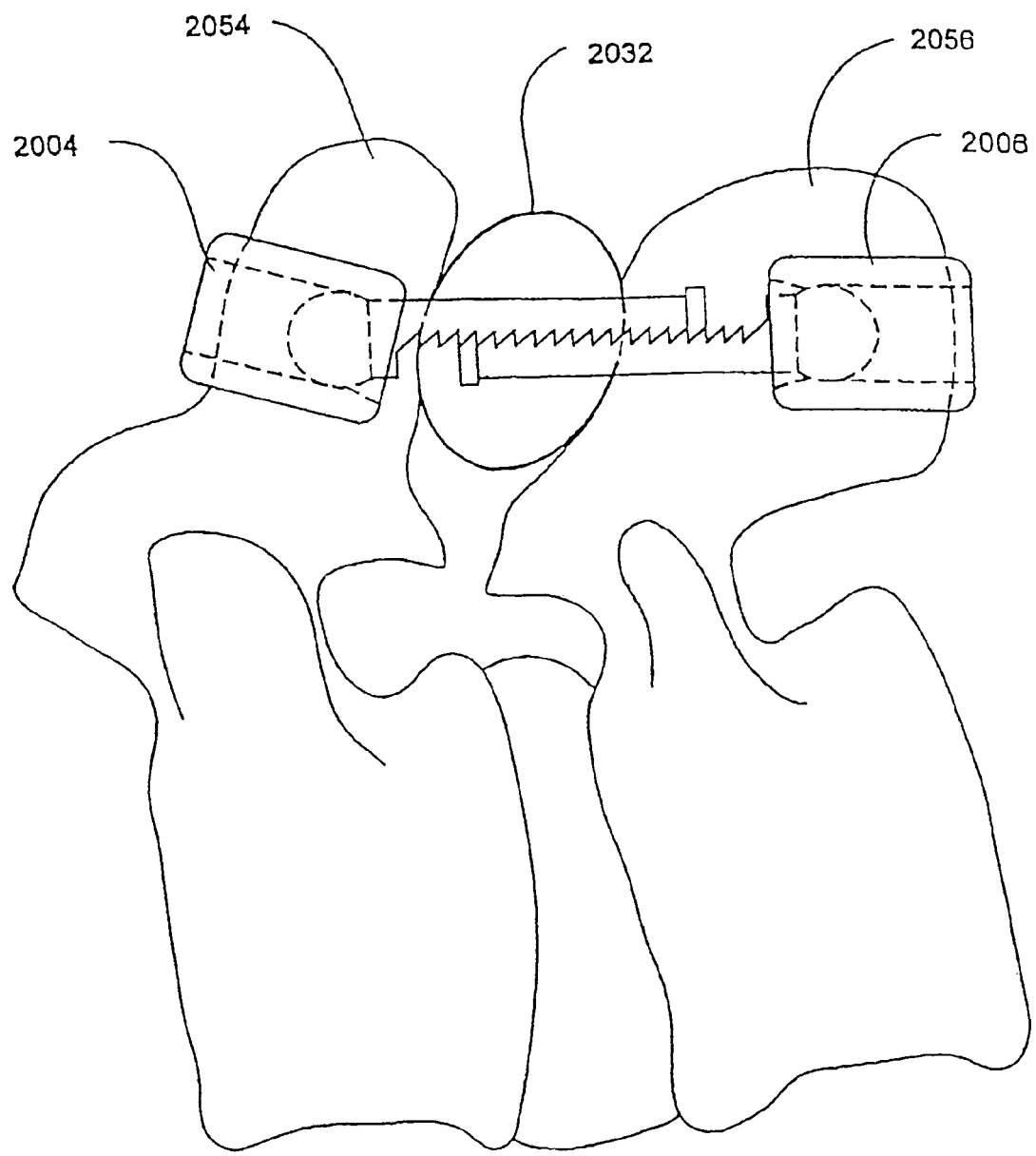
FIG. 136 is a schematical representation of an embodiment of the invention as positioned with respect to adjacent spinous processes.
Figure 137:
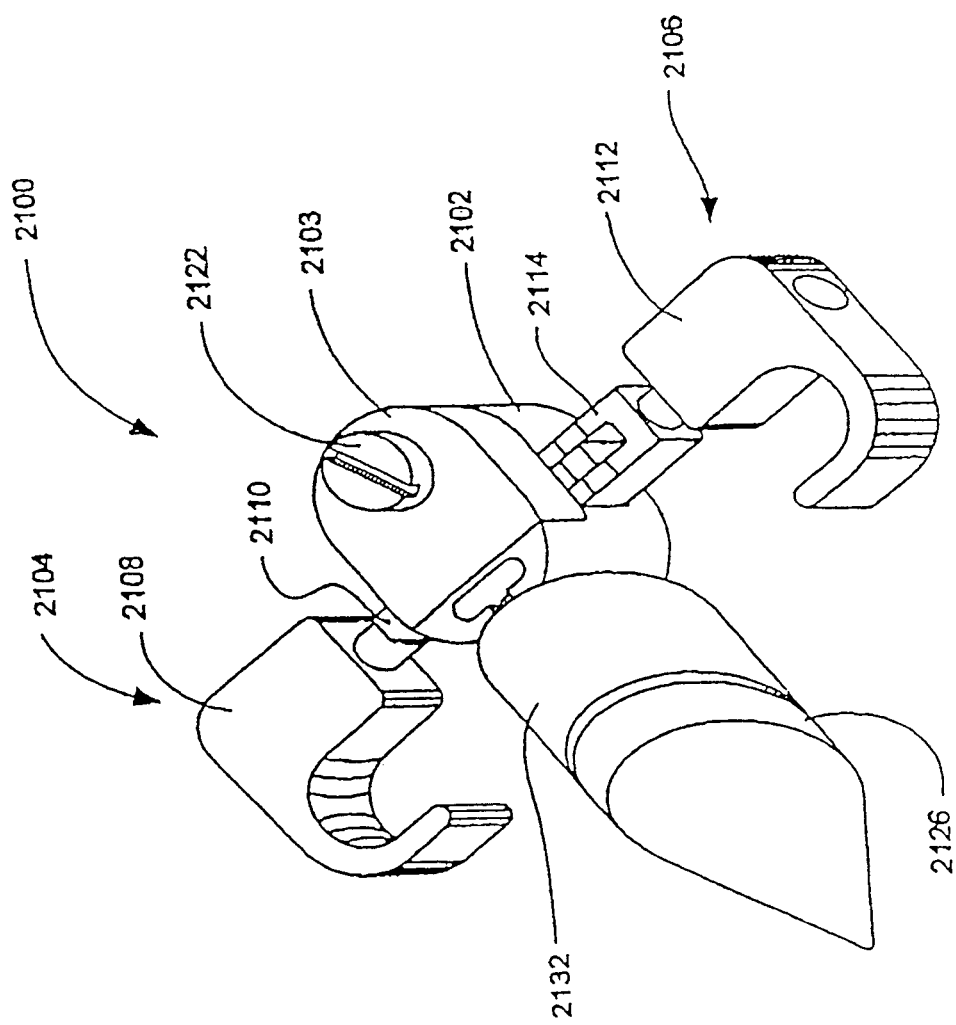
FIG. 137 is a perspective view of another embodiment of the invention.

The embodiment 2000 can be implanted in a number of methods, preferably, once a spine fixation device is implanted between the vertebral bodies. In this particular embodiment, through a small incision the hub, spacer, and guide are inserted with the guide and spacer inserted between the spinous processes. Once this is accomplished, a first hook member and then a second hook member is secured about the respective spinous processes. The shafts of the hook members are then inserted through the bore of the hub 2002 until the spinous processes are brought tight against the spacer. The hooks are appropriately positioned on the spinous processes as depicted in FIG. 136. After this has been accomplished, the securing mechanism 2022 is tightened in order to lock the hooks in place and to secure the spinous processes in a rigid manner relative to each other and relative to the distracting spacer 2032. Alternatively, the spinous ligaments can hold the spinous processes tightly against the spacer and the hooks can be moved and locked into tight contact with the spinous processes.

The above procedure can have variations. By way of example only, the hooks can be inserted first through the incision and then the guide, spacer and hub can be inserted. Once this is accomplished the hooks can be mated to the hub.

In another embodiment and method not depicted, the physician can insert the shaft 2024 on which the spacer 2032 is mounted into the slot 2030 of the hub 2002 and can close off the slot with a securing screw in order to retain shaft 2024. This process is in contrast to the shaft being secured in the slot during the manufacturing process. The securing screw would be similar to securing screw 2022 and would be placed in a bore made at the top of slot 2030. The physician could accordingly insert the tab 2028 of the shaft 2024 in the slot 2030, and then secure the tab in place with the securing screw.

Still an alternative method would be for the device 2000 to be inserted through a larger incision, with device 2000 fully assembled. Once inserted the screw 2022 could be loosened so that the hook members could be positioned around spinous processes at about the same time that the guide and spacer are inserted between the spinous processes. Once this is accomplished, the spinous processes could be drawn down tightly around the spacer, with the hooks tightly around the spinous processes and secured firmly into the hub 2002 with the securing screw 2022.

In all of the above procedures, it is advantageous that the device 2000 can address the adjacent spinous processes from one side of the spinous processes and not require exposure of both sides of the spinous processes and thus the procedure is less traumatic to the surgical site.

Still an alternate insertion method would be to insert the device fully assembled with the hook rotated at 90° to the final position shown in FIG. 130. Once the hooks are positioned adjacent to the spinous processes, the hooks could be rotated to the position shown in FIG. 130. Then simultaneously the guide and spacer could be inserted between the spinous processes, as the hooks are positioned about the spinous processes. The hooks are then drawn together, causing the spinous processes to be held firmly against the spacer. Once this is accomplished the screw 2022 can be securely fastened to the hub 2002.

With respect to the embodiment of FIG. 130, this embodiment as fully described above can be used as a supplemental fixation or augmentation device for the lumbar level fusion of the L4/L5 vertebrae and above vertebrae, and also for the L5/S1 and below vertebrae. Thus, this device 2000 can be used with respect to fusion of any of the vertebrae up and down the spinous processes.

Embodiments of FIGS. 137-140

Figure 138:
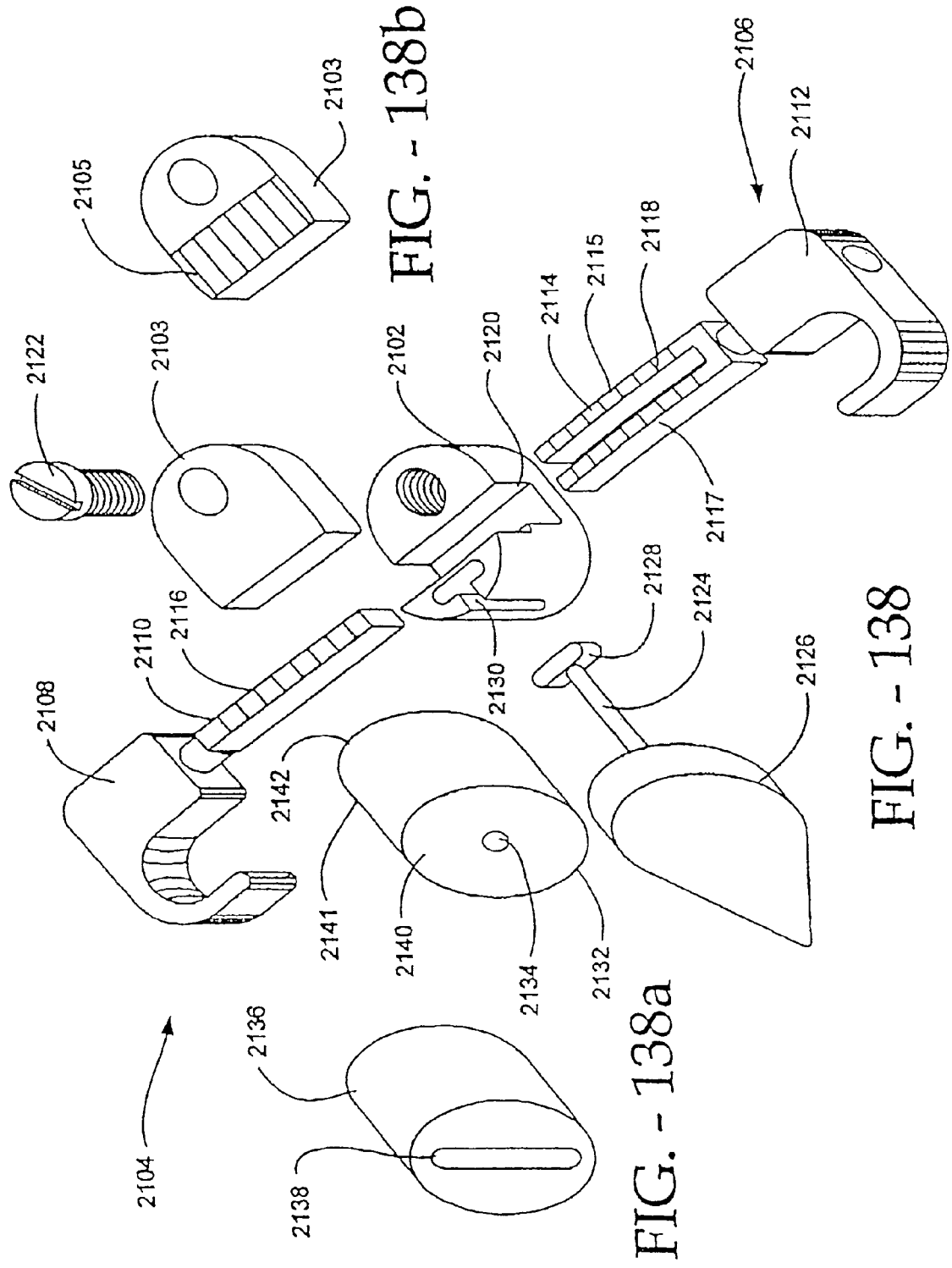
FIG. 138 is an exploded view of the embodiment of the invention of FIG. 137.
Figure 139:
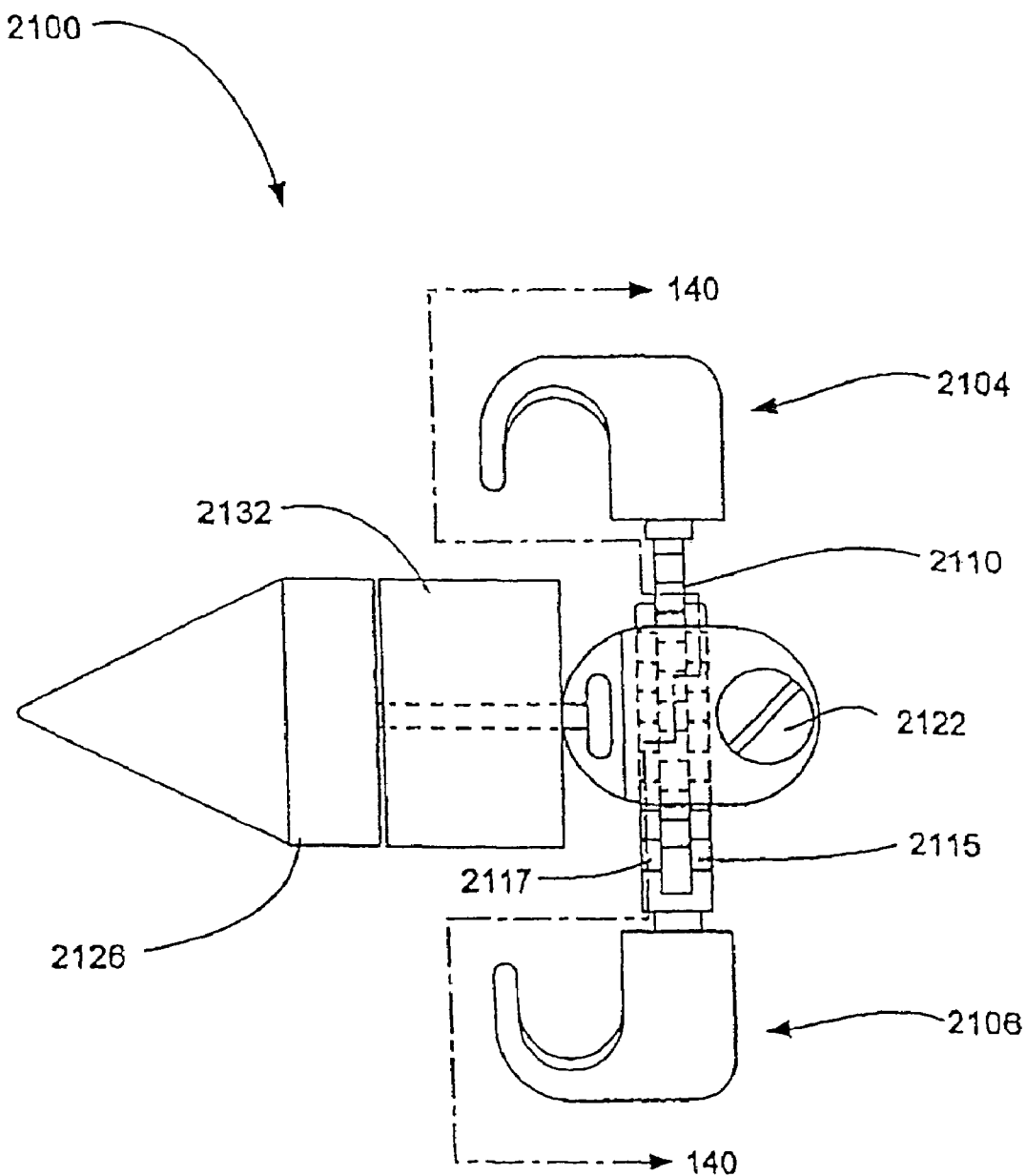
FIG. 139 is a plan view of the embodiment of the invention of FIG. 137.
Figure 140:
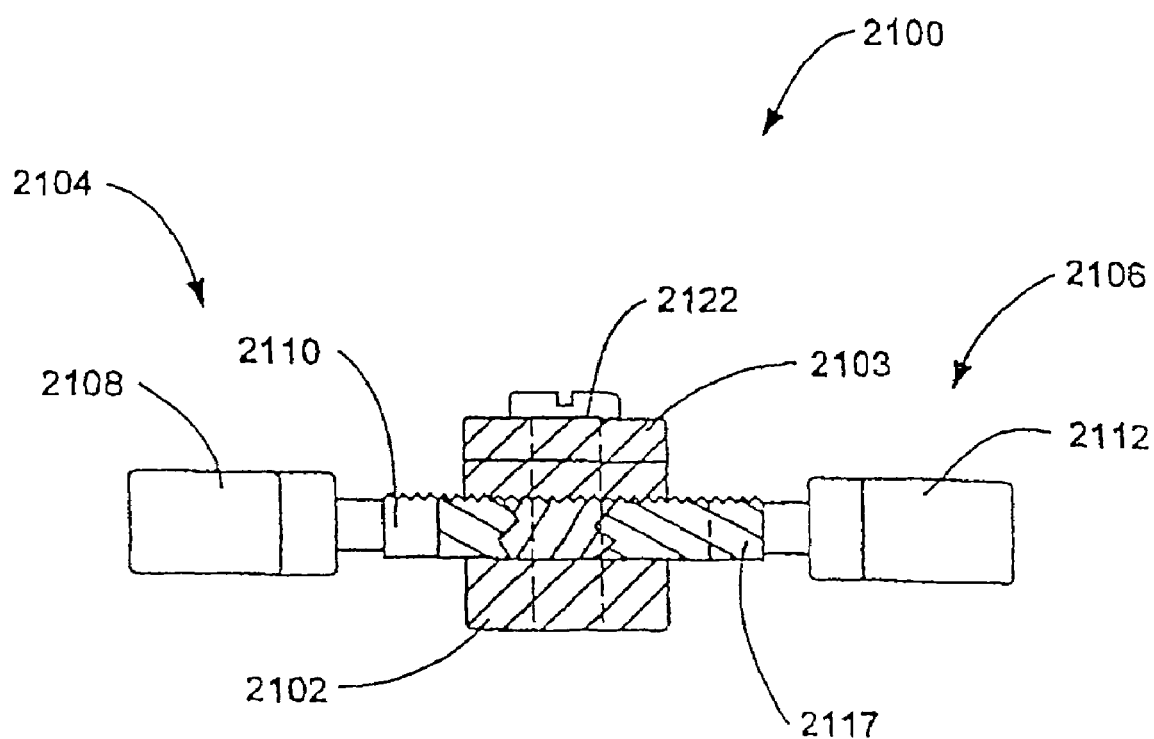
FIG. 140 is a partial section view taken through line 140-140 of FIG. 139.

Another embodiment 2100 of the invention can be seen in FIGS. 137-140. Components and features of this embodiment 2100 which are similar to components and features of the embodiment 2000 have similarly least significant digits. Thus the hub for embodiment 2100 would be 2102. The main difference between the embodiment 2100 and the previously described embodiment 2000 is directed to the hub 2102 and the shafts 2110 and 2114. In this embodiment, the shafts 2110, 2114 are substantially rectangular in cross-sections as opposed to semi-circular as in the previous embodiment of FIG. 130. As can be seen in FIG. 138, shaft 2110 is substantially rectangular in cross-section and include rack or teeth 2116. Shaft 2114 is shaped as a fork with two tines 2115 and 2117. Further, the two tines have rack or teeth 2118. The shaft 2110 of the first hook member 2104 slides between the two tines 2115 and 2117. As can be seen in FIG. 139, with the shaft 2110 slipped between the two tines 2115, 2117 and also with shafts 2110, 2114 located in the rectangular bore 2120 of the hub 2102, the top cap 2103 (which is shown both from the top side (FIG. 138) and from the bottom side (FIG. 138b)) can be placed over the hub 2102. The teeth or rack 2105 on the bottom side of the cap 2103, mesh with the teeth or rack 2116 and 2115, 2117 of the first and second hook members. Once this is accomplished, the screw 2122 can be inserted through the indicated bore so that the cap 2103 can tighten down on the hub 2102, locking the shafts 2110 and 2114 of the first and second hook members in place.

All the other features, dimensions, characteristics, materials, methods of insertion, and methods of operation of the embodiment shown in FIG. 138 are similar to or derivations from that shown in the embodiment of FIG. 130.

Figure 141:
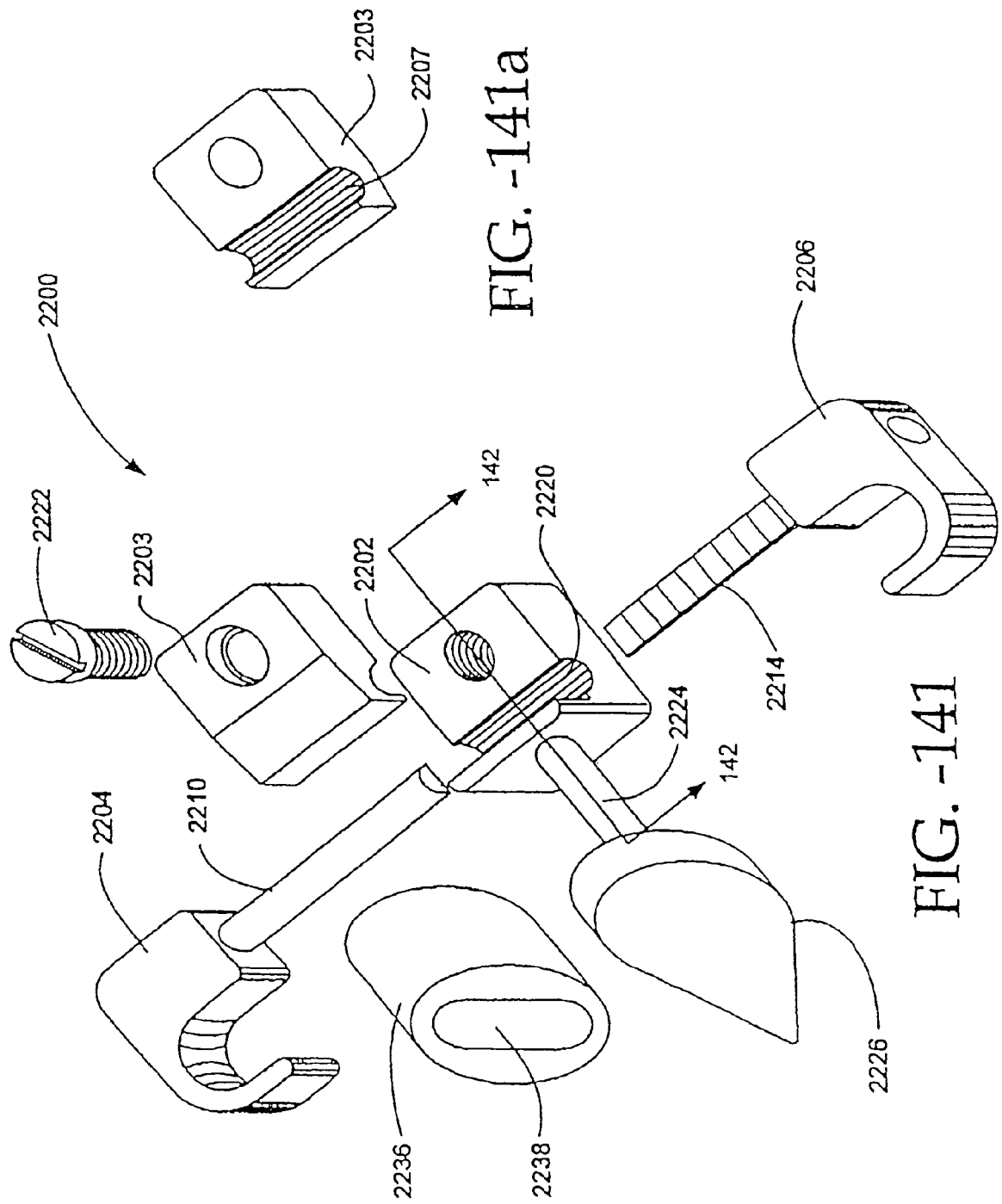
FIG. 141 is an exploded view of yet another embodiment of the invention.
Figure 142:
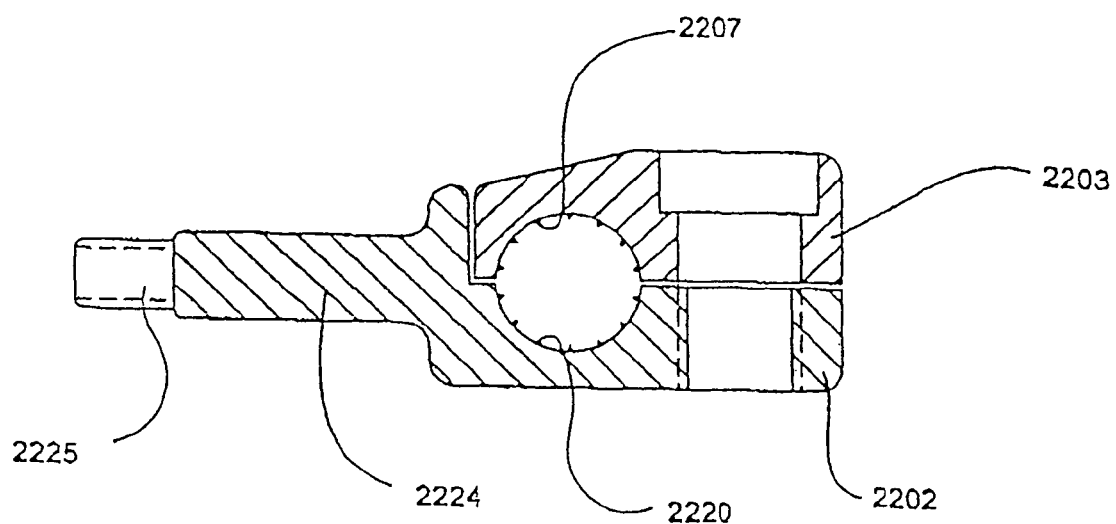
FIG. 142 is a sectional view of a body portion of the embodiment of the invention of FIG. 141 taken through line 142-142.
Figure 143:
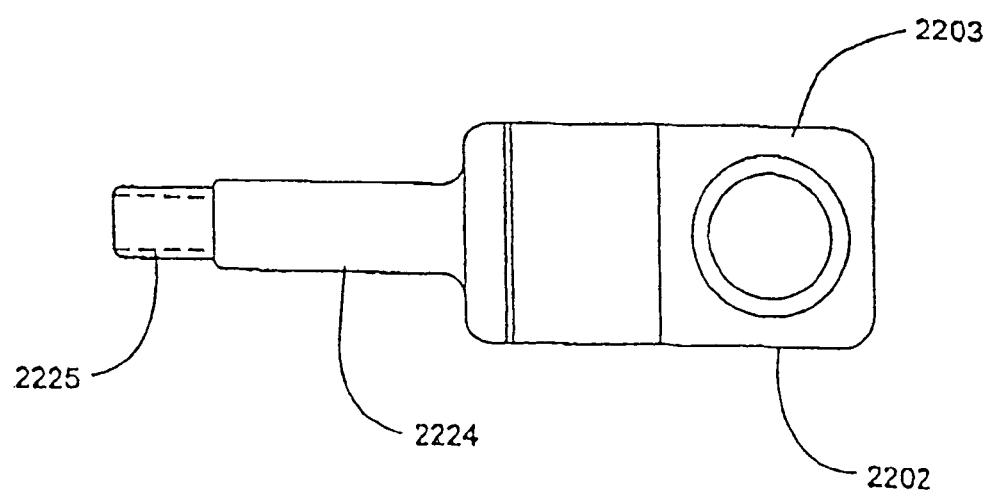
FIG. 143 is a top view of the body portion shown in FIG. 142.

Embodiments of FIGS. 141-143

Another embodiment of the invention is depicted in FIGS. 141-143. This embodiment is similar to the other embodiments 2000 and 2100. This embodiment is numbered 2200. Similar elements, features, methods and aspects have similar numerical designations with respect to the lowest two significant digits. Thus the hub of embodiment 2200 is identified as hub 2202.

In this particular embodiment, the hub has rigidly affixed thereto shaft 2224. Here shaft 2224 does not slide in a slot as happens with respect to the prior two embodiments 200 and 2100. Shaft 2224 can be screwed into hub 2202 or integrally formed with hub 2202. Additionally, the guide 2226 can be integrally formed with the shaft 2224 or in other manners fastened to the shaft 2224 as with a thread mechanism. In this particular embodiment, as can be seen in FIG. 143, the shaft 2224 is integrally formed with the hub 2202 and the shaft 2224 includes a threaded extension 2225 onto which is screwed the guide 2226. For this particular embodiment, the sleeve or spacer 2236 includes the elongated slot 2238 in order to provide for freedom of movement between the sleeve or spacer 2236, the hub 2202, and the first and second hook members 2204 and 2206.

In this particular embodiment the shaft 2210 and 2214 are similar to those depicted with respect to the embodiment 2000. In other words each has a rack or teeth which mate with the other. Shafts 2210 and 2214 are inserted through the semi-circular bore 2220 of the hub 2202, and then the cap 2203 is mated on top of the hub 2202. The cap includes a semi-circular bore 2207 which is positioned over the upper shaft 2210. Both bores 2207 and 2220 include ribs, teeth, or threads that run along the length of the bores. These ribs, teeth, or threads are urged against the shafts in order to assist in locking the shafts in place. Alternatively, the ribs, teeth, or threads of the bores can be across the length of the bores. The shafts 2210 and 2214 can have teeth, ribs, or threads that are positioned all about the shafts so that the shafts can lock to each other, and so that the teeth, racks or threads on the bores can lock the shafts in place. Once the cap 2203 is positioned over the hub 2202, the screw 2222 is positioned in the bore of the hub 2202 in order to lockingly position the first and second hook members 2204 and 2206 relative to the hub. In particular, with respect to embodiment 2200, the degrees of freedom are attributable to (1) the slot 2238 in the spacer 2236, (2) the shafts 2210 and 2224 which can be positioned relative to each other to position the hooks 2204 and 2206 relative to the hub, and accordingly relative to the spacer, and (3) the ability of the hooks 2204 and 2206 to swivel or pivot.

As indicated above, all the other features, materials, aspects, dimensions, and so forth, of the embodiment 2200 are similar to and can be specified according to the other embodiments 2000 and 2100.

A preferred method of insertion of this embodiment 2200 into a patient is as follows. Initially through a small incision the guide, spacer and hub are inserted so that the guide is positioned between and distracts apart adjacent spinous processes, allowing the spacer to come between the spinous processes. The spacer and guide can be moved in a posterior to anterior direction, and the spacer is able to rotate and translate in order to accommodate such movement. After this is accomplished, the first and second hook members are positioned through the incision and around upper and lower spinous processes. Once that is accomplished, the spinous processes are urged towards each other and about the spacer, if this is not already the condition caused by the insertion of the spacer in order to distract the spinous processes. Then the racks of the shafts are meshed together, and the cap is placed upon the hub in order to secure the hooks firmly to the hub and thus to secure the spinous processes rigidly in position about the spinous processes.

Embodiments of FIGS. 144-146*c*

Figure 144:
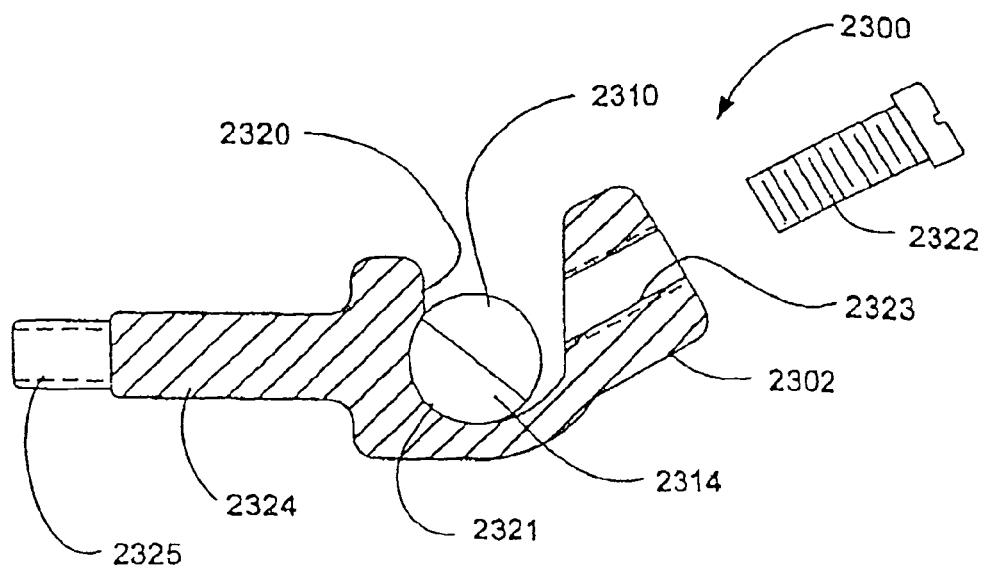
FIG. 144 is a sectional view of yet another embodiment of a body portion of the invention.

A further embodiment 2300 of the invention is depicted in FIG. 144. In FIG. 144, the hub 2302 of this embodiment is depicted. This hub could be used, for example, with the embodiment shown in FIG. 141 and similar components are similarly numbered. In this embodiment, the hub 2302 includes an integral shaft 2324 with a threaded end 2325 which can accept a guide such as guide 2226 of FIG. 141. Unlike the embodiment in FIG. 141, this hub 2203 does not have a cap. Instead hub 2302 includes an open bore 2320 which is shaped in order to receive shafts 2310 and 2314, which have mating notches or teeth. Bore 2320 has a portion 2321 which is circular and which receives the mated shaft 2310, 2324.

Once this is accomplished, a screw 2322 is received in the threaded bore 2323 in order to lockingly position the mated shafts 2310, 2324. As this embodiment has an open bore 2320 and no cap, mating of the shafts 2310, 2314 to the open bore 2320 of the hub 2302 can be done quickly and efficiently.

Figure 145:
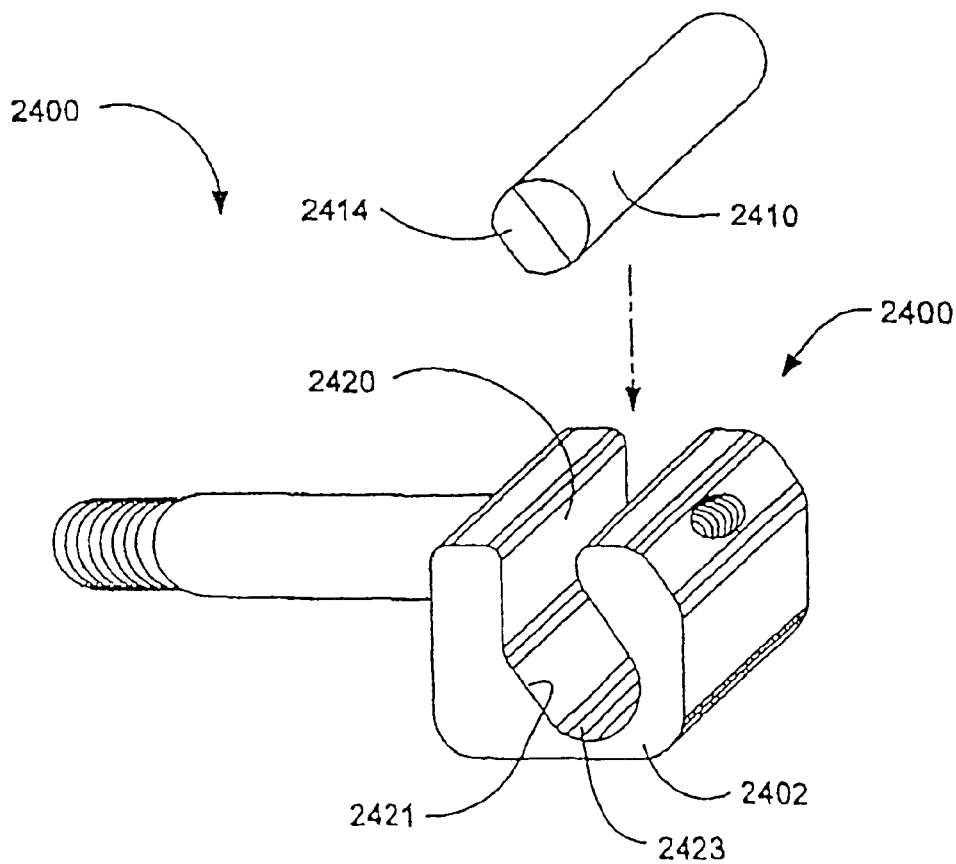
FIG. 145 is a perspective view of yet a further embodiment of the body portion of the invention.

FIG. 145 shows a hub 2402 of an embodiment 2400. This hub 2402 is similar to hub 2302, with the open bore 2420 having a shape which is different from the shape of bore 2320. In this embodiment bore 2420 includes a flat 2421 and a circular portion 2423. The shafts 2410 and 2414 when mated together would register in this open bore 2420. In particular, shaft 2414 has a flat which mates to flat 2421 and the combined shafts 2410 and 2424 have a circular portion which would mate to the circular portion 2423 of the bore 2420. Otherwise, hub 2202 would function similarly to hub 2302.

Figure 146A:
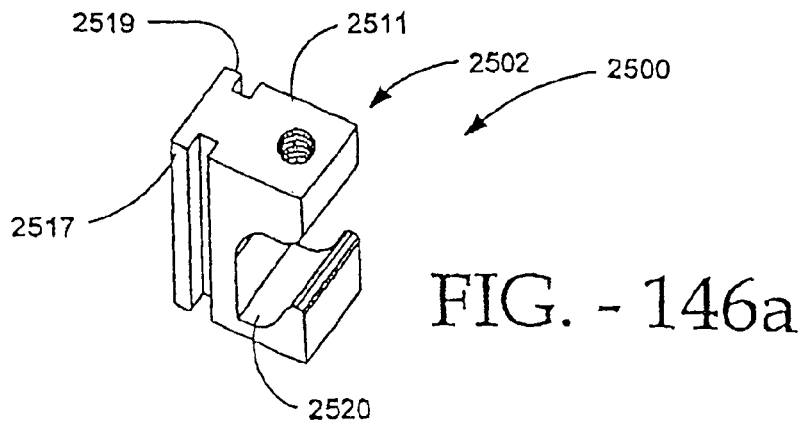
FIGS. 146a, 146b, and 146c depict yet a further embodiment of a body portion of the invention.
Figure 146B:
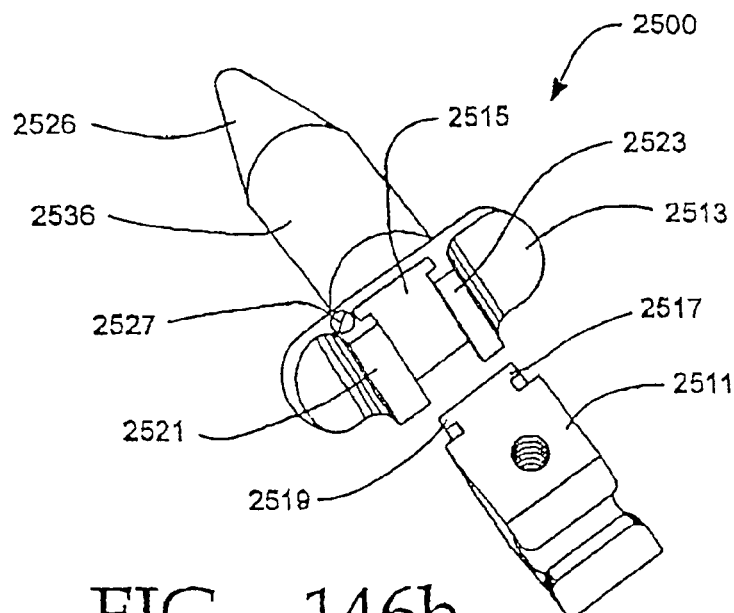
Figure 146C:
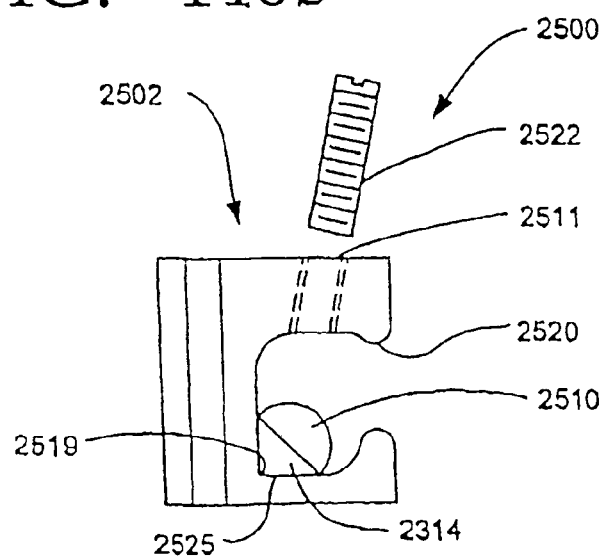

FIGS. 146*a*, 146*b*, and 146*c* depict a hub arrangement 2502 of an embodiment 2500 of the invention. In this embodiment, hub 2502 has two components 2511 and 2513. Component 2511 includes an open bore 2520 which is specially shaped in order to register shafts 2510, 2514 of the first and second hook members. In this particular embodiment, shaft 2510 is semi-circular in cross-section while shaft 2514 is triangular-shaped in cross-section. The triangular shape of shaft 2514 mates with the corner 2525 of the open bore 2520. The term open bore refers to 2520 and also to bores 2320 and 2420 in FIGS. 144 and 145, and means that not only are both ends of the bore open, but there is a longitudinal slot along the length of the bore which is open, allowing access to the bore from the side of the bore. Once the shafts 2510, 2514 are inserted as shown FIG. 146*c*, a screw 2522 can be tightened through a bore of the hub 2502, locking the shafts in place. Once this has occurred, the first portion 2511 of the hub 2502 can be mated into the second portion 2513 of the hub 2502. In this embodiment, the second portion of the hub 2513 includes a slot 2515 into which can be slid or snapped into the first portion 2511. The first portion 2511 includes tangs 2517 and 2519 which fit under lips 2521, 2523 respectively as the first portion 2511 of the hub 2502 is slid or alternatively snapped into engagement with the second portion 2513. Once this occurs, a locking cam 2527 is turned in order to cause a cam member to be urged against this portion 2511 of the hub in order to lock 2511 to the second portion 2513. Alternatively, it is to be understood that the act of sliding or snapping hub portion 2511 into hub portion 2513 can be sufficient to lock portion 2511 into portion 2513. This embodiment further includes spacer 2536 and cone shaped guide 2526.

Other features, functions, dimensions, and so forth of this embodiment are similar to the other embodiments as, for example, the embodiment of FIG. 141.

For purposes of insertion, one insertion methodology can be to insert the second hub portion 2513 with the guide 2526 into the position between the spinous processes. After this is accomplished, the hook members can be positioned about the spinous processes and locked into the first hub portion 2511. Then the first hub portion 2511 could be slid or snapped into engagement with the second hub portion 2513. Following that, the cam 2527 can be turned in order to secure the first hub portion 2511 to the second hub portion 2513.

Embodiments of FIGS. 147a-149b

Figure 147A:
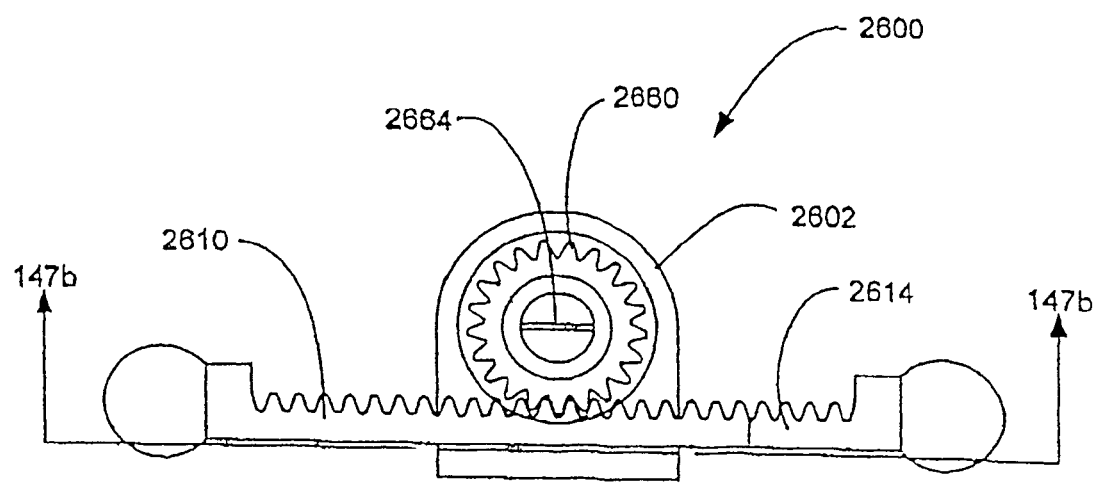
FIGS. 147a and 147b are side and top views of yet another embodiment of the invention depicting a mechanism for adjusting the positions of the hook mechanisms of, for example, the embodiment of the invention of FIGS. 130, 137, and 141.
Figure 147B:
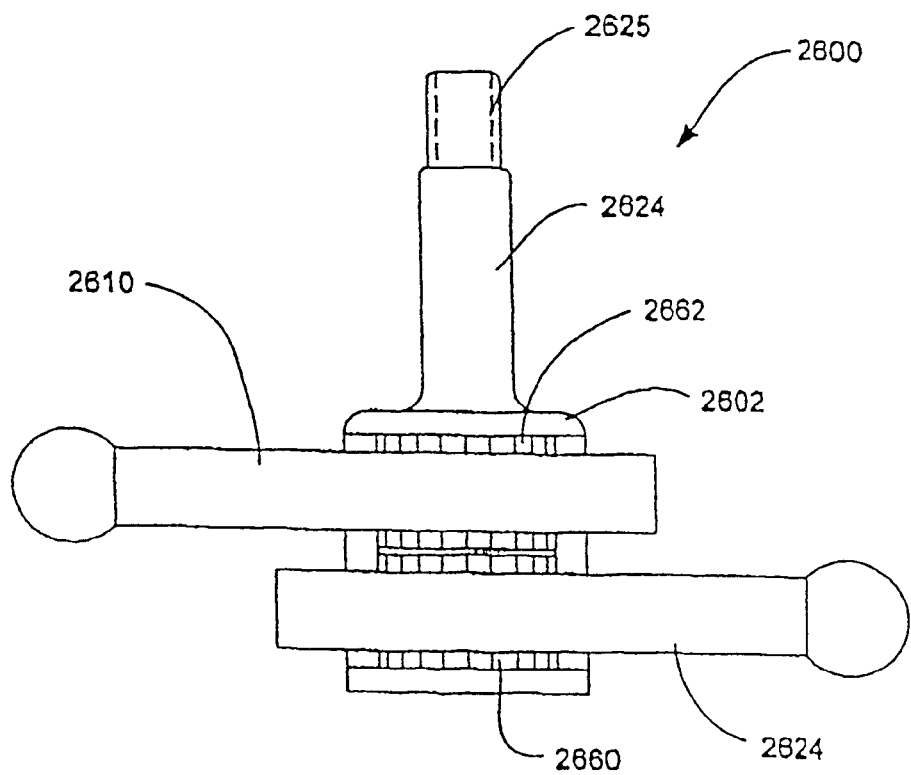

FIGS. 147a and 147b depict another embodiment 2600 of the invention. This embodiment 2600 includes a hub 2602 and a rack and pinion arrangement. The rack and pinion arrangement includes first and second pinions 2660 and 2662. These pinions engage shafts 2610 and 2614 respectively. In these embodiments, these shafts 2610 and 2614 have rounded ends to which the hook is secured as depicted in, for example, FIG. 131. For simplicity, these hooks have been left off of FIGS. 147a, 147b. The position of the shafts 2610 and 2614 can be adjusted relative to the hub. Once the shafts 2610, 2614 are appropriately positioned the pinions can be locked in position, locking the shafts in position. Pinions can be locked in position by tightening down screws such as screw 2664 against the pinion 2660. A similar screw, not shown, would tighten down pinion 2662.

Figure 148A:
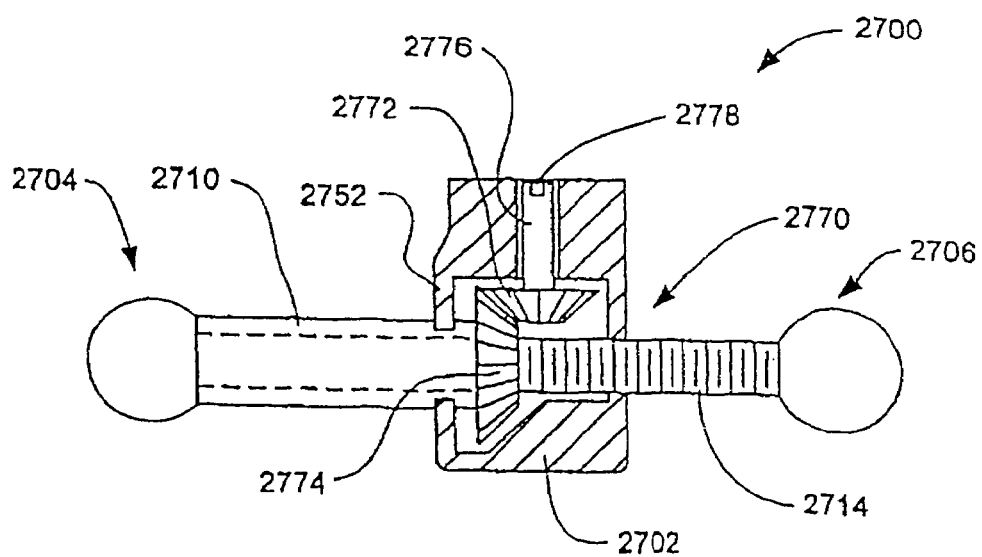
FIGS. 148a and 148b are sectional top and side views of yet another embodiment of the invention for adjusting the position of the hook mechanisms.
Figure 148B:
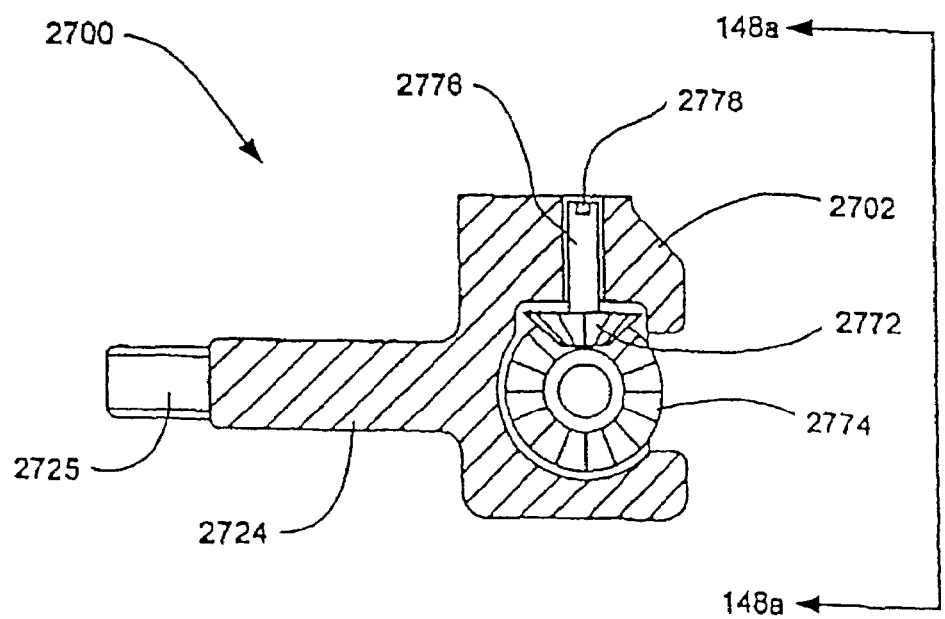

Another embodiment of the invention, embodiment 2700 is depicted in FIGS. 148a and 148b. In this embodiment a bevel gear arrangement 2770 is contained in the hub 2702. Bevel gear arrangement 2770 includes a first bevel gear 2772 and a second bevel gear 2774. Bevel gear 2772 has a shaft 2776 extending therefrom with a slot 2778. Slot 2778 can receive a tool for turning the bevel gear 2772. Bevel gear 2774 is mated to a threaded shaft 2710 of the hook member 2704. In this particular embodiment, the hook is not shown as is the case for the embodiment of FIGS. 147a and 147b. When the bevel gear 2772 is turned, it turns bevel gear 2774. The turning of bevel gear 2774 causes the threaded shaft 2714 to retreat into or extend out of the center of the other shaft 2710. With the hook members positioned around spinous processes, the bevel gear 2772 can be used to turn bevel gear 2774 in order to draw the hook member 2706 toward the hub 2702, tightening the hook members about the spinous processes.

In this embodiment 2700, a shaft 2724 extends therefrom in order to receive a spacer and a guide in the same manner that, for example, the embodiment of FIG. 144 receives a spacer and a guide.

Figure 149A:
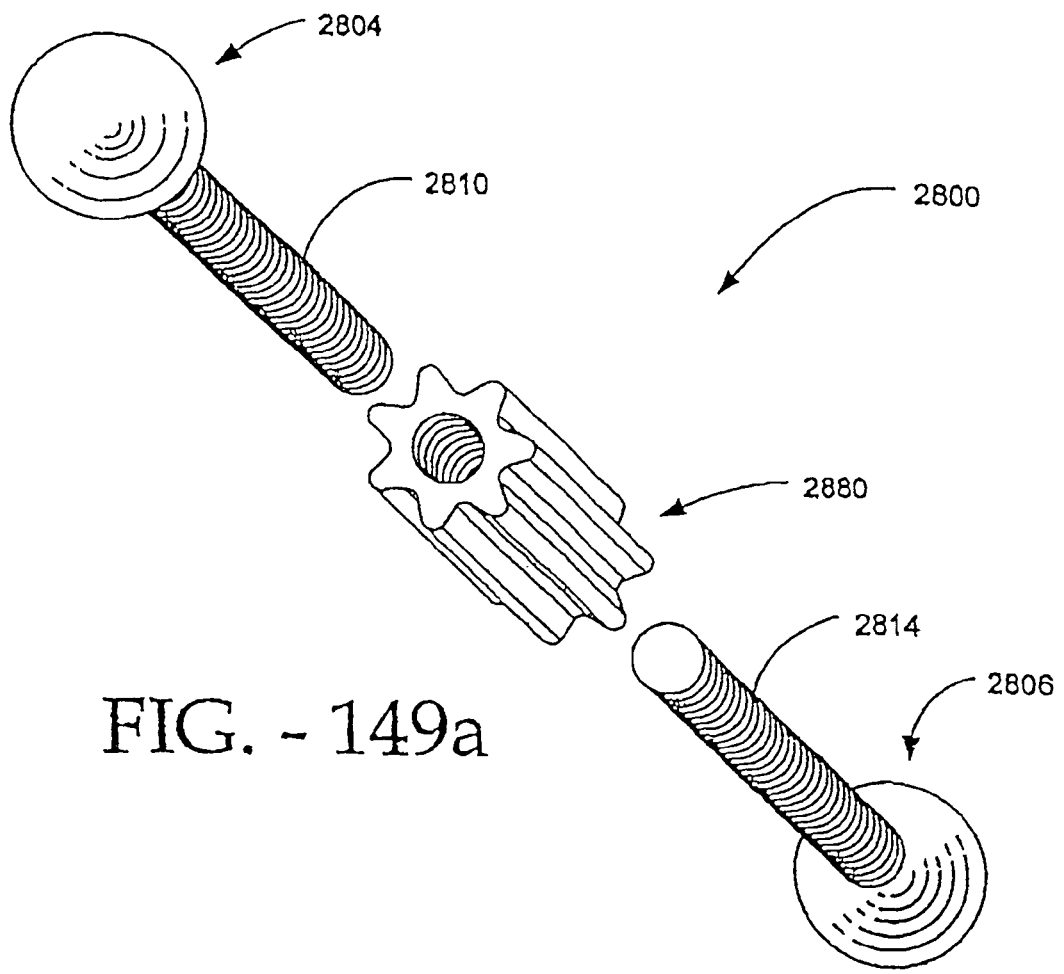
FIGS. 149a and 149b are perspective and side views of yet a further embodiment of an embodiment of the invention for adjusting the position of hook mechanisms of the invention.
Figure 149B:
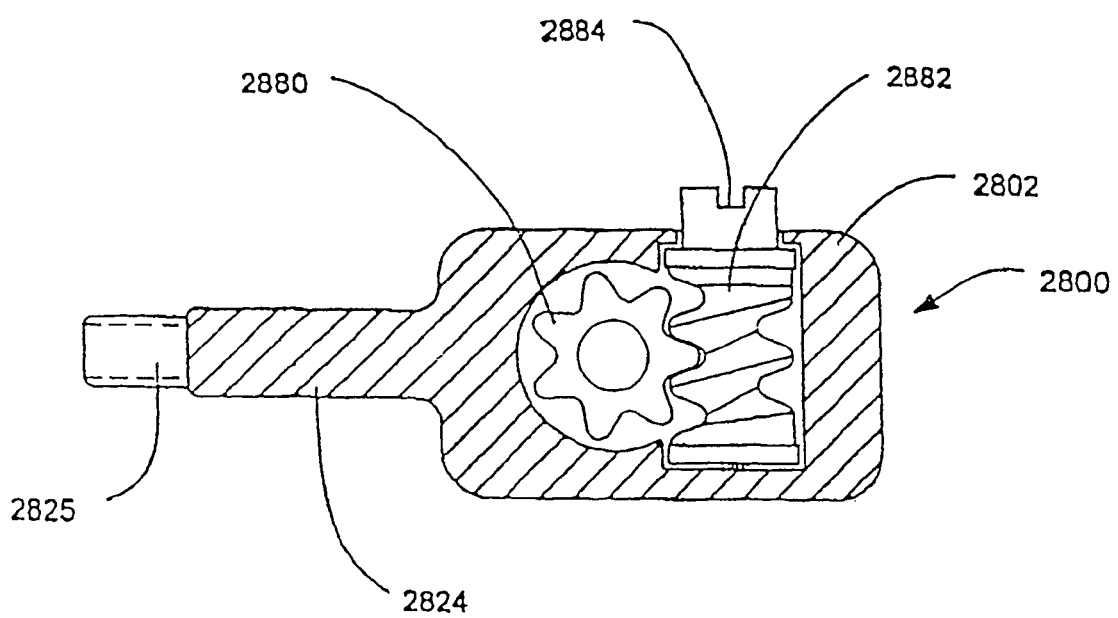

FIGS. 149a and 149b depict embodiment 2800 of the invention. Embodiment 2800 includes a hub 2802 which houses a turnbuckle arrangement 2880 which is actuated by a worm gear drive 2882. Turnbuckle 2880 receives the threaded shaft 2810 and 2814 of the hook members 2804, 2806 respectively. As with the past embodiments, the actual hooks of these hook members are not depicted in order to simplify the drawing. By turning the turnbuckle 2880, the threaded shafts 2810, 2814 are either drawn into or urged out of the turnbuckle. Thus, by turning the worm gear 2882 with a tool placed in the slot 2884, the turnbuckle turns, causing the hook members to extend out of or be urged into the hub 2802.

Extending from the hub is a shaft 2824 with a threaded end 2825. As with the other embodiments, such as the embodiment in FIG. 144, a spacer can be placed on the shaft 2824 and a guide can be placed on the threaded end 2825.

The preferred method of inserting this embodiment is to insert the embodiment as a whole, placing the guide and spacer between the spinous processes. The hooks would be initially rotated 90° from their final orientation. Once inserted adjacent to the spinous processes, the hooks would be rotated by 90° and the spacer and the hooks would be further urged into contact with the spinous processes. Once this has occurred, the turnbuckle would be turned in order to tighten the hooks about the spinous processes.

Figure 150:
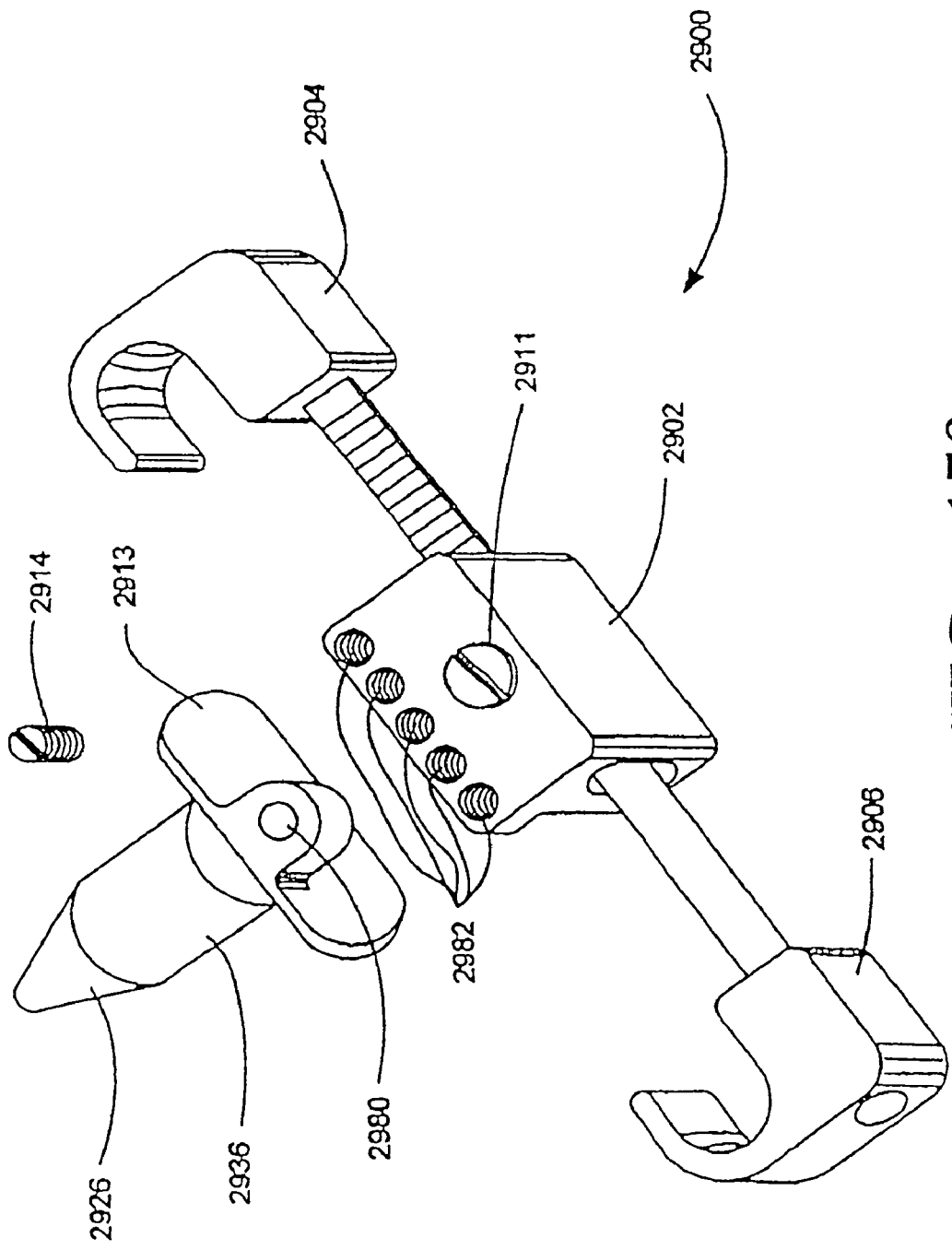
FIG. 150 is a perspective view of yet a further embodiment of the invention.

Embodiment of FIG. 150

Another embodiment 2900 of the invention is depicted in FIG. 150. This embodiment is similar to several of the other embodiments and, in particular, to the embodiment shown in FIG. 130. Accordingly, similar elements will have similar least significant numbers. By way of example, the hub is designated 2902. In this particular embodiment, the hub is comprised of two components, the first hub component 2911 and the second hub component 2913. This is somewhat similar to the hub components shown in FIG. 146b.

The two hook members are secured to the first hub component 2911 in much the same manner as the hook members of FIG. 130 are secured to the hub in FIG. 130.

The hub 2902 is divided into first hub component 2911 and second hub component 2913 in order to add flexibility in the positioning of the guide and spacer fitted to second hub component 2913 with respect to the first and second hook members 2904 and 2906 which are secured to the first hub component 2911. Thus, should the anatomy of the spine and in particular the spinous process require, the spacer 2936 and the guide 2926 can be moved relative to the first and second hook members 2904 and 2906 by selectively positioning the second hub component 2913 relative to the first hub component 2911. This can be accomplished by aligning the bore 2980 over one of the plurality of bores 2982 positioned through the first hub component 2911. After this is accomplished, a threaded screw 2984 can be inserted through smooth bore 2980 and engage one of the threaded bores 2982 in order to secure the second hub component 2913 to the first hub component 2911, thus positioning the sleeve or spacer 2936 in a desired location relative to the first and second hook members.

Figure 151:
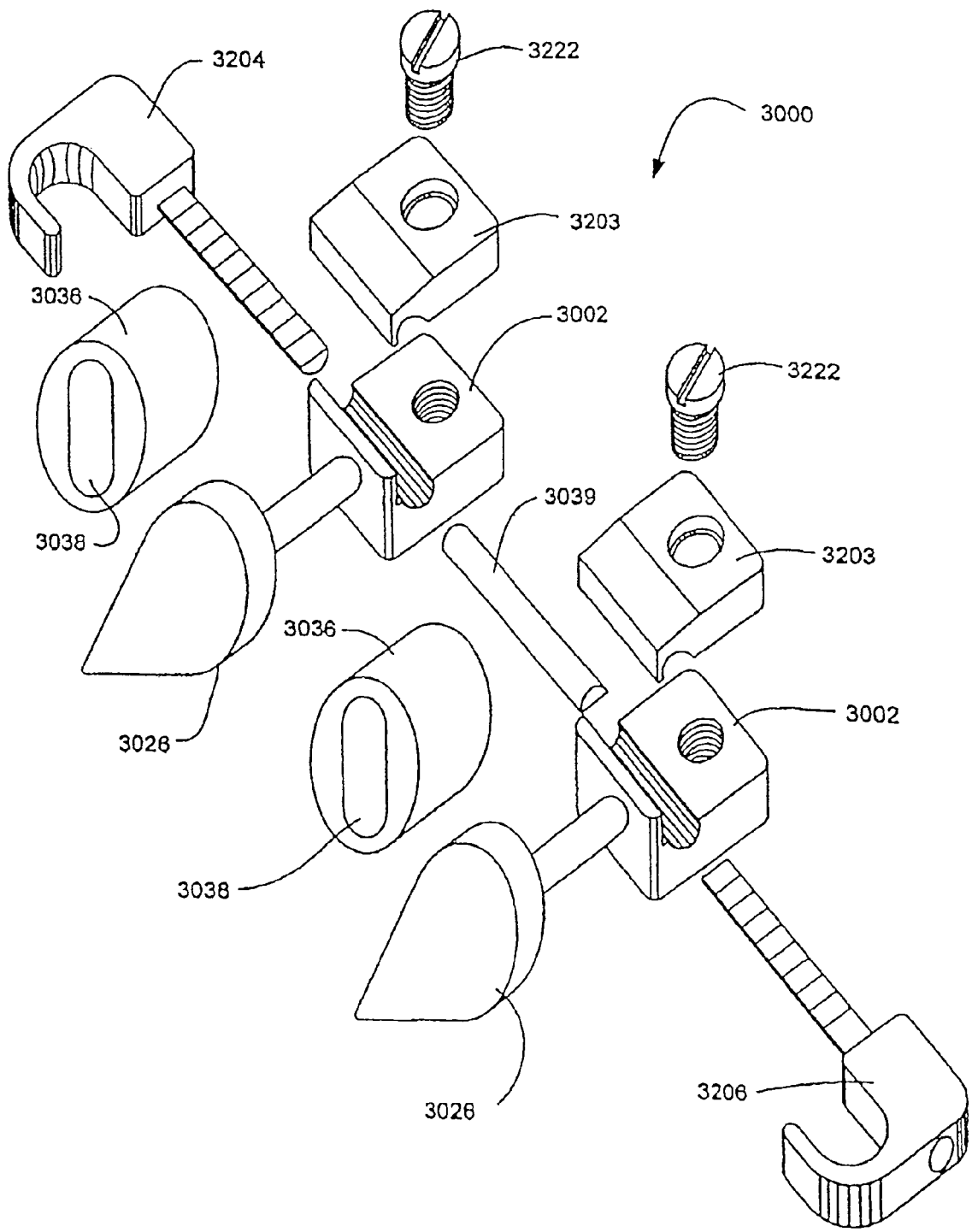
FIG. 151 is a perspective view of an embodiment of the invention which is addressable to multiple levels of spinous processes.

Embodiment of FIG. 151

Yet another embodiment of the invention 3000 is depicted in FIG. 151. Embodiment 3000 is meant for a double level spinous process fixation. That is to say that three spinous processes are engaged and rigidly fixed together. Such a situation would occur, for example, when there is a double level primary fusion. That is, three adjacent vertebral bodies are all fused together. In such a situation a double level supplemental spine fixation device 3000 would be used. This embodiment 3000 could be designed using any of the other embodiments depicted heretofore. Embodiment 3000 is in this particular instance modeled after the embodiment 2000 shown in FIG. 141. Accordingly, the elements that are similar to FIG. 141 have similarly least significant digits. By way of example, the hubs of FIG. 151 are both designated 3002 in accordance with the designation of FIG. 141. Similarly, the hub caps, sleeves, hook members, spacers, and guides are similarly numbered. In this embodiment two hubs, two spacers, and two guides are required as the first guide 3026 and the spacer 3036 would be inserted between first and second spinous processes, while the second guide 3026 and spacer 3036 would be inserted between the second and third spinous processes. The hook members 2004 and 2006 would hook about the first spinous process and the third spinous process respectively.

A preferred method of insertion of the device relative to three spinous processes would be to insert the guides and spacer between the first and second, and then the second and third spinous processes in order to distract apart the first and second spinous processes and also to distract apart the second and third spinous processes. After this is accomplished, the first hook member would be placed about the first spinous process and the second hook member would be placed about the third spinous process. The shafts of the hook members would be inserted in the respective hubs 3002. In this situation, the shafts are both up-facing racks or teeth as shown in FIG. 151. A linking shaft 3039 has downwardly facing racks or teeth. Thus the upwardly facing rack or teeth of the first hook member 2004 would be laid in the upper hub 3002 with the teeth facing up. The teeth of the member 3039 facing down would engage the rack or teeth of the first hook 2004. Once this is accomplished, the cap will be placed over the hub and the screw inserted in order to rigidly secure the hook member and the shaft 3039 relative to the upper hub 3002. Then the shaft of the second hook 2006 would be positioned in the lower hub 3002. The rack of shaft 3039 would mesh and lock with the rack of the shaft of the second hook member 2006. Once this is accomplished, the cap 3203 would be placed over the hub and the screw would be inserted through the cap into the hub in order to secure the shaft 3039 and the second member 2006 relative to the lower hub.

Embodiments of FIGS. 152-160

Figure 152:
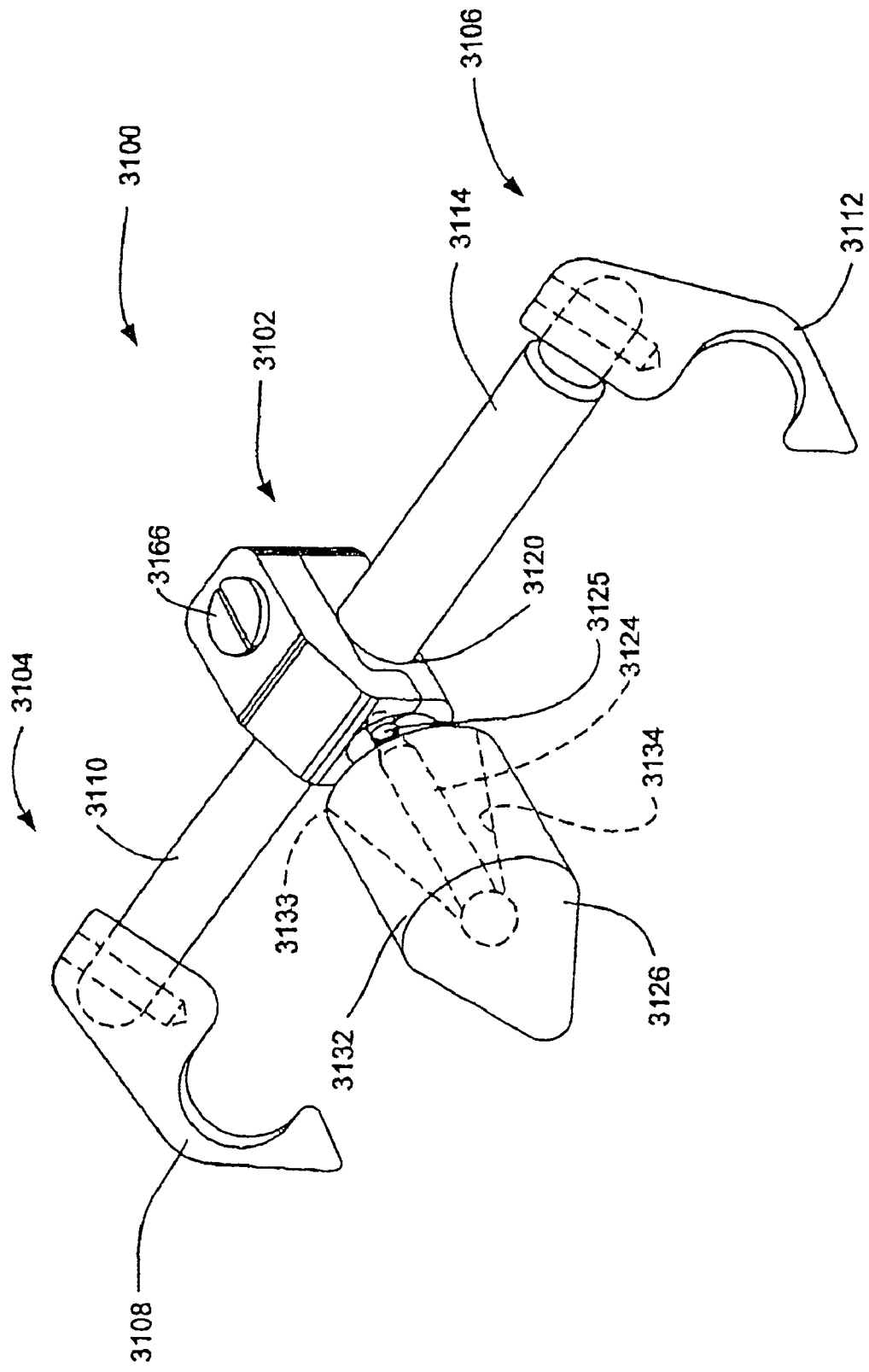
FIG. 152 is a perspective view of an alternative embodiment of the supplemental spine fixation device of the invention.

An alternate embodiment 3100 of the supplemental spine fixation device of the invention is depicted in FIG. 152. This embodiment 3100 includes a hub 3102 to which is adjustably secured a first hook member 3104 and second hook member 3106. First hook member 3104 includes a hook 3108 which is more fully described herein below, and a shaft 3110 extending therefrom. Similarly, second hook member 3106 includes a second hook 3112 and shaft 3114 extending therefrom. Shaft 3110 and 3114 are assembled together in a manner as will be described hereinbelow.

As described more fully below, hook 3108 is swivelly or pivotally mounted to shaft 3110. It is to be understood that the description and functionality of the first hook member 3108 applies equally well to that of the second hook member 3106. The shaft 3110, onto which hook 3108 is mounted in this embodiment, is received inside of the shaft 3114. Shaft 3110 can extend from shaft 3114 in a telescoping or sliding manner relative to shaft 3114 or alternatively shaft 3110 can be threaded into shaft 3114 and the rotation of shaft 3110 would allow it to extend from or be retracted into shaft 3114. Shafts 3110 and 3114 are received in a bore 3120 of the hub 3102. In this particular embodiment shaft 3114 can be press fit or otherwise secured in bore 3120. Shaft 3110 is thus free to move relative to the hub 3102 and the shaft 3114, until the hub 3102 is assembled, locking shaft 3110 into position in this particular embodiment. This locking arrangement will be discussed more fully below.

The hooks 3108 and 3112 are designed and shaped to fit to spinous processes. Further the hooks 3108 and 3112 are swivelly mounted to the shafts 3110 and 3114, respectively, in order to accommodate the various sizes, shapes, and positions of the spinous processes of the human population.

Swively mounted to the hub 3102 is a shaft 3124, and extending from the shaft 3124 is an inner-spinous process guide, or lead-in nose, or tissue expander 3126. The shaft 3124 at its proximal end includes a ball 3125, which is received in socket 3127 which is formed by the two portions of the hub 3102. At this ball and socket mechanism, the shaft 3124 is pivotable with respect to the hub 3102. With this arrangement, the tissue expand 3126 has some freedom of movement with respect to the hub 3102. The other end of the shaft 3124 (FIG. 154a) also includes a ball 3129 which fits into a socket arrangement 3131 created in the guide or tissue expander 3126. This arrangement allows the guide or tissue expander 3126 to pivot with respect to the shaft 3124. Accordingly the shaft 3124 is free to pivot relative to the hub and the guide or tissue expander 3126 is free to pivot relative to shaft 3124. This movement, as well as the ability of hooks 3108 and 3112 to swivel on the shaft 3110 and 3114, and the ability of the shaft to be positioned relative to each other allows the embodiment 3100 to conform to the spinous process anatomy.

In this particular embodiment, a sleeve or spacer 3132 is pivotally mounted on the shaft 3124 along with the guide 3126. In other embodiments as described below, the sleeve spacer 3132 is free to rotate relative to the guide 3126. Spacer 3132 includes a central bore 3134 in which the shaft 3124 extends. The spacer 3132 as well as guide 3136 are thus able to pivot and rotate about the shaft 3124. The spacer 3132 in this embodiment is cylindrical and in this particular embodiment is oval or elliptical in shape. For such shapes, the spacer can have minor diameters of 6 mm, 8 mm, 10 mm, and 12 mm. Smaller and larger diameters are within the spirit and scope of the invention. In addition, the spacer can be egg shaped as more fully described below. Further, the base of the guide 3126 is somewhat elliptical in shape in order to make a smooth transition between the guide 3126 and the spacer 3132 as the guide and spacer are inserted between the spinous processes in order to distract apart the spinous processes. As the guide 3126 and the spacer 3132 are rotatable and pivotable on the shaft 3124, and as the spacer 3132 is elliptically shaped, it can be inserted into one position and then as the entire embodiment 3100 is positioned to the final securing position, the spacer 3132 can be rotated about the shaft 3124 and pivoted relative thereto in order to accommodate the shape of the space between the spinous processes as the spacer is moved generally from a posturing position to an anterior position closer to the spine.

Figures 154A, 154B:
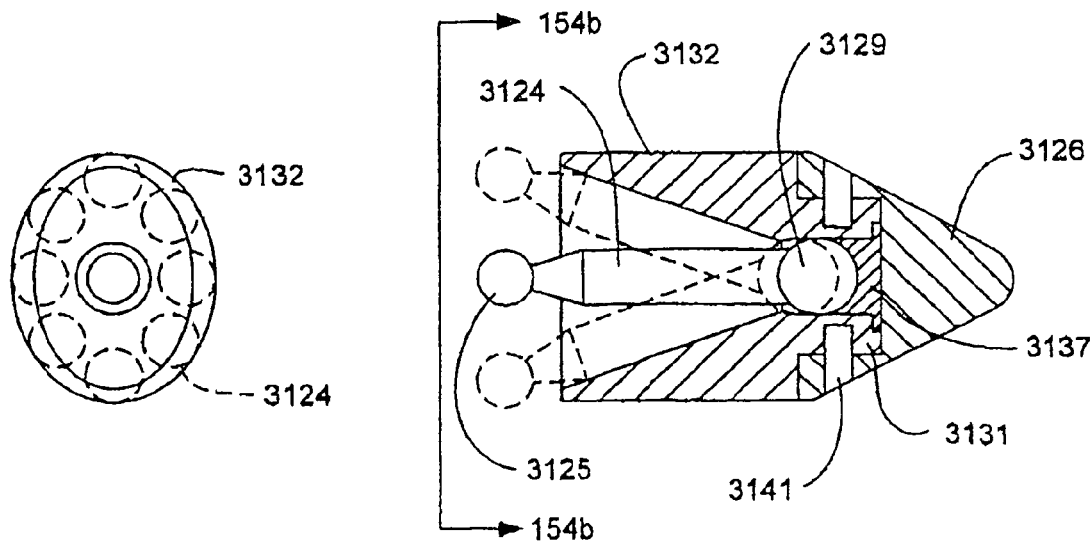
Figure 154C:
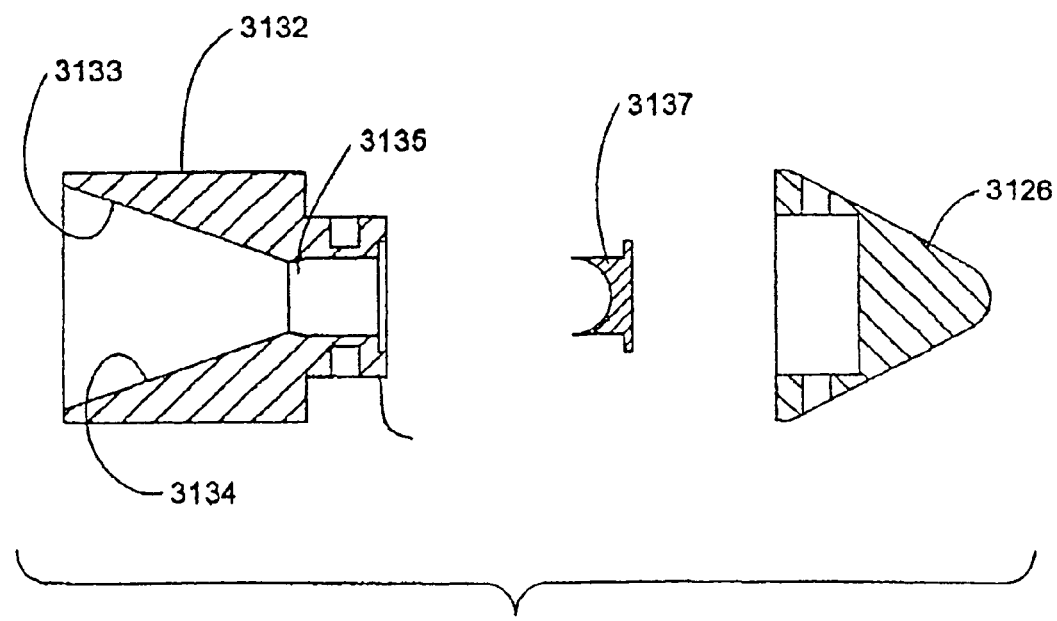
Figure 156:
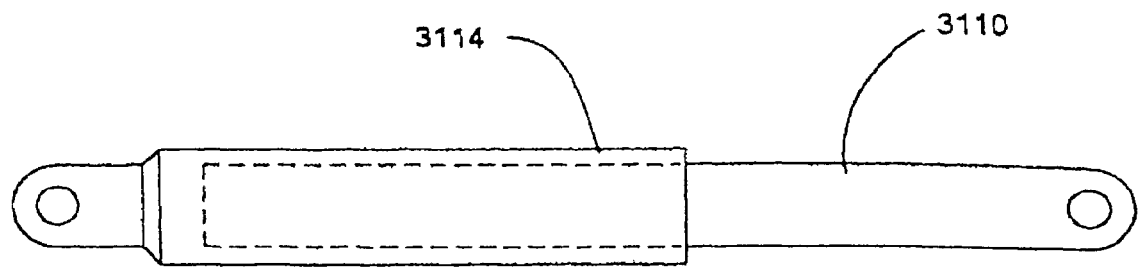
FIG. 156 is a view of an embodiment of a shaft arrangement of the invention upon which hooks can be mounted.

As can be seen in FIG. 152 and also in FIGS. 154a and 154c, the central bore 3134 of the spacer 3132 has a first end 3133 which is enlarged and in this particular embodiment substantially elliptical in shape. The second end 3135 is smaller. The reason for this arrangement is most evident in FIGS. 154a and 154b where in phantom various positions of the shaft 3124 are depicted demonstrating the pivotability of the guide 3124 and the sleeve 3132 relative to the hub 3102. As can be seen in FIGS. 154a and 154c, in this particular embodiment, the shaft 3124 is inserted into the small end 3135 of the sleeve 3132. A retainer 3137 is inserted relative to the ball 3129 of the shaft 3124. The lead-in nose or tissue expander 3126 is then inserted over the small end 3139 of the sleeve 3132 and pin 3141 is inserted into aligned slots in the guide 3126 and the sleeve 3132 in order to assemble together guide 3126, the retainer 3137 and the sleeve 3132 about the ball 3129 of the shaft 3124 to create a ball and socket arrangement, whereby the guide 3126 and sleeve 3132 are pivotable and rotatable about the ball 3129.

In this particular embodiment, a sleeve or spacer 3132 is pivotally mounted on the shaft 3124 along with the guide 3126. In other embodiments as described below, the sleeve spacer 3132 is free to rotate relative to the guide 3126. Spacer 3132 includes a central bore 3134 in which the shaft 3124 extends. The spacer 3132 as well as guide 3136 are thus able to pivot and rotate about the shaft 3124. The spacer 3132 in this embodiment is cylindrical and in this particular embodiment is oval or elliptical in shape. For such shapes, the spacer can have minor diameters of 6 mm, 8 mm, 10 mm, and 12 mm. Smaller and larger diameters are within the spirit and scope of the invention. In addition, the spacer can be egg shaped as more fully described below. Further, the base of the guide 3126 is somewhat elliptical in shape in order to make a smooth transition between the guide 3126 and the spacer 3132 as the guide and spacer are inserted between the spinous processes in order to distract apart the spinous processes. As the guide 3126 and the spacer 3132 are rotatable and pivotable on the shaft 3124, and as the spacer 3132 is elliptically shaped, it can be inserted into one position and then as the entire embodiment 3100 is positioned to the final securing position, the spacer 3132 can be rotated about the shaft 3124 and pivoted relative thereto in order to accommodate the shape of the space between the spinous processes as the spacer is moved generally from a posturing position to an anterior position closer to the spine. When the spacer 3132 is fully inserted between the spinous processes, the spacer 3132 extends through the sagittal plane defined by the adjacent spinous processes.

In another arrangement, the embodiment as shown in FIG. 154c could be modified to so that the small end 3139 of the spacer 3132 or of the spacer 3136 is severed from the remainder of the spacer 3132, 3136 and pinned by itself to the guide 3126 in order to capture the ball of the shaft. Thus the remainder of the spacer 3132, 3136 could rotate free of guide 3126.

Before proceeding to more specific details of this embodiment 3100, it is to be understood that the same features of the spacer, the shaft, and the lead-in guide, which are found on other embodiments such as by way of example only the embodiments of FIGS. 10, 16, 20, 22, 86, 88, 92 and 119b, and other figures can be incorporated into this embodiment. By way of example only, the implant 3100 can be comprised of stainless steel, titanium, or other biologically acceptable materials. The shape of the lead in plug can be cone shaped, pyramid shaped and other shapes with a small lead in cross-section expanding into a larger cross-section which is similar to the cross-section of the spacer 3132, in order to gradually distract apart the spinous processes to a sufficient distance so that the spacer 3132 or the spacer 3136 can conveniently fit between the spinous processes. Further, the spacer, as shown in the other embodiments, can include a spacer made of stainless steel or titanium or of a super-elastic material or of a silicone. The spacer besides being cylindrical, can be saddle-shaped along the surface which engages the spinous processes so that the high edges and the lower central portions can more fully accommodate the shape of the spinous process. This shape also aides in spreading the load across the broader contact area between the spinous processes and the spacer. For example, the spacer 3132 or 3136 could have a shape such as the saddle shape defined by the mated together components of the embodiment of FIGS. 16. Further, dimensions of this embodiment as applied to the guide 3106 and the spacer 3132 can be acquired from other embodiments presented herein. By way of example only, the guides and spacers can have multiple shapes with the small diameter of the elliptical shape being on the order of 6 mm, 8 mm, 10 mm, 12 mm and 14 mm.

The shape of the guide 3126 and the spacer 3132 or the spacer 3136 is such that for purposes of insertion between the spinous processes, the spinous processes do not need to be altered or cut away in any manner in order to accommodate this implant. Further, the associated ligaments do not need to be cut away and there would be very little or no damage to the other adjacent and surrounding tissues. Similarly, the hook members 3104 and 3106 are appropriately shaped, as described below and are also pivotable so that alterations of the spinous processes is not required.

Referring to FIG. 155a through 155e, the design and shape of the hook 3108 is more fully described and depicted. As indicated above, the description will be made with respect to the first hook 3108. This description applies equally well to second hook 3112. As can be seen in FIG. 155a, the first hook 3108 includes a bore 3144 into which the shaft 3110 is received. The shaft has a rounded end which has a bore provided therethrough. This bore mates with the bore 3145 associated with the bore 3144 of the hook 3108. When the bore of the shaft 3110 and the bore 3145 of the hook are aligned, a pin or screw can be inserted in order to lock the hook 3108 onto the shaft 3110. As can be seen in FIG. 155d, the lower end 3147 of the bore 3144 is oval or ob-round in shape allowing for the shaft to be pivotally received in the bore. Thus the hook 3108 is pivotable with respect to the end of the shaft 3110. The hook thus can pivot in order to accommodate the shape of the spinous process. Turning to FIG. 155a, the lead in nose or guide or tissue expander 3150 of the hook 3108 is pointed as can be additionally seen in FIGS. 155d and 155e. This allows the guide 3150 to be easily inserted between spinous processes and spread the tissue so that the concave recess 3152 can be received over the spinous process. The hook is then locked on the spinous process in order to retain the hook 3108 in place adjacent to the spinous process. The recess 3152 has a cross-section which is convex in shape in order to accommodate the various surface shapes of the spinous process and in order to even out the load transfer between the hook and the spinous process.

Again with respect to the lead in nose 3150 in a preferred embodiment, this nose is essentially shaped in the form of a pyramid with all of its sides rounded and curved. This allows the nose 3150 to easily be inserted over and past the spinous process, until the concave recess 3152 rests over the spinous process with the hook element 3154 caught by the spinous process in order to retain the hook 3108 in place.

Figure 153:
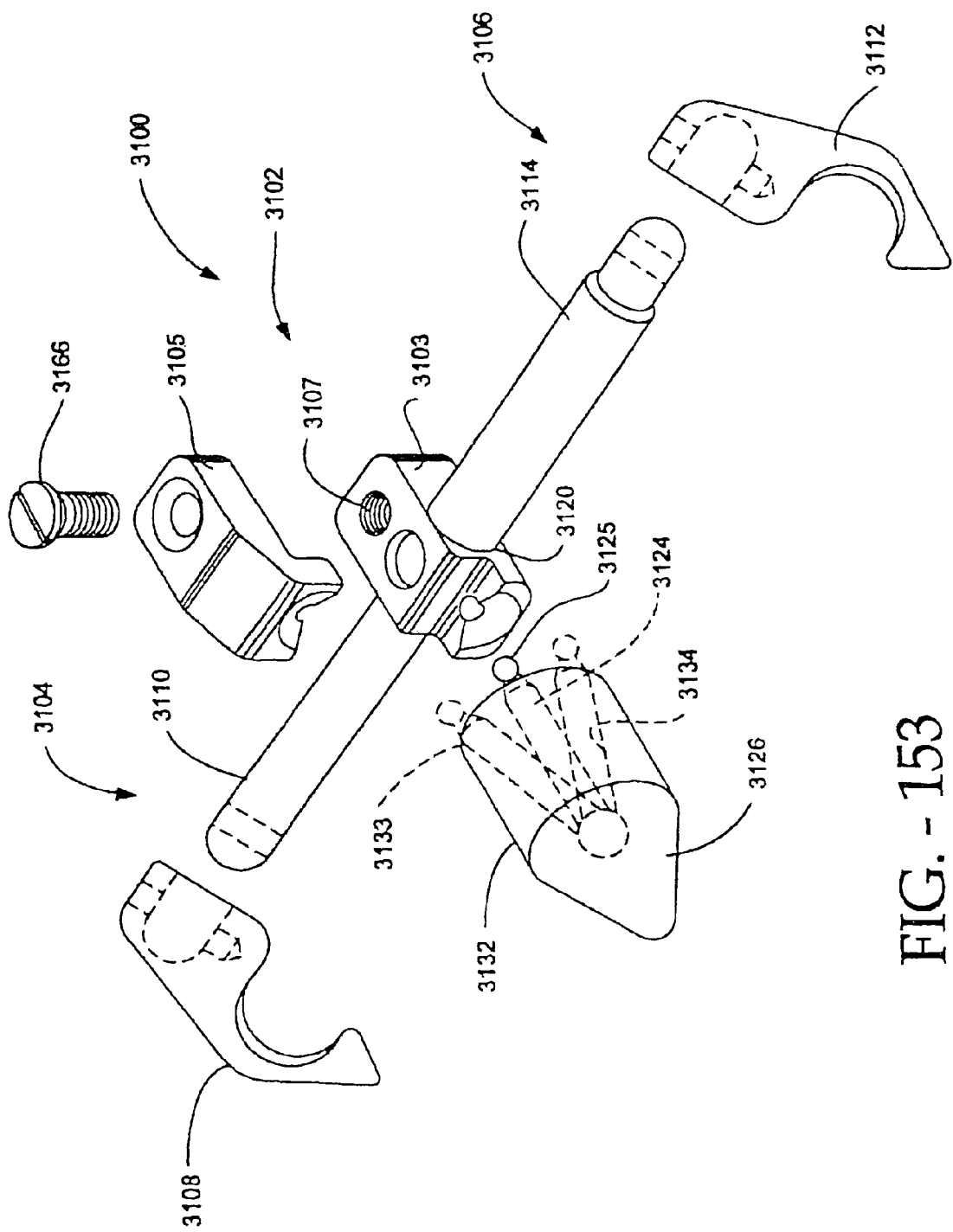
FIG. 153 is an exploded view of the embodiment of the invention of FIG. 152.
Figure 157:
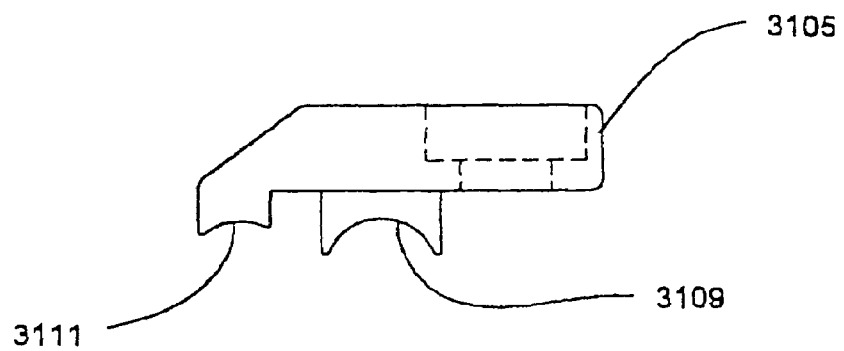
FIG. 157 is an alternate view of the top member of the hub showing the locking mechanism.

As can be seen in FIG. 153, the hub 3102 is comprised of two portions. The lower hub portion 3103 receives the shaft 3110 and 3114. The lower portion 3103 also receives the shaft 3124 upon which the nose and sleeve are mounted. The upper portion 3105 of the hub 3102 mates with a lower portion 3103 in order to lock the shaft 3110 and the shaft 3124 in place. The upper hub portion 3105 is secured to the lower portion 3103 with a screw through threaded bore 3107. As can be seen in FIG. 157, upper hub portion 3105 includes a locking projection 3109. This locking projection includes a concave surface. The locking projection 3109, with the upper hub portion 3105 is mated to lower hub portion 3107, bears down upon the shaft 3110 to lock it in position. Upper hub portion 3105 also includes a half spherical captured enclosure 3111. With the hub portions assembled, the enclosure 3111 captures the ball end of shaft 3124. It is to be understood that with respect to the embodiment of FIG. 153, that with the two halves of the hub 3102 mated together, a spherically shaped capture enclosure captures the ball end of shaft 3124.

Figure 158A:
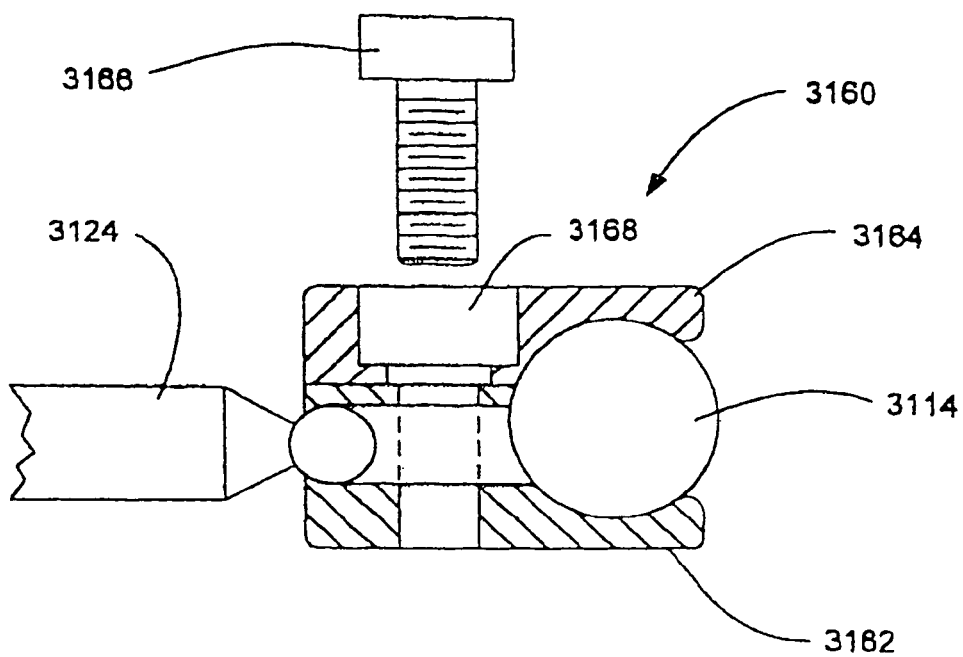
FIGS. 158a and 158b are sectioned views of an alternate embodiment of the hub mechanism of the invention.
Figure 158B:
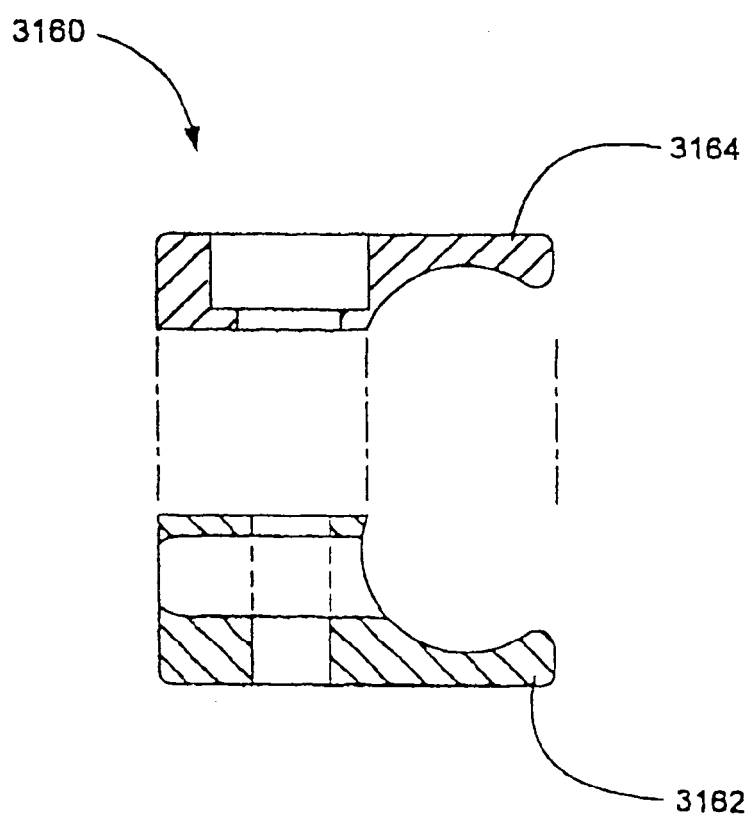

FIGS. 158*a* and 158*b* depict alternative embodiments of a hub arrangement. This alternative hub 3160 includes lower hub portion 3162 and upper hub portion 3164. In this embodiment, the ball end of the shaft 3124 is captured in the lower half of the hub 3160. The upper half 3164 of the hub is mated to the lower half with a screw 3166 which is placed through a leaf spring 3168 carried with the screw 3166. The leaf spring bias the upper hub portion 3164 towards the lower hub portion 3162 in order to trap and capture the shaft 3114. Once this is accomplished, the screw 3166 is tightened in order to complete the assembly.

Figure 159:
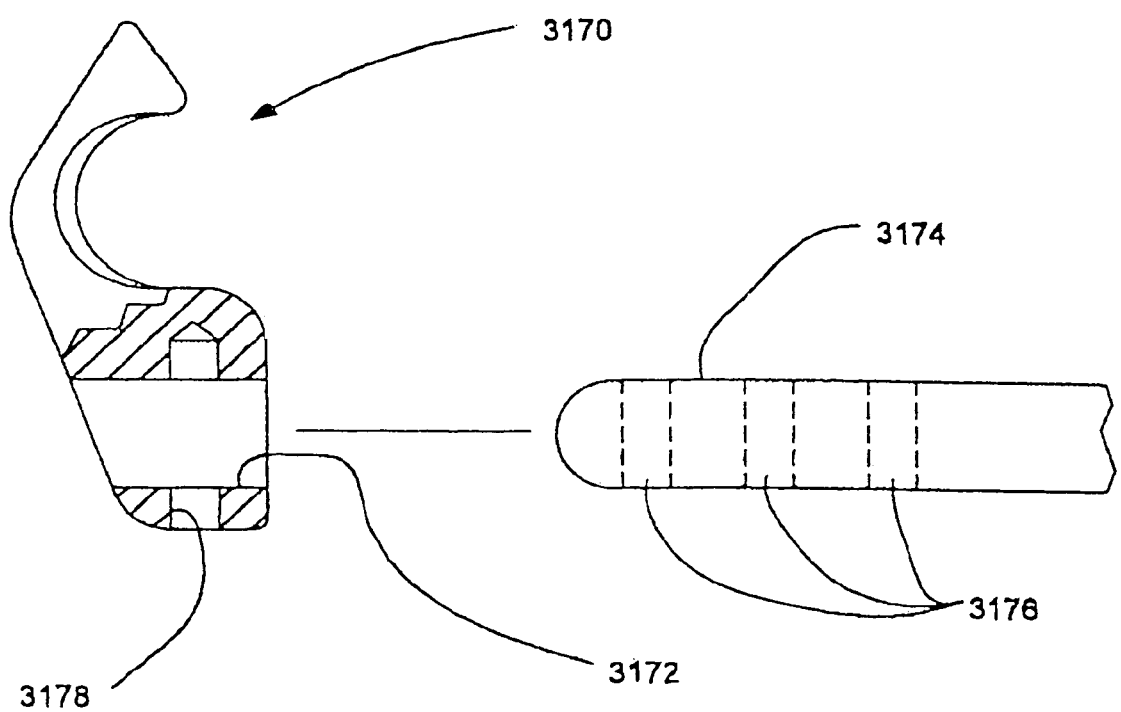
FIG. 159 is an alternate embodiment of the hook attached to a shaft of the invention.

FIG. 159 depicts yet an alternate embodiment of the hook and shaft arrangement which could be used instead of, byway of example only, hook 3108 and shaft 3110. In this arrangement the hook 3170 includes a bore 3172 which goes completely through the hook 3170. Both ends of the oval are oval or ob-round in order to allow the hook 3170 to pivot on shaft 3174. Shaft 3174 has a plurality of bores 3176 provided therethrough, any one of which can align with the bore 3178 which is provided across the bore 3172 of the hook 3170. When such an alignment is made a pin or screw can be inserted into bore 3178 in order to secure the shaft 3174 to the hub 3170. By selecting one of the several bores 3176 in the shaft 3174, the position of the hook relative to the hub can be adjusted in order to accommodate the shape and spacing of the various spinous processes.

Embodiment 3100 can be implanted in a number of methods in accordance with the teachings for the implantation of the embodiment 2000. Preferably this would occur once a spine fixation devices is implanted between the vertibral bodies in order to fuse together adjacent vertribral bodies.

In one preferred embodiment of implantation, in particular with respect to the embodiment of FIG. 153, the guide and sleeve or spacer can be inserted between adjacent spinous processes. Once this is accomplished, the hooks at the end of shafts could be positioned relative to the hub 3102 so that the hooks can grab about adjacent spinous processes. Once this has occurred, the shaft 3124 can be received in the lower portion of the hub. The upper portion of the hub 3105 can be mated with the lower portion in order (1) to capture and fix shaft 3124 in place, allowing for the movement of the shaft 3124, and also (2) to capture and fix the shaft 3110 in place to rigidly position the shaft 3110 relative to the hub 3102.

It is also to be understood that in other situations the fully assembled embodiment can be inserted in place relative to the adjacent spinous processes. Once this accomplished, a screw such as the screw in FIG. 153 can be tightened in order to secure the various shafts relative to the hub 3102.

In all of the above procedures, and also in the procedures with respect to prior embodiment 2000, it is advantageous that the embodiments can address the adjacent spinous processes from one side of the spinous processes and do not require exposure to both sides of the spinous processes. Thus, this procedure is less traumatic to the surgical site.

INDUSTRIAL APPLICABILITY

From the above, it can be seen that the present invention can be used to successfully provide for supplemental spine fixation as an adjunct to primary spine fixation. Also spinous fixation without vertebral body fusion could be accomplished if that is desired. The embodiments of the invention provides the correct amount of rigidity between spinous processes with a minimally invasive device and methodology. The present invention does not require that structures associated with the spinous process, including bone and ligament, be altered for purposes of implantation, thus the device and method do not add to the trauma associated with spinal fusion.

Other features, aspects and objects of the invention can be obtained from a review of the figures and the claims.

It is to be understood that other embodiments of the invention can be developed and fall within the spirit and scope of the invention and claims.

We claim:

1. A method for rigidly positioning a first spinous process relative to a second spinous process including the steps in any desired order of:
    placing a first hook around a first spinous process;
    placing a second hook around a second spinous process;
    interlocking the first hook relative to the second hook via a hub; and
    rotating and pivoting a spacer relative to the hub while the spacer is connected to the hub in order to place the spacer between the first spinous process and the second spinous process such that the spacer extends through a sagittal plane defined by the first and second spinous processes.

2. The method of claim 1 wherein the spacer is an egg-shaped spacer and the method further comprises directing a pointed end of the egg-shaped spacer toward the spine.

3. The method of claim 1 further comprising the step of:
    telescoping the position of one of the first hook and the second hook relative to the hub; and
    then locking the position of the one of the first hook and the second hook relative to the hub.

4. The method of claim 1 further comprising:
    adjusting the position of at least one of the spacer, the first hook, the second hook, and the hub, prior to using the hub to lock in the positions of the first hook and the second hook relative to the hub.

5. The method of claim 1 further comprising:
    implanting the first hook, the second hook, the hub, and the spacer without altering the first spinous process and the second spinous process.

6. A method for rigidly positioning a first spinous process relative to a second spinous process including the steps of:
    implanting a spinal fixation device to fuse adjacent vertebral bodies;
    placing a first hook around a first spinous process, wherein placing the first hook comprises pivoting the first hook relative to a first shaft while the first shaft supports the first hook in spaced relation to a hub;
    placing a second hook around a second spinous process;
    interlocking the first hook relative to the second hook via the hub; and
    rotating and pivoting a spacer relative to the hub while the spacer is connected to the hub in order to place the spacer between the first spinous process and the second spinous process such that the spacer extends through a sagittal plane defined by the first and second spinous processes.

7. The method as in claim 6 wherein the implanting comprises implanting the spinal fixation device from only one lateral side of the patient.

8. The method of claim 1 wherein the step of rotating and pivoting the spacer comprises placing the spacer in simultaneous contact with both the first spinous process and the second spinous process.

9. The method of claim 1 wherein the step of rotating and pivoting the spacer comprises rotating the spacer about an axis disposed generally transverse to the sagittal plane.

10. The method of claim 1 wherein the spacer includes a bore that is received over a shaft extending from the hub, and wherein the step of rotating and pivoting the spacer comprises rotating the spacer about the shaft and pivoting the spacer relative to the shaft.

11. The method as in claim 10 wherein the shaft includes a first end pivotably coupled to the hub and a second end opposite the first end; wherein the spacer is rotatably and pivotably mounted to the second end of the shaft; and wherein the step of rotating and pivoting the spacer comprises rotating the spacer about the shaft and pivoting the spacer about the second end of the shaft.

12. The method of claim 11 wherein the spacer defines a center axis and the bore is located off the center axis.

13. The method of claim 1 wherein the spacer includes a leading end opposite the hub, the leading end including a tissue expander tapered away from the hub, and further comprising advancing the tissue expander through a space between the first spinous process and the second spinous process in order to locate the spacer in the space.

14. The method of claim 6 wherein the step of rotating and pivoting the spacer comprises placing the spacer in simultaneous contact with both the first spinous process and the second spinous process.

15. The method of claim 6 wherein the step of rotating and pivoting the spacer comprises rotating the spacer about an axis disposed generally transverse to the sagittal plane.

16. The method as in claim 6 wherein the spacer includes a bore; and wherein a second shaft extending from the hub connects the spacer to the hub and extends through the bore, and wherein the step of rotating and pivoting the spacer comprises rotating the spacer about the second shaft and pivoting the spacer relative to the second shaft.

17. The method of claim 16 wherein the spacer defines a center axis and the bore is located off the center axis.

18. A method for positioning a first spinous process relative to a second spinous process including the steps of:
   adjusting the position of a shaft relative to a hub while the shaft is connected to the hub and is supporting a first hook;
   placing the first hook around a first spinous process;
   placing a second hook around a second spinous process;
   securing the position of the first hook relative to the second hook with the hub; and
   rotating and pivoting a spacer relative to the hub while the spacer is connected to the hub in order to place the spacer between the first spinous process and the second spinous process such that the spacer extends through a sagittal plane defined by the first and second spinous processes.

* * * * *

UNITED STATES PATENT AND TRADEMARK OFFICE
CERTIFICATE OF CORRECTION

| | |
|---|---|
| PATENT NO. | : 7,621,939 B2 |
| APPLICATION NO. | : 11/092862 |
| DATED | : November 24, 2009 |
| INVENTOR(S) | : Zucherman et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1075 days.

Signed and Sealed this

Twenty-sixth Day of October, 2010

David J. Kappos
*Director of the United States Patent and Trademark Office*

UNITED STATES PATENT AND TRADEMARK OFFICE
CERTIFICATE OF CORRECTION

PATENT NO. : 7,621,939 B2  
APPLICATION NO. : 11/092862  
DATED : November 24, 2009  
INVENTOR(S) : Zucherman et al.

Page 1 of 1

It is certified that error appears in the above-identified patent and that said Letters Patent is hereby corrected as shown below:

In Column 23, Lines 64-65, delete "For the above.................millimeters".

In Column 44, Line 50, after "spine.", insert -- When the spacer 3132 is fully inserted between the spinous processes, the spacer 3132 extends through the sagittal plane defined by the adjacent spinous processes. --.

Figure 160:
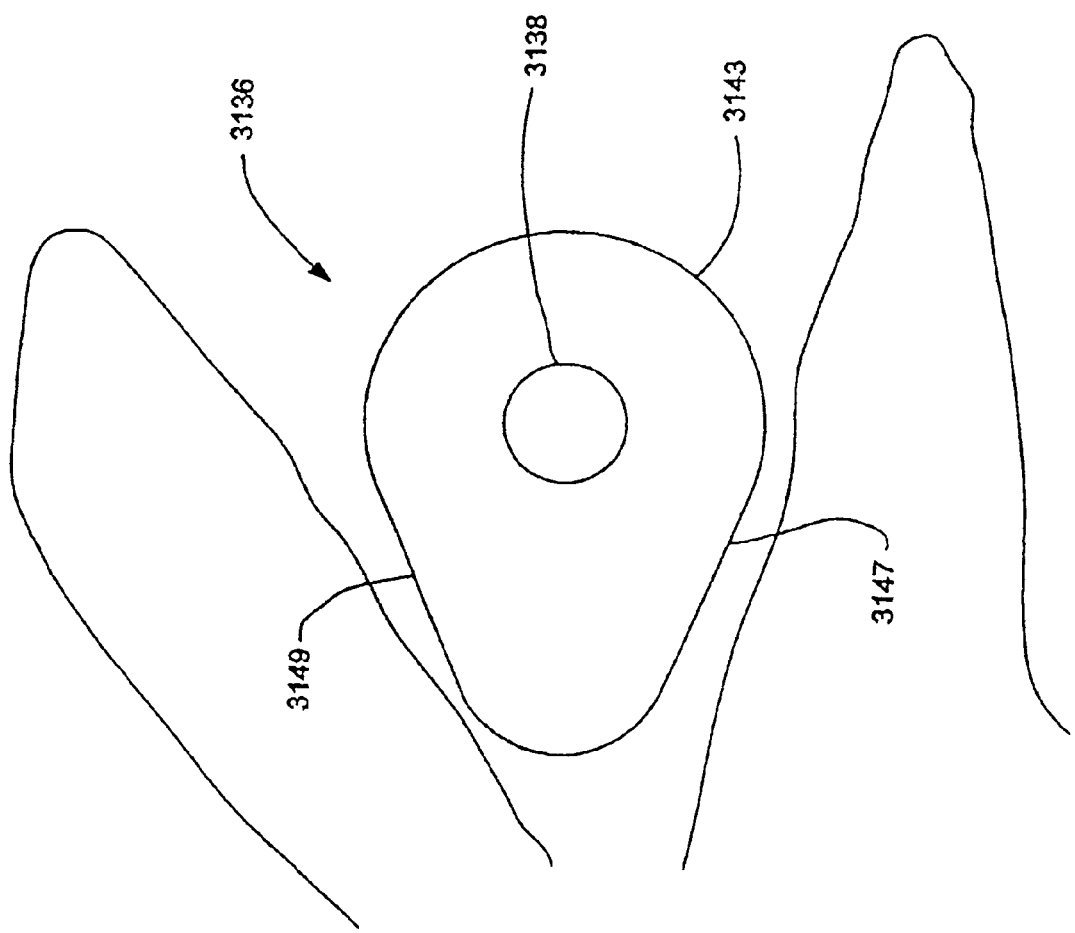
FIG. 160 is an alternate embodiment of a sleeve of the invention positioned between adjacent spinous processes.

In Column 45, Lines 3-32, delete "In this particular embodiment, a sleeve............ spinous processes" and insert -- The spacer 3132 can include an alternate embodiment spacer 3136 as shown in Fig. 160. This spacer 3136 can be substituted for spacer 3132. Spacer 3136 includes an egg-shape cross-section with a central bore 3138 upon which the shaft 3124 can be inserted so as to allow the spacer 3136 to rotate about the shaft 3124. As can be seen in Fig. 160, the egg-shaped spacer 3136 has a blunt end 3143 and a pointed end 3145. The center of the bore 3138 is off-center and more towards the front end 3134 in this preferred embodiment allowing the pointed nose end 3145 to be positionable more closely to the spine. This allows the flat sides 3147, 3149 between the blunt end 3143 and pointed end 3145 to be positioned closer to the spine and adjacent to portions of spinous processes which are generally comprised of stronger bone. In addition, these flat sides 3147 and 3149 can more easily accommodate and carry and thus spread the load placed thereupon by the adjacent spinous processes. The bore 3138 can be shaped like bore 3134 (Figure 154c) to allow for pivoting and rotating motion. Also, in order to accommodate bore 3138 of the egg-shaped spacer 3136 being off-center, the lead-in guide 3126 would also be egg-shaped and have an off-center position where shaft 3124 is attached. --, therefor.

Signed and Sealed this  
Twenty-third Day of August, 2011

David J. Kappos  
*Director of the United States Patent and Trademark Office*